(12) United States Patent
Jin et al.

(10) Patent No.: US 9,351,974 B2
(45) Date of Patent: May 31, 2016

(54) SUBSTITUTED PTERIDINONES FOR THE TREATMENT OF CANCER

(71) Applicant: OSI Pharmaceuticals, LLC, Farmingdale, NY (US)

(72) Inventors: Meizhong Jin, East Northport, NY (US); Mridula Kadalbajoo, Farmingdale, NY (US); An-Hu Li, Commack, NY (US); Mark J. Mulvihill, Concord, MA (US); Kam W. Siu, Farmingdale, NY (US); Arno G. Steinig, Carmel, NY (US); Jing Wang, Milford, CT (US)

(73) Assignee: OSI Pharmaceuticals, LLC, Northbrook, IL (US)

( * ) Notice: Subject to any disclaimer, the term of this patent is extended or adjusted under 35 U.S.C. 154(b) by 0 days.

(21) Appl. No.: 14/357,259

(22) PCT Filed: Nov. 12, 2012

(86) PCT No.: PCT/US2012/064596
§ 371 (c)(1),
(2) Date: May 9, 2014

(87) PCT Pub. No.: WO2013/071217
PCT Pub. Date: May 16, 2013

(65) Prior Publication Data
US 2014/0315911 A1    Oct. 23, 2014

Related U.S. Application Data

(60) Provisional application No. 61/558,223, filed on Nov. 10, 2011.

(51) Int. Cl.
| | |
|---|---|
| A61K 31/4985 | (2006.01) |
| C07D 475/00 | (2006.01) |
| A61K 31/519 | (2006.01) |
| C07D 487/04 | (2006.01) |
| C07D 471/04 | (2006.01) |
| C07D 519/00 | (2006.01) |
| A61K 45/06 | (2006.01) |
| C07D 475/12 | (2006.01) |
| A61K 31/5025 | (2006.01) |

(52) U.S. Cl.
CPC ........... *A61K 31/519* (2013.01); *A61K 31/4985* (2013.01); *A61K 45/06* (2013.01); *C07D 471/04* (2013.01); *C07D 475/00* (2013.01); *C07D 475/12* (2013.01); *C07D 487/04* (2013.01); *C07D 519/00* (2013.01); *A61K 31/5025* (2013.01)

(58) Field of Classification Search
CPC .......................... A61K 31/4985; C07D 475/00
USPC .......................... 514/249; 544/258
See application file for complete search history.

(56) References Cited

U.S. PATENT DOCUMENTS

| | | |
|---|---|---|
| 5,424,311 A | 6/1995 | Billhardt-Troughton |
| 6,806,272 B2 | 10/2004 | Bauer |
| 7,169,778 B2 | 1/2007 | Denny |
| 7,759,347 B2 | 7/2010 | Hoffmann |
| 2002/0086866 A1 | 7/2002 | Dudley |
| 2004/0029885 A1 | 2/2004 | Bauer et al. |
| 2006/0047118 A1 | 3/2006 | Stadtmueller |
| 2007/0155730 A1 | 7/2007 | Leit |
| 2008/0194572 A1 | 8/2008 | Nowak |
| 2009/0124628 A1 | 5/2009 | Hoffmann |
| 2010/0216726 A1 | 8/2010 | Fuchino |
| 2011/0124634 A1 | 5/2011 | Sun |

FOREIGN PATENT DOCUMENTS

| | | |
|---|---|---|
| WO | 2004076454 A1 | 9/2004 |
| WO | 2005018531 A2 | 3/2005 |
| WO | 2006002367 A1 | 1/2006 |
| WO | 2007014838 A1 | 2/2007 |
| WO | 2007135374 A1 | 11/2007 |
| WO | 2008009909 A1 | 1/2008 |
| WO | 2008040951 A1 | 4/2008 |
| WO | 2008092831 A1 | 8/2008 |

(Continued)

OTHER PUBLICATIONS

International Search Report and Written Opinion of the International Search Authority in PCT/US2012/064596, mailed Apr. 1, 2013 and received from the Korean Intellectual Property Office.

(Continued)

*Primary Examiner* — Douglas M Willis
(74) *Attorney, Agent, or Firm* — Brinks Gilson & Lione

(57) ABSTRACT

Compounds of Formula I, as shown below and defined herein:

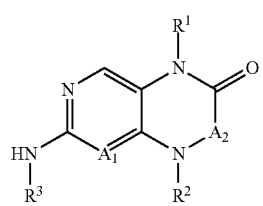

pharmaceutically acceptable salts thereof, synthesis, intermediates, formulations, and methods of disease treatment therewith, including treatment of cancers, such as tumors driven or mediated at least in part by RSK. This Abstract is not limiting of the invention.

10 Claims, No Drawings

(56) References Cited

FOREIGN PATENT DOCUMENTS

| | | |
|---|---|---|
| WO | 2009022185 A2 | 2/2009 |
| WO | 2009139834 A1 | 11/2009 |
| WO | 2010080712 A2 | 11/2010 |
| WO | 2011016472 A1 | 2/2011 |
| WO | 2011035534 A1 | 3/2011 |
| WO | 2011036566 A1 | 3/2011 |

OTHER PUBLICATIONS

Supplementary European Search Report in EP Application No. 12847823, completed Jun. 10, 2015.
Nguyen, Anti-Cancer Agents in Medicinal Chemistry (2008), vol. 8, No. 7, pp. 710-716.
Romeo et al., Expert Opin. Ther. Targets (2011), vol. 15, No. 1, pp. 5-9.
Sapkota et al., Biochem J. (2007), vol. 401, pp. 29-38.
Smith et al., Cancer Res. (2005), vol. 65, No. 3, pp. 1027-1034.

SUBSTITUTED PTERIDINONES FOR THE TREATMENT OF CANCER

CROSS-REFERENCE TO RELATED APPLICATIONS

This application is a national stage of PCT/US2012/064596, filed Nov. 12, 2012, which claims the benefit of U.S. Provisional Application No. 61/558,223, filed Nov. 10, 2011.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention pertains at least in part to cancer, chemical compounds, their preparation, formulation, and use in treating conditions such as cancer.

2. Description of the Related Art

RSK has emerged as an anti-cancer target. Ribosomal S6 protein kinases (RSKs) are a family of highly conserved protein serine/threonine kinases that includes subfamilies p90 RSK and p70 RSK and belong to the AGC super family. T. L. Nguyen, *Anti-Cancer Agents in Medicinal Chemistry*, 8, 710-716 (2008); Y. Romeo et al., *Expert Opin. Ther. Targets*, 15(1):5-9 (2011).

There are four isoforms of p90 RSK (RSK 1-4) in vertebrates, which exhibit variable tissue expression, and are activated in response to growth factors, polypeptide hormones, neurotransmitters, and chemokines. RSK lies downstream of the MAPK signaling pathway and is directly phosphorylated by ERK1/2. RSK activation was also found to be triggered by p38 and ERK5, and FGFR3. RSK regulates cellular processes such as cell growth, motility, survival, and proliferation. Nguyen, Romeo, above.

RSK contributes to antiapoptosis signaling by phosphorylating BAD, C/EBPβ, and DAP kinase. RSK is a mediator of FGFR3, being phosphorylated by it, and RSK is a regulator in cell transformations induced by tumor promoters. Some RSK substrates are themselves cancer targets of interest, such as Myt1 and GSK-3. Nguyen, Romeo, above.

Deregulated RSK expression or activity has been associated with several diseases, including cancers such as breast, multiple myeloma, acute myeloid leukemia, hand and neck cancer, osteosarcoma, and prostate. RSK has been linked to HIV and Coffin-Lowry syndrome (CLS), caused by a mutation in RSK2. A cardiovascular target of RSK is NHE1 and thus RSK inhibitors may be useful in treating cardiovascular disease.

RSK may be a promising target for treating cancers characterized by oncogenic Ras/MAPK signaling; and RSK2 has been the isoform most closely linked with human cancers. Nguyen, Romeo, above.

Compounds disclosed as inhibitors of RSK have come from various chemotypes. J. A. Smith et al., *Cancer Res.*, 65(3), 1027-1034 (2005); Nguyen, above. The dihydropteridinone BI-D1870 was found to be a potent inhibitor of RSK1-4. G. P. Sapkota et al., *Biochem J.*, 401, 29-38 (2007).

The reader may also take note of: U.S. Pat. No. 5,424,311; U.S. Pat. No. 6,806,272; U.S. Pat. No. 7,169,778; U.S. Pat. No. 7,759,347; US2002/0086866; US2006/0047118; US2007/0155730; US2008/0194572; US2009/0124628; US2010/0216726; US2011/0124634; WO2001/019825; WO2005/018531; WO2005/123736; WO2006/021547; WO2007/014838; WO2007/135374; WO2008/009909; WO2008/040951; WO2008/092831; WO2008/093075; WO2009/139834; WO2010/080712; WO2011/016472; WO2011/036566; EP0590428.

There is a need for effective therapies for use in proliferative disease, including treatments for primary cancers, prevention of metastatic disease, and targeted therapies, including tyrosine kinase inhibitors, such as RSK, including its individual isoforms. Thus, problems addressed by the present invention include the identification of potent and selective RSK inhibitors that further preferably possess other generally desirable drug-like physico-chemical and biological properties.

BRIEF SUMMARY OF THE INVENTION

The present invention includes all of the subject matter disclosed herein, including the compounds, their preparation and intermediates, formulations and products thereof, and their use in the treatment of disease, including in the treatment of cancers and other conditions, alone or in combination with other rationally selected active agents.

Among other things, the present invention addresses a desire for new anti-cancer agents, for small molecule agents that inhibit RSK, that selectively inhibit RSK, and that further possess a profile lending to effective pharmaceutical use, including physicochemical, PK, and PD properties suitable for an oral pharmaceutical product.

In some aspects, the present invention concerns compounds of Formula I, as shown below and defined herein:

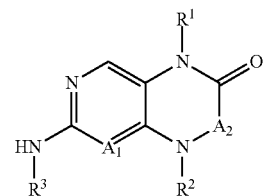

I or a pharmaceutically acceptable salt thereof, wherein:
$A_1$ is N or $C(R^4)$; $A_2$ is $C(O)$ or $C(R^5)(R^6)$;
$R^1$ is phenyl optionally fused to $_{5\text{-}10}$cyclic, or $R^1$ is $_{5\text{-}6}$heteroaryl optionally fused to $_{5\text{-}10}$cyclic, either of which is optionally substituted;
$R^2$ is optionally substituted phenyl or optionally substituted $_{5\text{-}6}$heteroaryl; or $R^2$ is H or optionally substituted $C_{1\text{-}8}$aliphatic that is optionally interrupted by one or more heteroatoms;
$R^3$ is $C_{4\text{-}8}$carbocyclic optionally fused to $_{5\text{-}10}$cyclic or is $_{5\text{-}6}$heteroaryl optionally fused to $_{5\text{-}10}$cyclic, either of which is optionally substituted;
$R^4$ is H, halo, $C_{1\text{-}3}$aliphatic, or $-OC_{1\text{-}3}$aliphatic; and each $R^5$ and $R^6$ is independently H, $C_{1-6}$aliphatic, or $_{3-10}$cyclic, any of which is optionally substituted, and wherein $R^5$ and $R^6$, together with the atom to which they are attached, can form a $_{3-6}$cyclic optionally including one or more heteroatoms; and $R^2$ and $R^5$, together with the atoms to which they are attached, can form a $_{3-6}$cyclic optionally including one or more heteroatoms.

In some aspects, compounds of the invention are inhibitors of kinases, including RSK1 and RSK2. In some aspects, compounds of the invention are selective inhibitors of one or more of RSK 1-4, or of all of RSK 1-4.

In some aspects, the invention includes treating disease, human disease, including cancers, mediated at least in part by RSK, characterized by deregulated RSK expression, oncogenic Ras/MAPK signaling, alone or in combination regimens with other active agents that are at any time known to effective in such combination.

The invention includes the compounds and salts thereof, and their physical forms, preparation of the compounds, useful intermediates, and pharmaceutical compositions and formulations thereof.

BRIEF DESCRIPTION OF THE SEVERAL VIEWS OF THE DRAWING(S)

Not Applicable

DETAILED DESCRIPTION OF THE INVENTION

Compounds

In some aspects, the present invention concerns compounds and any salts thereof of Formula I, as shown below and defined herein:

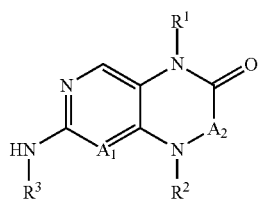

I wherein:
$A_1$ is N or $C(R^4)$; $A_2$ is C(O) or $C(R^5)(R^6)$;
$R^1$ is phenyl optionally fused to $_{5-10}$cyclic, or $R^1$ is $_{5-6}$heteroaryl optionally fused to $_{5-10}$cyclic, either of which is optionally substituted; $R^2$ is optionally substituted phenyl or optionally substituted $_{5-6}$heteroaryl; or $R^2$ is H or optionally substituted $C_{1-8}$aliphatic that is optionally interrupted by one or more heteroatoms;
$R^3$ is $C_{4-8}$carbocyclic optionally fused to $_{5-10}$cyclic or is $_{5-6}$heteroaryl optionally fused to $_{5-10}$cyclic, either of which is optionally substituted;
$R^4$ is H, halo, $C_{1-3}$aliphatic, or $-OC_{1-3}$aliphatic; and
each $R^5$ and $R^6$ is independently H, $C_{1-6}$aliphatic, or $_{3-10}$cyclic, any of which is optionally substituted, and wherein $R^5$ and $R^6$, together with the atom to which they are attached, can form a $_{3-6}$cyclic optionally including one or more heteroatoms; and $R^2$ and $R^5$, together with the atoms to which they are attached, can form a $_{3-6}$cyclic optionally including one or more heteroatoms.

The invention includes a subgenus 1 of Formula I, and its salts, wherein:

each $R^5$ and $R^6$ is independently H or $C_{1-6}$aliphatic optionally substituted by one or more halo, $-OH$, $-OC_{1-3}$aliphatic, $-NR^{40}R^{41}$, $_{5-6}$heteroaryl, or $-C(O)NR^{40}R^{41}$; and wherein $R^5$ and $R^6$, together with the atom to which they are attached, can form a $_{3-6}$cyclic optionally including one or more heteroatoms; and each $R^{40}$ and $R^{41}$ is independently H or $C_{1-3}$aliphatic, and $R^{40}$ and $R^{41}$, together with the atom to which they are attached, can form a $_{3-6}$cyclic optionally including one or more heteroatoms.

The invention includes a subgenus 2 of Formula I or of subgenus 1, and its salts, wherein:
$R^1$ is phenyl optionally fused to $_{5-10}$cyclic, or $R^1$ is $_{5-6}$heteroaryl optionally fused to $_{5-10}$cyclic, either of which is optionally substituted by one or more $R^7$;
each $R^7$ is independently halo, nitro, $-CN$, $-OR^{10}$, $-NR^{10}R^{11}$, $-C(O)R^{10}$, $-C(O)OR^{10}$, $-C(O)NR^{10}R^{11}$, $-SR^{10}$, $-R^{10}$, $-NR^{12}C(O)NR^{10}R^{11}$, $-OC(O)R^{10}$, $-NR^{12}C(O)R^1$, $-NR^{12}C(O)OR^{10}$, $-OC(O)NR^{10}R^{11}$, $-C(O)-C(O)OR^{10}$, $-S(O_{1-2})R^{10}$, $-S(O_{1-2})NR^{10}R^{11}$, $-NR^{12}S(O_{1-2})R^{10}$, $-NR^{12}S(O_{1-2})NR^{10}R^{11}$, $-NR^{12}S(O_{1-2})OR^{10}$, or $-OS(O_{1-2})NR^{10}R^{11}$; or $-PR^{10}R^{11}$, $-P(OR^{10})(OR^{11})$, $-PR^{10}(OR^{11})$, $-P(O)R^{10}R^{11}$, $-P(O)(OR^{10})(OR^{11})$, $-P(O)R^{10}(OR^{11})$, $-BR^{10}R^{11}$, $-B(OR^{10})(OR^{11})$, $-NHS(O)(R^{10})=NR^{11}$, or $-R^{10}-S(O)(R^{11})=NR^{12}$; wherein in the case of a non-aromatic moiety, an $R^7$ can also include oxo;
each $R^{10}$, $R^{11}$, and $R^{12}$ is independently H or $C_{1-6}$aliphatic, each independently optionally substituted by one or more halo, oxo, nitro, $-CN$, $-OR^{13}$, $-NR^{13}R^{14}$, $-C(O)R^{13}$, $-C(O)OR^{13}$, $-C(O)NR^{13}R^{14}$, $-SR^{13}$, $-R^{14}$, $-NR^{15}C(O)NR^{13}R^{14}$, $-OC(O)R^{13}$, $-NR^{14}C(O)R^{13}$, $-NR^{14}C(O)OR^{13}$, $-OC(O)NR^{13}R^{14}$, $-C(O)-C(O)OR^{13}$, $-S(O_{1-2})R^{13}$, $-S(O_{1-2})NR^{13}R^{14}$, or $-NR^{13}S(O_{1-2})R^{14}$; $-NR^{15}S(O_{1-2})NR^{13}R^{14}$, $-NR^{15}S(O_{1-2})OR^{13}$, or $-OS(O_{1-2})NR^{13}R^{14}$, or by $-PR^{13}R^{14}$, $-P(OR^{13})(OR^{14})$, $PR^{13}(OR^{14})$, $-P(O)R^{13}R^{14}$, $-P(O)(OR^{13})(OR^{14})$, $-P(O)R^{13}(OR^{14})$, $-BR^{13}R^{14}$, $-B(OR^{13})(OR^{14})$, $NHS(O)(R^{13})=NR^{14}$, or $-R^{13}-S(O)(R^{14})=NR^{15}$;

wherein any $R^{10}/R^{11}$ pair attached to the same atom, together with said atom to which they are attached, can form a $_{3-6}$cyclic that can include one or more heteroatoms selected from O, $NR^{18}$, or $S(O_{0-2})$;

each $R^{13}$, $R^{14}$, and $R^{15}$ is independently H or $C_{1-3}$aliphatic, each independently optionally substituted by one or more halo, $-CN$, $-OR^{16}$, $-NR^{16}R^{17}$, $-C(O)R^{16}$, $-C(O)OR^{16}$, $-C(O)NR^{16}$, or $-OC(O)R^{16}$;

wherein any $R^{13}/R^{14}$ pair attached to the same atom, together with said atom to which they are attached, can form a $_{3-6}$cyclic that can include one or more heteroatoms selected from O, $NR^{19}$, or $S(O_{0-2})$; and each $R^{16}$, $R^{17}$, $R^{18}$, and $R^{19}$ is independently H or $C_{1-3}$aliphatic.

The invention includes a subgenus 3 of Formula I or of subgenera 1 or 2, and its salts, wherein:
$R^2$ is phenyl or $_{5-6}$heteroaryl, each optionally substituted by one or more $R^{20}$;
or $R^2$ is $C_{1-8}$aliphatic optionally interrupted by one or more heteroatoms and optionally substituted by one or more $R^{21}$;
each $R^{20}$ and $R^{21}$ is independently oxo, $-R^{22}$, halo, $-CN$, $-OR^{22}$, $-SR^{22}$, $-NR^{22}R^{23}$, $-C(O)R^{22}$, $-C(O)OR^{22}$, $-C(O)NR^{22}$, $-OC(O)R^{22}$, $NR^{22}C(O)R^{23}$, $-S(O_{1-2})R^{22}$, $-S(O_{1-2})NR^{22}R^{23}$, or $-NR^{22}S(O_{1-2})R^{23}$;
each $R^{22}$ and $R^{23}$ is independently H or $C_{1-3}$aliphatic, each independently optionally substituted by one or more oxo, $-R^{50}$, halo, $-CN$, $-OR^{50}$, $-SR^{50}$, $-NR^{50}R^{51}$, $-C(O)$ $R^{50}$, —C(O)OR$^{50}$, —C(O)NR$^{50}$, —OC(O)R$^{50}$, NR$^{50}$C(O)R$^{51}$, —S(O$_{1-2}$)R$^{50}$, —S(O$_{1-2}$)NR$^{50}$R$^{51}$, or —NR$^{50}$S(O$_{1-2}$)R$^{51}$;

wherein any R$^{22}$/R$^{23}$ pair attached to the same atom, together with said atom to which they are attached, can form a $_{3-6}$cyclic that can include one or more heteroatoms selected from O, NR$^{52}$, or S(O$_{0-2}$); and each R$^{50}$, R$^{51}$ and R$^{52}$ is independently H or C$_{1-3}$aliphatic.

The invention includes a subgenus 4 of Formula I or of subgenera 1-3, and its salts, wherein:

R$^3$ is phenyl optionally fused to $_{5-10}$cyclic, or R$^3$ is $_{5-6}$heteroaryl optionally fused to $_{5-10}$cyclic, either of which is optionally substituted by one or more R$^8$;

each R$^8$ is independently halo, nitro, —CN, —OR$^{30}$, —NR$^{30}$R$^{31}$, —C(O)R$^{30}$, —C(O)OR$^{30}$, —C(O)NR$^{30}$R$^{31}$, —SR$^{30}$, —R$^{30}$, —NR$^{32}$C(O)NR$^{30}$R$^{31}$, —OC(O)R$^{30}$, —NR$^{32}$C(O)R$^{30}$, —NR$^{32}$C(O)OR$^{30}$, —OC(O)NR$^{30}$R$^{31}$, —C(O)—C(O)OR$^{30}$, —S(O$_{1-2}$)R$^{30}$, —S(O$_{1-2}$)NR$^{30}$R$^{31}$, —NR$^{32}$S(O$_{1-2}$)R$^{30}$, —NR$^{32}$S(O$_{1-2}$)NR$^{30}$R$^{31}$, —NR$^{31}$S(O$_{1-2}$)OR$^{32}$, or —OS(O$_{1-2}$)NR$^{30}$R$^{31}$; or —PR$^{30}$R$^{31}$, —P(OR$^{30}$)(OR$^{31}$), —PR$^{30}$(OR$^{31}$), —P(O)R$^{30}$R$^{31}$, —P(O)(OR$^{30}$)(OR$^{31}$), —P(O)R$^{30}$(OR$^{31}$), —BR$^{30}$R$^{31}$, —B(OR$^{30}$)(OR$^{31}$), —NHS(O)(R$^{30}$)=NR$^{31}$, or —R$^{30}$—S(O)(R$^{31}$)=NR$^{32}$; wherein in the case of a non-aromatic moiety, an R$^7$ can also include oxo;

each R$^{30}$, R$^{31}$, and R$^{32}$ is independently H or C$_{1-6}$aliphatic, each independently optionally substituted by one or more halo, oxo, nitro, —CN, —OR$^{33}$, —NR$^{33}$R$^{34}$, —C(O)R$^{33}$, —C(O)OR$^{33}$, —C(O)NR$^{33}$R$^{34}$, —SR$^{33}$, —R$^{34}$, —OC(O)R$^{33}$, —NR$^{34}$C(O)R$^{33}$, —NR$^{34}$C(O)OR$^{33}$, —N=CR$^{33}$R$^{34}$, —OC(O)NR$^{33}$R$^{34}$, —C(O)—C(O)OR$^{33}$, —S(O$_{1-2}$)R$^{33}$, —S(O$_{1-2}$)NR$^{33}$R$^{34}$, or —NR$^{33}$S(O$_{1-2}$)R$^{34}$; or by —PR$^{33}$R$^{34}$, —P(OR$^{33}$)(OR$^{34}$), —PR$^{33}$(OR$^{34}$), —P(O)R$^{33}$R$^{34}$, —P(O)(OR$^{33}$)(OR$^{34}$), —P(O)R$^{33}$(OR$^{34}$), —BR$^{33}$R$^{34}$, —B(OR$^{33}$)(OR$^{34}$), —NHS(O)(R$^{33}$)=NR$^{34}$, or —R$^{33}$—S(O)(R$^{34}$)=NR$^{35}$;

wherein any R$^{30}$/R$^{31}$ pair attached to the same atom, together with said atom to which they are attached, can form a $_{3-6}$cyclic that can include one or more heteroatoms selected from O, NR$^{38}$, or S(O$_{0-2}$);

each R$^{33}$, R$^{34}$, and R$^{35}$ is independently H or C$_{1-3}$aliphatic, each independently optionally substituted by one or more halo, —CN, —OR$^{36}$, —NR$^{36}$R$^{37}$, —C(O)R$^{36}$, —C(O)OR$^{36}$, —C(O)NR$^{36}$, or —OC(O)R$^{36}$;

wherein any R$^{33}$/R$^{34}$ pair attached to the same atom, together with said atom to which they are attached, can form a $_{3-6}$cyclic that can include one or more heteroatoms selected from O, NR$^{39}$, or S(O$_{0-2}$);

each R$^{36}$, R$^{37}$, R$^{38}$, and R$^{39}$ is independently H or C$_{1-3}$aliphatic.

The invention includes a subgenus 5 of subgenus 4, and its salts, wherein:

R$^8$ is independently halo, nitro, —CN, —OR$^{31}$, —NR$^{31}$R$^{32}$, —C(O)R$^{31}$, —C(O)OR$^{31}$, C(O)NR$^{31}$R$^{32}$, —SR$^{31}$, —R$^{31}$, —NR$^{33}$C(O)NR$^{31}$R$^{32}$, —OC(O)R$^{31}$, —NR$^{33}$C(O)R$^{31}$, —NR$^{33}$C(O)OR$^{31}$, OC(O)NR$^{31}$R$^{32}$, —C(O)—C(O)OR$^{31}$, —S(O$_{1-2}$)R$^{31}$, —S(O$_{1-2}$)NR$^{31}$R$^{32}$, —NR$^{33}$S(O$_{1-2}$)R$^{31}$, —NR$^{33}$S(O$_{1-2}$)NR$^{31}$R$^{32}$, or —OS(O$_{1-2}$)NR$^{31}$R$^{32}$;

in the case of a non-aromatic moiety, an R$^8$ can also include oxo;

each R$^{31}$, R$^{32}$, and R$^{33}$ is independently H or C$_{1-3}$aliphatic.

The invention includes a subgenus 6 of Formula I or of subgenera 1-5, and its salts, wherein: A$_1$ is C(R$^4$).

The invention includes a subgenus 7 of Formula I or of subgenera 1-5, and its salts, wherein: A$_1$ is N.

The invention includes a subgenus 8 of Formula I or of subgenera 1-7, and its salts, wherein: A$_2$ is C(O).

The invention includes a subgenus 9 of Formula I or of subgenera 1-8, and its salts, wherein: A$_2$ is C(H)((R)—R$^5$), wherein R$^5$ is C$_{1-3}$aliphatic optionally substituted by one halo, —OH, —OC$_{1-3}$aliphatic, or —NR$^{40}$R$^{41}$; and each R$^{40}$ and R$^{41}$ is independently H or C$_{1-3}$aliphatic.

The invention includes a subgenus 10 of Formula I or of subgenera 1-9, and its salts, wherein:

R$^2$ is phenyl optionally substituted by 1-3 independent R$^{20}$, or R$^2$ is C$_{3-8}$aliphatic containing at least one cyclic or branched moiety, optionally interrupted by 1-2 heteroatoms, and optionally substituted by 1-3 independent R$^{20}$;

each R$^{20}$ is independently —R$^{22}$, halo, —OR$^{22}$;

R$^{22}$ is H or C$_{1-3}$aliphatic, optionally substituted by 1-3 halo, —OC$_{1-3}$aliphatic.

The invention includes a subgenus 11 of Formula I or of subgenera 1-10, and its salts, wherein:

R$^3$ is phenyl or $_6$heteroaryl, either being optionally fused to $_{5-6}$cyclic and optionally substituted by one or more R$^8$;

each R$^8$ is independently halo, —CN, —OR$^{31}$, —NR$^{31}$R$^{32}$, —C(O)R$^{31}$, —C(O)OR$^{32}$, —C(O)NR$^{31}$R$^{32}$, —R$^{31}$, or —OC(O)R$^{31}$, or in the case of a non-aromatic moiety, an R$^8$ can also include oxo;

each R$^{31}$ and R$^{32}$ is independently H or C$_{1-3}$aliphatic.

The invention includes a subgenus 12 of Formula I or of subgenera 1-11, and its salts, wherein:

R$^1$ is phenyl or pyridyl, either of which is optionally substituted by 1-3 R$^7$;

each R$^7$ is independently halo, nitro, —CN, —OR$^{10}$, —R$^{10}$, —SR, —NR$^{10}$R$^{11}$, —C(O)R$^{10}$, —C(O)OR$^{10}$, —C(O)NR$^{10}$R$^{11}$, —NR$^{10}$C(O)R$^{11}$, —SO$_2$NR$^{10}$R$^{11}$, —NR$^{10}$SO$_2$R$^{11}$, —NR$^{10}$C(O)NR$^{11}$, or —SO$_2$R$^{10}$;

each R$^{10}$ and R$^{11}$ is independently H or C$_{1-3}$aliphatic, each independently optionally substituted by one or more halo, oxo, —CN, —OR$^{13}$, or —R$^{14}$;

wherein any R$^{10}$/R$^{11}$ pair attached to the same atom, together with said atom to which they are attached, can form a $_{3-6}$cyclic that can include one heteroatom selected from O, —NR$^{18}$, or S(O$_{0-2}$);

each R$^{13}$, R$^{14}$ and R$^{18}$ is independently H or C$_{1-3}$aliphatic.

The invention includes a subgenus 13 of Formula I, and its salts, wherein:

A$_1$ is N; A$_2$ is CH((R)-methyl);

R$^1$ is phenyl or pyridyl, either of which is optionally substituted by 1-2 independent halo, —CN, —CH$_3$, or —OCH$_3$;

R$^2$ is C$_{3-6}$aliphatic selected from branched and cyclic aliphatic optionally interrupted by 1-2 heteroatoms, and optionally substituted by 1-2 independent halo, —CH$_3$, or —OCH$_3$;

R$^3$ is selected from:

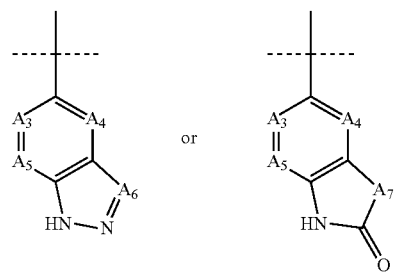

wherein each A$_3$-A$_6$ is independently CH or N;
A$_7$ is CH$_2$, O, or S;
and wherein either of the above is optionally substituted by 1-3 independent halo, —CH$_3$, or —OCH$_3$ groups.

The invention includes a subgenus 14 of Formula I or of subgenera 1-12, and its salts, having the formula:

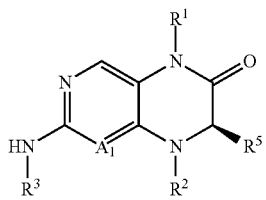

wherein R⁵ is $C_{1-3}$aliphatic.

The invention includes a subgenus 15 of subgenus 14, and its salts, wherein: R⁵ is methyl.

Each variable definition above includes any subset thereof and the compounds of Formula I include any combination of such variables or variable subsets.

In some aspects, the invention includes any of the compound examples herein and pharmaceutically acceptable salts thereof.

The invention includes the compound or salt of the invention, which is present as a material that is substantially stereochemically pure.

The invention includes the compounds and salts thereof per se, and their physical forms, preparation of the compounds, useful intermediates, and pharmaceutical compositions and formulations thereof.

The compounds of the invention and the term "compound" in the claims include any pharmaceutically acceptable salts or solvates, and any amorphous or crystal forms, or tautomers, whether or not specifically recited in context.

The invention includes the isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Included within the scope of the invention are all stereoisomers, geometric isomers and tautomeric forms of the inventive compounds, including compounds exhibiting more than one type of isomerism, and mixtures of one or more thereof.

When a tautomer of the compound of Formula (I) exists, the compound of formula (I) of the present invention includes any possible tautomers and pharmaceutically acceptable salts thereof, and mixtures thereof, except where specifically stated otherwise.

The compounds of the invention are not limited to those containing all of their atoms in their natural isotopic abundance. The present invention includes compounds wherein one or more hydrogen, carbon or other atoms are replaced by different isotopes thereof such as for labeling or other purposes. Such compounds can be useful as research and diagnostic tools in metabolism pharmacokinetic studies and in binding assays. A recitation of a compound or an atom within a compound includes isotopologs, i.e., species wherein an atom or compound varies only with respect to isotopic enrichment and/or in the position of isotopic enrichment. For non-limiting example, in some cases it may be desirable to enrich one or more hydrogen atoms with deuterium (D) or to enrich carbon with $^{13}C$. Other examples of isotopes suitable for inclusion in the compounds of the invention include isotopes of hydrogen, chlorine, fluorine, iodine, nitrogen, oxygen, phosphorus, and sulfur. Certain isotopically-labeled compounds of the invention may be useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Substitution with positron emitting isotopes may be useful in Positron Emission Topography (PET) studies for examining substrate receptor occupancy.

Further, the compounds may be amorphous or may exist or be prepared in various crystal forms or polymorphs, including solvates and hydrates. The invention includes any such forms provided herein, at any purity level. A recitation of a compound per se means the compound regardless of any unspecified stereochemistry, physical form and whether or not associated with solvent or water.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g., $D_2O$, d6-acetone, d6-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized.

The invention includes prodrugs of compounds of the invention which may, when administered to a patient, be converted into the inventive compounds, for example, by hydrolytic cleavage. Prodrugs in accordance with the invention can, for example, be produced by replacing appropriate functionalities present in the inventive compounds with certain moieties known to those skilled in the art as 'pro-moieties' as known in the art. Particularly favored derivatives and prodrugs of the invention are those that increase the bioavailability of the compounds when such compounds are administered to a patient, enhance delivery of the parent compound to a given biological compartment, increase solubility to allow administration by injection, alter metabolism or alter rate of excretion.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds that are basic are capable of forming a wide variety of salts with various inorganic and organic acids. The acids that can be used to prepare pharmaceutically acceptable acid addition salts of such basic compounds are those that form acceptable acid addition salts. When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Other salts are aspartate, besylate, bicarbonate/carbonate, bisulphate/sulfate, borate, camsylate, edisylate, gluceptate, glucuronate, hexafluorophosphate, hibenzate, hydrobromide/bromide, hydroiodide/iodide, malonate, methylsulfate, naphthylate, 2-napsylate, nicotinate, orotate, oxalate, palmitate, phosphate/hydrogen, phosphate/dihydrogen, phosphate, saccharate, stearate, tartrate, tosylate, and trifluoroacetate.

When the compound of the present invention is acidic, its corresponding salt can be conveniently prepared from pharmaceutically acceptable bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic bases include salts of primary, secondary, and tertiary amines, as well as cyclic amines and substituted amines such as naturally occurring and synthesized substituted amines. Other pharmaceutically acceptable organic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, trometamine and the like. Other examples include benzathine, diolamine, glycine, meglumine, and olamine.

Preparation

In some aspects, the invention includes the intermediates, examples, and synthetic methods described herein in all of their embodiments.

The compounds of the Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art [such as those methods disclosed in standard reference books such as the Compendium of Organic Synthetic Methods, Vol. I-VI (Wiley-Interscience); or the Comprehensive Organic Transformations, by R. C. Larock (Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons (1981); T. W. Greene and P. G. M. Wuts, Protective Groups in Organic Chemistry, John Wiley & Sons (1991), and T. W. Greene and P. G. M. Wuts, Protective Groups in Organic Chemistry, John Wiley & Sons, 1999, which are hereby incorporated by reference in their entireties.

Compounds of Formula I, or their pharmaceutically acceptable salts, and the intermediates used in the synthesis of the compounds of this invention can be prepared according to the reaction schemes discussed hereinbelow and the general skill in the art. Unless otherwise indicated, the substituents in the schemes are defined as above. Isolation and purification of the products is accomplished by standard procedures, which are known to a chemist of ordinary skill.

When a general or exemplary synthetic procedure is referred to, one skilled in the art can readily determine the appropriate reagents, if not indicated, extrapolating from the general or exemplary procedures. Some of the general procedures are given as examples for preparing specific compounds. One skilled in the art can readily adapt such procedures to the synthesis of other compounds. Representation of an unsubstituted position in structures shown or referred to in the general procedures is for convenience and does not preclude substitution as described elsewhere herein. For specific groups that can be present, either as R groups in the general procedures or as optional substituents not shown, refer to the descriptions in the remainder of this document, including the claims, summary and detailed description.

The process to produce compounds of the present invention is preferably carried out at about atmospheric pressure although higher or lower pressures can be used if desired. Substantially equimolar amounts of reactants are preferably used although higher or lower amounts can also be used.

General Schemes

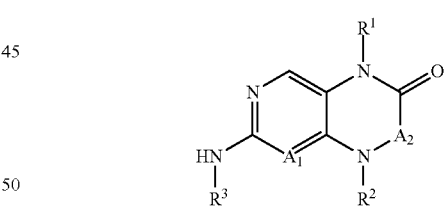

I

Method A may be used to prepare compounds of Formula I-A as shown below in Scheme 1:

Scheme 1

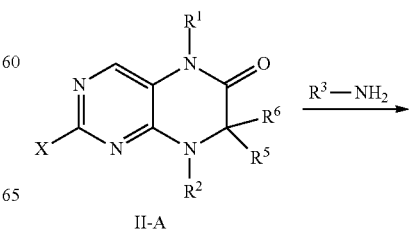

II-A $R^3$—$NH_2$ →

-continued

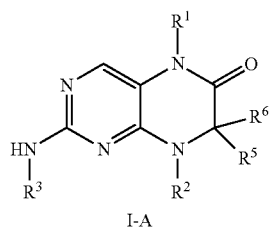

I-A where $R^1$, $R^2$, $R^3$, $R^5$, $R^6$ are as defined previously. X is halogen such as Cl, Br, I or other suitable leaving groups.

In a typical preparation of a compound of Formula I-A, a compound of Formula II-A is reacted with $R^3$—$NH_2$ in a suitable solvent. Suitable solvents include, but are not limited to, ethers such as THF, glyme, and the like; toluene, benzene and the like, DMF, DMSO, MeCN; alcohols such as MeOH, EtOH, IPA, trifluoroethanol, butanol and the like; if desired, mixtures of these solvents are used, however, the preferred solvents are trifluoroethanol or butanol. A certain amount of Brønsted acid (catalytic amount, stoichiometric amount or excessive amount) may be added to the reaction mixture to facilitate the reaction. Suitable Brønsted acids include, but are not limited to, HCl, TFA and the like. The above process may be carried out at temperatures between about −78° C. and about 150° C. Preferably, the reaction is carried out between about 80° C. and about 120° C. The above process is preferably carried out in a sealed reaction vessel such as, but not limited to, a thick walled glass reaction vessel. The above process could also be carried out in a microwave reactor under appropriate microwave reaction conditions.

Alternatively, compounds of Formula I-A could also be prepared by reacting a compound of Formula II-A (X is halogen such as Cl, Br, I or OTf) with $R^3$—$NH_2$ in a suitable solvent under transition metal catalysis (for example, Buchwald-Hartwig coupling or the like). Suitable solvents include, but are not limited to, ethers such as THF, glyme, and the like; toluene, benzene and the like, DMF. If desired, mixtures of these solvents are used, however, the preferred solvents are DMF or toluene. Suitable transition metal catalysts include, but are not limited to $Pd(PPh_3)_4$, $Pd(OAc)_2$, $Pd(dppf)Cl_2$, $Pd_2(dba)_3$ and the like. Additional ligands may be added to the reaction mixture. Suitable ligands include, but are not limited to 2,2'-bis(diphenylphosphino)-1,1'-binaphthyl (BINAP), 2-dicyclohexylphosphino-2',6'-dimethoxybiphenyl (SPhos), 2-dicyclohexylphosphino-2',4',6'-triisopropylbiphenyl (XPhos) and the like. Preferably, the reaction is carried out in the presence of a base such as, but not limited to, $Cs_2CO_3$, NaOtBu and the like. The above process may be carried out at temperatures between about −78° C. and about 150° C. Preferably, the reaction is carried out between about 80° C. and about 120° C. The above process is preferably carried out in a sealed reaction vessel such as, but not limited to, a thick walled glass reaction vessel. The above process could also be carried out in a microwave reactor under appropriate microwave reaction conditions.

Compounds of Formula II-A of Scheme 1 may be prepared as shown below in Scheme 2.

Scheme 2

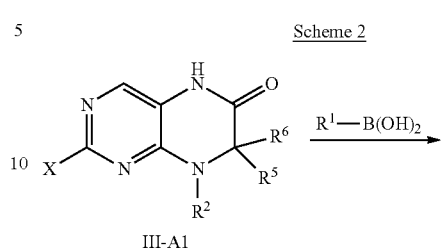

II-A where $R^1$, $R^2$, $R^5$, $R^6$ are as defined previously. X is halogen such as Cl, Br, I or other suitable leaving groups.

In a typical preparation of a compound of Formula II-A, an intermediate of Formula III-A1 is reacted with $R^1$—$B(OH)_2$ in a suitable solvent at a suitable reaction temperature in the presence of a metal coupling reagent and a base. Suitable solvents include, but are not limited to, ethers such as THF, glyme, and the like; toluene, benzene and the like, DMF, and chlorinated solvents such as DCM, 1,2-dichloroethane (DCE) or $CHCl_3$ and the like. If desired, mixtures of these solvents are used. The preferred solvents are DCM or DCE. The above process may be carried out at temperatures between about −78° C. and about 120° C. Preferably, the reaction is carried out between about 20° C. and about 50° C. Suitable metal coupling reagents include, but are not limited to, Copper(II) reagents such as $Cu(OAc)_2$; suitable bases include, but are not limited to, TEA, DIPEA. Molecular sieves may also be added to the reaction mixture to facilitate the reaction.

Alternatively, compounds of Formula II-A of Scheme 1 could also be prepared from an intermediate of Formula III-A2 as shown in Scheme 3.

Scheme 3

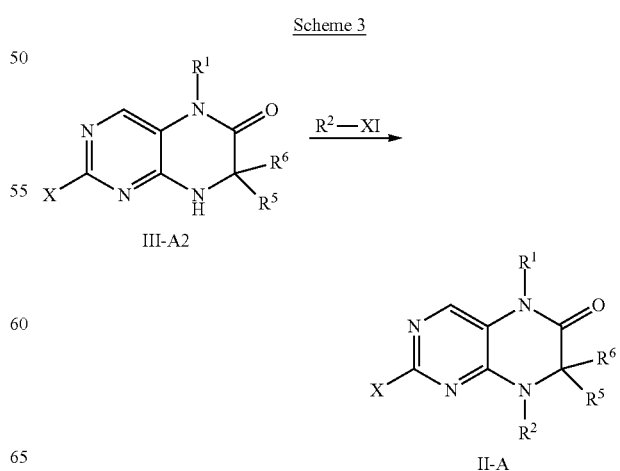

II-A where $R^1$, $R^2$, $R^5$, $R^6$ are as defined previously. X and XI are each independently halogens such as Cl, Br, I or other suitable leaving groups.

In a typical preparation of a compound of Formula II-A, an intermediate of Formula III-A2 is reacted with $R^2$—XI in a suitable solvent at a suitable reaction temperature in the presence of a base. Suitable solvents include, but are not limited to, ethers such as THF, glyme, and the like; DMF, DMSO. If desired, mixtures of these solvents are used. The preferred solvent is DMF. The above process may be carried out at temperatures between about −78° C. and about 150° C. Preferably, the reaction is carried out between about 20° C. and about 120° C. Suitable bases include, but are not limited to, NaH, NaOtBu and the like.

It would be appreciated by those skilled in the art that compounds of Formula II-A of Scheme 3 could also be prepared by other methods which include, but are not limited to, a reductive amination reaction between an intermediate of Formula III-A2 and an appropriate aldehyde or ketone, or a transition metal catalyzed coupling reaction between an intermediate of Formula III-A2 and $R^2$—XI (for example, Buchwald-Hartwig coupling or the like).

Compounds of Formula III-A1 of Scheme 2 may be prepared as shown below in Scheme 4.

Scheme 4

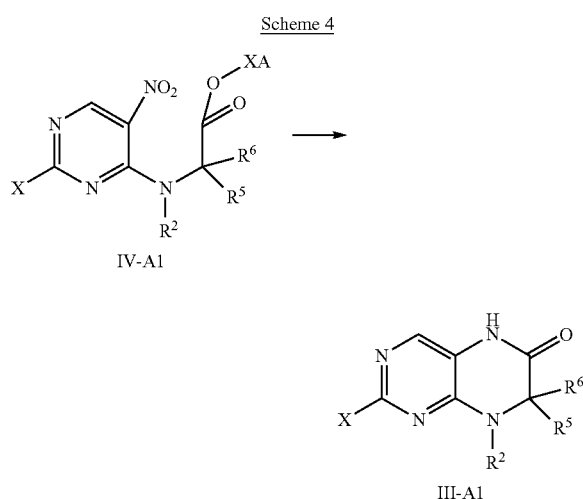

III-A1 where $R^2$, $R^5$, $R^6$ are as defined previously. X is halogen such as Cl, Br, I or other suitable leaving groups, XA is an alkyl group such as methyl, ethyl and the like.

In a typical preparation of a compound of Formula III-A1, an intermediate of Formula IV-A1 is reacted with a reducing reagent. Suitable solvents include, but are not limited to, alcohols such as MeOH, EtOH and the like. An acid is added to the reaction mixture. Suitable acids include, but are not limited to, HCl, acetic acid (AcOH) and the like. The reaction may also be carried out in neat AcOH without any other solvent. The above process may be carried out at temperatures between about −78° C. and about 150° C. Preferably, the reaction is carried out between about 50° C. and about 120° C. Suitable reducing agents include, but are not limited to, iron powder.

Compounds of Formula IV-A1 of Scheme 4 may be prepared as shown below in Scheme 5.

Scheme 5

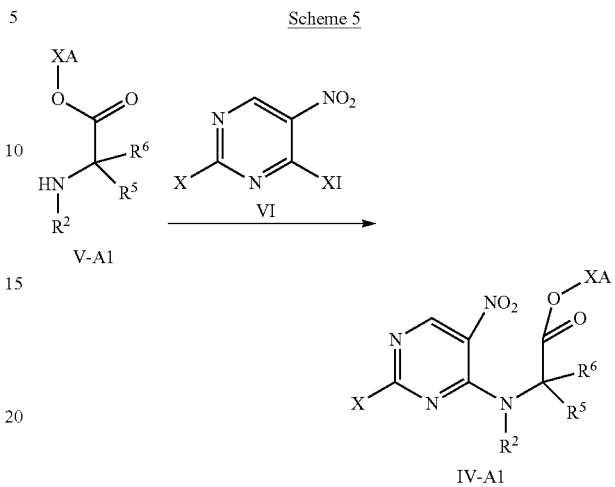

IV-A1 where $R^2$, $R^5$, $R^6$ are as defined previously. X, XI are each independently halogens such as Cl, Br, I or other suitable leaving groups, XA is an alkyl group such as methyl, ethyl and the like. The skilled artisan will recognize that a larger number of compounds V-A1, including cyclic compounds such as where $R^2$ and $R^5$ are linked, are commercially available or otherwise accessible.

In a typical preparation of a compound of Formula IV-A1, an intermediate of Formula V-A1 (in free base or a salt form) is reacted with an intermediate of Formula VI. Suitable solvents include, but are not limited to, water, ethers such as THF, glyme, and the like; toluene, benzene and the like, DMF, DMSO, MeCN. If desired, mixtures of these solvents are used, however, the preferred solvents are water and ether. A base may be added to the reaction to facilitate the reaction. Suitable bases include, but are not limited to, $Cs_2CO_3$, $K_2CO_3$, and the like. The above process may be carried out at temperatures between about −78° C. and about 100° C. Preferably, the reaction is carried out between about −20° C. and about 50° C.

Compounds of Formula V-A1 of Scheme 5 may be prepared as shown below in Scheme 6.

Scheme 6

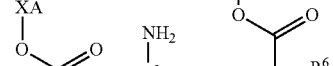

where $R^2$, $R^5$, $R^6$ are as defined previously. X is a halogen such as Cl, Br, I or other suitable leaving groups, XA is an alkyl group such as methyl, ethyl and the like.

In a typical preparation of a compound of Formula V-A1, an intermediate of Formula VII-A1 is reacted with an intermediate of Formula VIII (in free base or a salt form). Suitable solvents include, but are not limited to, water, ethers such as THF, glyme, and the like; toluene, benzene and the like, DMF, DMSO, MeCN, ethyl acetate. If desired, mixtures of these solvents are used. The preferred solvent is DMF. A base may be added to facilitate the reaction. Suitable bases include, but are not limited to, $Cs_2CO_3$, $K_2CO_3$, and the like. The above process may be carried out at temperatures between about −78° C. and about 120° C. Preferably, the reaction is carried out between about −20° C. and about 100° C.

It would be appreciated by those skilled in the art that compounds of Formula V-A1 of Scheme 5 could also be prepared by other methods which include, but are not limited to, a reductive amination reaction between an intermediate of Formula IX-A1 and an appropriate aldehyde or ketone, as shown in Scheme 7.

Scheme 7

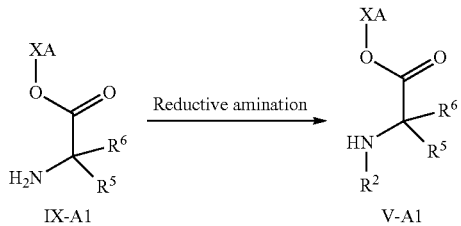

where $R^2$, $R^5$, $R^6$ are as defined previously. XA is an alkyl group such as methyl, ethyl and the like. The skilled artisan will recognize that a larger number of compounds IX-A1, including cyclic compounds such as where $R^5$ and $R^6$ are linked, are commercially available or otherwise accessible.

In a typical preparation of a compound of Formula V-A1, an intermediate of Formula IX-A1 (in free base or a salt form) is reacted with an appropriate aldehyde or ketone in the presence of a reducing reagent. Suitable solvents include, but are not limited to, water, ethers such as THF, glyme, and the like; toluene, benzene and the like, DMF, MeCN, ethyl acetate, alcohols such as MeOH, EtOH, and the like. If desired, mixtures of these solvents are used. The preferred solvents are alcohols. The suitable reducing reagents include, but are not limited to $NaBH_4$, $NaBH(OAc)_3$, $NaBH_3CN$, and the like. The above process may be carried out at temperatures between about −78° C. and about 100° C. Preferably, the reaction is carried out between about −20° C. and about 50° C.

Compounds of Formula III-A2 of Scheme 3 may be prepared as shown below in Scheme 8.

Scheme 8

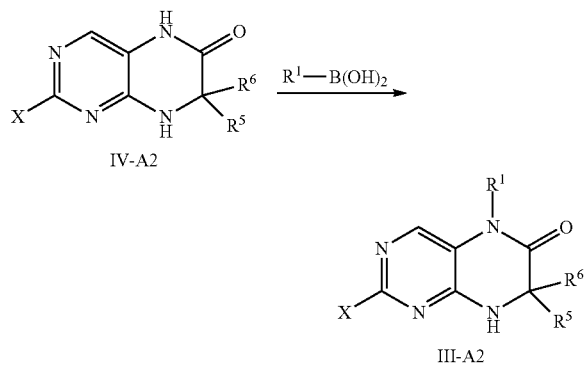

where $R^1$, $R^5$, $R^6$ are as defined previously. X is an halogen such as Cl, Br, I or other suitable leaving groups.

In a typical preparation of a compound of Formula III-A2, an intermediate of Formula IV-A2 is reacted with $R^1$—B$(OH)_2$ according to reaction conditions similar to the synthesis of compounds of Formula II-A from compounds of Formula III-A1 described above.

Compounds of Formula IV-A2 of Scheme 8 may be prepared as shown below in Scheme 9.

Scheme 9

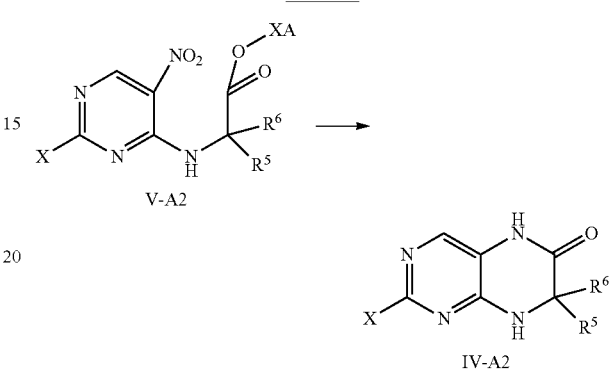

where $R^5$, $R^6$ are as defined previously. X is an halogen such as Cl, Br, I or other suitable leaving groups. XA is an alkyl group such as methyl, ethyl and the like.

In a typical preparation of a compound of Formula IV-A2, an intermediate of Formula V-A2 is reacted with an reducing reagent, according to reaction conditions similar to the synthesis of compounds of Formula III-A1 from compounds of Formula IV-A1 described above.

Compounds of Formula V-A2 of Scheme 9 may be prepared as shown below in Scheme 10.

Scheme 10

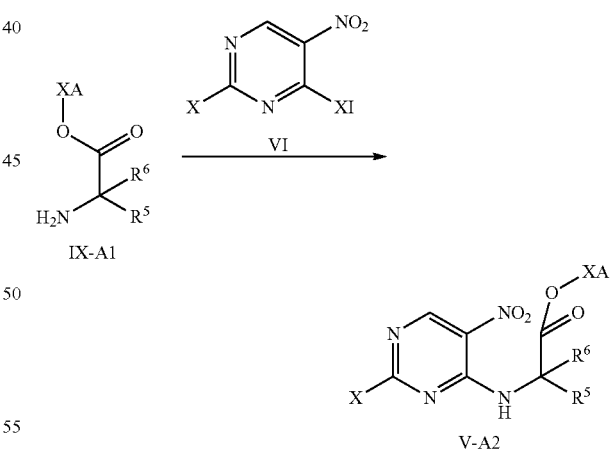

where $R^5$, $R^6$ are as defined previously. X, XI are each independently halogens such as Cl, Br, I or other suitable leaving groups, XA is an alkyl group such as methyl, ethyl and the like.

In a typical preparation of a compound of Formula V-A2, an intermediate of Formula IX-A1 (in free base or a salt form) is reacted with an intermediate of Formula VI, according to reaction conditions similar to the synthesis of compounds of Formula IV-A1 from compounds of Formula V-A1 described above.

Method B may be used to prepare compounds of Formula I-B as shown below in Scheme 11:

Scheme 11

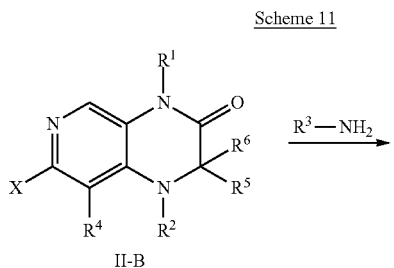

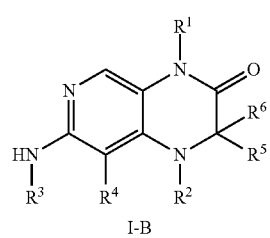
I-B where $R^1$, $R^2$, $R^3$, $R^4$, $R^5$, $R^6$ are as defined previously. X is halogen such as Cl, Br, I or OTf.

In a typical preparation of a compound of Formula I-B, a compound of Formula II-B is reacted with $R^3$—$NH_2$ in a suitable solvent under transition metal catalysis (for example, Buchwald-Hartwig coupling or the like). Suitable solvents include, but are not limited to, ethers such as THF, glyme, and the like; toluene, benzene and the like, DMF, DMSO. If desired, mixtures of these solvents are used, however, the preferred solvents are DMF or toluene. Suitable transition metal catalysts include, but are not limited to $Pd(PPh_3)_4$, $Pd(OAc)_2$, $Pd(dppf)Cl_2$, $Pd_2(dba)_3$ and the like. Additional ligands may be added to the reaction mixture. Suitable ligands include, but are not limited to BINAP, SPhos, XPhos and the like. Preferably, the reaction is carried out in presence of a base such as $Cs_2CO_3$, NaOtBu and the like. The above process may be carried out at temperatures between about −78° C. and about 150° C. Preferably, the reaction is carried out between about 80° C. and about 120° C. The above process is preferably carried out in a sealed reaction vessel such as, but not limited to, a thick walled glass reaction vessel. The above process could also be carried out in a microwave reactor under appropriate microwave reaction conditions.

Compounds of Formula II-B of Scheme 11 may be prepared as shown below in Scheme 12.

Scheme 12

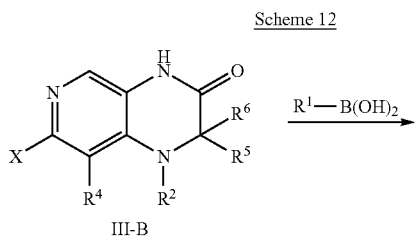

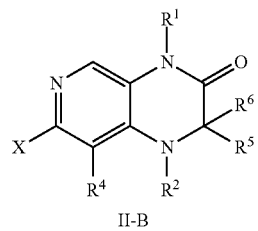
II-B where $R^1$, $R^2$, $R^4$, $R^5$, $R^6$ are as defined previously. X is halogen such as Cl, Br, I or OTf.

In a typical preparation of a compound of Formula II-B, an intermediate of Formula III-B is reacted with $R^1$—$B(OH)_2$, according to reaction conditions similar to the synthesis of compounds of Formula II-A from compounds of Formula III-A1 described above.

Compounds of Formula III-B of Scheme 12 may be prepared as shown below in Scheme 13.

Scheme 13

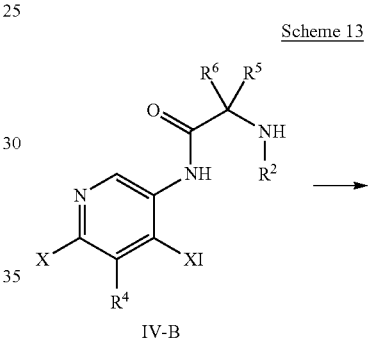
IV-B

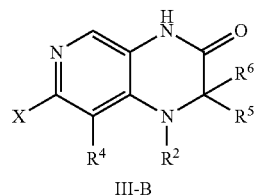
III-B where $R^2$, $R^4$, $R^5$, $R^6$ are as defined previously. X is a halogen such as Cl, Br, I or OTf.

Xl is halogen such as Cl, Br, I or other suitable leaving groups.

In a typical preparation of a compound of Formula III-B, an intermediate of Formula IV-B is treated with a base in a suitable solvent at a suitable reaction temperature. Suitable solvents include, but are not limited to, ethers such as THF, glyme, and the like; toluene, benzene and the like, DMF, DMSO, MeCN and chlorinated solvents such as DCM, DCE or $CHCl_3$ and the like. If desired, mixtures of these solvents are used. The preferred solvent is DMF. The above process may be carried out at temperatures between about −78° C. and about 150° C. Preferably, the reaction is carried out between about 50° C. and about 130° C. Suitable bases include, but are not limited to, $Cs_2CO_3$, $K_3PO_4$, NaOtBu and the like.

Compounds of Formula IV-B of Scheme 13 may be prepared as shown below in Scheme 14.

Scheme 14

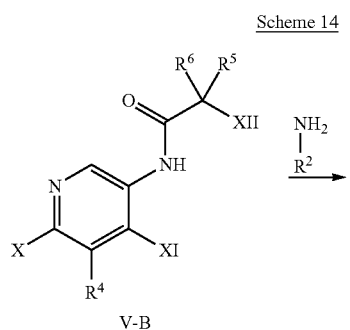

V-B

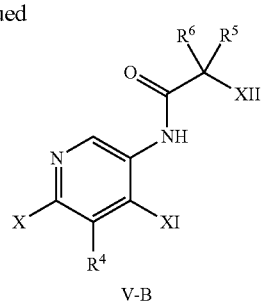

V-B where $R^4$, $R^5$, $R^6$ are as defined previously. X is a halogen such as Cl, Br, I or OTf. XI, XII, XIII are each independently halogens such as Cl, Br, I or other suitable leaving groups.

In a typical preparation of a compound of Formula V-B, an intermediate of Formula VI-B is reacted with intermediate of Formula VII-B. Suitable solvents include, but are not limited to, ethers such as THF, glyme, and the like; toluene, benzene and the like, DMF, DMSO, MeCN, ethyl acetate; chlorinated solvents such as DCM, DCE or CHCl$_3$ and the like. If desired, mixtures of these solvents are used. The preferred solvent is DMF. A base may be used to facilitate the reaction. Suitable bases include, but are not limited to, TEA, DIPEA and the like. The above process may be carried out at temperatures between about −78° C. and about 120° C. Preferably, the reaction is carried out between about −20° C. and about 100° C.

It would be appreciated by those skilled in the art that compounds of Formula V-B of Scheme 15 could also be prepared by other methods which include, but are not limited to, a amide coupling reaction between an intermediate of Formula VI-B and an appropriate acid in the presence of a amide coupling reagent. The suitable reaction conditions for amide couplings may be found in Larock, R. C. Comprehensive Organic Transformations, 2$^{nd}$ ed.; Wiley and Sons: New York, 1999, or in other similar literature sources.

It would be appreciated by those skilled in the art that compounds of Formula IV-B of Scheme 14 could also be prepared by other methods which include, but are not limited to, a reductive amination reaction between an intermediate of Formula VIII-B and an appropriate aldehyde or ketone, as shown in Scheme 16.

IV-B where $R^2$, $R^4$, $R^5$, $R^6$ are as defined previously. X is a halogen such as Cl, Br, I or OTf. XI, XII are each independently halogens such as Cl, Br, I or other suitable leaving groups.

In a typical preparation of a compound of Formula IV-B, an intermediate of Formula V-B is reacted with R$_2$—NH$_2$ (in free base or a salt form). Suitable solvents include, but are not limited to, water, ethers such as THF, glyme, and the like; toluene, benzene and the like, DMF, DMSO, MeCN, ethyl acetate; chlorinated solvents such as DCM, DCE or CHCl$_3$ and the like. If desired, mixtures of these solvents are used. The preferred solvent is DMF. A base may be used to facilitate the reaction. Suitable bases include, but are not limited to, Cs$_2$CO$_3$, K$_2$CO$_3$, and the like. The above process may be carried out at temperatures between about −78° C. and about 120° C. Preferably, the reaction is carried out between about −20° C. and about 100° C.

Compounds of Formula V-B of Scheme 14 may be prepared as shown below in Scheme 15.

Scheme 15

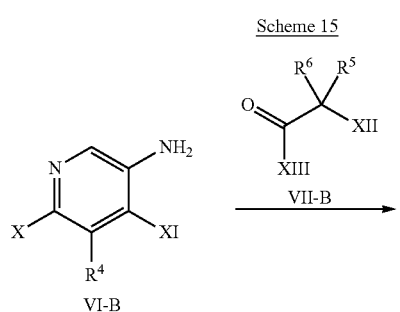

Scheme 16

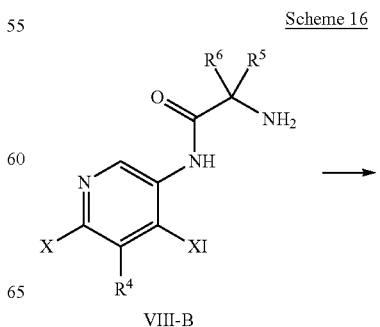

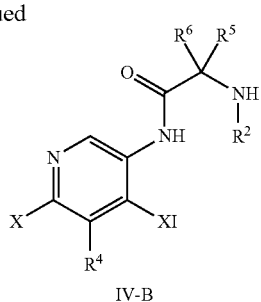

IV-B where $R^2$, $R^4$, $R^5$, $R^6$ are as defined previously. X is a halogen such as Cl, Br, I or OTf., XI is halogen such as Cl, Br, I or other suitable leaving groups.

In a typical preparation of a compound of Formula IV-B, an intermediate of Formula VIII-B (in free base or a salt form) is reacted with an appropriate aldehyde or ketone in the presence of a reducing reagent. Suitable solvents include, but are not limited to, water, ethers such as THF, glyme, and the like; toluene, benzene and the like, DMF, DMSO, MeCN, ethyl acetate, alcohols such as MeOH, EtOH and the like. If desired, mixtures of these solvents are used. The preferred solvents are alcohols. The suitable reducing reagents include, but are not limited to $NaBH_4$, $NaBH(OAc)_3$, $NaBH_3CN$, and the like. The above process may be carried out at temperatures between about –78° C. and about 100° C. Preferably, the reaction is carried out between about –20° C. and about 50° C.

It would be appreciated by those skilled in the art that compounds of Formula VIII-B of Scheme 16 could be prepared by methods which include, but are not limited to, a amide coupling reaction between an intermediate of Formula VI-B and an appropriate acid in the presence of a amide coupling reagent. The suitable reaction conditions for amide couplings can be found in Larock, R. C. Comprehensive Organic Transformations, $2^{nd}$ ed.; Wiley and Sons: New York, 1999, or in other similar literature sources.

Method C may be used to prepare compounds of Formula I-C as shown below in Scheme 17:

Scheme 17

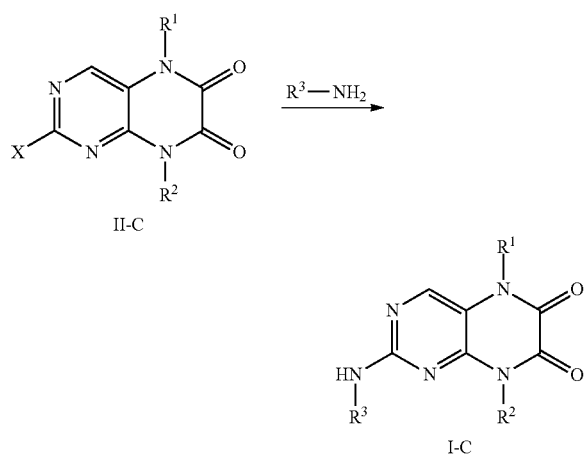

I-C where $R^1$, $R^2$, $R^3$ are as defined previously. X is halogen such as Cl, Br, I or other suitable leaving groups.

In a typical preparation of compounds of Formula I-C, compound of Formula II-C is reacted with $R^3$—$NH_2$, according to reaction conditions similar to the synthesis of compounds of Formula I-A from compounds of Formula II-A described above.

The compounds of Formula II-C of Scheme 17 may be prepared as shown below in Scheme 18.

Scheme 18

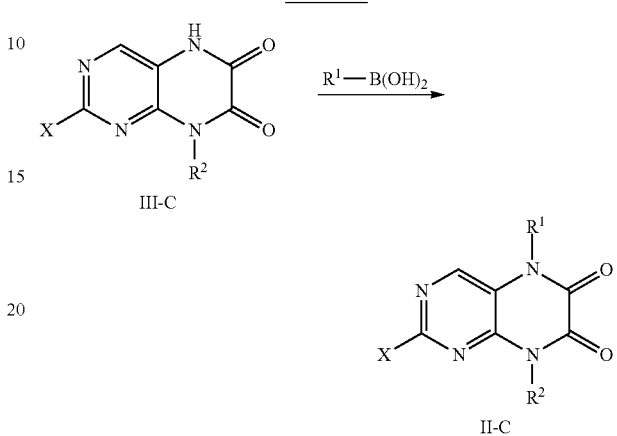

II-C where $R^1$, $R^2$ are as defined previously. X is halogen such as Cl, Br, I or other suitable leaving groups.

In a typical preparation of a compound of Formula II-C, an intermediate of Formula III-C is reacted with $R^1$—$B(OH)_2$, according to reaction conditions similar to the synthesis of compounds of Formula II-A from compounds of Formula III-A1 described above.

The compounds of Formula III-C of Scheme 18 may be prepared as shown below in Scheme 19.

Scheme 19

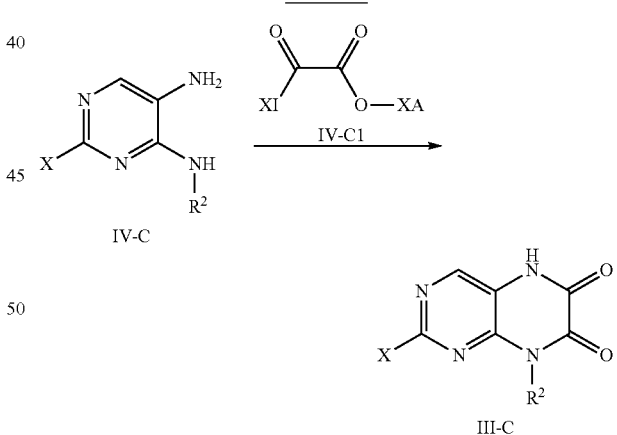

III-C where $R^2$ is as defined previously. X, XI are each independently halogens such as Cl, Br, I or other suitable leaving groups, XA is an alkyl group such as methyl, ethyl and the like.

In a typical preparation of a compound of Formula III-C, an intermediate of Formula IV-C is reacted with compound IV-C1 in a suitable solvent at a suitable reaction temperature in the presence of a base. Suitable solvents include, but are not limited to, ethers such as THF, glyme, and the like; toluene, benzene and the like, DMF, DMSO, MeCN and chlorinated solvents such as DCM, DCE or $CHCl_3$ and the like. If desired, mixtures of these solvents are used or no solvent is used. The preferred solvent is toluene. The above process may be carried out at temperatures between about −78° C. and about 120° C. Preferably, the reaction is carried out between about 20° C. and about 50° C. Suitable bases include, but are not limited to, TEA, DIPEA.

The compounds of Formula IV-C of Scheme 19 may be prepared as shown below in Scheme 20.

Scheme 20

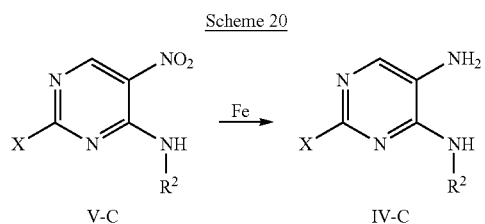

V-C    IV-C where $R^2$ is as defined previously. X is halogen such as Cl, Br, I or other suitable leaving groups.

In a typical preparation of a compound of Formula IV-C, an intermediate of Formula V-C is reacted with iron as reducing reagent. Suitable solvents include, but are not limited to, alcohols such as MeOH, EtOH and the like. An acid is added to the reaction mixture. Suitable acids include, but are not limited to, HCl, Acetic acid (AcOH) and the like. The above process may be carried out at temperatures between about −78° C. and about 150° C. Preferably, the reaction is carried out between about 50° C. and about 120° C.

It would be appreciated by those skilled in the art that the reduction reaction in Scheme 24 could also be achieved by various other methods described in literature using various reducing reagents such as, but not limited to, $SnCl_2$, $H_2$ (hydrogenation).

The compounds of Formula V-C of Scheme 20 may be prepared as shown below in Scheme 21.

Scheme 21

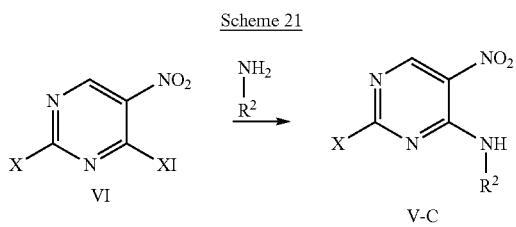

VI    V-C where $R^2$ is as defined previously. X, XI are each independently halogens such as Cl, Br, I or other suitable leaving groups.

In a typical preparation of a compound of Formula V-C, an intermediate of Formula VI is reacted with $R^2$—$NH_2$ (in free base or a salt form). Suitable solvents include, but are not limited to, water, ethers such as THF, glyme, and the like; toluene, benzene and the like, DMF, DMSO, MeCN. If desired, mixtures of these solvents are used, however, the preferred solvents are mixture of water and ether. A base may be added to the reaction to facilitate the reaction. Suitable bases include, but are not limited to, $Cs_2CO_3$, $K_2CO_3$, and the like. The above process may be carried out at temperatures between about −78° C. and about 100° C. Preferably, the reaction is carried out between about −20° C. and about 50° C.

Method D may be used to prepare compounds of Formula I-D as shown below in Scheme 22:

Scheme 22

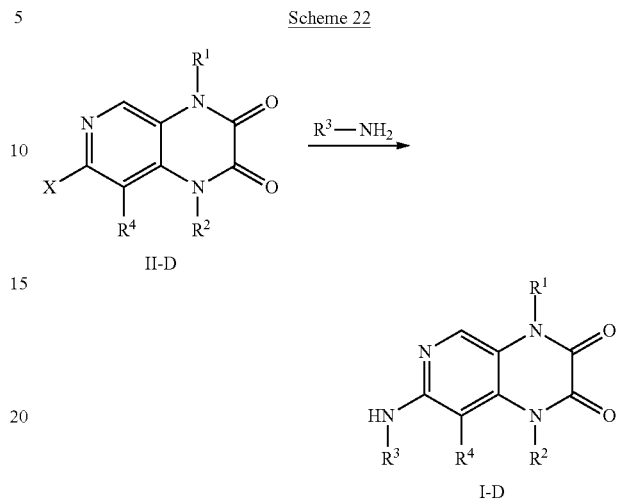

where $R^1$, $R^2$, $R^3$, $R^4$ are as defined previously for compound of Formula I. X is halogen such as Cl, Br, I or OTf.

In a typical preparation of a compound of Formula I-D, a compound of Formula II-D is reacted with $R^3$—$NH_2$ in a suitable solvent under transition metal catalysis (for example, Buchwald-Hartwig coupling or the like). Suitable solvents for use in the above process include, but are not limited to, ethers such as THF, glyme, and the like; toluene, benzene and the like, DMF, DMSO. If desired, mixtures of these solvents are used. Suitable transition metal catalyst for use in the above process include, but are not limited to $Pd(PPh_3)_4$, $Pd(OAc)_2$, $Pd(dppf)Cl_2$, $Pd_2(dba)_3$ and the like. Additional ligands may be added to the reaction mixture. Suitable ligands for use in the above process include, but are not limited to 2,2'-bis (diphenylphosphino)-1,1'-binaphthyl (BINAP), 2-dicyclohexylphosphino-2',6'-dimethoxybiphenyl (SPhos), 2-dicyclohexylphosphino-2',4',6'-triisopropylbiphenyl (XPhos) and the like. Preferably, the reaction is carried out in presence of a base such as $Cs_2CO_3$, NaOtBu and the like. The above process is carried out at temperatures between about −78° C. and about 150° C. Preferably, the reaction is carried out between 60° C. and about 120° C. The above process is preferably carried out in a sealed reaction vessel such as, but not limited to, a thick walled glass reaction vessel. The above process to produce compounds of the present invention could also be carried out in a microwave reactor under appropriate microwave reaction conditions.

The compounds of Formula II-D of Scheme 22 may be prepared as shown below in Scheme 23.

Scheme 23

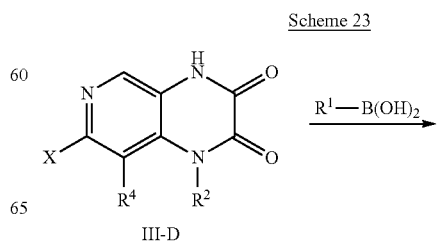

III-D

-continued

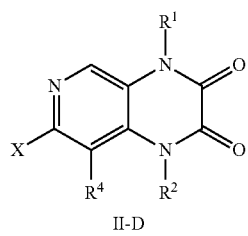
II-D where $R^1$, $R^2$, $R^4$ are as defined previously for compound of Formula I. X is halogen such as Cl, Br, I or OTf.

In a typical preparation of a compound of Formula II-D, an intermediate of Formula III-D is reacted with $R^1$—B(OH)$_2$, according to reaction conditions similar to the synthesis of compounds of Formula II-A from compounds of Formula III-A1 described above.

The compounds of Formula III-D of Scheme 23 may be prepared as shown below in Scheme 24.

Scheme 24

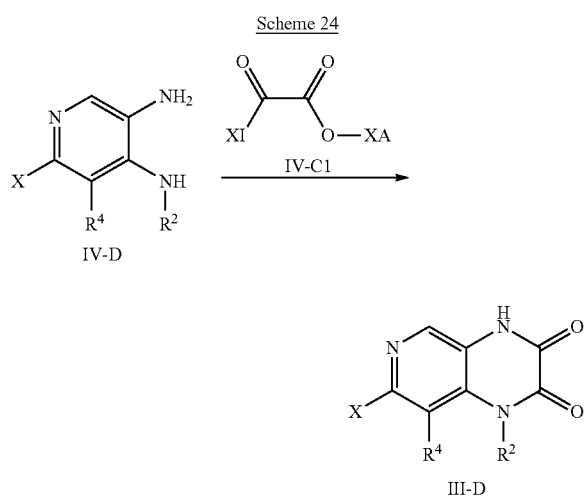

III-D where $R^2$, $R^4$ are as defined previously for compound of Formula I. X is halogen such as Cl, Br, I or OTf. XI is halogen such as Cl, Br, I or other suitable leaving groups, XA is an alkyl group such as methyl, ethyl and the like.

In a typical preparation of a compound of Formula III-D, an intermediate of Formula IV-D is reacted with compound IV-C1 in a suitable solvent at a suitable reaction temperature in the presence of a base. Suitable solvents for use in the above process include, but are not limited to, ethers such as THF, glyme, and the like; toluene, benzene and the like, dimethylformamide (DMF), dimethyl sulfoxide (DMSO), acetonitrile (MeCN) and chlorinated solvents such as dichloromethane (DCM), 1,2-dichloroethane (DCE) or chloroform (CHCl$_3$) and the like. If desired, mixtures of these solvents are used or no solvent is used. The above process is carried out at temperatures between about −78° C. and about 120° C. Preferably, the reaction is carried out between 20° C. and about 80° C. Suitable bases for use in the above process include, but are not limited to, triethylamine (TEA), diisopropylethylamine (DIPEA).

The compounds of Formula IV-D of Scheme 24 are prepared as shown below in Scheme 25.

Scheme 25

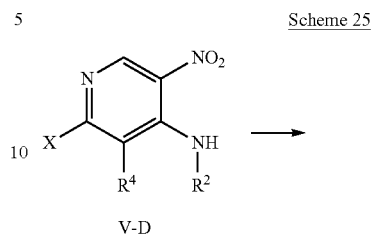
V-D

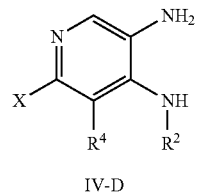
IV-D where $R^2$, $R^4$ are as defined previously for compound of Formula I. X is halogen such as Cl, Br, I or OTf.

In a typical preparation of a compound of Formula IV-D, an intermediate of Formula V-D is reacted with a suitable reducing reagent, according to reaction conditions similar to the synthesis of compounds of Formula IV-C from compounds of Formula V-C described above.

The compounds of Formula V-D of Scheme 25 are prepared as shown below in Scheme 26.

Scheme 26

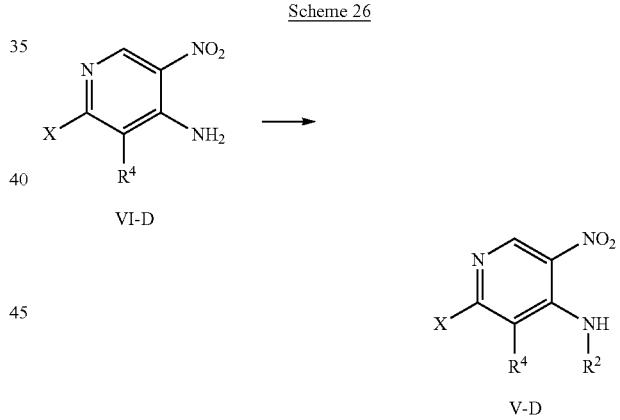

V-D where $R^2$, $R^4$ are as defined previously for compound of Formula I. X is halogen such as Cl, Br, I or OTf.

In a typical preparation of a compound of Formula V-D, an intermediate of Formula VI-D is reacted with an appropriate aldehyde or ketone in the presence of a reducing reagent.

Suitable solvents for use in the above process include, but are not limited to, water, ethers such as THF, glyme, and the like; toluene, benzene and the like, dimethylformamide (DMF), acetonitrile (MeCN), ethyl acetate, alcohols such as MeOH, EtOH, and the like. If desired, mixtures of these solvents are used. The preferred solvents are alcohols. The suitable reducing reagents for use in the above process include, but are not limited to NaBH$_4$, NaBH(OAc)$_3$, NaBH$_3$CN, and the like. The above process is carried out at temperatures between about −78° C. and about 100° C. Preferably, the reaction is carried out between −20° C. and about 50° C.

EXAMPLES

Unless otherwise noted, all materials/reagents were obtained from commercial suppliers and used without further purification. Reactions were monitored by thin layer chromatography (TLC) on silica gel 60 $F_{254}$ (0.2 mm) precoated aluminum foil or glass-backed and visualized using UV light. Flash chromatography (alternatively called "ISCO chromatography") was performed using an ISCO CombiFlash Rf 4× Organic Purification System or equivalent with RediSep normal-phase silica gel cartridges. Preparative TLC was performed on Whatman LK6F Silica Gel 60 Å size 20×20 cm plates with a thickness of 1000 µm or equivalent. Hydromatrix (=diatomaceous earth) was purchased from Varian.

$^1$H NMR (300 or 400 MHz) and $^{13}$C NMR (100.6 MHz) spectra were recorded on Bruker or Varian spectrometers at RT with TMS or the residual solvent peak as the internal standard. The line positions or multiples are given in (5) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 experiment and are abbreviated as follows: +(CH or $CH_3$), –($CH_2$), $C_{quart}$ (C).

Preparative HPLC purifications ("MDP") were performed on a Waters® Mass-Directed Purification System equipped with 2525 Binary Gradient Module, 2767 Sample Manager, a Column Fluidics Organizer (CFO), 2996 Photodiode Array Detector, a 515 pump for column regeneration, a reagent manager for the makeup flow, a 515 pump for at-column-dilution, ZQ™ single-quadrupole Mass Detector equipped with a Z-spray electrospray interface, controlled by MassLynx™ Version 4.1 with FractionLynx™ software. All purification work was completed using a parallel dual-column Luna C18(2) 21×150 mm, 5 µm LC/MS system and ARW (accelerated retention window). The mobile phases were water (0.1% TFA) and acetonitrile (0.1% TFA); all reagents used were of HPLC grade. The flow rate was 30 mL/min. After the columns, a 1:1000 LC packings flow splitter allowed transfer of a small portion of the eluent into the UV detector and, subsequently, a 10% portion into the ZQ MS. The electrospray source was set at 3.0 kV capillary voltage, 30 V cone voltage, 110° C. source temperature, 350° C. desolvation temperature, 600 L/h desolvation gas flow, and 60 L/h cone gas flow. For the analyzer, the multiplier was set at 550 for preparative tune method.

Analytical LC-MS data was collected on ZQ3, TOF, or UPLC instruments with a mobile phase of Acetonitrile (A) and 0.01% Formic Acid in HPLC grade water (B).

ZQ3 is an Agilent 1100 HPLC equipped with an ESA CAD secondary detector and Waters Micromass ZQ2000 for ionization. The system uses the following conditions for either 5 or 4 min run time.

5 minute run: Xterra MS C18 column, 5 µm, 4.6×50 mm. The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min; and 0.00 min 25% A, 3.00 min 99% A, 3.50 min 99% A, 4.00 min 25% A, 5.00 min 25% A for nonpolar_5 min. The flow rate is 1.0 mL/min, the run time is 5 min, and the gradient profiles are 0.00 min 1% A, 0.3 min 1% A, 3.00 min 90% A, 3.50 min 90% A, 4.00 min 1% A, 5.00 min 1% A for vvpolar_5 min. The Waters Micromass ZQ2000 instrument utilized electrospray ionization in positive (ES$^+$) or negative (ES$^-$) mode. The Waters Micromass ZQ2000 instrument can also utilize atmospheric pressure chemical ionization in positive (AP+) or negative (AP-) mode.

4 minute run: XTerra MS C18 column, 3.5 µm, 4.6×50 mm. The flow rate is 1.0 mL/min, the run time is 4 min, and the gradient profiles are 0.00 min 5% A, 2.00 min 90% A, 2.50 min 90% A, 3.00 min 5% A, 4.00 min 5% A for polar_4 min; and 0.00 min 25% A, 2.00 min 99% A, 2.50 min 99% A, 3.00 min 25% A, 4.00 min 25% A for nonpolar_4 min.

TOF is a Waters UPLC-LCT Premier system consisting of an ACQUITY UPLC equipped with an ACQUITY Sample Manager and LCT Premier XE MS for ionization. It uses an ACQUITY UPLC BEH® C18 2.1×50 mm, 1.7 µm column with a mobile phase of Acetonitrile (A) and 0.01% formic acid in water (B). The flow rate is 0.6 mL/min, run time is 3 min, and the gradient profile is 0.00 min 5% A, 0.2 min 5% A, 1.50 min 90% A, 2 min 90% A, 2.2 min 5% A, 3 min 5% A for polar_3 min; and 0.00 min 25% A, 0.2 min 25% A, 1.50 min 99% A, 2 min 99% A, 2.2 min 25% A, 3 min 25% A for nonpolar_3 min. Or, the flow rate is 0.7 mL/min, run time is 2 min, and the gradient profile is 0.00 min 10% A, 1 min 90% A, 1.5 min 90% A, 1.6 min 10% A, 2 min 10% A for polar_2 min; and 0.00 min 30% A, 1 min 90% A, 1.5 min 90% A, 1.6 min 30% A, 2 min 30% A for nonpolar_2 min. The LCT Premier XE MS utilized electrospray ionization in positive (ES$^+$) or negative (ES$^-$), as well positive (AP$^+$) or negative (AP$^-$) in W mode.

UPLC is an ACQUITY sample manager attached to an ACQUITY SQ detector. ACQUITY UPLC® BEH C18 1.7 µm 2.1×50 mm or 2.1×100 mm column was heated to 60° C. with detection at 254 nm and electrospray ionization in positive mode was used. The table below lists the mobile phase gradient (solvent A: 0.1% formic acid in water; solvent B: 0.1% formic acid in acetonitrile) and flow rate for the analytical UPLC program.

| Time (min) | A % | B % | Flow Rate (mL/min) |
|---|---|---|---|
| Analytical Method: Purity_2 min (column: 2.1 × 50 mm) | | | |
| 0.00 | 95.0 | 5.0 | 1.00 |
| 1.50 | 1.0 | 99.0 | 1.00 |
| 1.80 | 1.0 | 99.0 | 1.00 |
| 2.00 | 95.0 | 5.0 | 1.00 |
| Analytical Method: Analytical_2 min (column: 2.1 × 100 mm) | | | |
| 0.00 | 85.0 | 15.0 | 0.80 |
| 1.50 | 1.0 | 99.0 | 0.80 |
| 1.80 | 1.0 | 99.0 | 0.80 |
| 2.00 | 85.0 | 15.0 | 0.80 |

Unless otherwise noted, all HPLC retention times are reported using the ZQ3 polar_5 min gradient method.

All melting points were determined with a Mel-Temp II apparatus and are uncorrected. Elemental analyses were obtained by Atlantic Microlab, Inc., Norcross, Ga. Optical rotations were recorded on a Perkin-Elmer 241 polarimeter at room temperature.

Supercritical fluid chromatography (SFC, Thar/Waters) equipped with a Waters ZQ MS for ionization, is used for compound purifications, including separation of cis- and trans-isomers. Following conditions or similar conditions are followed for separation of cis- and trans-isomers:
SFC Analytical Chromatographic Conditions:
Column: CHIRALPACK IA 4.6×100 mm, 5u
Modifier: 0.2% IPAmine in MeOH
Flow Rate: 4 mL/min
Gradient: 10% to 60% modifier in 5 min
SFC Semi-Prep Chromatographic Conditions:

Column: CHIRALPACK IA 21×250 mm, 5u
Modifier: 0.2% IPAmine in MeOH
Flow Rate: 30 mL/min
Gradient: 35% to 50% modifier in 5 min followed by 50% isocratic.

Synthesis of Examples 1-12

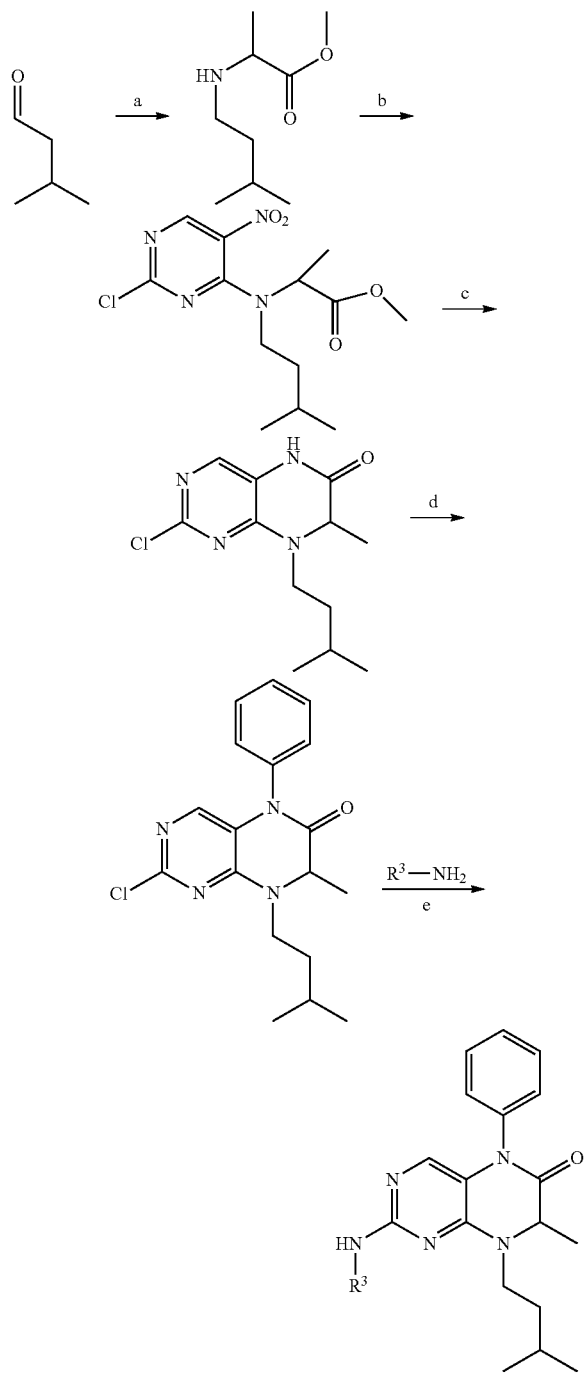

Examples 1-12

Example 1

2-(1H-indazol-5-ylamino)-7-methyl-8-(3-methylbutyl)-5-phenyl-7,8-dihydropteridin-6(5H)-one

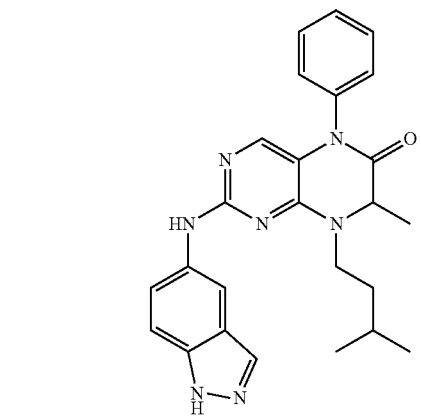 [SMILES: CC(C)CCN1c2nc(Nc3ccc4[nH]ncc4c3)ncc2N(c2ccccc2)C(=O)C1C]

Step e: A mixture of 2-chloro-7-methyl-8-(3-methylbutyl)-5-phenyl-7,8-dihydropteridin-6(5H)-one (172 mg, 0.50 mmol), 5-aminoindazole (100 mg, 0.75 mmol), trifluoroacetic acid (2.0 mmol) in trifluoroethanol (2.0 ml) was heated in a microwave reactor at 125° C. for 30 minutes. The reaction mixture was diluted with ethyl acetate (50 ml) and washed with aqueous saturated sodium bicarbonate, dried ($Na_2SO_4$) and evaporated. The residue was purified by column chromatography on silica gel using 2% methanol in dichloromethane as eluent to give the titled product. (yield: 54%). $^1$HNMR (300 MHz, $CDCl_3$): δ 0.96-1.0 (m, 6H), 1.54 (d, J=6.9 Hz, 3H), 1.62-1.67 (m, 3H), 3.10-3.16 (m, 1H), 4.15-4.22 (m, 1H), 4.36 (q, J=6.6 Hz, 1H), 7.03 (s, 1H), 7.23-7.54 (m, 8H), 7.98 (s, 1H). 8.08 (s, 1H) and 10.03 (s, 1H). $MS(ES^+)$: m/z=442.00 [$MH^+$]. HPLC: $t_R$=3.09 (ZQ3, Polar_5 min).

Step d: 2-Chloro-7-methyl-8-(3-methylbutyl)-5-phenyl-7,8-dihydropteridin-6(5H)-one To a stirred solution of 2-chloro-7-methyl-8-(3-methylbutyl)-7,8-dihydropteridin-6(5H)-one (2.0 g, 7.4 mmol) in dichloromethane (100 mL) was added triethylamine (10.4 ml, 74 mmol), cupric acetate (2.70 g, 14.8 mmol) and phenylboronic acid (1.81 g, 14.8 mmol) followed by 4 Å molecular sieves (3.0 g). The reaction mixture was stirred for 48 h at room temperature with an air balloon. The mixture was then filtered over celite. The filtrate was washed with aqueous saturated sodium bicarbonate (2×50 ml), dried over anhydrous sodium sulfate and evaporated. The residue was purified by column chromatography on silica gel using 2% methanol in dichloromethane as eluent to give the titled product. (yield: 39%). $^1$HNMR (300 MHz, $CDCl_3$): δ 0.91-1.01 (m, 6H), 1.49-1.75 (m, 6H), 3.12-3.20 (m, 1H), 4.18-4.21 (m, 1H), 4.30-4.45 (m, 1H), 7.10 (s, 1H), 7.20-7.39 (m, 2H), 7.42-7.65 (m, 3H).

Step c: 2-Chloro-7-methyl-8-(3-methylbutyl)-7,8-dihydropteridin-6(5H)-one

A mixture of methyl N-(2-chloro-5-nitropyrimidin-4-yl)-N-(3-methylbutyl)alaninate (16.2 g, 49 mmol), iron powder (6.9 g, 123 mmol) and glacial acetic acid (165 mL) was heated at 60° C. for 2 h. The reaction mixture was then filtered while hot over celite and washed with hot acetic acid (40 mL) followed by ethyl acetate (250 mL). The filtrate after evaporation was taken up in ethyl acetate and washed two times with aq. saturated sodium bicarbonate solution followed by brine. It was dried over sodium sulfate and evaporated. The residue was triturated with hot isopropyl ether to give titled product (yield: 61%). $^1$HNMR (300 MHz, CDCl$_3$): δ 0.92-1.01 (m, 7H), 1.43-1.75 (m, 5H), 3.01-3.20 (m, 1H), 4.10-4.25 (m, 2H), 7.63 (s, 1H), 9.13 (s, 1H).

Step b: Methyl N-(2-chloro-5-nitropyrimidin-4-yl)-N-(3-methylbutyl)alaninate A solution of 2,4-dichloro-5-nitropyrimidine (27.8 g, 144 mmol) in ether (350 mL) was cooled to −10° C. and was treated with methyl N-(3-methylbutyl)alaninate (20.8 g, 120 mmol). A solution of potassium bicarbonate (25.0 g in 180 mL water) was added drop wise maintaining the temperature below 0° C. Reaction mixture was then allowed to come to room temperature and stirred for 2 h. Ether layer was separated, the aq. layer was extracted with ether (3×100 mL). Combined ether solution was washed with brine, dried over anhydrous sodium sulfate and evaporated. The residue was purified by flash chromatography on silica gel using ethyl acetate-hexane mixture (v:v=5:95) to give titled product (yield: 51%). $^1$HNMR (300 MHz, CDCl$_3$): δ 0.90-1.01 (m, 6H), 1.40-1.61 (m, 6H), 3.10-3.21 (m, 1H), 3.39-3.45 (m, 1H), 3.78 (s, 3H), 4.41-4.50 (s, 1H), 8.71 (s, 1H).

Step a: Methyl N-(3-methylbutyl)alaninate

A suspension of DL-alanine methyl ester hydrochloride (41.8 g, 300 mmol) in dry dichloromethane (650 mL) was treated with potassium acetate (30.0 g, 306 mmol) and the reaction mixture stirred for ten minutes at rt. Reaction flask was then cooled to 10° C. and treated with 3-methylbutanal (25.8 g, 300 mmol). This was followed by the addition of sodium triacetoxyborohydride (82.5 g, 390 mmol) in portions over a period of ten minutes. Reaction mixture was stirred at room temperature for 16 h. Then saturated aqueous sodium bicarbonate solution was added to the reaction and the resulting mixture was stirred for another 30 minutes. The reaction mixture was then further basified with aqueous sodium carbonate to pH=~10. Dichloromethane layer was separated and the aqueous layer extracted with dichloromethane (3×100 mL). Organic layers were combined, washed with brine, dried over anhydrous sodium sulfate, and evaporated to give titled product as a colorless oil (yield: 72%). $^1$HNMR (300 MHz, CDCl$_3$): δ 0.92-0.98 (m, 6H), 1.28-1.41 (m, 5H), 2.48-2.68 (m, 3H), 3.30-3.40 (m, 1H), 3.74 (s, 3H).

Examples 2-12 were prepared from 2-chloro-7-methyl-8-(3-methylbutyl)-5-phenyl-7,8-dihydropteridin-6(5H)-one using corresponding R$^3$—NH$_2$, according to procedures similar for the preparation of Example 1 above. Examples 13 was prepared according to procedures similar for the preparation of Example 1 above using corresponding starting materials and intermediates. More specifically, acetone was used in the step a of the synthesis.

| Ex. # | Chemical Name | Analytical Data |
|---|---|---|
| 1 | 2-(1H-indazol-5-ylamino)-7-methyl-8-(3-methylbutyl)-5-phenyl-7,8-dihydropteridin-6(5H)-one | $^1$HNMR (300 MHz, CDCl$_3$): δ 0.96-1.0 (m, 6H), 1.54 (d, J = 6.9 Hz, 3H), 1.62-1.67 (m, 3H), 3.10-3.16 (m, 1H), 4.15-4.22 (m, 1H), 4.36 (q, J = 6.6 Hz, 1H), 7.03 (s, 1H), 7.23-7.54 (m, 8H), 7.98 (s, 1H). 8.08 (s, 1H) and 10.03 (s, 1H). MS(ES$^+$): m/z = 442.00 [MH$^+$]. HPLC: t$_R$ = 3.09 (ZQ3, Polar__5 min). |
| 2 | 2-[(3,5-difluoro-4-hydroxyphenyl)amino]-7-methyl-8-(3-methylbutyl)-5-phenyl-7,8-dihydropteridin-6(5H)-one | $^1$H NMR (CD$_3$OD, 400 MHz,) δ 1.00 (d, J = 5.81 Hz, 3 H), 1.03 (d, J = 6.06 Hz, 3 H), 1.53 (d, J = 6.82 Hz, 3 H), 1.60-1.80 (m, 3 H), 3.23-3.30 (m, 1 H), 4.10-4.20 (m, 1 H), 4.40 (q, J = 6.74 Hz, 1 H), 6.93 (s, 1 H), 7.18-7.35 (m, 4 H), 7.48-7.55 (m, 1 H), 7.56-7.64 (m, 2 H). MS (ES$^+$): m/z 453.93 (MH$^+$). HPLC: t$_R$ = 3.51 min (OpenLynx, polar__5 min, ZQ3). |
| 3 | 7-methyl-8-(3-methylbutyl)-2-[(2-oxo-2,3-dihydro-1H-indol-5-yl)amino]-5-phenyl-7,8-dihydropteridin-6(5H)-one | $^1$HNMR (300 MHz, CDCl$_3$) δ 0.97-1.01 (m, 6H), 1.50 (d, J = 6.6 Hz, 3H), 1.60-1.79 (m, 3H), 3.06-3.13 (m, 1H), 3.51 (s, 2H), 4.10-4.17 (m, 1H), 4.31 (q, J = 6.6 Hz, 1H), 6.73 (d, J = 8.4 Hz, 1H), 7.05 (s, 1H), 7.23 (s, 1H), 7.26-7.30 (m, 2H), 7.47-7.56 (m, 4H), 8.53 (s, 1H). MS (ES$^+$): m/z 456.89 [MH$^+$]. HPLC: t$_R$ = 3.00 min (OpenLynx, polar__5 min, ZQ3). |
| 4 | diethyl (4-{[7-methyl-8-(3-methylbutyl)-6-oxo-5-phenyl-5,6,7,8-tetrahydropteridin-2-yl]amino}benzyl)phosphonate | $^1$H NMR (CD$_3$OD, 400 MHz): δ 1.03 (d, J = 6.32 Hz, 3 H), 1.06 (d, J = 6.32 Hz, 3 H), 1.28 (t, J = 6.95 Hz, 6 H), 1.54 (d, J = 6.82 Hz, 3 H), 1.63-1.82 (m, 3 H), 3.14-3.19 (m, 1 H), 3.22 (s, 1 H), 3.25-3.31 (m, 1 H), 3.98-4.10 (m, 4 H), 4.20 (ddd, J = 13.71, 9.28, 6.32 Hz, 1 H), 4.42 (q, J = 6.82 Hz, 1 H), 6.97 (s, 1 H), 7.22 (dd, J = 8.59, 2.53 Hz, 2 H), 7.31 (d, J = 7.33 Hz, 2 H) 7.50-7.56 (m, 1 H). MS(ES$^+$): m/z 552.24 [MH$^+$]. HPLC: t$_R$ = 1.28 (TOF, Polar__3 min). |
| 5 | N-methyl-2-(4-{[7-methyl-8-(3-methylbutyl)-6-oxo-5-phenyl-5,6,7,8-tetrahydropteridin-2-yl]amino}phenyl)acetamide | $^1$H NMR (CDCl$_3$, 300 MHz): δ 0.97 (d, J = 6.3 Hz, 3H), 1.03 (d, J = 6.3 Hz, 3H), 1.51(d, J = 6.6 Hz, 3H), 1.63-1.76 (m, 3H), 2.74 (d, J = 4.8 Hz, 3H), 3.07-3.16 (m, 1H), 3.53 (s, 2H), 4.13-4.22 (m, 1H), 4.34 (q, J = 6.9 Hz, 1H), 5.36(s, 1H), 6.84 (s, 1H), 7.08(s, 1H), 7.13 |

-continued

| Ex. # | Chemical Name | Analytical Data |
|---|---|---|
| | | (s, 1H), 7.16 (s, 1H), 7.23 (s, 1H), 7.43-7.48 (m, 1H), 7.51-7.57 (m, 4H). ME(ES$^+$): m/z = 473.13 [MH$^+$]. HPLC: $t_R$ = 2.58 (ZQ3, Polar__5 min). |
| 6 | N,N-dimethyl-2-(4-{[7-methyl-8-(3-methylbutyl)-6-oxo-5-phenyl-5,6,7,8-tetrahydropteridin-2-yl]amino}phenyl)acetamide | $^1$H NMR (CD$_3$OD, 300 MHz): δ 0.95 (d, J = 6.3 Hz, 3H), 1.02 (d, J = 6.3 Hz, 3H), 1.50 (d, J = 6.6 Hz, 3H), 1.62-1.76 (m, 3H), 2.94 (s, 3H), 2.99(s, 3H), 3.05-3.17 (m, 1H), 3.69 (s, 2H), 4.14-4.20 (m, 1H), 4.38 (q, J = 6.9 Hz, 1H), 6.91(s, 1H), 7.13 (d, J = 8.4 Hz, 2H), 7.28 (d, J = 7.2 Hz, 2H), 7.48-7.60 (m, 5H). MS(ES$^+$): m/z = 487.16 (100) [MH$^+$]. HPLC: $t_R$ = 2.95 (ZQ3, Polar__5 min). |
| 7 | N-methyl-1-(4-{[7-methyl-8-(3-methylbutyl)-6-oxo-5-phenyl-5,6,7,8-tetrahydropteridin-2-yl]amino}phenyl)methanesulfonamide | $^1$H NMR (CDCl$_3$, 300 MHz): δ 0.95 (d, J = 6.3 Hz, 3H), 1.02 (d, J = 6.3 Hz, 3H), 1.51(d, J = 6.9 Hz, 3H), 1.63-1.70(m, 3H), 2.68 (d, J = 5.4 Hz, 3H), 3.11-3.16 (m, 1H), 4.19 (s, 2H), 4.31-4.35 (m, 2H), 7.06(s, 1H), 7.15(s, 1H), 7.23-7.28 (m, 3H), 7.44-7.59 (m, 5H). MS(ES$^+$): m/z = 509.01 [MH$^+$]. HPLC: $t_R$ = 3.12 (ZQ3, Polar__5 min). |
| 8 | N,N-dimethyl-1-(4-{[7-methyl-8-(3-methylbutyl)-6-oxo-5-phenyl-5,6,7,8-tetrahydropteridin-2-yl]amino}phenyl)methanesulfonamide | $^1$H NMR (CDCl$_3$, 300 MHz): δ 1.00 (t, J = 6.9 Hz, 6H), 1.51(d, J = 6.6 Hz, 3H), 1.63-1.74(m, 3H), 2.72 (s, 6H), 3.10-3.15 (m, 1H), 4.13-4.23 (m, 1H), 4.20 (s, 2H), 4.34 (q, J = 6.9 Hz, 1H), 6.94 (s, 1H), 7.09(s, 1H), 7.23-7.30(m, 3H), 7.44-7.62(m, 5H). MS(ES$^+$): m/z 523.14 [MH$^+$]. HPLC: $t_R$ = 3.33 (ZQ3, Polar__5 min). |
| 9 | methyl 4-{[7-methyl-8-(3-methylbutyl)-6-oxo-5-phenyl-5,6,7,8-tetrahydropteridin-2-yl]amino}benzoate | $^1$H NMR (CDCl$_3$, 400 MHz): δ 1.02 (d, J = 6.57 Hz, 3 H), 1.04 (d, J = 6.57 Hz, 3 H), 1.53 (d, J = 6.82 Hz, 3 H), 1.63-1.80 (m, 3 H), 3.09-3.22 (m, 1 H), 3.89 (s, 3 H), 4.12-4.24 (m, 1 H), 4.36 (q, J = 6.82 Hz, 1 H), 7.08 (s, 1 H), 7.11 (s, 1 H), 7.24 (s, 1 H), 7.44-7.50 (m, 1 H), 7.51-7.57 (m, 2 H), 7.61-7.67 (m, 2 H), 7.92-8.00 (m, 2 H). MS(ES$^+$): m/z 460.15 [MH$^+$]. HPLC: $t_R$ = 3.61 (ZQ3, Polar__5 min). |
| 10 | methyl 3-{[7-methyl-8-(3-methylbutyl)-6-oxo-5-phenyl-5,6,7,8-tetrahydropteridin-2-yl]amino}benzoate | MS(ES$^+$): m/z 460.21 [MH$^+$]. HPLC: $t_R$ = 1.46 (TOF, Polar__3 min). |
| 11 | 2-[(trans-4-hydroxycyclohexyl)amino]-7-methyl-8-(3-methylbutyl)-5-phenyl-7,8-dihydropteridin-6(5H)-one | $^1$H NMR (CD$_3$OD, 400 MHz): δ 1.03 (d, J = 6.50 Hz, 3 H), 1.05 (d, J = 6.50 Hz, 3 H), 1.27-1.44 (m, 4 H) 1.51 (d, J = 6.82 Hz, 3 H) 1.61-1.76 (m, 3 H), 1.95-2.08 (m, 4 H), 3.24 (ddd, J = 13.83, 9.03, 5.18 Hz, 1 H), 3.50-3.63 (m, 1 H), 3.64-3.75 (m, 1 H), 4.05-4.18 (m, 1 H), 4.36 (q, J = 6.74 Hz, 1 H), 6.78 (s, 1 H), 7.28 (d, J = 7.33 Hz, 2 H), 7.47-7.54 (m, 1 H), 7.54-7.63 (m, 2 H). MS(ES$^+$): m/z 424.24 [MH$^+$]. HPLC: $t_R$ = 0.99 (TOF, Polar__3 min). |
| 12 | 2-[(cis-4-hydroxycyclohexyl)amino]-7-methyl-8-(3-methylbutyl)-5-phenyl-7,8-dihydropteridin-6(5H)-one | $^1$H NMR (CD$_3$OD, 400 MHz): δ 1.02 (d, J = 6.80 Hz, 3 H), 1.04 (d, J = 6.80 Hz, 3 H), 1.51 (d, J = 6.57 Hz, 3 H), 1.62-1.80 (m, 11 H), 3.23 (ddd, J = 13.89, 8.97, 5.43 Hz, 1 H), 3.74-3.89 (m, 2 H), 4.07-4.18 (m, 1 H), 4.36 (q, J = 6.74 Hz, 1 H), 6.77-6.83 (m, 1 H), 7.24-7.33 (m, 2 H), 7.48-7.55 (m, 1 H) 7.55-7.63 (m, 2 H). MS(ES$^+$): m/z 424.22 [MH$^+$]. HPLC: $t_R$ = 2.50 (ZQ3, Polar__5 min). |
| 13 | 2-(1H-indazol-5-ylamino)-7-methyl-5-phenyl-8-(propan-2-yl)-7,8-dihydropteridin-6(5H)-one | $^1$H NMR (CDCl$_3$, 300 MHz): δ 1.38 (d, J = 6.50 Hz, 3 H), 1.42 (d, J = 6.50 Hz, 3 H), 1.50 (d, J = 6.9 Hz, 3H), 2.17 (s, 1H), 4.46 (q, J = 6.6 Hz, 1H), 4.75-4.84 (m, 1H), 7.03 (s, 1H), 7.16 (s, 1H), 7.23 (s, 1H), 7.39-7.41 (m, 2H), 7.43-7.54 (m, 3H), 7.98 (s, 1H), 8.11 (s, 1H), 10.18 (br. s, 1H). MS(ES$^+$): m/z = 414.03 [MH$^+$]. HPLC: $t_R$ = 2.47 (ZQ3, Polar__5 min). |

Examples 14: To a stirred solution of methyl 4-{[7-methyl-8-(3-methylbutyl)-6-oxo-5-phenyl-5,6,7,8-tetrahydropteridin-2-yl]amino}benzoate (46 mg, 0.1 mmol) in dioxane (contains 4N HCl, 5.0 mL) was added 6N aqueous HCl (1.0 mL) at rt. The resulting solution was stirred at 70° C. for 3 h. Then the solvent was removed under reduced pressure to give a residue, which was purified by recrystallization in acetonitrile to give titled compound (example 14, yield: 56%).

Example 15 was prepared from Example 10 according to procedures similar for the preparation of Example 14.

| Ex. # | Name | Analytical data |
|---|---|---|
| 14 | 4-{[7-methyl-8-(3-methylbutyl)-6-oxo-5-phenyl-5,6,7,8-tetrahydropteridin-2-yl]amino}benzoic acid | $^1$H NMR (DMSO-$d_6$, 400 MHz): δ 0.96 (d, J = 6.32 Hz, 3 H), 0.98 (d, J = 6.32 Hz, 3 H), 1.53 (d, J = 6.82 Hz, 3 H), 1.56-1.78 (m, 3 H), 3.31-3.42 (m, 1 H), 3.44-3.53 (m, 1 H), 4.55 (m, J = 6.80 Hz, 1 H), 6.87 (s, 1 H), 7.37 (d, J = 7.07 Hz, 2 H), 7.50-7.56 (m, 1 H), 7.57-7.64 (m, 2 H), 7.76 (d, J = 8.84 Hz, 2 H), 7.82-7.90 (m, 2 H). MS(ES$^+$): m/z 446.17 [MH$^+$]. HPLC: $t_R$ = 2.92 (ZQ3, Polar_5 min). |
| 15 | 3-{[7-methyl-8-(3-methylbutyl)-6-oxo-5-phenyl-5,6,7,8-tetrahydropteridin-2-yl]amino}benzoic acid | $^1$H NMR (DMSO-$d_6$, 400 MHz): δ 0.87 (d, J = 6.50 Hz, 3 H), 0.88 (d, J = 6.50 Hz, 3 H), 1.47-1.70 (m, 6 H), 3.30-3.41 (m, 1 H), 4.01-4.07 (m, 1H), 4.51-4.60 (m, 1 H), 6.81 (s, 1 H), 7.37 (d, J = 7.07 Hz, 2 H), 7.44 (t, J = 7.83 Hz, 1 H), 7.51-7.57 (m, 1 H), 7.57-7.68 (m, 3 H), 7.81 (d, J = 7.83 Hz, 1 H), 8.23 (s, 1 H). MS(ES$^+$): m/z 446.14 [MH$^+$]. HPLC: $t_R$ = 2.75 (ZQ3, Polar_5 min). |

Example 16 was prepared according to procedures similar for the preparation of Example 1 above using corresponding starting materials and intermediates. More specifically, D-alanine methyl ester hydrochloride was used in the step a of the synthesis.

Example 17 was prepared according to procedures similar for the preparation of Example 1 above using corresponding starting materials and intermediates. More specifically, L-alanine methyl ester hydrochloride was used in the step a of the synthesis.

| Ex. # | Chemical Name | Analytical data |
|---|---|---|
| 16 | (7R)-2-(1H-indazol-5-ylamino)-7-methyl-8-(3-methylbutyl)-5-phenyl-7,8-dihydropteridin-6(5H)-one | $^1$H NMR, Mass and HPLC are identical to Example 1 |
| 17 | (7S)-2-(1H-indazol-5-ylamino)-7-methyl-8-(3-methylbutyl)-5-phenyl-7,8-dihydropteridin-6(5H)-one | $^1$H NMR, Mass and HPLC are identical to Example 1 |

Synthesis of Examples 18-59

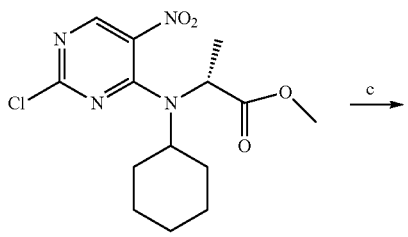

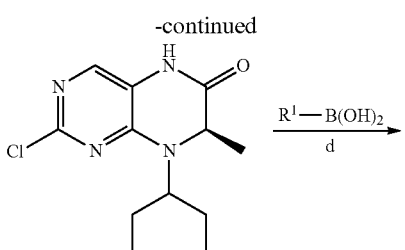

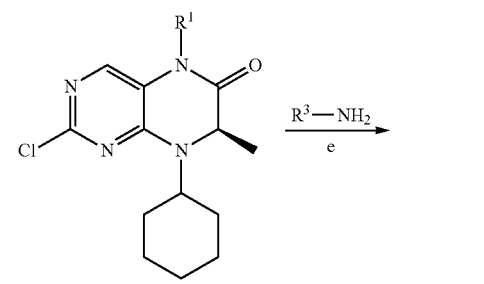

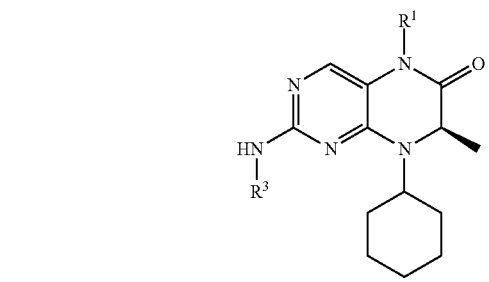

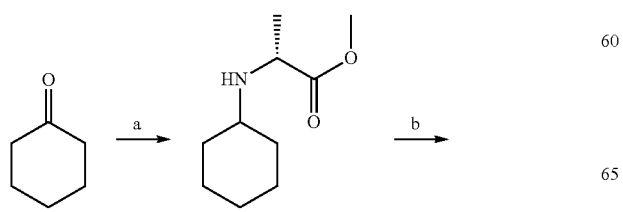

Examples 18-59

Example 18

(7R)-8-cyclohexyl-2-(1H-indazol-5-ylamino)-7-methyl-5-phenyl-7,8-dihydropteridin-6(5H)-one

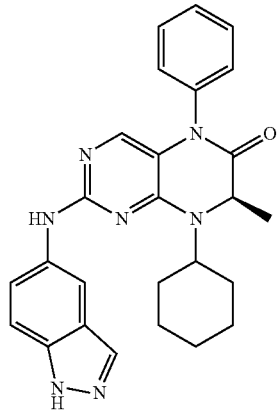 [SMILES: C[C@@H]1C(=O)N(c2ccccc2)c2cnc(Nc3ccc4[nH]ncc4c3)nc2N1C1CCCCC1]

Step e: Synthesis of Example 18

A mixture of (7R)-2-chloro-8-cyclohexyl-7-methyl-5-phenyl-7,8-dihydropteridin-6(5H)-one (114 mg, 0.32 mmol), 5-aminoindazole (53 mg, 0.40 mmol), trifluoroacetic acid (1.3 mmol) in trifluoroethanol (2.0 ml) was heated in a microwave reactor at 125° C. for 30 minutes. The reaction mixture was diluted with ethyl acetate (50 ml) and washed with aqueous saturated sodium bicarbonate, dried and evaporated. The residue was purified by column chromatography on silica gel using 3% methanol in dichloromethane as eluent to give the titled compound (yield: 41%).

Step d: synthesis of (7R)-2-chloro-8-cyclohexyl-7-methyl-5-phenyl-7,8-dihydropteridin-6(5H)-one To a solution of (7R)-2-chloro-8-cyclohexyl-7-methyl-7,8-dihydropteridin-6(5H)-one (280 mg, 1.0 mmol) in 10 mL of dry dichloromethane was added triethylamine (1.39 mL, 10 mmol), cupric acetate (363 mg, 2.0 mmol), phenylboronic acid (244 mg, 2.0 mmol) and 4 Å molecular sieves (2.0 g). The reaction mixture was allowed to stir at room temperature with air balloon on. The reaction mixture was then filtered over Celite, washed with dichloromethane and the organic layer was washed with aqueous sodium bicarbonate, dried over anhydrous sodium sulfate and evaporated. The residue was purified by silica gel flash chromatography, using dichloromethane-methanol mixture (v:v=99:1) as eluent, to give titled compound (yield: 39%). $^1$HNMR (300 MHz, CDCl$_3$): δ 1.20-1.22 (m, 1H), 1.47-1.49 (m, 6H), 1.72-1.77 (m, 3H), 1.87-1.89 (m, 2H), 2.10-2.13 (m, 1H), 4.44-4.49 (m, 2H), 7.17 (s, 1H), 7.20-7.24 (m, 2H), 7.48-7.56 (m, 3H).

Step c: Synthesis of (7R)-2-chloro-8-cyclohexyl-7-methyl-7,8-dihydropteridin-6(5H)-one To a solution of methyl N-(2-chloro-5-nitropyrimidin-4-yl)-N-cyclohexyl-D-alaninate (9.9 g, 29 mmol) in 100 mL of ethanol was added iron powder (16.2 g, 290 mmol). The resulting mixture was heated to reflux, then 2N HCl (10 mL) was added in small proportions. The reaction mixture was heated at reflux until the completion of the reaction as monitored by TLC. The reaction was cooled to room temperature and filtered. The filtrate was evaporated to give a residue which was triturated using isopropyl ether to give titled compound (yield: 62%). $^1$HNMR (300 MHz, DMSO-d$_6$): δ 1.11-1.20 (m, 1H), 1.25-1.34 (m, 6H), 1.59-1.60 (m, 3H), 1.75-1.90 (m, 3H), 4.05 (t, J=11.7 Hz, 1H), 4.25 (q, J=6.9 Hz, 1H), 7.60 (s, 1H), 10.23 (br s, 1H).

Step b: Synthesis of Methyl N-(2-chloro-5-nitropyrimidin-4-yl)-N-cyclohexyl-D-alaninate To a solution of 2,4-dichloro-5-nitropyrimidine (28.5 g, 146.9 mmol) in ether (200 mL) was added methyl N-cyclohexyl-D-alaninate (17.0 g, 91.8 mmol) at −10° C. To the resulting solution was then added aqueous potassium carbonate (19.0 g in 100 mL water) drop wise while maintaining the temperature below 0° C. Reaction mixture was then warmed to rt and stirred at rt for 16 h. The organic layer was separated and the aqueous layer was extracted with ether (3×75 mL). Combined ether solution was washed with brine, dried over anhydrous sodium sulfate and evaporated. The residue was purified by silica gel flash chromatography using ethyl acetate-hexane mixture (v:v=5:95) as eluent to give titled compound (yield, 41%). $^1$HNMR (300 MHz, CDCl$_3$): δ 1.06-1.29 (m, 3H), 1.43-1.53 (m, 2H), 1.58 (s, 1H), 1.64 (d, J=6.9 Hz, 3H), 1.90-1.82 (m, 2H), 2.02-1.98 (m, 1H), 2.17-2.14 (m, 1H), 3.09-3.01 (m, 1H), 3.73 (s, 3H), 4.13 (q, J=6.9 Hz, 1H), 8.59 (s, 1H).

Step a: Synthesis of methyl N-cyclohexyl-D-alaninate

To a suspension of D-Alanine methyl ester hydrochloride (16.0 g, 114.6 mmol) in dry dichloromethane (150 mL) was added potassium acetate (11.2 g, 114.6 mmol) and the reaction mixture stirred for ten minutes. The reaction mixture was then cooled to 10° C., cyclohexanone (11.8 mL, 114.6 mmol) was added, followed by sodium triacetoxyborohydride (30.3 g, 143.2 mmol) in portions over a period of ten minutes. Reaction mixture was stirred at room temperature for 16 h after which saturated sodium bicarbonate solution (60 mL) was added and stirred for another 30 minutes. The reaction mixture was further basified with aqueous sodium carbonate to pH=~10. The organic layer was separated and the aqueous layer extracted with dichloromethane (3×75 mL). The organic layers were combined, washed with brine, dried over anhydrous sodium sulfate, and evaporated to give titled compound (yield: 80%). $^1$HNMR (300 MHz, CDCl$_3$): δ 0.97-1.21 (m, 4H), 1.26 (d, J=6.9 Hz, 3H), 1.57-1.59 (m, 2H), 1.75-1.67 (m, 3H), 1.89-1.84 (m, 1H), 2.36-2.29 (m, 1H), 3.48 (q, J=6.9 Hz, 1H), 3.70 (s, 3H).

Examples 19-59 were prepared according to procedures similar for the preparation of Example 18 above, using corresponding R$^1$—B(OH)$_2$ and R$^3$—NH$_2$.

Examples 60 was prepared according to procedures similar for the preparation of Example 18 above using corresponding starting materials and intermediates. More specifically, DL-alanine methyl ester hydrochloride was used in the step a of the synthesis, 5-amino-1,3-dihydro-2H-indol-2-one as corresponding R$^3$—NH$_2$ was used in the step e of the synthesis.

Examples 61 was prepared according to procedures similar for the preparation of Example 18 above using corresponding starting materials. More specifically, DL-alanine methyl ester hydrochloride was used in the step a of the synthesis.

Examples 62 was prepared according to procedures similar for the preparation of Example 18 above using corresponding starting materials. More specifically, L-alanine methyl ester hydrochloride was used in the step a of the synthesis.

Synthesis of Example 63: To a stirred solution of methyl 4-[(7R)-8-cyclohexyl-2-(1H-indazol-5-ylamino)-7-methyl-6-oxo-7,8-dihydropteridin-5(6H)-yl]benzoate (51 mg, 0.1 mmol) in dioxane (contains 4N HCl, 5.0 mL) was added 6N aqueous HCl (1.0 mL) at rt. The resulting solution was stirred at 70° C. for 3 h. Then the solvent was removed under reduced pressure to give a residue, which was purified by recrystallization in acetonitrile to give titled compound (Example 63, yield: 45%).

| Ex. # | Chemical Name | Analytical data |
|---|---|---|
| 18 | (7R)-8-cyclohexyl-2-(1H-indazol-5-ylamino)-7-methyl-5-phenyl-7,8-dihydropteridin-6(5H)-one | $^1$H NMR (CDCl$_3$, 300 MHz): δ 1.23-1.26 (m, 1H), 1.45-1.50 (m, 6H), 1.69-1.87 (m, 3H), 1.92-1.96 (m, 2H), 2.23-2.25 (m, 1H), 4.41-4.50 (m, 2H), 7.07 (s, 1H), 7.15 (s, 1H), 7.22(s, 1H), 7.39-7.54 (m, 5H), 7.99 (s, 1H), 8.16 (s, 1H). MS(ES$^+$): m/z = 453.90 [MH$^+$]. HPLC: t$_R$ = 2.55 (ZQ3, Polar_5 min). |
| 19 | 4-[(7R)-8-cyclohexyl-2-(1H-indazol-5-ylamino)-7-methyl-6-oxo-7,8-dihydropteridin-5(6H)-yl]benzonitrile | $^1$H NMR (CDCl$_3$, 300 MHz): δ 1.24-1.27 (m, 1H), 1.46-1.53 (m, 6H), 1.66-1.80 (m, 3H), 1.92-1.96 (m, 2H), 2.23-2.28 (m, 1H), 4.42-4.46 (m, 2H), 7.01 (s, 1H), 7.17 (s, 1H), 7.37-7.45 (m, 4H), 7.81 (d, J = 8.7 Hz, 2H), 8.00 (s, 1H), 8.16 (s, 1H). MS(ES$^+$): m/z = 479.10 [MH$^+$]. HPLC: t$_R$ = 2.59 (ZQ3, Polar_5 min). Optical rotation: [α]$_D$ = +20.0 (C = 0.4 in CH$_2$Cl$_2$) |
| 20 | (7R)-8-cyclohexyl-2-(1H-indazol-5-ylamino)-7-methyl-5-(pyridin-4-yl)-7,8-dihydropteridin-6(5H)-one | $^1$H NMR (CDCl$_3$ and CD$_3$OD, 300 MHz): δ 1.12-1.13 (m, 1H), 1.34-1.40 (m, 6H), 1.58-1.71 (m, 3H), 1.82-1.86 (m, 2H), 2.11-2.14 (m, 1H), 4.32-4.38 (m, 2H), 7.10 (s, 1H), 7.21 (d, J = 6.3 Hz, 2H), 7.29-7.37 (m, 2H), 7.84 (s, 1H), 8.03 (s, 1H), 8.63 (d, J = 5.1 Hz, 2H). MS(ES$^+$): m/z = 455.18 [MH$^+$]. HPLC: t$_R$ = 2.31 (ZQ3, Polar_5 min). |
| 21 | (7R)-5-(4-chlorophenyl)-8-cyclohexyl-2-(1H-indazol-5-ylamino)-7-methyl-7,8-dihydropteridin-6(5H)-one | $^1$H NMR (CDCl$_3$, 300 MHz): δ 1.24-1.26 (m, 1H), 1.45-1.53 (m, 6H), 1.72-1.81(m, 3H), 1.92-1.96 (m, 2H), 2.24-2.26 (m, 1H), 4.43-4.48 (m, 2H), 6.99 (s, 1H), 7.16-7.20 (m, 3H), 7.40-7.50 (m, 4H), 7.99 (s, 1H), 8.16 (s, 1H). MS(ES$^+$): m/z = 488.09, 490.03 [MH$^+$]. HPLC: t$_R$ = 2.76 (ZQ3, Polar_5 min). Optical rotation: [α]$_D$ = −12.5 (C = 0.4 in CH$_2$Cl$_2$) |
| 22 | (7R)-8-cyclohexyl-2-(1H-indazol-5-ylamino)-7-methyl-5-(4-methylphenyl)-7,8-dihydropteridin-6(5H)-one | $^1$H NMR (CDCl$_3$, 300 MHz) δ: 1.19-2.22 (m, 2H), 1.46-1.53 (m, 6H), 1.68-1.96 (m, 4H), 2.24 (s, 1H), 2.41 (s, 3H), 4.45 (q, J = 6.9 Hz, 2H), 6.94 (s, 1H), 7.10-7.17 (m, 3H), 7.30-7.40 (m, 3H), 7.99 (s, 1H), 8.00 (s, 1H), 8.18 (s, 1H), 10.08 (s, 1H). MS(ES$^+$): m/z = 468.15 [MH$^+$]. HPLC: t$_R$ = 2.97 (ZQ3, Polar_5 min). |
| 23 | (7R)-8-cyclohexyl-2-(1H-indazol-5-ylamino)-7-methyl-5-(pyridin-3-yl)-7,8-dihydropteridin-6(5H)-one | $^1$H NMR (CDCl$_3$ and CD$_3$OD, 300 MHz) δ 1.07-1.28 (m, 1H), 1.28-1.46 (m, 6H), 1.54-1.78 (m, 3H), 1.80-1.89 (m, 2H), 2.09-2.20 (m, 1H), 4.32-4.39 (m, 2H), 6.97 (s, 1H), 7.32 (t, J = 8.1 Hz, 2H), 7.41-7.46 (m, 1H), 7.57 (d, J = 8.1 Hz, 1H), 7.81 (s, 1H), 8.01 (s, 1H), 8.37 (s, 1H), 8.54 (d, J = 4.8 Hz, 1H). MS(ES$^+$): m/z = 455.13 [MH$^+$]. HPLC: t$_R$ = 2.15 (ZQ3, Polar_5 min). Optical rotation: [α]$_D$ = −56.0 (C = 0.5 in 1N HCl). |
| 24 | (7R)-8-cyclohexyl-5-(4-fluorophenyl)-2-(1H-indazol-5-ylamino)-7-methyl-7,8-dihydropteridin-6(5H)-one | $^1$H NMR (CDCl$_3$, 300 MHz): δ 1.23-1.25 (m, 1H), 1.42-1.53 (m, 6H), 1.71-1.82 (m, 3H), 1.92-1.96 (m, 2H), 2.24 (s, 1H), 4.42-4.49 (m, 2H), 7.00 (s, 1H), 7.15 (s, 1H), 7.20-7.22 (m, 4H), 7.36-7.43 (m, 2H), 8.00 (s, 1H), 8.16 (s, 1H), 10.14 (br. s, 1H). MS(ES$^+$): m/z = 472.12 [MH$^+$]. HPLC: t$_R$ = 2.54 (Polar_5 min, ZQ3). Optical rotation: [α]$_D$ = − 47.5(C = 0.4 in CH$_2$Cl$_2$) |
| 25 | (7R)-8-cyclohexyl-5-(3-fluorophenyl)-2-(1H-indazol-5-ylamino)-7-methyl-7,8-dihydropteridin-6(5H)-one | $^1$H NMR (CDCl$_3$, 300 MHz): δ 1.23-1.25 (m, 1H), 1.42-1.53 (m, 6H), 1.72-1.81 (m, 3H), 1.92-1.96 (m, 2H), 2.23-2.35 (m, 1H), 4.42-4.49 (m, 2H), 6.98-7.06 (m, 3H), 7.13-7.18 (m, 2H), 7.37-7.41 (m, 2H), 7.44-7.53 (m, 1H), 8.00 (s, 1H), 8.16 (s, 1H), 10.11 (br. s, 1H). MS(ES$^+$): m/z = 472.12 [MH$^+$]. HPLC: t$_R$ = 2.58 (Polar_5 min, ZQ3). Optical rotation: [α]$_D$ = −48.0 (C = 0.5 in CH$_2$Cl$_2$) |
| 26 | (7R)-8-cyclohexyl-2-(1H-indazol-5-ylamino)-5-(4-methoxyphenyl)-7-methyl-7,8-dihydropteridin-6(5H)-one | $^1$H NMR (CDCl$_3$, 300 MHz) δ 1.26-1.40 (m, 1H), 1.50-1.57 (m, 4H), 1.72-2.03 (m, 7H), 2.30-3.36 (m, 1H), 3.92 (s, 3H), 4.50-4.57(m, 2H), 7.09 (d, J = 9 Hz, 2H), 7.21-7.26 (m, 2H), 7.33 (s, 1H), 7.46 (s, 2H), 8.07 (s, 1H), 8.25 (s, 1H). MS(ES$^+$): m/z = 484.15 [MH$^+$]. HPLC: t$_R$ = 2.55 (Polar_5 min, ZQ3). Optical rotation: [α]$_D$ = −17.0 (C = 0.7 in CH2Cl2). |
| 27 | 4-[(7R)-8-cyclohexyl-2-(1H-indazol-5-ylamino)-7-methyl-6-oxo-7,8-dihydropteridin-5(6H)-yl]-N,N-dimethylbenzamide | $^1$H NMR (CDCl$_3$ and CD$_3$OD, 300 MHz) δ 1.15-1.30 (m, 1H), 1.44-1.50 (m, 6H), 1.61-1.85 (m, 3H), 1.87-1.93 m, 2H), 2.22-2.35 (m, 1H), 3.01 (s, 3 H), 3.10 (s, 3H), 4.38-4.50 (m, 2H), 7.11 (s, 1H), 7.25-7.27 (m, 1H), 7.28 (s, 1H), 7.31-7.40 (m, 2H), 7.55 (d, J = 8.1 Hz, 1H), 7.92 (s, 1H), 8.14 (s, 1H). MS(ES$^+$): m/z = 525.15 [MH$^+$]. HPLC: t$_R$ = 2.15 (ZQ3, Polar_5 min). |

| Ex. # | Chemical Name | Analytical data |
|---|---|---|
| 28 | (7R)-8-cyclohexyl-2-(1H-indazol-5-ylamino)-5-(3-methoxyphenyl)-7-methyl-7,8-dihydropteridine-6(5H)-one | $^1$H NMR (CDCl$_3$, 300 MHz): δ 1.22-1.24 (m, 1H), 1.47-1.53 (m, 6H), 1.68-1.83 (m, 3H), 1.94-1.96 (m, 2H), 2.23-2.24 (m, 1H), 3.81 (s, 3H), 4.42-4.49 (m, 2H), 6.74 (s, 1H), 6.82 (d, J = 7.2 Hz, 1H), 6.96-7.00 (m, 2H), 7.18 (s, 1H), 7.36-7.44 (m, 3H), 7.99 (s, 1H), 8.17 (s, 1H), 10.10 (br. s, 1H). MS(ES$^+$): m/z = 484.28 [MH$^+$]. HPLC: $t_R$ = 2.47 (ZQ3, Polar_5 min). Optical rotation: [α]$_D$ = −20.0 (C = 0.4 in CH$_2$Cl$_2$) |
| 29 | 3-[(7R)-8-cyclohexyl-2-(1H-indazol-5-ylamino)-7-methyl-6-oxo-7,8-dihydropteridin-5(6H)-yl]benzonitrile | $^1$H NMR (CDCl$_3$, 300 MHz): δ 1.24-1.25 (m, 1H), 1.47-1.53 (m, 6H), 1.68-1.81 (m, 3H), 1.92-1.96 (m, 2H), 2.23-2.35 (m, 1H), 4.44-4.47 (m, 2H), 6.97 (s, 1H), 7.15 (s, 1H), 7.37-7.45 (m, 2H), 7.52 (d, J = 8.7 Hz, 1H), 7.59-7.66 (m, 2H), 7.72-7.75 (m, 1H), 8.00 (s, 1H), 8.15 (s, 1H), 10.07 (br. s, 1H). MS(ES$^+$): m/z = 479.24 [MH$^+$]. HPLC: $t_R$ = 2.48 (ZQ3, Polar_5 min). Optical rotation: [α]$_D$ = −50.0 (C = 0.4 in CH$_2$Cl$_2$) |
| 30 | (7R)-8-cyclohexyl-2-(1H-indazol-5-ylamino)-7-methyl-5-(3-methylphenyl)-7,8-dihydropteridine-6(5H)-one | $^1$H NMR (CDCl$_3$, 300 MHz): δ 1.19-1.23 (m, 1H), 1.47-1.53 (m, 6H), 1.68-1.83 (m, 3H), 1.92-1.96 (m, 2H), 2.24-2.25 (m, 1H), 2.38 (s, 3H), 4.42-4.49 (m, 2H), 6.95 (s, 1H), 7.03-7.04 (m, 2H), 7.15 (s, 1H), 7.23 (s, 1H), 7.36-7.42 (m, 3H), 7.99 (s, 1H), 8.17 (s, 1H), 10.09 (br. s, 1H). MS(ES$^+$): m/z = 468.21 [MH$^+$]. HPLC: $t_R$ = 2.75 (ZQ3, Polar_5 min). Optical rotation: [α]$_D$ = −30.0 (C = 0.4 in CH$_2$Cl$_2$) |
| 31 | (7R)-5-(3-chlorophenyl)-8-cyclohexyl-2-(1H-indazol-5-ylamino)-7-methyl-7,8-dihydropteridine-6(5H)-one | $^1$H NMR (CDCl$_3$, 300 MHz): δ 1.23-1.25 (m, 1H), 1.46-1.53 (m, 6H), 1.67-1.81 (m, 3H), 1.96-1.98 (m, 2H), 2.21-2.23 (m, 1H), 4.41-4.48 (m, 2H), 6.93 (s, 1H), 7.14-7.18 (m, 2H), 7.37-7.48 (m, 4H), 8.00 (s, 1H), 8.16 (s, 1H), 10.02 (br. s, 1H). MS(ES$^+$): m/z = 488.15, 490.12 [MH$^+$]. HPLC: $t_R$ = 2.75 (ZQ3, Polar_5 min). Optical rotation: [α]$_D$ = −27.5 (C = 0.4 in CH$_2$Cl$_2$) |
| 32 | 3-[(7R)-8-cyclohexyl-2-(1H-indazol-5-ylamino)-7-methyl-6-oxo-7,8-dihydropteridin-5(6H)-yl]-N,N-dimethylbenzamide | $^1$H NMR (CDCl$_3$, 300 MHz): δ 1.21-1.23 (m, 1H), 1.45-1.53 (m, 6H), 1.67-1.82 (m, 3H), 1.95-1.97 (m, 2H), 2.23-2.24 (m, 1H), 3.02 (s, 3H), 3.10 (s, 3H), 4.43-4.47 (m, 2H), 7.00 (s, 1H), 7.22 (s, 1H), 7.28-7.34 (m, 2H), 7.38-7.43 (m, 2H), 7.49-7.58 (m, 2H), 8.00 (s, 1H), 8.17 (s, 1H), 10.13 (br. s, 1H). Optical rotation: MS(ES$^+$): m/z = 525.21 [MH$^+$]. HPLC: $t_R$ = 2.22 (ZQ3, Polar_5 min). Optical rotation: [α]$_D$ = −23.33 (C = 0.6 in CH$_2$Cl$_2$) |
| 33 | (7R)-8-cyclohexyl-2-(1H-indazol-5-ylamino)-7-methyl-5-[4-(trifluoromethoxy)phenyl]-7,8-dihydropteridin-6(5H)-one | $^1$H NMR (CDCl$_3$ and CD$_3$OD, 300 MHz) δ 1.10-1.30 (m, 1H), 1.40-1.49 (m, 6H), 1.60-1.85 (3H), 1.89-1.92 (m, 2H), 2.19-2.30 (m, 1H), 4.39-4.45 (m, 2H), 7.06 (s, 1H), 7.23 (s, 1H), 7.32-7.41 (m, 5H), 7.92 (s, 1H), 8.11 (s, 1H); MS(ES$^+$): m/z = 538.13 [MH$^+$]. HPLC: $t_R$ = 3.04 (ZQ3, Polar_5 min). Optical rotation: [α]$_D$ = −52.0 (C = 0.25 in CH$_2$Cl$_2$) |
| 34 | (7R)-8-cyclohexyl-2-(1H-indazol-5-ylamino)-7-methyl-5-[3-(trifluoromethoxy)phenyl]-7,8-dihydropteridin-6(5H)-one | $^1$H NMR (CDCl$_3$, 300 MHz) δ 1.18-1.24 (m, 1H), 1.46-1.67 (m, 5H), 1.68-1.96 (m, 6H), 2.20-2.40 (m, 1H), 4.40-4.49 (m, 2H), 7.14-7.27 (m, 4H), 7.29-7.36 (m, 2H), 7.39 (s, 1H), 7.55 (t, J = 7.8 Hz, 1H), 8.00 (s, 1H), 8.16 (s, 1H), 10.4 (br. s, 1H). MS(ES$^+$) m/z = 538.16 [MH$^+$]. HPLC: $t_R$ = 3.01 (ZQ3, Polar_5 min). Optical rotation: [α]$_D$ = −66.0 (C = 0.5 in CH$_2$Cl$_2$). |
| 35 | (7R)-8-cyclohexyl-2-(1H-indazol-5-ylamino)-7-methyl-5-[4-(trifluoromethyl)phenyl]-7,8-dihydropteridin-6(5H)-one | $^1$H NMR (CDCl$_3$, 300 MHz) δ 1.15-1.30 (m, 1H), 1.46-1.57 (m, 6H), 1.60-2.00 (m, 5H), 2.20-2.40 (m, 1H), 4.42-4.51 (m, 2H), 7.08 (s, 1H), 7.19 (s, 1H), 7.38-7.41 (m, 4H), 7.78 (d, J = 8.1 Hz, 2H), 8.03 (s, 1H), 8.17 (s, 1H), 10.20 (br. s, 1H); MS(ES$^+$): m/z = 522.18 [MH$^+$]. HPLC: $t_R$ = 2.98 (ZQ3, Polar_5 min). Optical rotation: [α]$_D$ = −44.0 (C = 0.25 in CH$_2$Cl$_2$). |
| 36 | (7R)-8-cyclohexyl-2-(1H-indazol-5-ylamino)-7-methyl-5-[3-(trifluoromethyl)phenyl]-7,8-dihydropteridin-6(5H)-one | $^1$H NMR (CDCl$_3$, 300 MHz) δ 1.19-1.30 (m, 1H), 1.48-1.53 (m, 6H), 1.68-1.96 (m, 5H), 2.20-2.30 (m, 1H), 4.41-4.50 (m, 2H), 7.07 (s, 1H), 7.13 (s, 1H), 7.36-7.47 (m, 3H), 7.53 (s, 1H), 7.63-7.72 (m, 2H), 8.00 (s, 1H), 8.16 (s, 1H), 10.20 (br s, 1H); MS(ES$^+$): m/z = 522.18 [MH$^+$]. HPLC: $t_R$ = 2.94 (ZQ3, Polar_5 min). Optical rotation: [α]$_D$ = −58.0 (C = 0.5 in CH$_2$Cl$_2$) |
| 37 | 4-[(7R)-8-cyclohexyl-2-(1H-indazol-5-ylamino)- | $^1$H NMR (DMSO-d$_6$, 300 MHz) δ 1.20-1.30 (m, 1H), 1.36-1.45 (m, 4H), 1.59-1.84 (m, 7H), 2.02-2.18 (m, |

| Ex. # | Chemical Name | Analytical data |
|---|---|---|
| | 7-methyl-6-oxo-7,8-dihydropteridin-5(6H)-yl]-N-methylbenzenesulfonamide | 1H), 2.47-2.50 (m, 3H), 4.38-4.46 (m, 2H), 7.08 (s, 1H), 7.39 (d, J = 9.3 Hz, 1H), 7.51 (d, J = 9 Hz, 1H), 7.55-7.61 (m, 3H), 7.90 (m 3H), 8.22 (s, 1H), 9.18 (s, 1H). MS(ES$^+$): m/z = 547.18 [MH$^+$]. HPLC: t$_R$ = 2.40 (ZQ3, Polar_5 min). |
| 38 | (7R)-8-cyclohexyl-2-(1H-indazol-5-ylamino)-7-methyl-5-(3,4,5-trimethoxyphenyl)-7,8-dihydropteridin-6(5H)-one | $^1$H NMR (CDCl$_3$, 300 MHz): δ 1.22-1.24 (m, 1H), 1.42-1.54 (m, 6H), 1.70-1.97 (m, 5H), 2.23-2.25 (m, 1H), 3.84 (s, 6H), 3.88 (s, 3H), 4.44-4.49 (m, 2H), 6.42 (s, 2H), 7.08 (s, 1H), 7.20 (s, 1H), 7.37-7.43 (m, 2H), 8.00 (s, 1H), 8.18 (s, 1H), 10.07 (br. s, 1H). MS(ES$^+$): m/z = 544.24 [MH$^+$]. HPLC: t$_R$ = 2.41 (ZQ3, Polar_5 min). Optical rotation: [α]$_D$ = −11.66 (C = 0.6 in CH$_2$Cl$_2$) |
| 39 | (7R)-5-(1,3-benzodioxol-5-yl)-8-cyclohexyl-2-(1H-indazol-5-ylamino)-7-methyl-7,8-dihydropteridin-6(5H)-one | $^1$H NMR (CDCl$_3$, 300 MHz): δ 1.21-1.22 (m, 1H), 1.44-1.49 (m, 6H), 1.68-1.81 (m, 3H), 1.92-1.95 (m, 2H), 2.23-2.25 (m, 1H), 4.41-4.47 (m, 2H), 6.04 (s, 2H), 6.68-6.71 (m, 2H), 6.90-6.94 (m, 2H), 7.22 (s, 1H), 7.36-7.43 (m, 2H), 7.99 (s, 1H), 8.17 (s, 1H), 10.07 (br. s, 1H). MS(ES$^+$): m/z = 498.13 [MH$^+$]. HPLC: t$_R$ = 2.39 (Polar_5 min, ZQ3). Optical rotation: [α]$_D$ = −27.5 (C = 0.4 in CH$_3$OH) |
| 40 | (7R)-8-cyclohexyl-2-(1H-indazol-5-ylamino)-7-methyl-5-[4-(methylsulfonyl)phenyl]-7,8-dihydropteridin-6(5H)-one | $^1$H NMR (CDCl$_3$, 300 MHz): δ 1.10-1.19 (m, 1H), 1.42-1.46 (m, 6H), 1.70-1.78 (m, 3H), 1.87-1.89 (m, 2H), 2.20-2.22 (m, 1H), 3.09 (s, 3H), 4.40-4.43 (m, 2H), 7.07-7.11 (m, 1H), 7.38 (d, J = 7.8 Hz, 2H), 7.46 (d, J = 8.1 Hz, 2H), 7.90-7.92 (m, 1H), 8.05-8.09 (m, 3H). MS(ES$^+$): m/z = 532.14 [MH$^+$]. HPLC: t$_R$ = 2.33 (Polar_5 min, ZQ3). |
| 41 | (7R)-8-cyclohexyl-5-[4-(dimethylamino)phenyl]-2-(1H-indazol-5-ylamino)-7-methyl-7,8-dihydropteridin-6(5H)-one | $^1$H NMR (CDCl$_3$ and CD$_3$OD, 300 MHz): δ 1.20-1.22 (m, 1H), 1.33-1.42(m, 6H), 1.61-1.74(m, 3H), 1.83-1.87(m, 2H), 2.14-2.16 (m, 1H), 2.91(s, 6H), 4.32-4.38 (m, 2H), 6.71 (d, J = 9.0 Hz, 2H), 6.95(d, J = 8.1 Hz, 2H), 7.04(s, 1H), 7.29-7.37 (m, 2H), 7.85 (s, 1H), 8.06 (s, 1H). MS(ES$^+$): m/z = 497.19 [MH$^+$]. HPLC: t$_R$ = 2.61 (Polar_5 min, ZQ3). |
| 42 | 3-[(7R)-8-cyclohexyl-2-(1H-indazol-5-ylamino)-7-methyl-6-oxo-7,8-dihydropteridin-5(6H)-yl]-N-methylbenzenesulfonamide | $^1$H NMR (DMSO-d$_6$, 300 MHz) δ 1.15-1.26 (m, 1H), 1.32-1.51 (m, 4H), 1.59-1.87 (m, 7H), 2.07-2.10 (m, 1H), 2.44 (d, J = 4.5 Hz, 3H), 4.37-4.46 (m, 2H), 7.03 (s, 1 H), 7.40 (d, J = 8.7 Hz, 1H), 7.50 (d, J = 9 Hz, 1H), 7.58-7.64 (m, 2H), 7.70 (s, 1H), 7.78 (t, J = 7.8 Hz, 1H), 7.85-7.88 (m, 2H), 8.21 (s, 1H), 9.17 (s, 1H). MS(ES$^+$): m/z = 547.13 [MH$^+$]. HPLC: t$_R$ = 2.55 (Polar_5 min, ZQ3). |
| 43 | (7R)-8-cyclohexyl-2-(1H-indazol-5-ylamino)-7-methyl-5-[3-(methylsulfonyl)phenyl]-7,8-dihydropteridin-6(5H)-one | $^1$H NMR (CDCl$_3$ and CD$_3$OD, 300 MHz): δ 1.20-1.22 (m, 1H), 1.43-1.48(m, 6H), 1.64-1.78(m, 3H), 1.88-1.91(m, 2H), 2.18-2.19 (m, 1H), 3.08(s, 3H), 4.42 (q, J = 6.9 Hz, 2H), 7.05(s, 1H), 7.32-7.40 (m, 2H), 7.51(d, J = 7.5 Hz, 1H), 7.70(t, J = 7.8 Hz, 1H), 7.82(s, 1H), 7.91(s, 1 H), 7.97(d, J = 8.1 Hz, 1H), 8.10(s, 1H). MS(ES$^+$): m/z = 532.14 [MH$^+$]. HPLC: t$_R$ = 2.33 (Polar_5 min, ZQ3). |
| 44 | (7R)-8-cyclohexyl-5-[3-(dimethylamino)phenyl]-2-(1H-indazol-5-ylamino)-7-methyl-7,8-dihydropteridin-6(5H)-one | $^1$H NMR (CDCl$_3$, 300 MHz): δ 1.23-1.28 (m, 1H), 1.47-1.53(m, 6H), 1.69-1.84(m, 3H), 1.93-1.95(m, 2H), 2.25-2.27(m, 1H), 2.94(s, 6H), 4.43-4.49 (m, 2H), 6.46 (s, 1H), 6.53-6.55 (m, 1H), 6.74-7.77 (m, 1H), 7.14(s, 1H), 7.22(s, 1H), 7.31-7.38 (m, 3H), 7.99(s, 1H), 8.18(s, 1H), 10.39 (br. s, 1H). MS(ES$^+$): m/z = 497.23 [MH$^+$]. HPLC: t$_R$ = 2.56 (Polar_5 min, ZQ3). Optical rotation: [α]$_D$ = −26.66 (C = 0.6 in CH$_2$Cl$_2$). |
| 45 | (7R)-8-cyclohexyl-2-(1H-indazol-5-ylamino)-7-methyl-5-(naphthalen-2-yl)-7,8-dihydropteridin-6(5H)-one | $^1$H NMR (CDCl$_3$, 300 MHz) δ 1.20-1.33 (m, 1H), 1.43-1.55 (m, 6H), 1.71-1.97 (m, 5H), 2.24-2.29 (m, 1H), 4.47-4.52 (m, 2H), 7.19 (s, 1H), 7.27-7.30 (m, 2H), 7.37 (s, 2H), 7.53-7.58 (m, 2H), 7.77 (s, 1H), 7.83-7.92 (m, 2H), 7.98 (d, J = 8.7 Hz, 2H), 8.17 (s, 1H)., 10.20 (br. s, 1H); MS(ES$^+$): m/z = 504.23 [MH$^+$]. HPLC: t$_R$ = 2.86 (Polar_5 min, ZQ3). Optical rotation: [α]$_D$ = −36.0 (C = 0.25 in CH$_2$Cl$_2$). |
| 46 | 3-[(7R)-8-cyclohexyl-2-(1H-indazol-5-ylamino)-7-methyl-6-oxo-7,8-dihydropteridin-5(6H)-yl]-N-methylbenzamide | $^1$H NMR (CDCl$_3$ and CD$_3$OD, 300 MHz) δ 1.15-1.22 (m, 1H), 1.39-1.44 (m, 6H), 1.60-1.95 (m, 5H), 2.17-2.24 (m, 1H), 2.89 (s, 3H), 4.39-4.41 (m, 2H), 7.02 (s, 1H), 7.27-7.35 (m, 3H), 7.51 (d, J = 8.1 Hz, 1H), 7.55-7.57 (m, 1H), 7.81(d, J = 3.3 Hz, 1H), 7.85 (s, 1H), 8.08 (s, 1H); MS(ES$^+$): m/z = 511.23 [MH$^+$]. HPLC: t$_R$ = 2.15 (Polar_5 min, ZQ3). |

| Ex. # | Chemical Name | Analytical data |
|---|---|---|
| 47 | N-{4-[(7R)-8-cyclohexyl-2-(1H-indazol-5-ylamino)-7-methyl-6-oxo-7,8-dihydropteridin-5(6H)-yl]phenyl}methanesulfonamide | $^1$H NMR (CDCl$_3$ and CD$_3$OD, 300 MHz): δ 0.97-0.99 (m, 1H), 1.21-1.30(m, 6H), 1.47-1.57(m, 3H), 1.66-1.70(m, 2H), 1.97-1.99(m, 1H), 2.78 (s, 3H), 4.16-4.22 (m, 2H), 6.82(s, 1H), 6.94(d, J = 8.1 Hz, 2H), 7.13-7.22 (m, 4H), 7.66 (s, 1H), 7.86(s, 1H). MS(ES$^+$): m/z = 547.07 [MH$^+$]. HPLC: t$_R$ = 2.25 (ZQ3, Polar_5 min). |
| 48 | (7R)-8-cyclohexyl-2-(1H-indazol-5-ylamino)-5-(6-methoxypyridin-3-yl)-7-methyl-7,8-dihydropteridin-6(5H)-one | $^1$H NMR (CDCl$_3$, 300 MHz) δ: 1.18-1.27 (m, 1 H), 1.46-1.53 (m, 5 H), 1.68-1.83 (m, 4 H), 1.87-1.96 (m, 2 H), 2.20-2.60 (m, 1 H), 3.98 (s, 3 H), 4.43-4.49 (m, 2 H), 6.88 (s, 1 H), 7.04 (s, 1 H), 7.20 (s, 1 H), 7.36-7.45 (m, 3 H), 8.01 (s, 1 H), 8.05 (d, J = 2.1 Hz, 1 H), 8.16 (s, 1 H), 10.10 (br. s, 1 H); MS(ES$^+$): m/z = 485.11 [MH$^+$]. HPLC: t$_R$ = 2.39 (ZQ3, Polar_5 min). |
| 49 | (7R)-8-cyclohexyl-5-(3,4-difluorophenyl)-2-(1H-indazol-5-ylamino)-7-methyl-7,8-dihydropteridin-6(5H)-one | $^1$H NMR (CDCl$_3$, 300 MHz) δ: 1.18-1.23 (m, 1 H), 1.45-1.52 (m, 5 H), 1.68-1.85 (m, 4 H), 1.90-2.01 (m, 2 H), 2.20-2.38 (m, 1 H), 4.41-4.48 (m, 2 H), 6.99-7.05 (m, 1 H), 7.06-7.15 (m, 2 H), 7.18 (s, 1 H), 7.31 (d, J = 9.3 Hz, 1 H), 7.35-7.43 (m, 2 H), 8.00 (s, 1 H), 8.16 (s, 1 H), 10.20 (br. s, 1 H); MS(ES$^+$): m/z = 490.07 [MH$^+$]. HPLC: t$_R$ = 2.69 (ZQ3, Polar_5 min). Optical rotation: [α]$_D$ = −65 (C = 0.4 in CH2Cl2). |
| 50 | (7R)-8-cyclohexyl-2-(1H-indazol-5-ylamino)-7-methyl-5-(quinolin-3-yl)-7,8-dihydropteridin-6(5H)-one | $^1$H NMR (CDCl$_3$ and CD$_3$OD, 300 MHz) δ: 1.14-1.25 (m, 1H), 1.40-1.50 (m, 6H), 1.60-1.79 (m, 3H), 1.81-1.92 (m, 2H), 2.19-2.22 (m, 1H), 4.37-4.49 (m, 2H), 7.10 (s, 1H), 7.32-7.40 (m, 2H), 7.60 (t, J = 7.2 Hz, 1H), 7.75-7.84 (m, 2H), 7.88 (s, 1H), 8.11 (d, J = 9.3 Hz, 3H), 8.65 (d, J = 2.1 Hz, 1H); MS(ES$^+$): m/z = 505.19 [MH$^+$]. HPLC: t$_R$ = 2.51 (ZQ3, Polar_5 min). |
| 51 | 3-[(7R)-8-cyclohexyl-7-methyl-6-oxo-2-[(2-oxo-2,3-dihydro-1H-indol-5-yl)amino]-7,8-dihydropteridin-5(6H)-yl]benzonitrile | $^1$H NMR (CDCl$_3$, 300 MHz) δ: 1.22-1.24 (m, 1 H), 1.39-1.50 (m, 6H), 1.65-1.84 (m, 3H), 1.91-1.95 (m, 2H), 2.18-2.28 (m, 1H), 3.54 (s, 2H), 4.39-4.48 (m, 2H), 6.77 (d, J = 8.7 Hz, 1H), 7.11 (s, 2H), 7.27-7.31(m, 1H), 7.49-7.52(m, 1H), 7.58 (s, 1H), 7.61-7.66 (m, 2H), 7.71-7.74 (m, 1H), 8.81 (br. s, 1H); MS(ES$^+$): m/z = 494.16 [MH$^+$]. HPLC: t$_R$ = 2.42 (ZQ3, Polar_5 min). Optical rotation: [α]$_D$ = −48.88 (C = 0.9 in CH$_2$Cl$_2$) |
| 52 | methyl 4-[(7R)-8-cyclohexyl-2-(1H-indazol-5-ylamino)-7-methyl-6-oxo-7,8-dihydropteridin-5(6H)-yl]benzoate | $^1$H NMR (CDCl$_3$, 300 MHz) δ: 1.20-1.26 (m, 1H), 1.47-1.53 (m, 6H), 1.67-1.86 (m, 3H), 1.80-1.96 (m, 2H), 2.42-2.58 (m, 1H), 3.95 (s, 3H), 4.42-4.49 (m, 2H), 6.99 (s, 1H), 7.17 (s, 1H), 7.32-7.44 (m, 4H), 8.00 (s, 1H), 8.17-8.20 (m, 3H), 10.10 (br s, 1H); MS(ES$^+$): m/z = 512.19 [MH$^+$]. HPLC: t$_R$ = 2.62 (ZQ3, Polar_5 min). |
| 53 | 5-[(7R)-8-cyclohexyl-2-(1H-indazol-5-ylamino)-7-methyl-6-oxo-7,8-dihydropteridin-5(6H)-yl]-2-methylbenzonitrile | $^1$H NMR (CDCl$_3$, 300 MHz) δ: 1.18-1.24 (m, 1H), 1.46-1.52 (m, 6H), 1.70-1.86 (m, 3H), 1.80-2.01 (m, 2H), 2.42-2.57 (m, 1H), 2.61 (s, 3H), 4.39-4.48 (m, 2H), 7.04 (s, 1H), 7.14 (s, 1H), 7.36-7.39 (m, 2H), 7.41 (s, 1H), 7.44-7.48 (m, 1H), 7.52 (d, J = 2.4 Hz, 1H), 8.00 (s, 1H), 8.16 (s, 1H), 10.19 (br. s, 1H). MS(ES$^+$): m/z = 493.19 [MH$^+$]. HPLC: t$_R$ = 2.62 (ZQ3, Polar_5 min). Optical rotation: [α]$_D$ = −77.5 (C = 0.4 in CH$_2$Cl$_2$). |
| 54 | (7R)-8-cyclohexyl-5-(4-fluoro-3-methoxyphenyl)-2-(1H-indazol-5-ylamino)-7-methyl-7,8-dihydropteridin-6(5H)-one | $^1$H NMR (CDCl$_3$, 300 MHz) δ: 1.19-1.27 (m, 1H), 1.47-1.64 (m, 6H), 1.73-1.83 (m, 3H), 1.96-2.00 (m, 2H), 2.21-2.35 (m, 1H), 3.87 (s, 3H), 4.42-4.49 (m, 2H), 6.78-6.70 (m, 2H), 7.01 (s, 1H), 7.11-7.25 (m, 2H), 7.36-7.44 (m, 2H), 8.01 (s, 1H), 8.17 (s, 1H), 10.11 (br. s, 1H). MS(ES$^+$): m/z = 502.18 [MH$^+$]. HPLC: t$_R$ = 2.53 (ZQ3, Polar_5 min). |
| 55 | (7R)-8-cyclohexyl-5-(3-fluoro-4-methoxyphenyl)-2-(1H-indazol-5-ylamino)-7-methyl-7,8-dihydropteridin-6(5H)-one | $^1$H NMR (CDCl$_3$, 300 MHz) δ: 1.16-1.25 (m, 1H), 1.45-1.52 (m, 6H), 1.72-1.83 (m, 3H), 1.91-1.98 (m, 2H), 2.23-2.29 (m, 1H), 3.94 (s, 3H), 4.40-4.61 (m, 2H), 6.97-7.01 (m, 3H), 7.07 (t, J = 8.4 Hz, 1H), 7.19 (s, 1H), 7.36-7.44 (m, 2H), 7.99 (s, 1H), 8.16 (s, 1H), 10.10 (br. s, 1H). MS(ES$^+$): m/z = 502.16 [MH$^+$]. HPLC: t$_R$ = 2.49 (ZQ3, Polar_5 min). |
| 56 | 3-[(7R)-8-cyclohexyl-2-[(6-fluoro-1H-indazol-5-yl)amino]-7-methyl-6-oxo-7,8-dihydropteridin-5(6H)-yl]benzonitrile | $^1$H NMR (CDCl$_3$, 300 MHz) δ: 1.20-1.26 (m, 1 H), 1.47-1.62 (m, 6H), 1.73-1.83 (m, 3H), 1.97-1.99 (m, 2H), 2.25-2.27 (m, 1H), 4.45-4.49 (m, 2H), 7.11 (s, 1H), 7.18-7.22 (m, 2H), 7.51-7.54 (m, 1H), 7.60-7.62 (m, 1H), 7.65-7.67 (m, 1H), 7.73-7.75 (m, 1H), 7.99 (s, 1H), 8.69 (d, J = 7.8 Hz, 1H), 10.21 (br. s, |

| Ex. # | Chemical Name | Analytical data |
|---|---|---|
| | | 1H). MS(ES$^+$): m/z = 497.12 [MH$^+$]. HPLC: $t_R$ = 2.65 (ZQ3, Polar_5 min). Optical rotation: $[\alpha]_D$ = −55.55 (C = 0.9 in CH$_2$Cl$_2$). |
| 57 | (7R)-8-cyclohexyl-2-(1H-indazol-5-ylamino)-7-methyl-5-(thiophen-3-yl)-7,8-dihydropteridin-6(5H)-one | $^1$H NMR (CDCl$_3$, 300 MHz) δ: 1.18-1.25 (m, 1 H), 1.44-1.52 (m, 3H), 1.60-1.70 (m, 3H), 1.72-1.81 (m, 3H), 1.91-1.98 (m, 2H), 2.20-2.36 (m, 1H), 4.41-4.47 (m, 2H), 6.96 (dd, J = 5.4, 1.2 Hz, 1H), 7.00 (s, 1H), 7.31-7.33 (m, 2H), 7.40-7.41 (m, 2H), 7.44-7.47 (m, 1H), 8.00 (s, 1H), 8.17 (m, 1H); MS(ES$^+$): m/z = 460.16 [MH$^+$]. HPLC: $t_R$ = 2.35 (ZQ3, Polar_5 min). Optical rotation: $[\alpha]_D$ = −51.0 (C = 1.0 in CH$_2$Cl$_2$). |
| 58 | (7R)-8-cyclohexyl-2-(1H-indazol-5-ylamino)-7-methyl-5-(1-methyl-1H-pyrazol-4-yl)-7,8-dihydropteridin-6(5H)-one | $^1$H NMR (CDCl$_3$, 300 MHz) δ: 1.22-1.27 (m, 1 H), 1.39-1.66 (m, 6H), 1.69-1.84 (m, 3H), 1.97-2.27 (m, 2H), 2.22-2.28 (m, 1H), 3.95 (s, 3H), 4.40-4.45 (m, 2H), 7.15 (s, 1H), 7.39-7.44 (m, 2H), 7.49-7.52 (m, 3H), 8.00 (s, 1H), 8.18 (s, 1H). MS(ES$^+$): m/z = 458.14 [MH$^+$]. HPLC: $t_R$ = 2.09 (ZQ3, Polar_5 in). Optical rotation: $[\alpha]_D$ = −24.0 (C = 0.5 in CH$_2$Cl$_2$). |
| 59 | 3-[(7R)-8-cyclohexyl-7-methyl-2-[(7-methyl-1H-indazol-5-yl)amino]-6-oxo-7,8-dihydropteridin-5(6H)-yl]benzonitrile | $^1$H NMR (CDCl$_3$, 300 MHz) δ: 0.87-0.89 (m, 1 H), 1.42-1.48 (m, 6H), 1.74-1.80 (m, 3H), 1.92-2.04 (m, 2H), 2.22-2.26 (m, 1H), 2.53 (s, 3H), 4.42-4.49 (m, 2H), 6.97-7.05(m, 1H), 7.14 (s, 2H), 7.50-7.53 (m, 1H), 7.59-7.65 (m, 2H), 7.71-7.74 (m, 1H), 8.00 (s, 2H), 10.41 (br. s, 1H). MS(ES$^+$): m/z = 493.16 [MH$^+$]. HPLC: $t_R$ = 2.56 (ZQ3, Polar_5 min). Optical rotation: $[\alpha]_D$ = −38.88 (C = 0.6 in CH$_2$Cl$_2$) |
| 60 | 8-cyclohexyl-7-methyl-2-[(2-oxo-2,3-dihydro-1H-indol-5-yl)amino]-5-phenyl-7,8-dihydropteridin-6(5H)-one | $^1$H NMR (300 MHz, DMSO-d$_6$): δ: 1.21-1.22 (m, 1H), 1.34-1.38 (m, 6H), 1.61-1.82 (m, 5H), 2.04-2.07 (m, 1H), 3.41 (s, 2H), 4.20-4.32 (m, 2H), 6.66 (d, J = 8.7 Hz, 1H), 6.92 (s, 1H), 7.28 (d, J = 7.5 Hz, 2H), 7.46-7.54 (m, 4H), 7.60 (s, 1H), 9.02 (s, 1H), 10.17 (br s, 1H). MS(ES$^+$): m/z = 469.10 [MH$^+$]. HPLC: $t_R$ = 2.45 (ZQ3, Polar_5 min). |
| 61 | 8-cyclohexyl-2-(1H-indazol-5-ylamino)-7-methyl-5-phenyl-7,8-dihydropteridin-6(5H)-one | $^1$H NMR, Mass and HPLC data: identical to Example 18 |
| 62 | (7S)-8-cyclohexyl-2-(1H-indazol-5-ylamino)-7-methyl-5-phenyl-7,8-dihydropteridin-6(5H)-one | $^1$H NMR, Mass and HPLC data: identical to Example 18 |
| 63 | 4-[(7R)-8-cyclohexyl-2-(1 H-indazol-5-ylamino)-7-methyl-6-oxo-7,8-dihydropteridin-5(6H)-yl]benzoic acid | $^1$H NMR (DMSO-d$_6$, 300 MHz) δ: 1.21-1.26 (m, 2H), 1.50-1.52 (m, 4H), 1.65-1.81 (m, 4H), 1.86-1.89 (m, 1H), 1.92-2.03 (m, 2H), 4.10-4.19 (m, 1H), 4.54-4.63 (m, 1H), 6.89 (s, 1H), 7.38 (d, J = 9 Hz, 1H), 7.49-7.57 (m, 3H), 7.94(s, 1H), 8.03 (s, 1H), 8.11-8.14 (m, 2H), 10.09 (br s, 1H). MS(ES$^+$): m/z = 498.14 [MH$^+$]. HPLC: $t_R$ = 2.27 (ZQ3, Polar_5 min). |

Example 64 was prepared according to procedures similar for the preparation of Example 18 above using corresponding starting materials and intermediates. More specifically, DL-alanine methyl ester hydrochloride and cyclopentanone was used in the step a of the synthesis.

Example 65 was prepared according to procedures similar for the preparation of Example 18 above using corresponding starting materials and intermediates. More specifically, DL-alanine methyl ester hydrochloride and cyclopentanone was used in the step a of the synthesis. 5-amino-1,3-dihydro-2H-indol-2-one as corresponding R$^3$—NH$_2$ was used in the step e of the synthesis.

Example 66 was prepared according to procedures similar for the preparation of Example 18 above using corresponding starting materials and intermediates. More specifically, cyclopentanone was used in the step a of the synthesis.

Example 67 was prepared according to procedures similar for the preparation of Example 18 above using corresponding starting materials and intermediates. More specifically, L-alanine methyl ester hydrochloride and cyclopentanone was used in the step a of the synthesis.

Example 68 was prepared according to procedures similar for the preparation of Example 18 above using corresponding starting materials and intermediates. More specifically, cyclopentanone was used in the step a of the synthesis. 5-amino-1,3-dihydro-2H-indol-2-one as corresponding R$^3$—NH$_2$ was used in the step e of the synthesis.

Example 69 was prepared according to procedures similar for the preparation of Example 18 above using corresponding starting materials and intermediates. More specifically, cyclopentanone was used in the step a of the synthesis. (3-Cyanophenyl)boronic acid as corresponding R$^1$—B(OH)$_2$ was used in the step d of the synthesis.

| Ex. # | Chemical Name | Analytical data |
|---|---|---|
| 64 | 8-cyclopentyl-2-(1H-indazol-5-ylamino)-7-methyl-5-phenyl-7,8-dihydropteridin-6(5H)-one | $^1$HNMR (CDCl$_3$, 300 MHz): δ 1.47 (d, J = 6.6 Hz, 3H), 1.68-1.81 (m, 6H), 2.04-2.13 (m, 2H), 4.43(q, J = 6.9 Hz, 1H), 4.46-4.59 (m, 1H), 7.01 (s, 1H), 7.16 (s, 1H), 7.24 (s, 1H), 7.38 (s, 2H), 7.41-7.46(m, 1H), 7.49-7.54(m, 2H), 7.98 (s, 1H), 8.11 (s, 1H), 10.18 (br. s, 1H). MS(ES$^+$): m/z = 439.98 [MH$^+$]. HPLC: t$_R$ = 2.33 (ZQ3, Polar_5 min). |
| 65 | 8-cyclopentyl-7-methyl-2-[(2-oxo-2,3-dihydro-1H-indol-5-yl)amino]-5-phenyl-7,8-dihydropteridin-6(5H)-one | $^1$H NMR (CDCl$_3$, 300 MHz): δ 1.46 (d, J = 6.9 Hz, 3H), 1.68-1.80 (m, 6H), 2.04-2.11 (m, 2H), 3.51(s, 2H), 4.41(q, J = 6.6 Hz, 1H), 4.51-4.55 (m, 1H), 6.74-6.76 (m, 2H), 7.12(s, 1H), 7.22 (s, 1H), 7.41-7.49(m, 3H), 7.60 (s, 1H), 7.70 (s, 1H). MS(ES$^+$): m/z = 454.90 [MH$^+$]. HPLC: t$_R$ = 2.21 (ZQ3, Polar_5 min). |
| 66 | (7R)-8-cyclopentyl-2-(1H-indazol-5-ylamino)-7-methyl-5-phenyl-7,8-dihydropteridin-6(5H)-one | $^1$HNMR, Mass, HPLC are identical to example 64. |
| 67 | (7S)-8-cyclopentyl-2-(1H-indazol-5-ylamino)-7-methyl-5-phenyl-7,8-dihydropteridin-6(5H)-one | $^1$HNMR, Mass, HPLC are identical to example 64. |
| 68 | (7R)-8-cyclopentyl-7-methyl-2-[(2-oxo-2,3-dihydro-1H-indol-5-yl)amino]-5-phenyl-7,8-dihydropteridin-6(5H)-one | $^1$HNMR, Mass, HPLC are identical to example 65. |
| 69 | 3-[(7R)-8-cyclopentyl-2-(1H-indazol-5-ylamino)-7-methyl-6-oxo-7,8-dihydropteridin-5(6H)-yl]benzonitrile | $^1$H NMR (CDCl$_3$, 300 MHz) δ: 1.46-1.48 (m, 4H), 1.61-1.62 (m, 2H), 1.68-1.81 (m, 4H), , 2.06-2.15 (m, 1H), 4.42 (q, , J = 6.9 Hz, 1H), 4.46-4.57 (m, 1H), 6.91-6.94 (m, 1H), 7.15 (s, 1H), 7.36-7.44 (m, 2H), 7.52-7.66 (m, 3H), 7.72-7.56 (s, 1H), 7.99 (s, 1H), 8.09 (s, 1H). MS(ES$^+$): m/z = 465.13 [MH$^+$]. HPLC: t$_R$ = 2.36 (ZQ3, Polar_5 min). |

Example 70 was prepared from methyl 2-methylalaninate hydrochloride using procedures shown below:

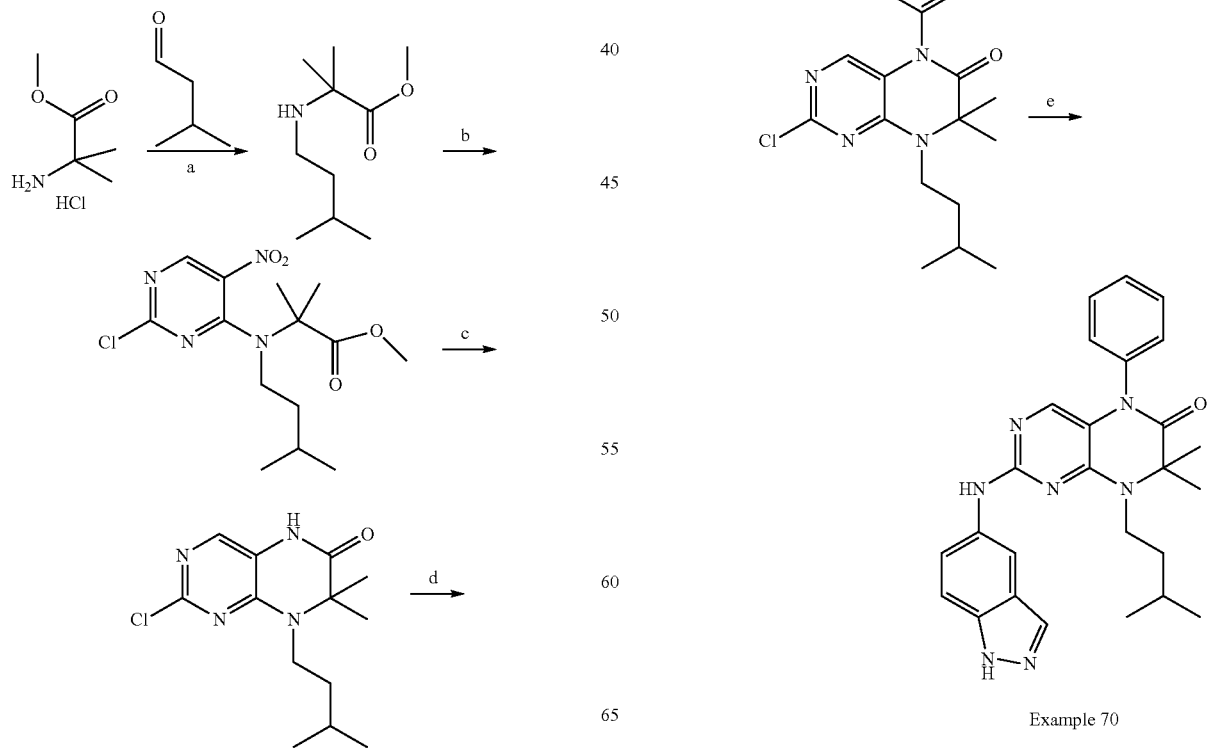

Example 70

Step a: Methyl 2-methyl-N-(3-methylbutyl)alaninate

A suspension of methyl 2-methylalaninate hydrochloride (6.9 g, 45 mmol) in dry dichloromethane (180 mL) was treated with potassium acetate (4.4 g, 45 mmol) and the reaction mixture stirred for ten minutes. The reaction mixture was then cooled to 10° C. and treated with 3-methylbutanal (4.8 g, 56 mmol). This was followed by the addition of sodium triacetoxyborohydride (11.91 g, 56 mmol) in portions over a period of ten minutes. Reaction mixture was stirred at room temperature for 16 h. Then saturated aqueous sodium bicarbonate solution was added to the reaction and resulting mixture was stirred for another 30 minutes. The reaction mixture was further basified with aqueous sodium carbonate to pH=~10. Dichloromethane layer was separated and the aqueous layer extracted with dichloromethane (3×50 mL). Organic layers were combined, washed with brine, dried over anhydrous sodium sulfate, and evaporated to give titled product as colorless oil which was used as such for the next step. $^1$HNMR (300 MHz, CDCl$_3$): δ 0.95 (s, 3H), 0.96 (s, 3H), 1.25-1.35 (m, 7H), 1.55-1.65 (m, 1H), 1.80 (s, 1H), 2.40-2.48 (m, 2H), 3.63 (s, 3H).

Step b: Methyl N-(2-chloro-5-nitropyrimidin-4-yl)-2-methyl-N-(3-methylbutyl)alaninate To a stirred suspension of 2,4-dichloro-5-nitropyrimidine (7.5 g, 38.5 mmol), anhydrous potassium carbonate (10.0 g) in dry acetone (150 mL) was added a solution of methyl 2-methyl-N-(3-methylbutyl)alaninate (5.6 g, 30.0 mmol) in dry acetone (9 mL) at 0° C. The reaction was then allowed to warm up to room temperature and stirred at rt for 16 h. The reaction mixture was filtered and evaporated. The residue was purified by flash chromatography on silica gel (eluent: ethyl acetate-hexane mixture (v:v=5:95)) to give titled product (yield: 15%). $^1$HNMR (300 MHz, CDCl$_3$): δ 0.85 (s, 3H), 0.88 (s, 3H), 1.30-1.36 (m, 2H), 1.60-1.65 (m, 7H), 3.37-3.42 (m, 2H), 3.72 (s, 3H) and 8.56 (s, 1H).

Step c: 2-Chloro-7,7-dimethyl-8-(3-methylbutyl)-7,8-dihydropteridin-6(5H)-one To a stirred solution of methyl N-(2-chloro-5-nitropyrimidin-4-yl)-2-methyl-N-(3-methylbutyl)alaninate (2.0 g, 5.8 mmol) in ethanol (125 mL) was added iron powder (3.2 g, 58 mmol), the resulting mixture was heated to reflux. 1N aqueous hydrochloric acid was added to the reaction mixture (added in small portions, 5.0 ml total), The reaction mixture was heated at reflux until the completion of the reaction as monitored by TLC. The reaction was cooled to room temperature and filtered. The filtrate was evaporated to give a residue which was triturated using isopropyl ether to give titled compound (yield: 65%). $^1$HNMR (300 MHz, CDCl$_3$): δ 0.97 (s, 3H), 1.0 (s, 3H), 1.37-1.56 (m, 7H), 1.65-1.80 (m, 2H), 3.52-3.58 (m, 2H), 7.62 (s, 1H), 9.13 (br s, 1H).

Step d: 2-Chloro-7,7-dimethyl-8-(3-methylbutyl)-5-phenyl-7,8-dihydropteridin-6(5H)-one To a stirred solution of 2-chloro-7,7-dimethyl-8-(3-methylbutyl)-7,8-dihydropteridin-6(5H)-one (707 mg, 2.5 mmol) in dichloromethane (50 mL) was added triethylamine (25.0 mmol), cupric acetate (908 mg, 5.0 mmol) and phenylboronic acid (610 mg, 5.0 mmol) followed by 4 Å molecular sieves (2.0 g). The reaction mixture was stirred for 48 h at room temperature with an air balloon. Then the reaction mixture was filtered over celite. The filtrate was washed with aqueous saturated sodium bicarbonate (2×30 mL), dried over anhydrous sodium sulfate and evaporated. The residue was purified by column chromatography on silica gel (Eluent: 2% methanol in dichloromethane) to give titled product (yield; 46%). $^1$HNMR (300 MHz, CDCl$_3$): δ 1.0 (s, 3H), 1.02 (s, 3H), 1.61-1.65 (m, 9H), 3.64 (q, J=5.1 Hz, 2H), 7.06 (s, 1H), 7.18-7.21 (m, 2H) and 7.48-7.57 (m, 3H).

Step e: 2-(1H-indazol-5-ylamino)-7,7-dimethyl-8-(3-methylbutyl)-5-phenyl-7,8-dihydropteridin-6(5H)-one Example 70

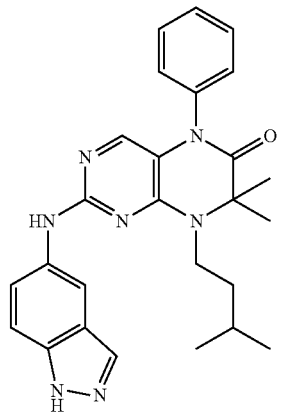 [SMILES: CC(C)CCN1c2nc(Nc3ccc4[nH]ncc4c3)ncc2N(c2ccccc2)C(=O)C1(C)C]

A mixture of 2-chloro-7,7-dimethyl-8-(3-methylbutyl)-5-phenyl-7,8-dihydropteridin-6(5H)-one (89 mg, 0.25 mmol), 5-aminoindazole (41 mg, 0.31 mmol), trifluoroacetic acid (1.0 mmol) in trifluoroethanol (1.5 mL) was heated in a microwave reactor at 125° C. for 35 minutes. The reaction mixture was diluted with ethyl acetate (30 ml) and washed with aqueous saturated sodium bicarbonate, dried over anhydrous sodium sulfate and evaporated. The residue was purified by column chromatography on silica gel using 2% methanol in dichloromethane as eluent to give titled compound (yield: 30%). $^1$HNMR (300 MHz, CDCl$_3$): δ 0.98 (s, 3H), 1.0 (s, 3H), 1.64-1.85 (m, 9H), 3.64-3.69 (m, 2H), 7.05 (s, 1H), 7.18-7.24 (m, 2H), 7.40-7.55 (m, 5H), 7.98 (s, 1H), 8.08 (s, 1H), 10.04 (br. s, 1H). MS(ES$^+$): m/z=456.10 [MH$^+$]. HPLC: t$_R$=2.76 (ZQ3, Polar_5 min).

| Ex. # | Chemical Name | Analytical data |
|---|---|---|
| 71 | 3-[(7R)-8-(cyclobutylmethyl)-2-(1H-indazol-5-ylamino)-7-methyl-6-oxo-7,8-dihydropteridin-5(6H)-yl]benzonitrile | $^1$H NMR (CDCl$_3$, 300 MHz): δ 1.54 (d, J = 6.9 Hz, 3H), 1.83-2.08 (m, 4H), 2.17-2.30 (m, 2H), 2.82-2.92 (m, 1H), 3.23 (q, J = 7.5 Hz, 1H), 4.27-4.40 (m, 2H), 7.17 (s, 1H), 7.24 (s, 1H), 7.42-7.49 (m, 2H), 7.59-7.63 (m, 1H), 7.68-7.71 (m, 2H), 7.79-7.83 (m, 1H), 8.07 (s, 1H), 8.20 (s, |

| Ex. # | Chemical Name | Analytical data |
|---|---|---|
| 72 | (7R)-8-(cyclohexylmethyl)-2-(1H-indazol-5-ylamino)-7-methyl-5-phenyl-7,8-dihydropteridin-6(5H)-one | 1H), 10.53 (br s 1H). MS(ES+): m/z = 465.13 [MH+]. HPLC: $t_R$ = 2.25 (ZQ3, Polar_5 min) $^1$HNMR (300 MHz, CDCl$_3$): δ 1.02-1.06 (m, 3H), 1.20-1.24 (m, 3H), 1.47 (d, J = 6.6 Hz, 3H), 1.76-1.89 (m, 5H), 2.73 (q, J = 7.8 Hz, 1H), 4.18 (q, J = 6.6 Hz, 1H), 4.28 (q, J = 6.9 Hz, 1H), 6.86 (s, 1H), 7.14 (s, 1H), 7.28 (s, 1H), 7.34-7.56 (m, 5H), 7.98 (s, 1H), 8.14 (s, 1H) and 10.1 (br s, 1H). MS(ES+): m/z = 468.28 [MH+]. HPLC: $t_R$ = 2.70 (ZQ3, Polar_5 min). |
| 73 | (7R)-8-[2-(dimethylamino)ethyl]-2-(1H-indazol-5-ylamino)-7-methyl-5-phenyl-7,8-dihydropteridin-6(5H)-one | $^1$HNMR (300 MHz, CDCl$_3$ + CD$_3$OD): δ 1.08-1.09 (m, 1H), 1.47 (d, J = 6.9 Hz, 3H), 2.24 (s, 6H), 2.61 (t, J = 7.2 Hz, 2H), 4.14-4.18, (m, 1H), 4.30 (q, J = 6.9 Hz, 1H), 6.98 (s, 1H), 7.19 (d, J = 6.0 Hz, 2H), 7.35-7.49 (m, 5H), 7.87 (s, 1H) 7.97 (s, 1H). MS(ES+): m/z = 443.22 [MH+]. HPLC: $t_R$ = 0.75 (TOF, Polar3 min). |
| 74 | (7R)-2-(1H-indazol-5-ylamino)-7-methyl-5-phenyl-8-(tetrahydro-2H-pyran-4-ylmethyl)-7,8-dihydropteridin-6(5H)-one | $^1$HNMR (300 MHz, CDCl$_3$ + CD$_3$OD): δ 1.29-1.34 (m, 2H), 1.31 (d, J = 6.6 Hz, 3H), 1.41-1.70 (m, 2H), 1.90-2.10 (m, 1H), 2.70 (q, J = 7.5 Hz, 1H), 3.71-3.89 (m, 3H), 4.17-4.19 (m, 3H), 6.90 (s, 1H), 7.16 (q, J = 8.4 Hz, 2H), 7.30-7.49 (m, 5H), 7.82 (s, 1H), 7.95 (s, 1H). MS(ES+): m/z = 470.18 (100) [MH+]. HPLC: $t_R$ = 2.15 (ZQ3, Polar_5 min). |
| 75 | (7R)-8-(cyclopentylmethyl)-2-(1H-indazol-5-ylamino)-7-methyl-5-phenyl-7,8-dihydropteridin-6(5H)-one | $^1$HNMR (300 MHz, CDCl$_3$): δ 1.23-1.40 (m, 3H), 1.48 (d, J = 6.9 Hz, 3H), 1.56-1.69 (m, 4H), 1.80-1.86 (m, 1H), 2.44 (q, J = 7.5 Hz, 1H), 2.85-2.95 (M, 1H), 4.22-4.36 (m, 2H), 7.02 (s, 1H), 7.11 (s, 1H), 7.24-7.38 (m, 2H), 7.38-7.39 (m, 1H), 7.41-7.56 (m, 3H), 7.98 (s, 1H), 8.13-8.14 (m, 1H), 10.20-10.30 (br s, 1H). ME(ES)+: m/z = 454.14 (100) [MH+]. HPLC: $t_R$ = 2.45 (ZQ3, Polar_5 min). |
| 76 | (7R)-8-benzyl-2-(1H-indazol-5-ylamino)-7-methyl-5-phenyl-7,8-dihydropteridin-6(5H)-one | $^1$HNMR (300 MHz, CDCl$_3$ + CD$_3$OD): δ 1.42 (d, J = 6.9 Hz, 3H), 4.22-4.44 (m, 1H), 4.33 (d, J = 15.6 Hz, 1H), 5.34 (d, J = 15.3 Hz, 1H), 7.04 (s, 1H), 7.20-7.23 (m, 2H), 7.26-7.34(m, 6H), 7.42-7.52 (m, 4H), 7.78 (s, 1H) and 7.91-7.92 (m, 1H). MS: m/z = 462.2 [M + H+]. |
| 77 | (7R)-8-(3-hydroxypropyl)-2-(1H-indazol-5-ylamino)-7-methyl-5-phenyl-7,8-dihydropteridin-6(5H)-one | $^1$HNMR (300 MHz, CDCl$_3$ + CD$_3$OD): δ 1.25 (s, 1H), 1.52 (d, J = 6.6 Hz, 3H), 1.86-1.88 (m, 2H), 3.37-3.44 (m 2H), 4.08 (q, J = 6.3 Hz, 1H), 4.30 (q, J = 6.3 Hz 1H), 7.10 (s, 1H), 7.22-7.30 (m, 4H), 7.33-7.53 (m, 3H) and 7.93 (s, 2H). MS: m/z = 430.2 [M + H+]. |
| 78 | (7R)-2-(1H-indazol-5-ylamino)-7-methyl-5-phenyl-8-(piperidin-4-ylmethyl)-7,8-dihydropteridin-6(5H)-one | $^1$HNMR (300 MHz, CDCl$_3$) δ 1.48 (d, J = 6.9 Hz, 3H), 1.98-2.12 (m, 4H), 2.58-2.75 (m, 2H), 2.78-2.85 (m, 2H), 3.20-3.29 (m, 4H), 4.18-4.29 (m, 2H), 7.06 (s, 1H), 7.25 (d, J = 7.5 Hz, 2H), 7.33-7.58 (m, 5H) and 7.95 (d, J = 11.4 Hz, 2H). MS(ES+): m/z 469.23 [MH+]. HPLC: $t_R$ = 2.29 (vvPolar_5 min, ZQ3). |
| 79 | (7R)-2-(1H-indazol-5-ylamino)-7-methyl-8-(2-methylpropyl)-5-phenyl-7,8-dihydropteridin-6(5H)-one | $^1$H NMR (CDCl$_3$, 300 MHz) δ: 1.02 (d, J = 4.8 Hz, 3H), 1.04 (d, J = 4.8 Hz, 3H), 1.47 (d, J = 6.9 Hz, 3H), 2.17-2.23 (m, 1H), 2.69 (q, J = 8.1 Hz, 1H), 4.16 (q, J = 6.9 Hz, 1H), 4.30-4.32 (m, 1H), 7.13 (s, 1H), 7.28-7.35 (m, 2H), 7.36 (d, J = 1.5 Hz, 2H), 7.42-7.56 (m, 3H), 7.99 (s, 1H) and 8.12 (t, J = 1.2 Hz, 1H). MS(ES+): m/z = 428.15 (100) [MH+]. HPLC: $t_R$ = 2.39 (ZQ3, Polar_5 min). [α]$_D$ = +43.1 (C = 0.53 in CH$_2$Cl$_2$) |
| 80 | 3-[(7R)-2-(1H-indazol-5-ylamino)-7-methyl-6-oxo-8-(tetrahydro-2H-pyran-4-ylmethyl)-7,8-dihydropteridin-5(6H)-yl]benzonitrile | $^1$H NMR (CDCl$_3$, 300 MHz): δ 1.90 (d, J = 6.0 Hz, 1H), 1.48-1.57 (m, 6H), 2.01-2.02 (m, 1H), , 2.84 (q, J = 7.8 Hz, 1H), 3.45 (t, J = 10.2 Hz, 2H), 4.06-4.11 (m, 2H), 4.27-4.38 (m, 2H), 6.98-7.0 (m, 1H), 7.20 (s, 1H), 7.44-7.52 (m, 2H), 7.60-7.63 (m, 1H), 7.70-7.84 (m, 3H), 8.05 (s, 1H) and 8.14 (s, 1H). MS(ES+): m/z = 495.11 [MH+]. HPLC: $t_R$ = 1.97 (ZQ3, Polar_5 min). |
| 81 | 3-[(7R)-8-(cyclopentylmethyl)-2-(1H-indazol-5-ylamino)-7-methyl-6-oxo-7,8-dihydropteridin-5(6H)-yl]benzonitrile | $^1$H NMR (CDCl$_3$, 300 MHz): δ 1.13 (d, J = 6.0 Hz, 2H), 1.25-1.34 (m, 4H), 1.48 (d, J = 6.9 Hz, 3H), 1.80-1.84 (m, 2H), 2.39-2.45 (m, 1H), 2.87 (q, J = 6.9 Hz, 1H), 4.25 (q, J = 7.5 Hz, 1H), 4.36 (d, J = 6.9 Hz, 1H), 7.10 (s, 2H), 7.38-7.41 (m, 2H), 7.56-7.68 (m, 3H), 7.73-7.76 (m, 1H), 7.99 (s, 1H), 8.12 (s, 1H). MS(ES+): m/z = 479.50 [MH+] |

| Ex. # | Chemical Name | Analytical data |
|---|---|---|
| 82 | 3-[(7R)-2-(1H-indazol-5-ylamino)-7-methyl-6-oxo-8-(tetrahydrofuran-3-ylmethyl)-7,8-dihydropteridin-5(6H)-yl]benzonitrile | $^1$H NMR (CDCl$_3$, 300 MHz) δ 1.48 (d, J = 6.6 Hz, 3H), 1.69-1.76 (m, 1H), 2.04-2.15 (m, 1H), 2.81-2.83 (m, 1H), 2.91-3.01 (m, 1H), 3.66-3.84 (m, 3H), 3.86-3.96 (m, 1H), 4.20-4.34 (m, 2H), 7.14 (s, 1H), 7.35-7.42 (m, 2H), 7.53-7.56 (m, 1H), 7.62-7.67 (m, 2H), 7.73-7.76 (m, 1H), 8.00-8.10 (m, 2H). MS(ES$^+$): m/z = 481.13 (100), [MH$^+$]. HPLC: t$_R$ = 2.78 (ZQ3, Polar_5 min). |
| 83 | 3-[(7R)-8-[(3,3-difluorocyclobutyl)methyl]-2-(1H-indazol-5-ylamino)-7-methyl-6-oxo-7,8-dihydropteridin-5(6H)-yl]benzonitrile | $^1$H NMR (CDCl$_3$, 300 MHz) δ 1.48 (d, J = 6.6 Hz, 3H), 2.37-2.43 (m, 2H), 2.68-2.77 (m, 3H), 3.17 (q, J = 6.6 Hz, 1H), 4.27-4.38 (m, 2H), 7.07 (s, 1H), 7.15 (s, 1H), 7.37-7.45 (m, 2H), 7.53--7.56 (m, 1H), 7.62-7.68 (m, 2H), 7.75 (d, J = 7.5 Hz, 1H), 8.02 (d, J = 7.5 Hz, 2H). MS(ES$^+$): m/z = 501.16 [MH$^+$]. HPLC: t$_R$ = 2.28 (ZQ3, Polar_5 min). |
| 84 | 3-[(6aR)-2-[(7-fluoro-1H-indazol-5-yl)amino]-6-oxo-6a,7,8,9-tetrahydropyrrolo[2,1-h]pteridin-5(6H)-yl]benzonitrile | $^1$H NMR (DMSO-d6, 300 MHz) δ 2.04 (s, 3H), 2.30 (s, 1H), 3.66-3.75 (m, 2H), 4.41 (m, 1H), 6.93 (s, 1H), 7.58 (d, J = 13.5 Hz, 1H), 7.73-7.76 (m, 2H), 7.94-8.04 (m, 4H), 9.28 (s, 1H), 13.34 (s, 1H). MS(ES$^+$): m/z = 441.40 [MH$^+$]. |
| 85 | (7R)-5-(3,4-dimethoxyphenyl)-2-[(7-fluoro-1H-indazol-5-yl)amino]-7-methyl-8-(3-methylbutyl)-7,8-dihydropteridin-6(5H)-one | $^1$H NMR (CDCl$_3$, 300 MHz) δ 1.06 (t, J = 6.3 Hz, 6H), 1.60 (d, J = 6.9 Hz, 3H), 1.68-1.84 (m, 3H), 3.18-3.22 (m, 1H), 3.94 (s, 3H), 4.0 (s, 3H), 4.18-4.30 (m, 1H), 4.42 (q, J = 6.9 Hz, 1H), 6.77 (s, 1H), 6.80-6.90 (m, 1H), 7.06 (d, J = 7.7 Hz, 1H), 7.19 (s, 1H), 7.48 (dd,, J = 10.8 and 1.5 Hz, 1H), 7.78 (d, J = 1.5 Hz, 1H) and 8.07 (d, J = 1.5 Hz, 1H). MS(ES$^+$): m/z = 520.85 [MH$^+$]. HPLC: t$_R$ = 2.43 (ZQ3, Polar_5 min). |
| 86 | 3-[(7R)-2-[(7-fluoro-1H-indazol-5-yl)amino]-7-methyl-8-(3-methylbutyl)-6-oxo-7,8-dihydropteridin-5(6H)-yl]benzonitrile | $^1$H NMR (CDCl$_3$, 300 MHz) δ 0.99 (t, J = 6.3 Hz, 6H), 1.52 (d, J = 6.6 Hz, 3H), 1.62-1.72 (m, 3H), 3.10-3.16 (m, 1H), 4.12-4.16 (m, 1H), 4.35-4.37 (m, 1H), 7.10 (s, 1H), 7.36-7.40 (m, 2H), 7.52-7.56 (m, 1H), 7.61-7.67 (m, 2H), 7.72-7.76 (m, 2H) and 8.01 (d, J = 3.3 Hz, 1H). MS(ES$^+$): m/z = 485.92 [MH$^+$]. HPLC: t$_R$ = 2.45 (ZQ3, Polar_5 min). |
| 87 | (7R)-2-[(7-fluoro-1H-indazol-5-yl)amino]-7-methyl-8-(3-methylbutyl)-5-(pyridin-3-yl)-7,8-dihydropteridin-6(5H)-one | $^1$H NMR (CDCl$_3$ + CD$_3$OD, 300 MHz) δ: 0.90 (t, J = 3.3 Hz, 6H), 1.45 (d, J = 6.6 Hz, 3H),1.55-1.66 (m, 3H), 3.05-3.12 (m, 1H), 4.04-4.14 (m, 1H), 4.25-4.31 (m, 1H), 6.95 (s, 1H), 7.28-7.32 (m, 1H), 7.45-7.50 (m, 1H), 7.61-7.63 (m, 2H), 7.87 (d, J = 3.0 Hz, 1H), 8.44 (s, 1H), and 8.60 (d, J 3.6 Hz, 1H). MS(ES$^+$): m/z = 461.90 [MH$^+$]. HPLC: t$_R$ = 2.17 (ZQ3, Polar_5 min). |
| 88 | (7R)-5-(3,4-dimethoxyphenyl)-2-[(4-fluoro-2-oxo-2,3-dihydro-1,3-benzoxazol-6-yl)amino]-7-methyl-8-(3-methylbutyl)-7,8-dihydropteridin-6(5H)-one | $^1$H NMR (400 MHz, CD$_3$OD): δ 0.88-1.08 (m, 5H), 0.91-1.07 (m, 6H), 1.27 (br. s., 2H), 1.43-1.57 (m, 3H), 1.67 (br. s., 3H), 3.78-3.95 (m, 6H), 4.13 (br. s., 1H), 4.37 (br. s., 1H), 6.83 (br. s., 2H), 6.96-7.14 (m, 2H), 7.30 (d, J = 11.37 Hz, 1H), 7.49 (br. s., 1H). MS(ES$^+$): m/z = 537.67 [MH$^+$]. HPLC: t$_R$ = 0.91 min (analytical_2 min, UPLC). |
| 89 | 3-[(7R)-2-[(3,5-difluoro-4-hydroxyphenyl)amino]-7-methyl-8-(3-methylbutyl)-6-oxo-7,8-dihydropteridin-5(6H)-yl]benzonitrile | $^1$H NMR (400 MHz, CD$_3$OD): δ 7.84-7.90 (m, 1H), 7.79 (s, 1H), 7.75 (t, J = 8.0 Hz, 1H), 7.62-7.67 (m, 1H), 7.17-7.29 (m, 2H), 6.96 (s, 1H), 4.41 (q, J = 6.8 Hz, 1H), 4.13 (ddd, J = 6.2, 9.4, 13.7 Hz, 1H), 3.23-3.28 (m, 1H), 1.59-1.79 (m, 3H), 1.52 (d, J = 6.8 Hz, 3H), 1.00 (t, J = 5.9 Hz, 6H). MS (ES$^+$): m/z = 479.71 [MH$^+$]. UPLC: t$_R$ = 1.00 min (TOF: polar_2 min). |
| 90 | 3-[(7R)-2-[(4-fluoro-2-oxo-2,3-dihydro-1,3-benzoxazol-6-yl)amino]-7-methyl-8-(3-methylbutyl)-6-oxo-7,8-dihydropteridin-5(6H)-yl]benzonitrile | $^1$H NMR (400 MHz, CDCl$_3$) δ 0.96-1.04 (m, 6H), 1.56 (d, J = 6.82 Hz, 3H), 1.61-1.79 (m, 3H), 3.13-3.25 (m, 1H), 4.07-4.24 (m, 1H), 4.27-4.43 (m, 1H), 7.23 (d, J = 11.12 Hz, 1H), 7.50 (s, 1H), 7.55 (d, J = 8.08 Hz, 1H), 7.61 (s, 1H), 7.70 (t, J = 7.96 Hz, 1H), 7.75-7.83 (m, 1H), 9.05 (br. s., 1H). MS(ES$^+$): m/z = 502.20[MH$^+$]. HPLC: t$_R$ = 0.97 min (analytical_2 min, UPLC). |
| 91 | 5-[(7R)-2-[(7-fluoro-1H-indazol-5-yl)amino]-7-methyl-8-(3-methylbutyl)-6-oxo-7,8-dihydropteridin-5(6H)-yl]-2-methoxybenzonitrile | $^1$H NMR (CDCl$_3$, 300 MHz) δ: 0.98 (t, J = 6.3 Hz, 6H), 1.51 (d, J = 6.9 Hz, 3H), 1.62-1.71 (m, 3H), 3.12-3.15, (m, 1H), 3.97 (s, 3H), 4.12-4.19 (m, 1H), 4.31-4.38 (m, 1H), 7.10-7.13 (m, 2H), 7.36-7.50 (m, 4H), 7.74 (s, 1H), 8.01 (d, J = 3.0 Hz, 1H). MS(ES$^+$): m/z = 515.89 [MH$^+$]. HPLC: t$_R$ = 2.50 (ZQ3, Polar_5 min). |

| Ex. # | Chemical Name | Analytical data |
|---|---|---|
| 92 | 2-ethoxy-5-[(7R)-2-[(7-fluoro-1H-indazol-5-yl)amino]-7-methyl-8-(3-methylbutyl)-6-oxo-7,8-dihydropteridin-5(6H)-yl]benzonitrile | $^1$H NMR (CDCl$_3$, 300 MHz) δ: 0.98 (t, J = 6.6 Hz, 6H), 1.49-1.51 (m, 6H), 1.61-1.74 (m, 3H), 3.09-3.15 (m, 1H), 4.15-4.23 (m, 3H), 4.31-4.35 (m, 1H), 7.05-7.12 (m, 2H), 7.26-7.42 (m, 2H), 7.43-7.49 (m, 1H), 7.72(d, J = 1.5 Hz, 1H), 8.01 (d, J = 2.2 Hz, 1H). MS(ES$^+$): m/z = 529.88 [MH$^+$]. HPLC: t$_R$ = 2.65 (ZQ3, Polar_5 min). |
| 93 | 5-[(7R)-2-[(7-fluoro-1H-indazol-5-yl)amino]-7-methyl-8-(3-methylbutyl)-6-oxo-7,8-dihydropteridin-5(6H)-yl]-2-(propan-2-yloxy)benzonitrile | $^1$H NMR (CDCl$_3$, 300 MHz) δ: 0.98 (t, J = 6.3 Hz, 6H), 1.43-1.52 (m, 9H), 1.60-1.75 (m, 3H), 3.07-3.17, (m, 1H), 4.10-4.21 (m, 1H), 4.30-4.37 (m, 1H), 4.65-4.73 (m, 1H), 7.06-7.17 (m, 3H), 7.38-7.48 (m, 3H), 7.71 (d, J = 1.8 Hz, 1H), 8.01 (d, J = 2.2 Hz, 1H). MS(ES$^+$): m/z = 543.87 [MH$^+$]. HPLC: t$_R$ = 2.86 (ZQ3, Polar_5 min). |
| 94 | 7-methyl-2-[(2-oxo-2,3-dihydro-1H-indol-5-yl)amino]-5-phenyl-8-(propan-2-yl)-7,8-dihydropteridin-6(5H)-one | 1H NMR (CDCl$_3$, 300 MHz): δ 1.36-1.42 (m, 6H), 1.49 (d, J = 6.6 Hz, 3H), 3.50 (s, 2H), 4.45 (q, J = 6.9 Hz, 1H), 4.72-4.79 (m, 1H), 6.71 (d, J = 8.4 Hz, 1H), 7.11(s, 1H), 7.22-7.43 (m, 4H), 7.46-7.55(m, 4H), 9.26 (brs, 1H). MS(ES$^+$): m/z = 429.04 [MH$^+$]. HPLC: t$_R$ = 2.29 (ZQ3, Polar_5 min). |

Example 71 was prepared by following procedure:

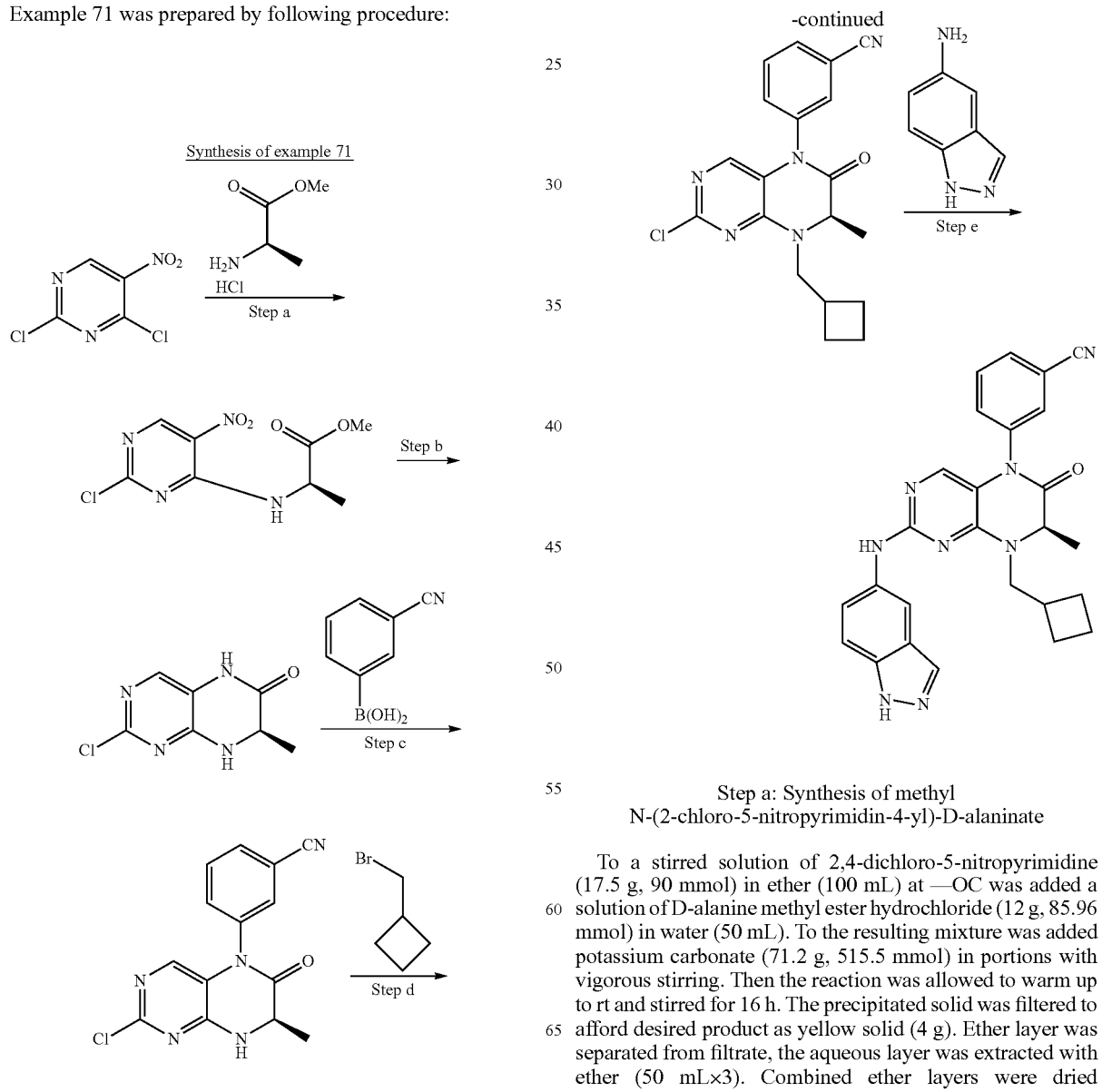

Step a: Synthesis of methyl N-(2-chloro-5-nitropyrimidin-4-yl)-D-alaninate

To a stirred solution of 2,4-dichloro-5-nitropyrimidine (17.5 g, 90 mmol) in ether (100 mL) at —0C was added a solution of D-alanine methyl ester hydrochloride (12 g, 85.96 mmol) in water (50 mL). To the resulting mixture was added potassium carbonate (71.2 g, 515.5 mmol) in portions with vigorous stirring. Then the reaction was allowed to warm up to rt and stirred for 16 h. The precipitated solid was filtered to afford desired product as yellow solid (4 g). Ether layer was separated from filtrate, the aqueous layer was extracted with ether (50 mL×3). Combined ether layers were dried (Na₂SO₄), evaporated to give a crude residue, which was then purified by silica gel flash chromatography to give another 2.7 g of desired product. ¹HNMR (300 MHz, CDCl₃): δ 1.61 (d, J=7.2 Hz, 3H), 3.82 (s, 3H), 4.90-5.0 (m, 1H), 8.75 (br s 1H) and 9.07 (s, 1H).

Step b: synthesis of (7R)-2-chloro-7-methyl-7,8-dihydropteridin-6(5H)-one

To a stirred solution of methyl N-(2-chloro-5-nitropyrimidin-4-yl)-D-alaninate (5 g, 19.2 mmol) in ethanol (400 mL) was added iron powder (7.14 g, 127 mmol). The resulted mixture was heated to reflux, followed by addition of 1M aqueous hydrochloric acid (15 ml) in small portions. The mixture was refluxed for 2 h. Then it was cooled to rt, the insoluble material was filtered off to give a clear solution. The solvent was evaporated to give a crude residue, which was then purified by silica gel flash chromatography (eluent: 5% methanol in dichloromethane) to give desired product (Yield: 81%). ¹HNMR (300 MHz, DMSO d₆): δ 1.34 (d, J=6.9 Hz, 3H), 4.22 (q, J=1.2 Hz, 1H), 7.50 (s, 1H), 8.45 (s, 1H) and 10.59 (s, 1H).

Step c: Synthesis of 3-[(7R)-2-chloro-7-methyl-6-oxo-7,8-dihydropteridin-5(6H)-yl]benzonitrile To a stirred solution of (7R)-2-chloro-7-methyl-7,8-dihydropteridin-6(5H)-one (4.2 g, 21.15 mmol) in dichloromethane (350 mL) was added triethylamine (29.61 ml, 211.5 mmol), cupric acetate (7.69 g, 42.30 mmol) and 3-cyanophenyl boronic acid (6.62 g, 42.30 mmol) followed by 4 Å molecular sieves (2.0 g). The reaction mixture was stirred for 24 h at rt with an air balloon on the top. The reaction mixture was then filtered over celite to give a clear solution. The solution was washed with aqueous saturated sodium bicarbonate (50 mL×2), dried over anhydrous sodium sulfate and evaporated to give a crude material, which was purified by silica gel column chromatography (eluent: 2% methanol in dichloromethane) to give the desired product (Yield: 39%). ¹HNMR (300 MHz, CDCl₃): δ 1.66 (d, J=6.9 Hz, 3H), 4.55 (q, J=5.1 Hz, 1H), 5.98 (br s 1H), 7.16 (s, 1H), 7.50-7.53 (m, 1H), 7.59-7.68 (m, 1H), 7.72 (t, J=7.8 Hz, 1H) and 7.81-7.83 (m, 1H).

Step d: Synthesis of 3-[(7R)-2-chloro-8-(cyclobutylmethyl)-7-methyl-6-oxo-7,8-dihydropteridin-5(6H)-yl]benzonitrile To a stirred solution of 3-[(7R)-2-chloro-7-methyl-6-oxo-7,8-dihydropteridin-5(6H)-yl]benzonitrile (120 mg, 0.4 mmol) in anhydrous DMF (3 ml) was added cyclobutyl methyl bromide (119 mg, 0.8 mmol) at 0° C. under nitrogen. To the resulting solution was added sodium hydride (32 mg of 60% dispersion in oil, 0.8 mmol) at 0° C. The reaction was then allowed to warm up to rt in 20 min and then heated at 50° C. for 3 h. The reaction mixture was diluted with water (20 ml) and extracted with ethyl acetate (30 mL×3). The organic layers were combined, dried (Na₂SO₄) and evaporated to give a crude residue, which was then purified by silica gel flash chromatography (eluent: 2% methanol in dichloromethane) to give desired product (Yield: 41%). ¹HNMR (300 MHz, CDCl₃) δ 1.50 (d, J=6.9 Hz, 3H), 1.78-1.94 (m, 4H), 1.96-2.21 (m, 2H), 2.68-2.87 (m, 1H), 3.17 (q, J=6.9 Hz, 1H), 4.22-4.36 (m, 2H), 7.10 (s, 1H), 7.50 (d, J=7.8 Hz, 1H), 7.58 (s, 1H), 7.66-7.78 (m, 1H) and 7.79-7.81 (m, 1H).

Step e: Synthesis of 3-[(7R)-8-(cyclobutylmethyl)-2-(1H-indazol-5-ylamino)-7-methyl-6-oxo-7,8-dihydropteridin-5(6H)-yl]benzonitrile Example 71

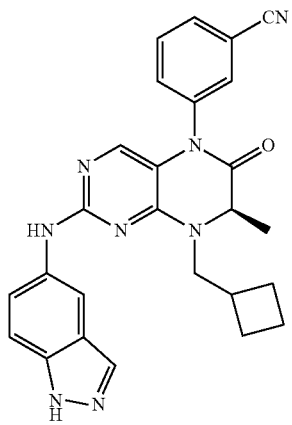 [SMILES: C[C@@H]1C(=O)N(c2cccc(C#N)c2)c2cnc(Nc3ccc4[nH]ncc4c3)nc2N1CC1CCC1]

To a solution of 3-[(7R)-2-chloro-8-(cyclobutylmethyl)-7-methyl-6-oxo-7,8-dihydropteridin-5(6H)-yl]benzonitrile (60 mg, 0.16 mmol) and 5-aminoindazole (22.3 mg, 0.17 mmol) in trifluoroethanol (2 mL) in a microwave reactor vial was added trifluoroacetic acid (55 mg). The vial was then sealed and heated in a microwave reactor at 125° C. for 35 minutes. The reaction mixture was then diluted with ethyl acetate (25 mL) and washed with aqueous saturated aq. sodium bicarbonate. The organic layer was dried (Na₂SO₄) and evaporated to give a crude residue, which was then purified by silica gel column chromatography (eluent: 2% methanol in dichloromethane) to give the desired product (Yield: 61%).

Examples 72-83 were synthesized according to procedures similar to the preparation of Example 71, using corresponding starting materials and intermediates. For example, for the synthesis of example 72, phenyl boronic acid was used in the step c of the synthesis, and (bromomethyl)cyclohexane was used in the step d of the synthesis.

Examples 84 were synthesized according to chemistry showed in the following scheme. The procedures for steps a, b, c, d for synthesis of example 84 are similar to that of steps b, c, d, e for the preparation of Example 18, respectively.

Synthesis of example 84

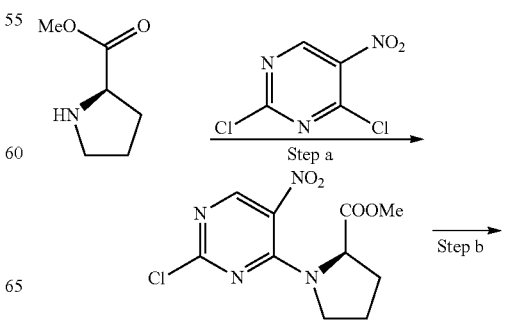

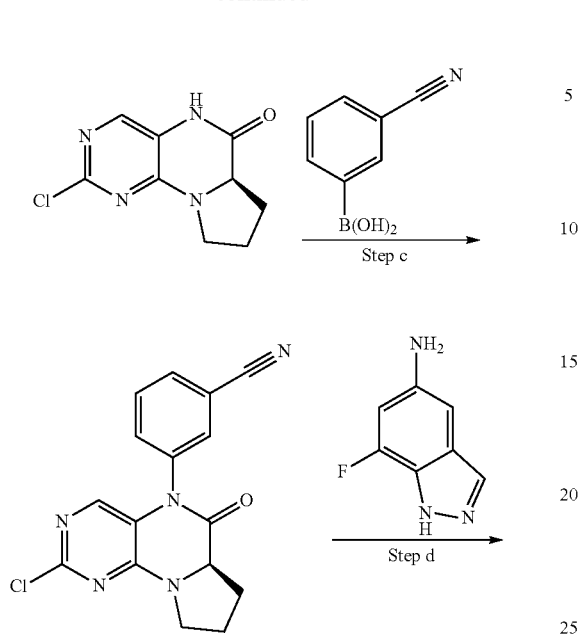
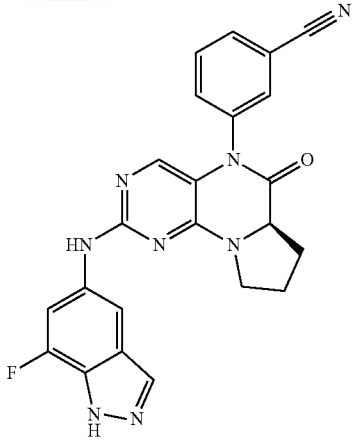

Examples 85-94 were synthesized according to procedures similar for the preparation of Example 1, using corresponding starting materials and intermediates. For example, for the synthesis of example 85, D-alanine methyl ester hydrochloride was used in the step a of the synthesis; (3,4-dimethoxyphenyl)boronic acid was used in the step d of the synthesis, and 7-fluoro-1H-indazol-5-amine was used in the step e of the synthesis.

| Ex. # | Chemical Name | Analytical data |
|---|---|---|
| 95 | (7R)-8-cyclohexyl-5-(3,5-difluorophenyl)-2-(1H-indazol-5-ylamino)-7-methyl-7,8-dihydropteridin-6(5H)-one | $^1$H NMR (CDCl$_3$, 300 MHz) δ 1.21-1.28 (m, 1H), 1.45-1.49 (m, 6H), 1.67-1.80 (m, 3H), 1.91-1.98 (m, 2H), 2.20-2.28 (m, 1H), 4.43-4.57 (m, 2H), 6.81-6.89 (m, 2H), 6.90-6.98 (m, 2H), 7.23-7.24 (m, 1H), 7.37-7.45 (m, 2H), 8.00 (s, 1H), 8.16 (s, 1H), 9.99 (br s, 1H). MS(ES$^+$): m/z = 490.13 [MH$^+$]. HPLC: t$_R$ = 2.66 (ZQ3, Polar__5 min). |
| 96 | 5-[(7R)-8-cyclohexyl-2-(1H-indazol-5-ylamino)-7-methyl-6-oxo-7,8-dihydropteridin-5(6H)-yl]-2-fluorobenzonitrile | $^1$H NMR (CDCl$_3$, 300 MHz) δ 1.18-1.24 (m, 1H), 1.46-1.52 (m, 6H), 1.63-1.81 (m, 3H), 1.92-1.96 (m, 2H), 2.20-2.29 (m, 1H), 4.39-4.49 (m, 2H), 7.08 (s, 1H), 7.16 (s, 1H), 7.34-7.45 (m, 3H), 7.49-7.54 (m, 1H), 7.56-7.59 (m, 1H), 8.01 (s, 1H), 8.15 (s, 1H). MS(ES$^+$): m/z = 497.12 [MH$^+$]. HPLC: t$_R$ = 2.61 (ZQ3, Polar__5 min). |
| 97 | 3-[(7R)-2-[(7-chloro-1H-indazol-5-yl)amino]-8-cyclohexyl-7-methyl-6-oxo-7,8-dihydropteridin-5(6H)-yl]benzonitrile | $^1$H NMR (CDCl$_3$, 300 MHz) δ: 0.85-0.87 (m, 1H), 1.39-1.49 (m, 6H), 1.63-1.85 (m, 3H), 1.91-1.95 (m, 2H), 2.19-2.23 (m, 1H), 4.43-4.50 (m, 2H), 7.16 (s, 1H), 7.30 (s, 1H), 7.50-7.53 (m, 1H), 7.59-7.66 (m, 3H), 7.72-7.75 (m, 1H), 7.88 (s, 1H), 8.04 (s, 1H), 10.79 (brs, 1H). MS(ES$^+$): m/z = 513.12 [MH$^+$]. HPLC: t$_R$ = 2.79 (ZQ3, Polar__5 min). |
| 98 | (7R)-8-cyclohexyl-2-(1H-indazol-5-ylamino)-7-methyl-5-[6-(methylsulfanyl)pyridin-3-yl]-7,8-dihydropteridin-6(5H)-one | $^1$H NMR (CDCl$_3$, 300 MHz) δ 1.19-1.24 (m, 1H), 1.47-1.53 (m, 6H), 1.67-1.83 (m, 3H), 1.89-1.96 (m, 2H), 2.22-2.30 (m, 1H), 2.59 (s, 3H), 4.43-4.47 (m, 2H), 7.07 (s, 1H), 7.21 (s, 1H), 7.31 (dd, J = 0.6, 8.4 Hz, 1H), 7.36 (d, J = 2.4 Hz, 1H), 7.39-7.41 (m, 2H), 8.01 (s, 1H), 8.16 (s, 1H), 8.33 (s, 1H), 10.03 (br s, 1H); MS(ES$^+$): m/z = 501.10 [MH$^+$]. |
| 99 | (7R)-8-cyclohexyl-5-(3-fluoro-5-methoxyphenyl)-2-(1H-indazol-5-ylamino)-7-methyl-7,8-dihydropteridin-6(5H)-one | $^1$H NMR (CDCl$_3$, 300 MHz) δ: 1.13-1.27 (m, 1H), 1.46-1.52 (m, 6H), 1.64-1.87 (m, 3H), 1.91-2.01 (m, 2H), 2.21-2.29 (m, 1H), 3.80 (s, 3H), 4.41-4.46 (m, 2H), 6.56-6.59 (m, 2H), 6.68-6.73 (m, 1H), 7.11 (s 1H), 7.21 (s 1H), 7.37-7.45 (m, 2H), 8.01 (s, 1H), 8.16 (s, 1H), 10.10 (br s, 1H); MS(ES$^+$): m/z = 502.40 [MH$^+$]. |
| 100 | 3-[(7R)-8-cyclohexyl-2-[(4-fluoro-1H-indazol-5-yl)amino]-7-methyl-6-oxo-7,8-dihydropteridin-5(6H)-yl]benzonitrile | $^1$H NMR (CDCl$_3$, 400 MHz): δ 1.16 (m, 1 H), 1.30-1.48 (m, 2 H), 1.49 (d, J = 6.8 Hz, 3 H), 1.64-1.74 (m, 2 H), 1.80-1.93 (m, 4 H), 2.16 (d, J = 11.2 Hz, 1 H), 4.32 (m, 1 H), 4.45 (q, J = 6.8 Hz, 1 H), 6.96 (s, br, 1 H), 7.12 (s, 1 H), 7.25 (d, J = 8.8 Hz, 1 H), 7.52 (m, 1 H), 7.59 (m, 1 H), 7.65 (t, J = 8.0 Hz, 1 |

-continued

| Ex. # | Chemical Name | Analytical data |
|---|---|---|
| | | H), 7.74 (dt, J = 1.2, 7.6 Hz, 1 H), 8.09 (dd, J = 7.6, 9.1 Hz, 1 H), 8.13 (d, J = 1.2 Hz, 1 H), 10.22 (s, br, 1 H). MS (ES⁺): m/z = 497.19 [MH⁺]. HPLC: t_R = 1.14 min (TOF, polar__3 min). |
| 101 | 3-[(7R)-2-[(4-chloro-1H-indazol-5-yl)amino]-8-cyclohexyl-7-methyl-6-oxo-7,8-dihydropteridin-5(6H)-yl]benzonitrile | ¹H NMR (CDCl₃, 400 MHz): δ 1.19 (m, 1 H), 1.34-1.49 (m, 3 H), 1.51 (d, J = 6.8 Hz, 3 H), 1.66 (m, 1 H), 1.72-1.81 (m, 2 H), 1.89-1.93 (m, 1 H), 2.12 (d, J = 11.6 Hz, 1 H), 4.34 (m, 1 H), 4.47 (q, J = 6.8 Hz, 1 H), 7.05 (d, J = 7.6 Hz, 1 H), 7.10 (s, br, 1 H), 7.14 (s, 1 H), 7.35 (m, 1 H), 7.51 (d, J = 8.0 Hz, 1 H), 7.59 (m, 1 H), 7.66 (t, J = 8.4 Hz, 1 H), 7.76 (dt, J = 1.2, 8.0 Hz, 1 H), 8.11 (s, 1 H), 12.40 (s, br, 1 H). MS (ES⁺): m/z = 513.16 [MH⁺, ³⁵Cl], 515.18 [MH⁺, ³⁷Cl]. HPLC: t_R = 1.52 min (TOF, polar__3 min). |
| 102 | 3-[(7R)-8-cyclohexyl-2-[(4-methoxy-1H-indazol-5-yl)amino]-7-methyl-6-oxo-7,8-dihydropteridin-5(6H)-yl]benzonitrile | ¹H NMR (DMSO-d₆, 400 MHz): δ 1.06 (m, 1 H), 1.18-1.30 (m, 2 H), 1.36 (d, J = 6.4 Hz, 3 H), 1.54-1.58 (m, 2 H), 1.64 (m, 1 H), 1.72-1.81 (m, 3 H), 1.94 (d, J = 11.6 Hz, 1 H), 4.11 (m, 1 H), 4.12 (s, 3 H), 4.39 (q, J = 6.8 Hz, 1 H), 6.96 (s, 1 H), 7.09 (d, J = 8.8 Hz, 1 H), 7.69 (d, J = 8.0 Hz, 1 H), 7.73-7.77 (m, 3 H), 7.84 (s, 1 H), 7.94-7.96 (m, 2 H), 8.25 (s, 1 H). MS (ES⁺): m/z = 509.20 [MH⁺]. HPLC: t_R = 1.08 min (TOF, polar__3 min). |
| 103 | 3-[(7R)-8-cyclohexyl-7-methyl-2-[(3-methyl-1H-indazol-5-yl)amino]-6-oxo-7,8-dihydropteridin-5(6H)-yl]benzonitrile | ¹H NMR (CDCl₃, 300 MHz) δ 1.12-1.19 (m, 1H), 1.42-1.48 (m, 6H), 1.65-1.70 (m, 3H), 1.79-1.89 (m, 2H), 2.13-2.16 (m, 1H), 2.57 (s, 3H), 4.41-4.47 (m, 2H), 6.88-6.95 (m, 1H), 7.15 (s, 1H), 7.34-7.37 (m, 1H), 7.45-7.53 (m, 2H), 7.59-7.66 (m, 2H), 7.72-7.74 (m, 1H), 7.86 (s, 1H), 9.77 (br. s, 1H). MS(ES⁺): m/z = 493.22 (100) [MH⁺]. HPLC: t_R = 2.51 (ZQ3, Polar__5 min). |
| 104 | 5-[(7R)-8-cyclohexyl-2-(1H-indazol-5-ylamino)-7-methyl-6-oxo-7,8-dihydropteridin-5(6H)-yl]-2-methoxybenzonitrile | ¹H NMR (CDCl₃, 300 MHz) δ 1.14-1.23 (m, 1H), 1.45-1.52 (m, 6H), 1.67-1.80 (m, 3H), 1.93-1.95 (m, 2H), 2.22-2.24 (m, 1H), 3.99 (s, 3H), 4.41-4.48 (m, 2H), 6.93 (s, 1H), 7.09 (d, J = 9.3 Hz, 1H), 7.16 (s, 1H), 7.40-7.47 (m, 4H), 8.00 (s, 1H), 8.15 (s, 1H), 10.01 (br. s, 1H). MS(ES⁺): m/z = 509.34 [MH⁺]. HPLC: t_R = 2.52 (ZQ3, Polar__5 min). [α]_D = −44.66 (C = 1.5 in CH₂Cl₂) |
| 105 | 2-chloro-5-[(7R)-8-cyclohexyl-2-(1H-indazol-5-ylamino)-7-methyl-6-oxo-7,8-dihydropteridin-5(6H)-yl]benzonitrile | ¹H NMR (CDCl₃, 300 MHz) δ 1.18-1.23 (m, 1H), 1.41-1.52 (m, 6H), 1.63-1.85 (m, 3H), 1.89-2.00 (m, 2H), 2.20-2.28 (m, 1H), 4.39-4.49 (m, 2H), 7.07 (s, 1H), 7.19 (s, 1H), 7.36-7.47 (m, 3H), 7.61 (d, J = 2.1 Hz, 1 H), 7.65 (d, J = 8.4 Hz, 1H), 8.00 (s, 1H), 8.16 (s, 1H), 10.20 (br s, 1H). MS(ES⁺): m/z = 513.25, 515.20 [MH⁺]. HPLC: t_R = 2.79 (ZQ3, Polar__5 min). [α]_D = −34.28 (C = 0.7 in CH₂Cl₂). |
| 106 | 3-[(7R)-8-cyclohexyl-2-[(7-fluoro-1H-indazol-5-yl)amino]-7-methyl-6-oxo-7,8-dihydropteridin-5(6H)-yl]benzonitrile | ¹H NMR (CDCl₃, 400 MHz): δ 1.22 (m, 1 H), 1.43-1.53 (m, 2 H), 1.52 (d, J = 6.4 Hz, 3 H), 1.67-1.87 (m, 4 H), 1.94-1.96 (m, 2 H), 2.22 (d, J = 11.2 Hz, 1 H), 4.44 (m, 1 H), 4.49 (q, J = 6.4 Hz, 1 H), 7.10 (s, 1 H), 7.46 (dd, J = 1.6, 12.4 Hz, 1 H), 7.52 (d, J = 8.0 Hz, 1 H), 7.59 (m, 1 H), 7.67 (t, J = 8.0 Hz, 1 H), 7.72 (d, J = 2.0 Hz, 1 H), 7.77 (dt, J = 1.2, 7.6 Hz, 1 H), 8.04 (d, J = 3.2 Hz, 1 H). MS (ES⁺): m/z = 497.59 [MH⁺]. HPLC: t_R = 0.93 min (TOF, polar__2 min). |
| 107 | 3-[(7R)-8-cyclohexyl-2-[(7-fluoro-1H-indazol-4-yl)amino]-7-methyl-6-oxo-7,8-dihydropteridin-5(6H)-yl]benzonitrile | ¹H NMR (CDCl₃, 400 MHz): δ 1.25 (m, 1 H), 1.46-1.53 (m, 3 H), 1.53 (d, J = 6.8 Hz, 3 H), 1.71 (m, 1 H), 1.81 (m, 1 H), 1.90 (m, 1 H), 1.97-2.00 (m, 2 H), 2.23 (d, J = 11.2 Hz, 1 H), 4.49-4.56 (m, 2 H), 7.02 (dd, J = 8.8, 10.4 Hz, 1 H), 7.58 (d, J = 7.6 Hz, 1 H), 7.67 (s, 1 H), 7.70 (t, J = 8.4 Hz, 1 H), 7.80 (dt, J = 1.2, 7.6 Hz, 1 H), 8.03 (dd, J = 3.2, 8.4 Hz, 1 H), 9.00 (d, J = 2.8 Hz, 1 H), 9.39 (s, 1 H). MS (ES⁺): m/z = 497.58 [MH⁺]. HPLC: t_R = 0.97 min (TOF, polar__2 min). |
| 108 | 3-[(7R)-2-[(3-chloro-1H-indazol-5-yl)amino]-8-cyclohexyl-7-methyl-6-oxo-7,8-dihydropteridin-5(6H)-yl]benzonitrile | ¹H NMR (CDCl₃, 400 MHz): δ 1.20 (m, 1 H), 1.46-1.57 (m, 3 H), 1.49 (d, J = 7.2 Hz, 3 H), 1.83-1.93 (m, 3 H), 2.17 (d, J = 6.4 Hz, 1 H), 4.48 (q, J = 7.2 Hz, 1 H), 4.54 (m, 1 H), 7.18 (s, 1 H), 7.38 (d, J = 8.8 Hz, 1 H), 7.43 (dd, J = 2.4, 9.1 Hz, 1 H), 7.47 (s, br, 1 H), 7.53 (d, J = 8.4 Hz, 1 H), 7.61 (s, 1 H), 7.64 (t, J = 8.0 Hz, 1 H), 7.30 (dt, J = 1.6, 8.0 Hz, 1 H), 8.08 (d, J = 1.2 Hz, 1 H), 10.85 (s, br, 1 H). |

| Ex. # | Chemical Name | Analytical data |
|---|---|---|
| 109 | 3-[(7R)-2-(1,2-benzothiazol-5-ylamino)-8-cyclohexyl-7-methyl-6-oxo-7,8-dihydropteridin-5(6H)-yl]benzonitrile | MS (ES$^+$): m/z = 513.57 [MH$^+$, $^{35}$Cl], 515.55 [MH$^+$, $^{35}$Cl]. HPLC: t$_R$ = 1.00 min (TOF, polar_2 min). $^1$H NMR (CDCl$_3$, 300 MHz) δ 1.25-1.26 (m, 1H), 1.48-1.52 (m, 6H), 1.69-1.83 (m, 3H), 1.97-1.99 (m, 2H), 2.25-2.27 (m, 1H), 4.44-4.51 (m, 2H), 7.05 (brs, 1H), 7.18(s, 1H), 7.51-7.54 (m, 2H), 7.59 (s, 1H), 7.65 (t, J = 7.8 Hz, 1H), 7.74-7.76 (m, 1H), 7.85 (d, J = 8.7 Hz, 1H), 8.56 (s, 1H), 8.83 (s, 1H). MS(ES$^+$): m/z = 496.12 [MH$^+$]. HPLC: t$_R$ = 3.45 (ZQ3, Polar_5 min). [α]$_D$ = −47.5 (C = 0.8 in CH$_2$Cl$_2$). |
| 110 | (7R)-8-cyclohexyl-2-(1H-indazol-5-ylamino)-5-[3-(methoxymethyl)phenyl]-7-methyl-7,8-dihydropteridin-6(5H)-one | $^1$H NMR (CDCl$_3$, 300 MHz) δ 1.23-1.24 (m, 1H), 1.47-1.53 (m, 6H), 1.68-1.83 (m, 3H), 1.94-1.96 (m, 2H), 2.24-2.25(m, 1H), 3.40 (s, 3H), 4.44-4.46 (m, 2H), 4.50 (s, 2H), 6.92 (s, 1H), 7.14-7.18 (m, 2H), 7.22 (s, 1H), 7.38-7.41 (m, 3H), 7.50 (t, J = 7.5 Hz, 1H), 7.99 (s, 1H), 8.17 (s, 1H), 10.04 (brs, 1H). MS(ES$^+$): m/z = 498.60 [MH$^+$]. HPLC: t$_R$ = 2.51 (ZQ3, Polar_5 min). [α]$_D$ = −32.22 (C = 0.9 in CH$_2$Cl$_2$). |
| 111 | (7R)-8-cyclohexyl-5-(3,4-dimethoxyphenyl)-2-(1H-indazol-5-ylamino)-7-methyl-7,8-dihydropteridin-6(5H)-one | $^1$H NMR (CDCl$_3$, 300 MHz) δ 1.19-1.25 (m, 1H), 1.47-1.53 (m, 6H), 1.74-1.88 (m, 3H), 1.90-1.98 (m, 2H), 2.40-2.59 (m, 1H), 3.86 (s, 3H), 3.92 (s, 3H), 4.43-4.49 (m, 2H), 6.67 (s, 1H), 6.79-6.82 (m, 1H), 6.96-7.03 (m, 2H), 7.17 (s, 1H), 7.36-7.43 (m, 2H), 7.99 (s, 1H), 8.17 (s, 1H), 10.10 (br s, 1H). MS(ES$^+$); m/z = 514.19 [MH$^+$]. HPLC: t$_R$ = 2.41 (ZQ3, Polar_5 min). |
| 112 | 3-[(7R)-8-cyclohexyl-2-(1H-indazol-5-ylamino)-7-methyl-6-oxo-7,8-dihydropteridin-5(6H)-yl]-5-fluorobenzonitrile | $^1$H NMR (CDCl$_3$, 300 MHz) δ 1.19-1.23(m, 1H), 1.45-1.52 (m, 6H), 1.66-1.80 (m, 3H), 1.92-1.96 (m, 2H), 2.22-2.24 (m, 1H), 4.42-4.49 (m, 2H), 7.04 (brs, 1H), 7.21 (s, 1H), 7.28-7.32 (m, 1H), 7.37-7.45 (m, 4H), 8.01 (s, 1H), 8.15 (s, 1H), 10.15(brs, 1H). MS(ES$^+$): m/z = 496.75 [MH$^+$]. HPLC: t$_R$ = 2.68 (ZQ3, Polar_5 min). [α]$_D$ = −44.0 (C = 2.0 in CH$_2$Cl$_2$) |
| 113 | (7R)-8-cyclohexyl-2-(1H-indazol-5-ylamino)-7-methyl-5-(6-methylpyridin-3-yl)-7,8-dihydropteridin-6(5H)-one | $^1$H NMR (CDCl$_3$, 300 MHz) δ 1.22-1.24 (m, 1H), 1.47-1.53 (m, 6H), 1.69-1.84 (m, 3H), 1.94-1.96 (m, 2H), 2.25-2.27 (m, 1H), 2.64 (s, 3H), 4.41-4.49 (m, 2H), 7.00 (brs, 1H), 7.17 (s, 1H), 7.30-7.33 (m, 1H), 7.37-7.44 (m, 2H), 7.47-7.50 (m, 1H), 8.00 (s, 1H), 8.16 (s, 1H), 8.39 (d, J = 2.4 Hz, 1H). MS(ES$^+$): m/z = 469.10 [MH$^+$]. HPLC: t$_R$ = 2.30 (ZQ3, Polar_5 min). [α]$_D$ = −23.33 (C = 0.6 in CH$_2$Cl$_2$) |
| 114 | (7R)-8-cyclohexyl-2-(1H-indazol-5-ylamino)-7-methyl-5-[3-(methylsulfinyl)phenyl]-7,8-dihydropteridin-6(5H)-one | 1H NMR (CDCl$_3$, 300 MHz) δ 0.81-0.84 (m, 1H), 1.47-1.52 (m, 6H), 1.67-1.83 (m, 3H), 1.88-1.99 (m, 2H), 2.20-2.26 (m, 2H), 2.78(s, 3H), 4.45-4.47 (m, 2H), 7.12 (s, 1H), 7.30-7.41 (m, 3H), 7.60-7.66 (m, 3H), 7.60-7.66 (m, 3H), 8.00 (s, 1H), 8.15 (s, 1H). MS(ES$^+$): m/z = 516.67 [MH$^+$]. HPLC: t$_R$ = 2.50 (ZQ3, Polar_5 min). |
| 115 | 3-[(7R)-8-cyclohexyl-2-[(3-fluoro-1H-indazol-5-yl)amino]-7-methyl-6-oxo-7,8-dihydropteridin-5(6H)-yl]benzonitrile | $^1$H NMR (CDCl$_3$, 400 MHz): δ 1.22 (m, 1 H), 1.45-1.55 (m, 3 H), 1.49 (d, J = 6.8 Hz, 3 H), 1.69 (m, 1 H), 1.74-1.86 (m, 2 H), 1.92-1.95 (m, 2 H), 2.21 (m, 1 H), 4.51 (m, 1 H), 4.48 (q, J = 6.8 Hz, 1 H), 7.16 (m, 1 H), 7.19 (s, br, 1 H), 7.30 (d, J = 1.6, 8.8 Hz, 1 H), 7.36 (dd, J = 2.0, 8.8 Hz, 1 H), 7.53 (d, J = 8.0 Hz, 1 H), 7.60 (m, 1 H), 7.66 (t, J = 8.0 Hz, 1 H), 7.75 (dt, J = 1.6, 7.6 Hz, 1 H), 8.18 (s, 1 H), 9.30 (s, br, 1 H). MS (ES$^+$): m/z = 497.56 [MH$^+$]. HPLC: t$_R$ = 0.96 min (TOF, polar_2 min). |
| 116 | 3-[(7R)-8-cyclohexyl-2-[(3-methoxy-1H-indazol-5-yl)amino]-7-methyl-6-oxo-7,8-dihydropteridin-5(6H)-yl]benzonitrile | $^1$H NMR (CDCl$_3$, 400 MHz): δ 1.21 (m, 1 H), 1.42-1.59 (m, 3 H), 1.47 (d, J = 6.8 Hz, 3 H), 1.60-1.72 (m, 2 H), 1.75-1.92 (m, 3 H), 2.17 (m, 1 H), 4.09 (s, 3 H), 4.47 (q, J = 6.8 Hz, 1 H), 4.53 (m, 1 H), 7.15 (s, 1 H), 7.17 (d, J = 8.8 Hz, 1 H), 7.26 (dd, J = 1.2, 8.8 Hz, 1 H), 7.51 (d, J = 8.0 Hz, 1 H), 7.56-7.62 (m, 3 H), 7.70 (dt, J = 1.6, 7.6 Hz, 1 H), 8.14 (s, 1 H), 9.48 (m, 1 H). MS (ES$^+$)\ m/z = 509.53 [MH$^+$]. HPLC: t$_R$ = 0.96 min (TOF, polar_2 min). |
| 117 | 3-[(7R)-8-cyclohexyl-7-methyl-2-[(4-methyl-1H-indazol-5-yl)amino]-6-oxo-7,8-dihydropteridin-5(6H)-yl]benzonitrile | $^1$H NMR (CDCl$_3$, 400 MHz): δ 1.08 (m, 1 H), 1.19-1.46 (m, 3 H), 1.48 (d, J = 6.8 Hz, 3 H), 1.61-1.71 (m, 2 H), 1.76-1.87 (m, 3 H), 2.07 (d, J = 11.6 Hz, 1 H), 2.54 (s, 3 H), 4.23 (m, 1 H), 4.40 (q, J = 6.8 Hz, 1 H), 6.72 (s, br, 1 H), 7.09 (s, 1 H), 7.26 (d, J = 8.8 Hz, 1 H), 7.51 (dq, J = 1.2, 8.0 Hz, 1 H), |

| Ex. # | Chemical Name | Analytical data |
|---|---|---|
| | | 7.59 (t, J = 2.0 Hz, 1 H), 7.60-7.64 (m, 2 H), 7.71 (dt, J = 1.2, 7.2 Hz, 1 H), 8.06 (d, J = 0.8 Hz, 1 H), 10.65 (s, br, 1 H). MS (ES$^+$): m/z = 493.56 [MH$^+$]. HPLC: t$_R$ = 0.89 min (TOF, polar__2 min). |
| 118 | 3-[(7R)-2-[(6-chloro-1H-indazol-5-yl)amino]-8-cyclohexyl-7-methyl-6-oxo-7,8-dihydropteridin-5(6H)-yl]benzonitrile | $^1$H NMR (CDCl$_3$, 400 MHz): δ 1.23 (m, 1 H), 1.43-1.54 (m, 2 H), 1.51 (d, J = 6.8 Hz, 3 H), 1.56-1.88 (m, 4 H), 1.95-2.03 (m, 2 H), 2.22 (m, 1 H), 4.44 (m, 1 H), 4.45 (q, J = 6.8 Hz, 1 H), 7.21 (s, br, 1 H), 7.35 (s, 1 H), 7.54 (d, J = 8.4 Hz, 1 H), 7.59-7.62 (m, 2 H), 7.66 (t, J = 7.6 Hz, 1 H), 7.76 (dt, J = 1.2, 8.0 Hz, 1 H), 8.01 (d, J = 0.8 Hz, 1 H), 8.75 (s, 1 H), 10.21 (s, br, 1 H). MS (ES$^+$): m/z = 513.51 [MH$^+$, $^{35}$Cl], 515.48 [MH$^+$, $^{37}$Cl]. HPLC: t$_R$ = 0.96 min (TOF, polar__2 min). |
| 119 | 3-[(7R)-8-cyclohexyl-2-[(6-methoxy-1H-indazol-5-yl)amino]-7-methyl-6-oxo-7,8-dihydropteridin-5(6H)-yl]benzonitrile | $^1$H NMR (CDCl$_3$, 400 MHz): δ 1.27 (m, 1 H), 1.50 (d, J = 6.8 Hz, 3 H), 1.53-1.64 (m, 3 H), 1.73 (m, 1 H), 1.82-1.90 (m, 2 H), 1.97-2.04 (m, 2 H), 2.33 (d, J = 11.2 Hz, 1 H), 3.96 (s, 3 H), 4.50 (q, J = 6.8 Hz, 1 H), 4.55 (m, 1 H), 6.91 (s, br, 1 H), 7.21 (s, 1 H), 7.54 (d, J = 8.0 Hz, 1 H), 7.60-7.62 (m, 2 H), 7.65 (t, J = 8.4 Hz, 1 H), 7.74 (dt, J = 1.2, 7.6 Hz, 1 H), 7.95 (s, 1 H), 8.74 (s, 1 H). MS (ES$^+$): m/z = 509.55 [MH$^+$]. HPLC: t$_R$ = 0.92 min (TOF, polar__2 min). |
| 120 | (7R)-8-cyclohexyl-2-[(4-fluoro-1H-indazol-5-yl)amino]-5-(3-fluorophenyl)-7-methyl-7,8-dihydropteridin-6(5H)-one | $^1$H NMR (CDCl$_3$, 300 MHz) δ 1.17-1.24 (m, 1H), 1.41-1.47 (m, 6H), 1.62-1.78 (m, 3H), 1.82-1.95 (m, 2H), 2.14-2.17 (m, 1 H), 4.29-4.46 (m, 2H), 6.86 (s, 1H), 6.97-7.00 (m, 1H), 7.04 (d, J = 7.8 Hz, 1H), 7.12-7.17 (m, 2H), 7.22 (d, J = 9 Hz, 1H), 7.44-7.52 (m, 1H), 8.10-8.16 (m, 2H), 10.23 (br s, 1H). MS(ES$^+$): m/z = 490.13 [MH$^+$]. HPLC: t$_R$ = 2.65 (ZQ3, Polar__5 min). |
| 121 | (7R)-8-cyclohexyl-5-(3-fluoro-4-methylphenyl)-2-(1H-indazol-5-ylamino)-7-methyl-7,8-dihydropteridin-6(5H)-one | $^1$H NMR (CDCl$_3$, 300 MHz) δ: 1.19-1.23 (m, 1H), 1.45-1.53 (m, 6H), 1.71-1.88 (m, 3H), 1.90-1.99 (m, 2H), 2.20-2.39 (m, 1 H), 2.32 (s, 3H), 4.41-4.48 (m, 2H), 6.92-6.95 (m, 2H), 7.01 (s, 1H), 7.19 (s, 1H), 7.29-7.35 (m, 1H), 7.39-7.43 (m, 2H), 8.00 (s, 1H), 8.17 (s, 1H), 10.19 (br s, 1H), MS(ES$^+$): m/z = 486.35 [MH$^+$]. HPLC: t$_R$ = 2.75 (ZQ3, Polar__5 min). [α]$_D$ = −26.6(C = 0.6 in CH$_2$Cl$_2$) |
| 122 | (7R)-8-cyclohexyl-2-[(4-fluoro-1H-indazol-5-yl)amino]-7-methyl-5-(pyridin-3-yl)-7,8-dihydropteridin-6(5H)-one | $^1$H NMR (CDCl$_3$, 300 MHz) δ 0.80-0.90 (m, 1H), 1.40-1.49 (m, 6H), 1.58-1.70 (m, 3H), 1.81-1.88 (m, 2H), 2.11-2.14 (m, 1 H), 4.27-4.33 (m, 1H), 4.40-4.45 (m, 1H), 6.91 (s, 1H), 7.11 (s, 1H), 7.19-7.21 (d, J = 6.6 Hz, 1H), 7.42-7.45 (m, 1H), 7.58 (d, J = 6 Hz, 1H), 8.05-8.09 (m, 2H), 8.51 (s, 1H), 8.66 (d, J = 3.3 Hz, 1H). MS(ES$^+$): m/z = 473.32 [MH$^+$]. HPLC: t$_R$ = 2.22 (ZQ3, Polar__5 min). |
| 123 | 3-[(7R)-8-cyclohexyl-2-[(7-methoxy-1H-indazol-5-yl)amino]-7-methyl-6-oxo-7,8-dihydropteridin-5(6H)-yl]benzonitrile | $^1$H NMR (CDCl$_3$, 400 MHz): δ 1.24 (m, 1 H), 1.52 (d, J = 6.8 Hz, 3 H), 1.42-1.61 (m, 2 H), 1.61-1.86 (m, 4 H), 1.93-2.00 (m, 2 H), 2.23 (d, J = 9.2 Hz, 1 H), 3.97 (s, 3 H), 4.42 (m, 1 H), 4.45 (q, J = 6.8 Hz, 1 H), 6.74 (d, J = 1.6 Hz, 1 H), 7.07 (s, 1 H), 7.16 (s, 1 H), 7.53 (dd, J = 1.2, 8.0 Hz, 1 H), 7.61 (d, J = 1.6 Hz, 1 H), 7.65 (t, J = 8.0 Hz, 1 H), 7.74 (dt, J = 1.2, 7.6 Hz, 1 H), 7.76 (d, J = 1.6 Hz, 1 H), 7.96 (s, 1 H), 10.48 (s, br, 1 H). MS (ES$^+$): m/z = 509.48 [MH$^+$]. HPLC: t$_R$ = 0.90 min (TOF, polar__2 min). |
| 124 | 4-[(7R)-8-cyclohexyl-2-(1H-indazol-5-ylamino)-7-methyl-6-oxo-7,8-dihydropteridin-5(6H)-yl]thiophene-2-carboxylic acid | $^1$H NMR (DMSO-d$_6$, 300 MHz) δ 0.98-1.08 (m, 1H), 1.15-1.40 (m, 2H), 1.45-1.59 (m, 5H), 1.61-1.82 (m, 4H), 1.90-2.00 (m, 1H), 4.10-4.21 (m, 1H), 4.52-4.62 (m, 1H), 7.07 (s, 1H), 7.19-7.24 (m, 1H), 7.33-7.42 (m, 1H), 7.54-7.58 (m, 1H), 7.73 (s, 1H), 7.95-8.05 (s, 3H), 10.43 (br s, 1H). MS(ES$^+$): 504.19 [MH$^+$]. HPLC: t$_R$ = 2.41 (ZQ3, Polar__5 min). |
| 125 | (7R)-8-cyclohexyl-2-(1H-indazol-5-ylamino)-5-(3-methoxy-4-methylphenyl)-7-methyl-7,8-dihydropteridin-6(5H)-one | $^1$H NMR (CDCl$_3$, 300 MHz) δ 1.21-1.27 (m, 1H), 1.45-1.53 (m, 6H), 1.68-1.83 (m, 3H), 1.91-1.98 (m, 2H), 2.24 (m, 4H), 3.80 (s, 3H), 4.41-4.50 (m, 2H), 6.61 (s, 1H), 6.73 (d, J = 6.9 Hz, 1H), 6.99 (s, 1H), 7.19 (s, 1H), 7.24-7.25 (m, 1H), 7.35-7.45 (m, 2H), 7.99 (s, 1H), 8.18 (s, 1H), 10.19 (br s, 1H). MS(ES$^+$): m/z = 498.01 [MH$^+$]. HPLC: t$_R$ = 2.64 (ZQ3, Polar__5 min). |

| Ex. # | Chemical Name | Analytical data |
|---|---|---|
| 126 | (7R)-8-cyclohexyl-2-(1H-indazol-5-ylamino)-7-methyl-5-[4-(morpholin-4-yl)phenyl]-7,8-dihydropteridin-6(5H)-one | $^1$H NMR (CDCl$_3$, 300 MHz) δ 1.20-1.22 (m, 1H), 1.46-1.57 (m, 6H), 1.73-1.96 (m, 5H), 2.24 (br s, 1H), 3.57 (t, J = 4.2 Hz, 4H), 3.84 (t, J = 4.2 Hz, 4H), 4.42-4.49 (m, 2H), 6.73 (d, J = 9.6 Hz, 1H), 6.90 (d, J = 2.4 Hz, 1H), 7.27-7.42 (m, 3H), 7.99 (s, 1H), 8.05 (d, J = 2.4 Hz, 1H), 8.18 (s, 1H). MS(ES$^+$): m/z = 540.84[MH$^+$]. HPLC: t$_R$ = 2.40 (Polar_5 min, ZQ3). |
| 127 | (7R)-8-cyclohexyl-5-[3-(hydroxymethyl)phenyl]-2-(1H-indazol-5-ylamino)-7-methyl-7,8-dihydropteridin-6(5H)-one | MS(ES$^+$): m/z = 485.00 [MH$^+$]. HPLC: t$_R$ = 2.25 (ZQ3, Polar_5 min). |
| 128 | 5-[(7R)-8-cyclohexyl-2-(1H-indazol-5-ylamino)-7-methyl-6-oxo-7,8-dihydropteridin-5(6H)-yl]pyridine-3-carbonitrile | MS(ES$^+$): m/z = 480.11 [MH$^+$]. HPLC: t$_R$ = 2.45 (ZQ3, Polar_5 min). |
| 129 | (7R)-8-cyclohexyl-5-[6-(dimethylamino)pyridin-3-yl]-2-(1H-indazol-5-ylamino)-7-methyl-7,8-dihydropteridin-6(5H)-one | $^1$H NMR (CDCl$_3$, 300 MHz) δ 1.15-1.19 (m, 2H), 1.43 (d, J = 6.9 Hz, 6H), 1.70-1.79 (m, 2H), 1.92-1.93 (m, 2H), 2.21 (br s, 1H), 3.10 (s, 3H), 3.11 (s, 3H), 4.40-4.20 (m, 2H), 6.58 (d, J = 8.7 Hz, 1H), 7.15 (s, 1H), 7.26 (s, 1H), 7.27-7.39 (m, 2H), 7.92 (d, J = 7.8 Hz, 2H), 8.12 (s, 1H). MS(ES$^+$): m/z = 497.90 [MH$^+$]. HPLC: t$_R$ = 2.32 (ZQ3, Polar_5 min). |
| 130 | 3-[(7R)-8-cyclohexyl-2-[(4,7-difluoro-1H-indazol-5-yl)amino]-7-methyl-6-oxo-7,8-dihydropteridin-5(6H)-yl]benzonitrile | $^1$H NMR (CDCl$_3$, 400 MHz): δ 1.16 (m, 1 H), 1.43-1.58 (m, 3 H), 1.51 (d, J = 6.8 Hz, 3 H), 1.71 (m, 1 H), 1.80-1.94 (m, 4 H), 2.16 (m, 1 H), 4.34 (m, 1 H), 4.49 (q, J = 6.8 Hz, 1 H), 7.07 (d, J = 4.0 Hz, 1 H), 7.27 (s, br, 1 H), 7.51 (dd, J = 1.2, 8.4 Hz, 1 H), 7.58 (m, 1 H), 7.67 (t, J = 7.6 Hz, 1 H), 7.77 (dt, J = 1.2, 7.6 Hz, 1 H), 8.02 (m, 1 H), 8.15 (d, J = 3.2 Hz, 1 H), 10.21 (s, br, 1 H). MS (ES$^+$): m/z = 515.39 [MH$^+$]. HPLC: t$_R$ = 0.97 min (TOF, polar_2 min). |
| 131 | 3-[(7R)-8-cyclohexyl-2-[(3,7-difluoro-1H-indazol-5-yl)amino]-7-methyl-6-oxo-7,8-dihydropteridin-5(6H)-yl]benzonitrile | $^1$H NMR (CDCl$_3$, 400 MHz): δ 1.14 (m, 1 H), 1.39-1.50 (m, 3 H), 1.43 (d, J = 6.8 Hz, 3 H), 1.62-1.80 (m, 3 H), 1.86-1.89 (m, 2 H), 2.15 (m, 1 H), 4.41 (m, 1 H), 4.42 (q, J = 6.8 Hz, 1 H), 7.71 (s, 1 H), 7.31-7.40 (m, 2 H), 7.47 (d, J = 7.2 Hz, 1 H), 7.54 (s, 1 H), 7.59 (t, J = 8.0 Hz, 1 H), 7.68 (dt, J = 1.2, 8.0 Hz, 1 H), 7.70 (d, J = 2.4 Hz, 1 H), 9.83 (s, br, 1 H). MS (ES$^+$): m/z = 515.39 [MH$^+$]. HPLC: t$_R$ = 1.07 min (TOF, polar_2 min). |
| 132 | (7R)-8-cyclohexyl-5-(3,4-dimethoxyphenyl)-2-[(7-fluoro-1H-indazol-5-yl)amino]-7-methyl-7,8-dihydropteridin-6(5H)-one | $^1$H NMR (CDCl$_3$, 400 MHz): δ 1.16 (m, 1 H), 1.36-1.50 (m, 2 H), 1.46 (d, J = 6.8 Hz, 3 H), 1.64-1.74 (m, 3 H), 1.79-1.90 (m, 3 H), 2.19 (m, 1 H), 3.81 (s, 3 H), 3.87 (s, 3 H), 4.39 (m, 1 H), 4.42 (q, J = 6.8 Hz, 1 H), 6.63 (s, 1 H), 6.75 (d, J = 7.2 Hz, 1 H), 6.92 (d, J = 8.8 Hz, 1 H), 7.15 (d, J = 11.6 Hz, 1 H), 7.41 (dd, J = 1.6, 13.2 Hz, 1 H), 7.67 (d, J = 1.6 Hz, 1 H), 7.95 (d, J = 3.6 Hz, 1 H), 10.32 (s, br, 1 H). MS (ES$^+$): m/z = 532.44 [MH$^+$]. HPLC: t$_R$ = 0.91 min (TOF, polar_2 min). |
| 133 | (7R)-8-cyclohexyl-2-[(7-fluoro-1H-indazol-5-yl)amino]-7-methyl-5-(quinolin-7-yl)-7,8-dihydropteridin-6(5H)-one | $^1$H NMR (400 MHz, CD$_3$OD): δ 8.95 (dd, J = 1.5, 4.3 Hz, 1H), 8.49 (d, J = 8.3 Hz, 1H), 8.17 (d, J = 8.6 Hz, 1H), 7.96-8.02 (m, 2H), 7.80 (d, J = 1.0 Hz, 1H), 7.65 (dd, J = 4.3, 8.3 Hz, 1H), 7.46-7.55 (m, 2H), 7.11 (s, 1H), 4.45-4.59 (m, 2H), 2.22 (d, J = 11.6 Hz, 1H), 1.95 (d, J = 13.4 Hz, 2H), 1.82-1.91 (m, 2H), 1.62-1.80 (m, 2H), 1.50 (d, J = 3.3 Hz, 2H), 1.23-1.35 (m, 2H). MS (ES$^+$): m/z = 523.50 [MH$^+$]. UPLC: t$_R$ = 0.88 min (TOF: polar_2 min). |
| 134 | (7R)-8-cyclohexyl-2-[(7-fluoro-1H-indazol-5-yl)amino]-7-methyl-5-[4-(morpholin-4-yl)phenyl]-7,8-dihydropteridin-6(5H)-one | $^1$H NMR (CDCl$_3$, 400 MHz) δ 1.04-1.29 (m, 2 H) 1.32-1.53 (m, 6 H) 1.58-1.82 (m, 3 H) 1.87 (d, J = 10.3 Hz, 2 H) 2.16 (d, J = 9.6 Hz, 1 H) 3.44-3.61 (m, 4 H) 3.69-3.85 (m, 4 H) 4.22-4.60 (m, 2 H) 6.69 (d, J = 8.8 Hz, 1 H) 7.09 (br. s., 1 H) 7.28 (dd, J = 8.9, 2.40 Hz, 1 H) 7.39 (d, J = 12.6 Hz, 1 H) 7.66 (d, J = 1.2 Hz, 1 H) 7.86-8.07 (m, 1 H). MS(ES$^+$): m/z = 558.46 (100 [MH$^+$]. HPLC: t$_R$ = 0.89 (Polar_2 min, UPLC). |
| 135 | (7R)-8-cyclohexyl-2-[(7-fluoro-1H-indazol-5-yl)amino]-7-methyl-5-(pyridin-3-yl)-7,8-dihydropteridin-6(5H)-one | $^1$H NMR (400 MHz, CD$_3$OD): δ 1.50 (d, J = 6.82 Hz, 3H), 1.53-1.79 (m, 3H), 1.79-1.88 (m, 2H), 1.94 (d, J = 12.3 Hz, 2H), 2.01 (s, 2H), 2.20 (d, J = 11.1 Hz, 1H), 4.10 (q, J = 7.0 Hz, 1H), 4.49-4.59 (m, 1H), 7.09 (s, 1H), 7.49 (d, J = 12.8 Hz, 1H), 7.65 (dd, J = 8.0, 4.80 Hz, 1H), 7.80 (d, J = 1.5 |

| Ex. # | Chemical Name | Analytical data |
|---|---|---|
| | | Hz, 1H), 7.86 (dt, J = 8.2, 1.83 Hz, 1H), 7.99 (d, J = 2.5 Hz, 1H), 8.53 (d, J = 2.2 Hz, 1H), 8.67 (dd, J = 4.9, 1.39 Hz, 1H). MS(ES$^+$): m/z = 473.36[MH$^+$]. HPLC: t$_R$ = 0.81 min (analytical_2 min, UPLC). |
| 136 | 5-[(7R)-8-cyclohexyl-2-[(7-fluoro-1H-indazol-5-yl)amino]-7-methyl-6-oxo-7,8-dihydropteridin-5(6H)-yl]-2-methoxybenzonitrile | $^1$H NMR (CDCl$_3$, 400 MHz) δ 1.28-1.50 (m, 7 H) 1.51-1.81 (m, 4 H) 1.86 (d, J = 9.3 Hz, 2 H) 2.13 (br. s., 1 H) 3.91 (s, 3 H) 4.21-4.50 (m, 2 H) 7.02 (d, J = 9.0 Hz, 1 H) 7.06 (s, 1 H) 7.24 (br. s., 1 H) 7.31-7.44 (m, 3 H) 7.64 (d, J = 1.7 Hz, 1 H) 7.93 (d, J = 3.5 Hz, 1 H). MS(ES$^+$): m/z = 527.45 [MH$^+$]. HPLC: t$_R$ = 0.93 (Polar_2 min, ZQ3) |
| 137 | (7R)-8-cyclohexyl-2-[(7-fluoro-1H-indazol-5-yl)amino]-5-(3-fluorophenyl)-7-methyl-7,8-dihydropteridin-6(5H)-one | 1H NMR (400 MHz, CD$_3$OD): δ 1.28 (br. s., 1H), 1.41-1.56 (m, 5H), 1.58-1.98 (m, 6H), 2.19 (d, J = 11.1 Hz, 1H), 4.39-4.53 (m, 2H), 7.08 (s, 1H), 7.11-7.19 (m, 2H), 7.23-7.33 (m, 1H), 7.49 (d, J = 12.8 Hz, 1H), 7.56-7.65 (m, 1H), 7.79 (d, J = 1.5 Hz, 1H), 7.99 (d, J = 3.0 Hz, 1H). MS(ES$^+$): m/z = 490.40 [MH$^+$]. HPLC: t$_R$ = 0.94 (analytical_2 min, UPLC). |
| 138 | (7R)-8-cyclohexyl-2-[(7-fluoro-1H-indazol-5-yl)amino]-5-(6-methoxypyridin-3-yl)-7-methyl-7,8-dihydropteridin-6(5H)-one | $^1$H NMR (400 MHz, CD$_3$OD): δ 7.95-8.00 (m, 1H), 7.90-7.95 (m, 1H), 7.75-7.80 (m, 1H), 7.43-7.51 (m, 1H), 7.34-7.41 (m, 1H), 7.12-7.17 (m, 1H), 6.89-6.95 (m, 1H), 4.37-4.51 (m, 2H), 3.58-3.65 (m, 4H), 2.14-2.23 (m, 1H), 1.87-1.96 (m, 2H), 1.77-1.86 (m, 2H), 1.57-1.77 (m, 8H), 1.42-1.56 (m, 4H), 1.21-1.33 (m, 2H). MS (ES$^+$): m/z = 503.42 [MH$^+$]. UPLC: t$_R$ = 0.90 min (TOF: polar_2 min). |
| 139 | (7R)-8-cyclohexyl-2-[(7-fluoro-1H-indazol-5-yl)amino]-7-methyl-5-[6-(4-methylpiperazin-1-yl)pyridin-3-yl]-7,8-dihydropteridin-6(5H)-one. | $^1$H NMR (400 MHz, CD$_3$OD): δ 7.95-8.00 (m, 1H), 7.90-7.95 (m, 1H), 7.75-7.80 (m, 1H), 7.43-7.51 (m, 1H), 7.34-7.41 (m, 1H), 7.12-7.17 (m, 1H), 6.89-6.95 (m, 1H), 4.37-4.51 (m, 2H), 3.58-3.65 (m, 4H), 2.14-2.23 (m, 1H), 1.87-1.96 (m, 2H), 1.77-1.86 (m, 2H), 1.57-1.77 (m, 8H), 1.42-1.56 (m, 4H), 1.21-1.33 (m, 2H). MS (ES$^+$): m/z = 571.41 [MH$^+$]. UPLC: t$_R$ = 0.65 min (TOF: polar_2 min). |
| 140 | 3-[(7R)-8-cyclopentyl-7-ethyl-2-(1H-indazol-5-ylamino)-6-oxo-7,8-dihydropteridin-5(6H)-yl]benzonitrile | $^1$H NMR (400 MHz, CD$_3$OD): δ 7.95-8.00 (m, 1H), 7.90-7.95 (m, 1H), 7.75-7.80 (m, 1H), 7.43-7.51 (m, 1H), 7.34-7.41 (m, 1H), 7.12-7.17 (m, 1H), 6.89-6.95 (m, 1H), 4.37-4.51 (m, 2H), 3.58-3.65 (m, 4H), 2.14-2.23 (m, 1H), 1.87-1.96 (m, 2H), 1.77-1.86 (m, 2H), 1.57-1.77 (m, 8H), 1.42-1.56 (m, 4H), 1.21-1.33 (m, 2H). MS (ES$^+$): m/z = 479.48 [MH$^+$]. UPLC: t$_R$ = 0.89 min (TOF: polar_2 min). |
| 141 | (7R)-8-cyclohexyl-2-[(7-fluoro-1H-indazol-5-yl)amino]-7-methyl-5-[6-(pyrrolidin-1-yl)pyridin-3-yl]-7,8-dihydropteridin-6(5H)-one | $^1$H NMR (400 MHz, CD$_3$OD): δ 7.98 (d, J = 3.0 Hz, 1H), 7.89 (br. s., 1H), 7.78 (d, J = 1.5 Hz, 1H), 7.48 (d, J = 13.6 Hz, 1H), 7.40 (d, J = 10.6 Hz, 1H), 7.15 (s, 1H), 6.64 (d, J = 9.1 Hz, 1H), 4.41-4.52 (m, 2H), 3.46-3.53 (m, 5H), 2.19 (d, J = 10.9 Hz, 1H), 2.03-2.10 (m, 4H), 1.92 (br. s., 2H), 1.86 (br. s., 2H), 1.74 (d, J = 12.9 Hz, 1H), 1.59-1.67 (m, 1H), 1.50 (br. s., 1H), 1.29 (s, 3H), 0.90 (dd, J = 3.4, 6.4 Hz, 1 H). MS (ES$^+$): m/z = 542.40 [MH$^+$]. UPLC: t$_R$ = 0.78 min (TOF: polar_2 min). |
| 142 | (7R)-8-cyclohexyl-2-[(7-fluoro-1H-indazol-5-yl)amino]-7-methyl-5-[6-(piperidin-1-yl)pyridin-3-yl]-7,8-dihydropteridin-6(5H)-one | $^1$H NMR (400 MHz, CD$_3$OD): δ 7.95-8.00 (m, 1H), 7.90-7.95 (m, 1H), 7.75-7.80 (m, 1H), 7.43-7.51 (m, 1H), 7.34-7.41 (m, 1H), 7.12-7.17 (m, 1H), 6.89-6.95 (m, 1H), 4.37-4.51 (m, 2H), 3.58-3.65 (m, 4H), 2.14-2.23 (m, 1H), 1.87-1.96 (m, 2H), 1.77-1.86 (m, 2H), 1.57-1.77 (m, 8H), 1.42-1.56 (m, 4H), 1.21-1.33 (m, 2H). MS (ES$^+$): m/z = 556.49 [MH$^+$]. UPLC: t$_R$ = 0.97 min (TOF: polar_2 min). |
| 143 | (7R)-8-cyclohexyl-5-[6-(dimethylamino)pyridin-3-yl]-2-[(7-fluoro-1H-indazol-5-yl)amino]-7-methyl-7,8-dihydropteridin-6(5H)-one | $^1$H NMR (CDCl3, 300 MHz) δ 0.85-0.88 (m, 1H), 1.46-1.53 (m, 6H), 1.64-1.83 (m, 3H), 1.84-1.95 (m, 2H), 2.21-2.32 (m, 1H), 3.13 (s, 6H), 4.43-4.47 (m, 2H), 6.59 (d, J = 9 Hz, 1H), 7.20-7.22 (m, 1H), 7.28-7.29 (m, 1H), 7.46 (dd, J = 12.6, 1.5 Hz, 1H), 7.72 (d, J = 1.8 Hz, 1H), 8.01 (br s, 2H). MS(ES$^+$): m/z = 515.47 (60) [MH+]. HPLC: t$_R$ = 2.27 (ZQ3, Polar_5 min). |

| Ex. # | Chemical Name | Analytical data |
|---|---|---|
| 144 | 3-[(7R)-8-cyclohexyl-2-[(3,4-difluoro-1H-indazol-5-yl)amino]-7-methyl-6-oxo-7,8-dihydropteridin-5(6H)-yl]benzonitrile | $^1$H NMR (CDCl$_3$, 400 MHz): δ 1.18 (m, 1 H), 1.34-1.52 (m, 3 H), 1.48 (d, J = 6.4 Hz, 3 H), 1.66-1.74 (m, 2 H), 1.80 (m, 1 H), 1.87-1.93 (m, 2 H), 2.15 (m, 1 H), 4.33 (m, 1 H), 4.45 (q, J = 6.8 Hz, 1 H), 6.96 (s, 1 H), 7.08 (dd, J = 2.0, 9.2 Hz, 1 H), 7.12 (s, 1 H), 7.52 (d, J = 8.4 Hz, 1 H), 7.58 (s, 1 H), 7.64 (t, J = 8.0 Hz, 1 H), 7.73 (dt, J = 1.8, 8.0 Hz, 1 H), 8.10 (dd, J = 6.8, 8.4 Hz, 1 H), 9.62 (s, br, 1 H). MS (ES$^+$): m/z = 515.39 [MH$^+$]. HPLC: t$_R$ = 0.94 min (TOF, polar__2 min). |
| 145 | 3-[(7R)-8-cyclohexyl-2-[(7-fluoro-2-oxo-2,3-dihydro-1H-indol-5-yl)amino]-7-methyl-6-oxo-7,8-dihydropteridin-5(6H)-yl]benzonitrile | $^1$H NMR (CDCl$_3$, 400 MHz): δ 1.23 (m, 1 H), 1.47-1.52 (m, 3 H), 1.48 (d, J = 6.4 Hz, 3 H), 1.69 (m, 1 H), 1.77-1.86 (m, 2 H), 1.90-1.95 (m, 2 H), 2.21 (m, 1 H), 3.57 (s, 2 H), 4.43 (m, 1 H), 4.47 (q, J = 6.8 Hz, 1 H), 7.14 (s, 1 H), 7.15 (d, J = 2.8 Hz, 1 H), 7.21 (d, J = 0.8 Hz, 1 H), 7.51-7.53 (m, 2 H), 7.58 (m, 1 H), 7.65 (t, J = 8.0 Hz, 1 H), 7.75 (dt, J = 1.2, 7.6 Hz, 1 H), 8.32 (s, br, 1 H). MS (ES$^+$): m/z = 512.39 [MH$^+$]. HPLC: t$_R$ = 0.88 min (TOF, polar__2 min). |
| 146 | 3-[(7R)-8-cyclohexyl-7-methyl-6-oxo-2-[(3,4,7-trifluoro-1H-indazol-5-yl)amino]-7,8-dihydropteridin-5(6H)-yl]benzonitrile | $^1$H NMR (CDCl$_3$, 400 MHz): δ 1.16 (m, 1 H), 1.43-1.58 (m, 3 H), 1.50 (d, J = 6.8 Hz, 3 H), 1.74 (m, 1 H), 1.81-1.93 (m, 4 H), 2.17 (m, 1 H), 4.40 (m, 1 H), 4.47 (q, J = 7.2 Hz, 1 H), 6.89 (m, 1 H), 7.15 (s, 1 H), 7.52 (dd, J = 1.2, 8.4 Hz, 1 H), 7.59 (m, 1 H), 7.65 (t, J = 8.0 Hz, 1 H), 7.75 (dt, J = 1.2, 7.6 Hz, 1 H), 8.27 (dd, J = 5.2, 12.0 Hz, 1 H), 9.23 (s, br, 1 H). MS (ES$^+$): m/z = 533.35 [MH$^+$]. HPLC: t$_R$ = 1.06 min (TOF, polar__2 min). |
| 147 | (7R)-8-cyclohexyl-2-[(7-fluoro-1H-indazol-5-yl)amino]-5-[6-(4-hydroxypiperidin-1-yl)pyridin-3-yl]-7-methyl-7,8-dihydropteridin-6(5H)-one. | $^1$H NMR (400 MHz, CDCl$_3$): δ 7.95-8.09 (m, 2H), 7.71-7.76 (m, 1H), 7.43-7.51 (m, 1H), 7.04-7.26 (m, 2H), 6.78 (d, J = 9.1 Hz, 1H), 4.34-4.57 (m, 3H), 3.92-4.18 (m, 3H), 3.31 (ddd, J = 3.2, 9.7, 13.2 Hz, 2H), 2.16-2.28 (m, 1H), 1.85-2.06 (m, 6H), 1.69-1.82 (m, 3H), 1.60-1.68 (m, 3H), 1.38-1.54 (m, 6H). MS (ES$^+$): m/z = 572.34 [MH$^+$]. UPLC: t$_R$ = 0.82 min (TOF: polar__2 min). |
| 148 | 4-{[(7R)-8-cyclohexyl-5-(3,4-dimethoxyphenyl)-7-methyl-6-oxo-5,6,7,8-tetrahydropteridin-2-yl]amino}benzoic acid | $^1$H NMR (CD$_3$OD and CDCl$_3$, 300 MHz) δ: 1.20-1.26 (m, 1H), 1.44-1.57 (m, 6H), 1.72-1.81 (m, 3H), 1.90-1.94 (m, 2H), 2.21-2.22 (m, 1H), 3.79 (s, 3H), 3.86 (s, 3H), 4.41-4.46 (m, 2H), 6.73-6.78 (m, 2H), 7.01-7.06 (m, 2H), 7.66-7.70 (m, 2H), 7.88 (d, J = 8.7 Hz, 2H). MS (ES$^+$): m/z = 517.73 [MH$^+$]. UPLC: t$_R$ = 2.68 min (ZQ3: polar__5 min). |
| 149 | 3-[(7R)-8-cyclohexyl-7-methyl-6-oxo-2-[(2-oxo-2,3-dihydro-1,3-benzoxazol-6-yl)amino]-7,8-dihydropteridin-(6H)-yl]benzonitrile | $^1$H NMR (400 MHz, CD$_3$OD): δ 7.83-7.90 (m, 2H), 7.71-7.80 (m, 2H), 7.64 (d, J = 8.3 Hz, 1H), 7.20 (dd, J = 2.0, 8.6 Hz, 1H), 7.06 (s, 1H), 6.97 (d, J = 8.3 Hz, 1H), 4.50 (d, J = 6.8 Hz, 2H), 2.14-2.24 (m, 2H), 1.94 (d, J = 12.4 Hz, 2H), 1.80-1.87 (m, 2H), 1.76 (d, J = 13.1 Hz, 1H), 1.46-1.70 (m, 6H). MS (ES$^+$): m/z = 496.31 [MH$^+$]. UPLC: t$_R$ = 0.87 min (TOF: polar__2 min). |
| 150 | (7R)-8-cyclohexyl-5-(3,4-dimethoxyphenyl)-7-methyl-2-[(2-oxo-2,3-dihydro-1,3-benzoxazol-6-yl)amino]-7,8-dihydropteridin-6(5H)-one | $^1$H NMR (400 MHz, CD$_3$OD): δ 7.85 (d, J = 2.0 Hz, 1H), 7.19 (dd, J = 2.0, 8.3 Hz, 1H), 7.11 (d, J = 8.3 Hz, 1H), 7.07 (s, 1H), 6.97 (d, J = 8.3 Hz, 1H), 6.76-6.88 (m, 2H), 4.36-4.52 (m, 2H), 3.89 (s, 3H), 3.82 (s, 3H), 2.20 (d, J = 10.9 Hz, 1H), 1.94 (d, J = 10.1 Hz, 2H), 1.72-1.87 (m, 3H), 1.58 (br. s., 6H), 1.23-1.35 (m, 1 H). MS (ES$^+$): m/z = 531.35 [MH$^+$]. UPLC: t$_R$ = 0.84 min (TOF: polar__2 min). |
| 151 | (7R)-8-cyclohexyl-7-methyl-2-[(2-oxo-2,3-dihydro-1,3-benzoxazol-6-yl)amino]-5-(pyridin-3-yl)-7,8-dihydropteridin-6(5H)-one | $^1$H NMR (400 MHz, CD$_3$OD): δ 8.66 (dd, J = 1.5, 4.8 Hz, 1H), 8.52 (d, J = 2.3 Hz, 1H), 7.82-7.88 (m, 2H), 7.65 (dd, J = 4.9, 8.2 Hz, 1H), 7.20 (dd, J = 2.0, 8.6 Hz, 1H), 7.08 (s, 1H), 6.97 (d, J = 8.6 Hz, 1H), 4.40-4.57 (m, 2H), 2.20 (d, J = 11.1 Hz, 1H), 1.95 (d, J = 11.4 Hz, 2H), 1.72-1.88 (m, 3H), 1.65 (d, J = 12.6 Hz, 1H), 1.47-1.61 (m, 5H), 1.26-1.32 (m, 1H). MS (ES$^+$): m/z = 472.29 [MH$^+$]. UPLC: t$_R$ = 0.75 min (TOF: polar__2 min). |
| 152 | 3-[(7R)-8-cyclohexyl-7-methyl-6-oxo-2-(1H-pyrazolo[3,4- | $^1$H NMR (400 MHz, CD$_3$OD): δ 8.63 (d, J = 2.0 Hz, 1H), 8.54 (d, J = 1.8 Hz, 1H), 8.01 (s, 1H), 7.88 (d, |

| Ex. # | Chemical Name | Analytical data |
|---|---|---|
| | b]pyridin-5-ylamino)-7,8-dihydropteridin-5(6H)-yl]benzonitrile | J = 7.6 Hz, 1H), 7.72-7.80 (m, 2H), 7.61-7.68 (m, 1H), 7.07 (s, 1H), 4.50 (q, J = 6.7 Hz, 1H), 4.38 (br. s., 1H), 2.15 (s, 1H), 1.78-1.95 (m,4H), 1.56-1.76 (m, 2H), 1.37-1.52 (m, 5H), 1.20-1.29 (m, 1H). MS (ES$^+$): m/z = 480.31 [MH$^+$]. UPLC: $t_R$ = 0.83 min (TOF: polar_2 min). |
| 153 | (7R)-8-cyclohexyl-5-(3,4-dimethoxyphenyl)-7-methyl-2-(1H-pyrazolo[3,4-B]pyridin-5-ylamino)-7,8-dihydropteridin-6(5H)-one. | $^1$H NMR (400 MHz, CD$_3$OD): δ 8.48-8.65 (m, 2H), 8.01 (s, 1H), 7.04-7.15 (m, 2H), 6.86 (br. s., 2H), 4.47 (d, J = 6.6 Hz, 1H), 4.37 (br. s., 1H), 3.90 (s, 3H), 3.83 (s, 3H), 2.15 (d, J = 12.4 Hz, 1H), 1.77-1.95 (m, 4H), 1.57-1.76 (m, 2H), 1.37-1.52 (m, 5H), 1.28 (br. s., 1H). MS (ES$^+$): m/z = 515.35 [MH$^+$]. UPLC: $t_R$ = 0.80 min (TOF: polar_2 min). |
| 154 | (7R)-8-cyclohexyl-7-methyl-2-(1H-pyrazolo[3,4-b]pyridin-5-ylamino)-5-(pyridin-3-yl)-7,8-dihydropteridin-6(5H)-one | $^1$H NMR (400 MHz, CD$_3$OD): δ 8.65-8.69 (m, 1H), 8.63 (d, J = 2.3 Hz, 1H), 8.51-8.55 (m, 2H), 8.01 (s, 1H), 7.86 (td, J = 1.1, 8.1 Hz, 1H), 7.65 (dd, J = 4.8, 8.1 Hz, 1H), 7.09 (d, J = 1.0 Hz, 1H), 4.51 (d, J = 6.8 Hz, 1H), 4.33-4.45 (m, 1H), 2.15 (br. s., 1H), 1.78-1.97 (m, 4H), 1.71 (d, J = 1.0 Hz, 3H), 1.38-1.52 (m, 5H). MS (ES$^+$): m/z = 456.45 [MH$^+$]. UPLC: $t_R$ = 0.67 min (TOF: polar_2 min) |
| 155 | 4-{[(7R)-5-(3-cyanophenyl)-8-cyclohexyl-7-methyl-6-oxo-5,6,7,8-tetrahydropteridin-2-yl]amino}benzoic acid. | $^1$H NMR (400 MHz, CD$_3$OD): δ 7.85-7.95 (m, 3H), 7.71-7.81 (m, 4H), 7.65 (d, J = 8.1 Hz, 1H), 7.11 (s, 1H), 4.41-4.58 (m, 2H), 2.24 (br. s., 1H), 1.92-2.03 (m, 2H), 1.75-1.89 (m, 3H), 1.47-1.72 (m, 6H), 1.26-1.36 (m, 1 H). MS (ES$^+$): m/z = 483.09 [MH$^+$]. UPLC: $t_R$ = 1.01 min (TOF: polar_2 min). |
| 156 | 3-[(7R)-8-cyclohexyl-7-methyl-6-oxo-2-(phenylamino)-7,8-dihydropteridin-5(6H)-yl]benzonitrile | $^1$H NMR (400 MHz, CD$_3$OD) δ 7.87 (d, J = 7.8 Hz, 1H), 7.71-7.80 (m, 2H), 7.55-7.67 (m, 3H), 7.26 (t, J = 7.3 Hz, 2H), 6.88-7.09 (m, 2H), 4.37-4.56 (m, 2H), 2.21 (d, J = 11.4 Hz, 1H), 1.95 (d, J = 11.9 Hz, 2H), 1.72-1.87 (m, 2H), 1.59-1.69 (m, 1H), 1.44-1.54 (m, 5H), 1.30 (d, J = 12.1 Hz, 2H). MS (ES$^+$): m/z = 439.17 [M + H]$^+$. UPLC: $t_R$ = 1.11 min (TOF: polar_2 min). |
| 157 | 5-{[(7R)-5-(3-cyanophenyl)-8-cyclohexyl-7-methyl-6-oxo-5,6,7,8-tetrahydropteridin-2-yl]amino}-1H-indazole-3-carbonitrile. | $^1$H NMR (400 MHz, CD$_3$OD): δ 8.19-8.23 (m, 1H), 7.83-7.90 (m, 1H), 7.71-7.81 (m, 2H), 7.61-7.68 (m, 1H), 7.51-7.59 (m, 2H), 7.12 (s, 1H), 4.51 (q, J = 6.8 Hz, 2H), 2.11-2.21 (m, 1H), 1.69-1.94 (m, 5H), 1.44-1.67 (m, 6H), 1.19-1.28 (m, 1H). MS (ES$^+$): m/z = 504.30 [MH$^+$]. UPLC: $t_R$ = 0.97 min (TOF: polar_2 min). |
| 158 | 3-[(7R)-8-cyclohexyl-2-[(3,5-difluoro-4-hydroxyphenyl)amino]-7-methyl-6-oxo-7,8-dihydropteridin-5(6H)-yl]benzonitrile | $^1$H NMR (400 MHz, CD$_3$OD): δ 7.86 (d, J = 7.8 Hz, 1H), 7.68-7.79 (m, 2H), 7.62 (d, J = 7.6 Hz, 1H), 7.22-7.32 (m, 2H), 7.05 (s, 1H), 4.40-4.53 (m, 2H), 2.19 (d, J = 10.6 Hz, 1H), 1.92 (br. s., 2H), 1.69-1.86 (m, 3H), 1.42-1.68 (m, 6H), 1.21-1.37 (m, 1H). MS (ES$^+$): m/z = 490.96 [MH$^+$]. UPLC: $t_R$ = 1.00 min (TOF: polar_2 min). |
| 159 | (7R)-8-cyclohexyl-2-[(3,5-difluoro-4-hydroxyphenyl)amino]-5-(3,4-dimethoxyphenyl)-7-methyl-7,8-dihydropteridin-6(5H)-one | $^1$H NMR (400 MHz, CD$_3$OD): δ 7.22-7.32 (m, 2H), 7.05-7.13 (m, 2H), 6.75-6.88 (m, 2H), 4.47 (q, J = 6.7 Hz, 2H), 3.89 (s, 3H), 3.82 (s, 3H), 2.18 (t, J = 11.0 Hz, 1H), 1.88-1.98 (m, 2H), 1.71-1.86 (m, 3H), 1.43-1.66 (m, 6H), 1.30 (dd, J = 3.3, 12.6 Hz, 1H). MS (ES$^+$): m/z = 526.21 [MH$^+$]. UPLC: $t_R$ = 0.94 min (TOF: polar_2 min). |
| 160 | (7R)-8-cyclohexyl-2-[(3,5-difluoro-4-hydroxyphenyl)amino]-7-methyl-5-(pyridin-3-yl)-7,8-dihydropteridin-(5H)-one. | $^1$H NMR (400 MHz, CD$_3$OD): δ 8.66 (dd, J = 1.5, 4.8 Hz, 1H), 8.52 (d, J = 2.3 Hz, 1H), 7.84 (td, J = 1.8, 8.2 Hz, 1H), 7.64 (dd, J = 4.9, 8.2 Hz, 1H), 7.22-7.32 (m, 2H), 7.08 (s, 1H), 4.43-4.55 (m, 2H), 2.20 (d, J = 11.9 Hz, 1H), 1.88-1.99 (m, 2H), 1.71-1.86 (m, 3H), 1.45-1.70 (m, 6H), 1.25-1.34 (m, 1H). MS (ES$^+$): m/z = 467.35 [MH$^+$]. UPLC: $t_R$ = 0.86 min (TOF: polar_2 min). |
| 161 | 3-[(7R)-8-cyclohexyl-7-methyl-6-oxo-2-[(1-oxo-2,3-dihydro-1H-isoindol-5-yl)amino]-7,8-dihydropteridin-5(6H)-yl]benzonitrile | $^1$H NMR (400 MHz, CD$_3$OD): δ 8.04 (d, J = 0.8 Hz, 1H), 7.85-7.90 (m, 1H), 7.73-7.81 (m, 2H), 7.62-7.71 (m, 3H), 7.39-7.52 (m, J = 6.6 Hz, 1H), 7.20-7.42 (m, 1H), 7.13 (s, 1H), 4.53 (q, J = 6.8 Hz, 2H), 2.23 (d, J = 10.6 Hz, 1H), 1.92-2.03 (m, 2H), 1.74-1.88 (m, 3H), 1.60-1.73 (m, 1H), 1.45-1.59 (m, 5H), 1.29 (br. s., 1H). MS (ES$^+$): m/z = 494.34 [MH$^+$]. UPLC: $t_R$ = 0.88 min (TOF: polar_2 min). |
| 162 | (7R)-8-cyclohexyl-5-(3,4-dimethoxyphenyl)-7-methyl-2-[(pyridin-4-ylmethyl)amino]-7,8-dihydropteridin-6(5H)-one | $^1$H NMR (400 MHz, CD$_3$OD): δ 8.43 (d, J = 5.3 Hz, 2H), 7.38 (d, J = 5.8 Hz, 2H), 7.09 (d, J = 8.6 Hz, 1H), 6.93 (s, 1H), 6.70-6.85 (m, 2H), 4.56 (s, 2H), 4.36 (q, J = 6.8 Hz, 1H), 4.06 (br. s., 1H), 3.88 (s, 3H), 3.81 (s, 3H), 1.72-1.90 (m, 4H), 1.58-1.69 (m, |

| Ex. # | Chemical Name | Analytical data |
|---|---|---|
| | | 2H), 1.43-1.57 (m, 1H), 1.40 (d, J = 6.6 Hz, 3H), 1.13-1.34 (m, 3H). MS (ES+): m/z = 489.81 [MH+]. UPLC: $t_R$ = 0.61 min (TOF: polar_2 min). |
| 163 | (7R)-8-cyclohexyl-5-(3,4-dimethoxyphenyl)-7-methyl-2-[(1H-pyrazol-4-ylmethyl)amino]-7,8-dihydropteridin-6(5H)-one. | $^1$H NMR (400 MHz, CD$_3$OD): δ 7.53 (br. s., 2H), 7.09 (d, J = 8.1 Hz, 1H), 6.93 (s, 1H), 6.81 (br. s., 2H), 4.30-4.45 (m, 4H), 3.88 (s, 3H), 3.80 (s, 3H), 2.08 (d, J = 10.6 Hz, 1H), 1.57-1.94 (m, 6H), 1.44 (d, J = 5.8 Hz, 5H), 1.20-1.32 (m, 1H). MS (ES+): m/z = 478.73 [MH+]. UPLC: $t_R$ = 0.78 min (TOF: polar_2 min). |
| 164 | 5-[(7R)-8-cyclohexyl-7-methyl-6-oxo-2-(1H-pyrazolo[3,4-b]pyridin-5-ylamino)-7,8-dihydropteridin-5(6H)-yl]-2-methoxybenzonitrile. | $^1$H NMR (400 MHz, CD$_3$OD): δ 8.62 (d, J = 2.3 Hz, 1H), 8.53 (d, J = 2.3 Hz, 1H), 8.01 (s, 1H), 7.65 (d, J = 2.3 Hz, 1H), 7.56 (d, J = 6.8 Hz, 1H), 7.36 (d, J = 8.8 Hz, 1H), 7.09 (s, 1H), 4.48 (q, J = 6.7 Hz, 1H), 4.37 (br. s., 1H), 4.03 (s, 3H), 2.14 (d, J = 11.4 Hz, 1H), 1.76-1.95(m,4H), 1.71 (d, J = 12.6 Hz, 1H), 1.62 (dd, J = 3.3, 12.1 Hz, 1H), 1.37-1.50 (m, 5H), 1.17-1.30 (m, 1H). MS (ES+): m/z = 510.39 [MH+]. UPLC: $t_R$ = 0.83 min (TOF: polar_2 min). |
| 165 | 5-[(7R)-8-cyclohexyl-7-methyl-6-oxo-2-[(2-oxo-2,3-dihydro-1,3-benzoxazol-6-yl)amino]-7,8-dihydropteridin-5(6H)-yl]-2-methoxybenzonitrile | $^1$H NMR (400 MHz, CD$_3$OD): δ 7.85 (s, 1H), 7.64 (br. s., 1H), 7.55 (d, J = 9.9 Hz, 1H), 7.35 (d, J = 9.1 Hz, 1H), 7.14-7.21 (m, 1H), 7.07 (s, 1H), 6.97 (d, J = 8.3 Hz, 1H), 4.37-4.52 (m, 2H), 4.03 (s, 3H), 2.19 (d, J = 11.6 Hz, 1H), 1.94 (d, J = 10.1 Hz, 2H), 1.70-1.87 (m, 3H), 1.59-1.66 (m, 1H), 1.47 (d, J = 6.8 Hz, 5H), 1.28 (d, J = 12.6 Hz, 1H). MS (ES+): m/z = 526.38 [MH+]. UPLC: $t_R$ = 0.87 min (TOF: polar_2 min). |
| 166 | 3-[(7R)-8-cyclohexyl-7-methyl-6-oxo-2-[(3-oxo-2,3-dihydro-1,2-benzoxazol-6-yl)amino]-7,8-dihydropteridin-5(6H)-yl]benzonitrile | $^1$H NMR (400 MHz, CD$_3$OD): δ 7.83-7.90 (m, 1 H), 7.70-7.80 (m, 2H), 7.59-7.67 (m, 2H), 7.48 (d, J = 2.0 Hz, 1H), 7.11 (s, 1H), 7.05 (dd, J = 2.1, 8.7 Hz, 1H), 4.48-4.60 (m, 2H), 2.24 (br. s., 1H), 1.90-1.99 (m, 2H), 1.72-1.87 (m, 3H), 1.60-1.71 (m, 2H), 1.49 (d, J = 6.6 Hz, 3H), 1.25-1.34 (m, 2H). MS (ES+): m/z = 496.78 [MH+]. UPLC: $t_R$ = 0.99 min (TOF: polar_2 min). |
| 167 | 3-[(7R)-8-cyclohexyl-7-methyl-6-oxo-2-(1H-pyrazolo[4,3-b]pyridin-5-ylamino)-7,8-dihydropteridin-5(6H)-yl]benzonitrile | $^1$H NMR (CDCl$_3$, 400 MHz): δ 1.25 (m, 1 H), 1.49 (d, J = 6.8 Hz, 3 H), 1.42-1.56 (m, 2 H), 1.67-1.87 (m, 4 H), 1.94-1.99 (m, 2 H), 2.25 (d, J = 9.2 Hz, 1 H), 4.38 (m, 1 H), 4.49 (q, J = 6.8 Hz, 1 H), 7.30 (s, 1 H), 7.54 (d, J = 8.0 Hz, 1 H), 7.61-7.66 (m, 2 H), 7.72 (dt, J = 1.2, 7.6 Hz, 1 H), 7.81 (d, J = 9.2 Hz, 1 H), 8.06 (s, 1 H), 8.48 (d, J = 9.2 Hz, 1 H), 8.68 (s, 1 H), 11.11 (s, br, 1 H). MS (ES+): m/z = 480.60 [MH+]. HPLC: $t_R$ = 0.84 min (TOF, polar_2 min). |
| 168 | 3-[(7R)-8-cyclohexyl-2-[(5-hydroxypyridin-2-yl)amino]-7-methyl-6-oxo-7,8-dihydropteridin-5(6H)-yl]benzonitrile | $^1$H NMR (DMSO-d$_6$, 400 MHz): δ 1.26 (m, 1 H), 1.39 (d, J = 6.8 Hz, 3 H), 1.37-1.48 (m, 2 H), 1.62-1.75 (m, 4 H), 1.85-1.88 (m, 2 H), 2.08 (d, J = 10.8 Hz, 1 H), 4.28 (m, 1 H), 4.46 (q, J = 6.8 Hz, 1 H), 7.07 (d, J = 1.2 Hz, 1 H), 7.15 (dd, J = 3.2, 9.2 Hz, 1 H), 7.71-7.79 (m, 2 H), 7.81 (d, J = 2.4 Hz, 1 H), 7.96-8.00 (m, 3 H), 9.03 (s, 1 H), 9.36 (d, J = 0.8 Hz, 1 H). MS (ES+): m/z = 456.62 [MH+]. HPLC: $t_R$ = 0.85 min (TOF, polar_2 min). |
| 169 | 3-[(7R)-8-cyclohexyl-2-[(4-fluoro-2-oxo-2,3-dihydro-1,3-benzoxazol-6-yl)amino]-7-methyl-6-oxo-7,8-dihydropteridin-5(6H)-yl]benzonitrile | $^1$H NMR (400 MHz, CD$_3$OD): δ 1.31 (d, J = 12.63 Hz, 1H), 1.42-1.71 (m, 6H), 1.73-1.88 (m, 3H), 1.96 (d, J = 10.86 Hz, 2H), 2.22 (d, J = 10.86 Hz, 1H), 4.41-4.58 (m, 2H), 7.09 (s, 1H), 7.36 (d, J = 12.63 Hz, 1H), 7.55 (s, 1H), 7.65 (d, J = 7.83 Hz, 1H), 7.71-7.76 (m, 1H), 7.77-7.81(m, 1H), 7.88 (dd, J = 7.83, 1.01 Hz, 1H). MS(ES+): m/z = 514.64[MH+]. HPLC: $t_R$ = 0.98 min (analytical_2 min, UPLC). |
| 170 | (7R)-8-cyclohexyl-5-(3,4-dimethoxyphenyl)-7-methyl-2-{[2-(1H-pyrazol-4-yl)ethyl]amino}-7,8-dihydropteridin-6(5H)-one. | $^1$H NMR (400 MHz, CD$_3$OD): δ 8.44 (br. s., 1H), 7.75 (br. s., 1H), 7.26 (br. s., 1H), 7.14 (d, J = 7.6 Hz, 1H), 6.89 (br. s., 2H), 4.59 (br. s., 2H), 3.91 (s, 3H), 3.83 (br. s., 3H), 3.21 (q, J = 7.3 Hz, 2H), 2.94 (br. s., 2H), 2.17 (d, J = 9.9 Hz, 1H), 1.91-1.98 (m, 3H), 1.87 (br. s., 1H), 1.77 (d, J = 12.6 Hz, 2H), 1.54 (d, J = 6.6 Hz, 3H), 1.31 (t, J = 7.3 Hz, 2H). MS (ES+): m/z = 492.37 [MH+]. UPLC: $t_R$ = 0.77 min (TOF: polar_2 min). |

| Ex. # | Chemical Name | Analytical data |
|---|---|---|
| 171 | 3-[(7R)-8-cyclohexyl-2-{[4-(hydroxymethyl)phenyl]amino}-7-methyl-6-oxo-7,8-dihydropteridin-5(6H)-yl]benzonitrile | $^1$H NMR (CDCl$_3$, 400 MHz): δ 1.24 (m, 1 H), 1.48 (d, J = 6.8 Hz, 3 H), 1.42-1.53 (m, 2 H), 1.65-1.86 (m, 4 H), 1.95-1.97 (m, 2 H), 2.25 (d, J = 5.6 Hz, 1 H), 4.42 (m, 1 H), 4.47 (q, J = 6.8 Hz, 1 H), 4.64 (s, 2 H), 7.13 (s, 2 H), 7.30 (d, J = 8.0 Hz, 1 H), 7.51 (d, J = 8.0 Hz, 1 H), 7.56-7.59 (m, 3 H), 7.64 (t, J = 8.0 Hz, 1 H), 7.74 (dt, J = 0.8, 7.6 Hz, 1 H). MS (ES$^+$): m/z = 469.80 [MH$^+$]. HPLC: t$_R$ = 0.91 min (TOF, polar_2 min). |
| 172 | 3-[(7R)-8-cyclohexyl-7-methyl-6-oxo-2-[(2-oxo-2,3-dihydro[1,3]oxazolo[4,5-b]pyridin-6-yl)amino]-7,8-dihydropteridin-5(6H)-yl]benzonitrile | $^1$H NMR (CDCl$_3$, 400 MHz): δ 1.23 (m, 1 H), 1.42-1.54 (m, 2 H), 1.53 (d, J = 6.8 Hz, 3 H), 1.66-1.76 (m, 2 H), 1.80-1.88 (m, 2 H), 1.96-1.99 (m, 2 H), 2.26 (m, 1 H), 4.41 (m, 1 H), 4.53 (q, J = 6.8 Hz, 1 H), 7.22 (s, 1 H), 7.26 (s, 1 H), 7.57 (d, J = 8.0 Hz, 1 H), 7.60 (s, 1 H), 7.69 (t, J = 7.6 Hz, 1 H), 7.78 (dt, J = 1.2, 7.6 Hz, 1 H), 8.13 (d, J = 2.0 Hz, 1 H), 8.57 (d, J = 2.0 Hz, 1 H), 9.13 (s, br, 1 H). MS (ES$^+$): m/z = 497.35 [MH$^+$]. HPLC: t$_R$ = 0.92 min (TOF, polar_2 min). |
| 173 | 5-[(7R)-8-cyclohexyl-2-[(7-fluoro-1H-indazol-5-yl)amino]-7-methyl-6-oxo-7,8-dihydropteridin-5(6H)-yl]-2-(4-methylpiperazin-1-yl)benzonitrile | $^1$H NMR (CDCl$_3$, 400 MHz): δ 1.24 (m, 1 H), 1.48 (d, J = 6.8 Hz, 3 H), 1.49-1.53 (m, 2 H), 1.69-1.87 (m, 4 H), 1.94-2.00 (m, 2 H), 2.25 (m, 1 H), 2.41 (s, 3 H), 2.69 (t, J = 4.8 Hz, 4 H), 3.35 (t, J = 4.8 Hz, 4 H), 4.45 (m, 1 H), 4.48 (q, J = 6.8 Hz, 1 H), 7.11 (d, J = 9.2 Hz, 1 H), 7.20 (s, 1 H), 7.35 (dd, J = 1.6, 8.8 Hz, 1 H), 7.40 (s, 1 H), 7.42 (dd, J = 1.6, 12.8 Hz, 1 H), 7.46 (d, J = 1.6 Hz, 1 H), 7.76 (d, J = 1.6 Hz, 1 H), 8.03 (d, J = 2.8 Hz, 1 H), 11.31 (s, br, 1 H). MS (ES$^+$): m/z = 595.43 [MH$^+$]. HPLC: t$_R$ = 0.74 min (TOF, polar_2 min). |
| 174 | 3-[(7R)-8-cyclohexyl-2-[(2,2-dioxido-1,3-dihydro-2,1-benzothiazol-5-yl)amino]-7-methyl-6-oxo-7,8-dihydropteridin-5(6H)-yl]benzonitrile. | $^1$H NMR (400 MHz, CD$_3$OD): δ 7.86 (d, J = 7.8 Hz, 1H), 7.71-7.79 (m, 2H), 7.63 (d, J = 8.1 Hz, 1H), 7.57 (d, J = 1.0 Hz, 1H), 7.46 (dd, J = 1.5, 8.6 Hz, 1H), 7.02 (s, 1H), 6.81 (d, J = 8.6 Hz, 1H), 4.39-4.52 (m, 2H), 2.15 (d, J = 10.1 Hz, 1H), 1.89-1.98 (m, 2H), 1.57-1.86 (m, 5H), 1.47 (d, J = 6.8 Hz, 5H), 0.87-0.92 (m, 2H). MS (ES$^+$): m/z = 530.41[MH$^+$]. UPLC: t$_R$ = 0.88 min (TOF: polar_2 min). |
| 175 | (7R)-8-cyclohexyl-7-methyl-5-(1-methyl-2-oxo-1,2-dihydropyridin-4-yl)-2-(1H-pyrazolo[3,4-b]pyridin-5-ylamino)-7,8-dihydropteridin-6(5H)-one | $^1$H NMR (400 MHz, CD$_3$OD): δ 7.99 (br. s., 1H), 7.87 (d, J = 8.3 Hz, 1H), 7.71-7.81 (m, 3H), 7.65 (d, J = 8.6 Hz, 1H), 7.50 (d, J = 13.6 Hz, 1H), 7.08 (s, 1H), 4.49-4.63 (m, 2H), 2.19 (d, J = 10.9 Hz, 1H), 1.93-2.08 (m, 3H), 1.73-1.84 (m, 2H), 1.50 (d, J = 6.6 Hz, 3H), 1.00-1.10 (m, 2H), 0.28-0.41 (m, 4H). MS (ES$^+$): m/z = 486.23 [MH$^+$]. UPLC: t$_R$ = 1.00 min (TOF: polar_2 min). |
| 176 | (7R)-8-cyclohexyl-2-[(7-fluoro-1H-indazol-5-yl)amino]-7-methyl-5-(1-methyl-2-oxo-1,2-dihydropyridin-4-yl)-7,8-dihydropteridin-6(5H)-one | $^1$H NMR (400 MHz, CD$_3$OD): δ 7.99 (br. s., 1H), 7.75-7.84 (m, 2H), 7.50 (d, J = 12.6 Hz, 1H), 7.40 (s, 1H), 6.56 (br. s., 1H), 6.29 (d, J = 6.8 Hz, 1H), 4.46 (d, J = 6.1 Hz, 2H), 3.62 (s, 3H), 2.16 (d, J = 9.6 Hz, 1H), 1.92 (d, J = 11.1 Hz, 2H), 1.68-1.84 (m, 3H), 1.60 (br. s., 1H), 1.38-1.54 (m, 5H), 1.29 (br. s., 1H). MS (ES$^+$): m/z = 503.72 [MH$^+$]. UPLC: t$_R$ = 0.75 min (TOF: polar_2 min). |
| 177 | methyl 4-[(7R)-8-cyclohexyl-2-(1H-indazol-5-ylamino)-7-methyl-6-oxo-7,8-dihydropteridin-5(6H)-yl]thiophene-2-carboxylate | $^1$H NMR (CDCl$_3$, 300 MHz) δ 1.18-1.22 (m, 1H), 1.43-1.52 (m, 6H), 1.65-1.80 (m, 3H), 1.90-1.98 (m, 2H), 2.19-2.25 (m, 1H), 3.89 (s, 3H), 4.40-4.47 (m, 2H), 6.99 (s, 1H), 7.35 (s, 1H), 7.40-7.43 (m, 2H), 7.54 (d, J = 1.8 Hz, 1H), 7.68 (d, J = 1.5 Hz, 1H), 8.02 (br s, 1H), 8.16 (s, 1H), 10.02 (br s, 1H). MS(ES$^+$): m/z = 518.35 [MH$^+$]. HPLC: t$_R$ = 2.54 (ZQ3, Polar_5 min). |
| 178 | 2-(1H-indazol-5-ylamino)-7-methyl-5,8-diphenyl-7,8-dihydropteridin-6(5H)-one | $^1$HNMR (300 MHz, DMSO-d$_6$): δ 1.47 (d, J = 6.6 Hz, 3H), 4.77-4.99 (m, 1H), 7.05 (s, 1H), 7.20-7.31 (m, 2H), 7.43-7.63 (m, 10H), 7.81 (s, 2H), 9.15 (s, 1H). MS(ES$^+$): m/z = 448.00 [MH$^+$]. HPLC: t$_R$ = 2.51 (ZQ3, Polar_5 min). |
| 179 | 7-methyl-2-[(2-oxo-2,3-dihydro-1H-indol-5-yl)amino]-5,8-diphenyl-7,8-dihydropteridin-6(5H)-one | $^1$HNMR (300 MHz, CDCl$_3$) δ 1.63 (d, J = 6.6 Hz, 3H), 3.33 (s, 2H), 4.68-4.75 (m, 1H), 6.66 (d, J = 8.4 Hz, 1H), 6.75 (s, 1H), 6.93 (d, J = 8.1 Hz, 1H) and 7.31-7.59 (m, 12H). MS(ES$^+$): m/z = 463.07 [MH$^+$]. HPLC: t$_R$ = 2.39 (ZQ3, Polar_5 min). |
| 180 | 3-[(7R)-2-[(7-fluoro-1H-indazol-5-yl)amino]-8-(4-fluorophenyl)-7-methyl-6-oxo- | $^1$H NMR (DMSO-d$_6$, 300 MHz) δ: 1.46 (d, J = 6.9 Hz, 3H), 4.77 (q, J = 6.9, 13.8 Hz, 1H), 7.13 (s, 1H), 7.25 (d, J = 13.2 Hz, 1H), 7.44 (t, J = 8.7 Hz, |

-continued

| Ex. # | Chemical Name | Analytical data |
|---|---|---|
| | 7,8-dihydropteridin-5(6H)-yl]benzonitrile | 2H), 7.57-7.60 (m, 2H), 7.74 (s, 1H), 7.81 (d, J = 5.4 Hz, 2H), 7.98-8.04 (m, 2H), 9.30 (s, 1H). MS(ES$^+$): m/z = 509.62[MH$^+$]. HPLC: t$_R$ = 0.93 min (analytical_2 min, UPLC). |
| 181 | 3-[(7R)-2-[(7-fluoro-1H-indazol-5-yl)amino]-8-(3-methoxyphenyl)-7-methyl-6-oxo-7,8-dihydropteridin-5(6H)-yl]benzonitrile | $^1$H NMR (DMSO-d$_6$, 300 MHz) δ: 1.46 (d, J = 6.9 Hz, 3H), 3.87 (s, 3H), 4.71 (q, 1H), 7.08 (s, 1H), 7.15 (d, J = 9 Hz, 2H), 7.23 (d, J = 13.5 Hz, 1H), 7.44 (d, J = 8.7 Hz, 1H), 7.57 (s, 1H), 7.68 (s, 1H), 7.80-7.82 (m, 2H), 7.99-8.03 (m, 2H), 9.24 (s, 1H). MS(ES$^+$): m/z = 521.65[MH$^+$]. HPLC: t$_R$ = 0.92 min (analytical_2 min, UPLC). |
| 182 | 3-[(7R)-2-[(7-fluoro-1H-indazol-5-yl)amino]-8-(4-methoxyphenyl)-7-methyl-6-oxo-7,8-dihydropteridin-5(6H)-yl]benzonitrile | $^1$H NMR (DMSO-d$_6$, 300 MHz) δ: 1.46 (d, J = 6.9 Hz, 3H), 3.87 (s,3H), 4.71 (q, 1H), 7.15 (d, J = 9 Hz, 2H), 7.20-7.25 (m, 1H), 7.44 (d, J = 8.7 Hz, 2H), 7.57 (s, 1H), 7.66-7.70 (m, 1H), 7.80-7.82 (m, 2H), 7.99-8.02 (m, 2H), 9.24 (br s, 1H). MS(ES$^+$): m/z = 521.76[MH$^+$]. HPLC: t$_R$ = 2.61 min (ZQ3, Polar_5 min). |
| 183 | 3-[(7R)-2-[(7-fluoro-1H-indazol-5-yl)amino]-8-(3-fluorophenyl)-7-methyl-6-oxo-7,8-dihydropteridin-5(6H)-yl]benzonitrile | $^1$H NMR (CDCl$_3$, 300 MHz) δ: 1.62 (d, J = 6.9 Hz, 3H), 4.74 (q, J = 16.8, 6.9 Hz, 1H), 7.09-7.22 (m, 4H), 7.31 (s, 1H), 7.42-7.62 (m, 3H), 7.68-7.72 (m, 2H), 7.78-7.80 (m, 1H), 7.89 (s, 1H), 10.32 (br s, 1H). MS(ES$^+$): m/z = 509.76 [MH$^+$]. HPLC: t$_R$ = 2.78 min (ZQ3, Polar_5 min). |

Examples 95-177 were prepared according to procedures similar to the preparation of Example 18, using corresponding starting materials and intermediates. For example, for the synthesis of example 100, (3-cyanophenyl)boronic acid was used in the step d of the synthesis, 4-fluoro-1H-indazol-5-amine was used in the step e of the synthesis.

Example 178 was prepared by the following procedures:

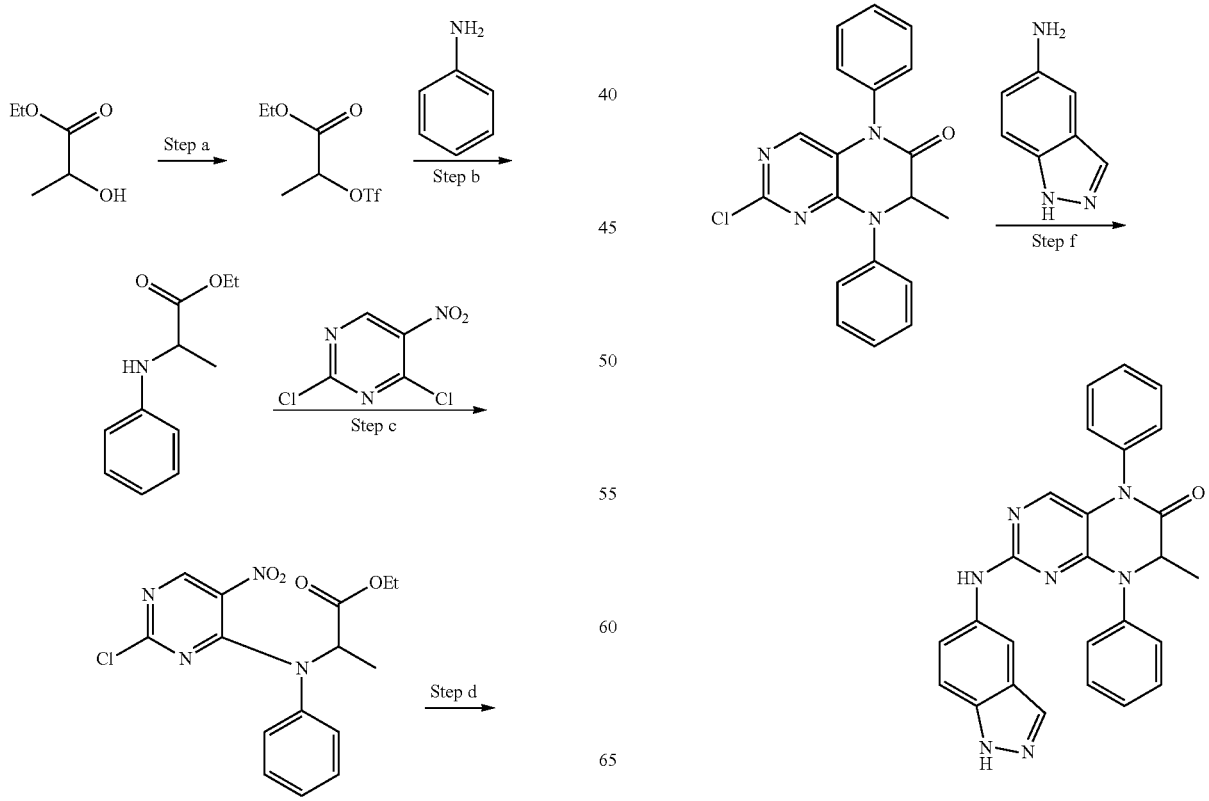

Step a: Synthesis of ethyl 2-{[(trifluoromethyl)sulfonyl]oxy}propanoate

To a stirred solution of trifluoromethanesulfonic anhydride (30 mL, 170 mmol) in anhydrous dichloromethane (50 mL) was added drop-wise a solution of 2-hydroxypropanoic acid ethyl ester (20 g, 170 mmol) and pyridine (14 mL) in dichloromethane (50 mL) at 0° C. (Ice bath) over a period of 1 h under nitrogen. The ice bath was then removed and the reaction mixture was stirred for additional 2 h. The inorganic salt was then filtered off and the organic solution was washed with water, dried over sodium sulfate, and evaporated to give desired product as pink colored oil (37.4 g, 88%) which was used as such for the next step. $^1$HNMR (300 MHz, CDCl$_3$): δ 1.38 (t, J=4.8 Hz, 3H), 1.77 (d, J=4.8 Hz, 3H), 4.32-4.37 (m, 2H) and 5.28 (q, J=6.9 Hz, 1H).

Step b: Synthesis of ethyl N-phenylalaninate

To a stirred solution of aniline (4.55 mL, 50 mmol) and triethylamine (7 mL, 50 mmol) in anhydrous dichloromethane (120 mL) was added a solution of ethyl 2-{[(trifluoromethyl)sulfonyl]oxy}propanoate (12.5 g, 50 mmol) in dichloromethane (60 mL) at 0° C. (Ice bath) over a period of 30 minutes under nitrogen. The ice bath was then removed and the reaction mixture was stirred at 35° C. for 2 h. The reaction mixture was cooled to rt, washed with water, dried over sodium sulfate, and evaporated to give desired product as oil (8.9 g, 92%) which was used as such for the next step. $^1$HNMR (300 MHz, CDCl$_3$): δ 1.19-1.67 (m, 6H), 4.17-4.38 (m, 3H), 6.65-6.80 (m, 3H), 7.20-7.35 (m, 2H).

Step c: Synthesis of ethyl N-(2-chloro-5-nitropyrimidin-4-yl)-N-phenylalaninate A solution of ethyl N-phenylalaninate (9.65 g, 50 mmol) and 2,4-dichloro-5-nitropyrimidine (9.7 g, 50 mmol) in anhydrous dichloromethane (100 mL) was stirred for 5 minutes at rt under nitrogen. The solution was then cooled to 0° C. (Ice bath) followed by addition of imidazole (3.41 g, 50 mmol). The resulting reaction mixture was allowed to warm up to rt in 30 min and further heated at 50° C. for 2 h. The reaction was then cooled to rt, washed with water, dried over sodium sulfate and evaporated to give a crude residue, which was purified by silica gel flash chromatography (eluent: ethyl acetate-hexane mixture (5:95)) to afford desired product (22%). $^1$HNMR (300 MHz, CDCl$_3$): δ 1.29 (t, J=7.2 Hz, 3H), 1.63 (d, J=7.5 Hz, 3H), 4.18-4.27 (m, 2H), 4.90 (q, J=7.2 Hz, 1H), 7.19 (d, J=6.9 Hz, 2H), 7.26-7.39 (m, 3H) and 8.52 (s, 1H).

Step d: 2-chloro-7-methyl-8-phenyl-7,8-dihydropteridin-6(5H)-one

To a stirred solution of ethyl N-(2-chloro-5-nitropyrimidin-4-yl)-N-phenylalaninate (1.6 g, 4.56 mmol) in glacial acetic acid (35 mL) was added iron powder (1.6 g, 28.57 mmol). The resulting mixture was heated at 70° C. for 2 h. The insoluble material was then filtered off celite to give a clear solution. The bulk of solvent was evaporated to give a crude residue, which was purified by silica gel flash chromatography (eluent: 2% methanol in dichloromethane) to afford desired product (75%). $^1$HNMR (300 MHz, DMSOd$_6$): δ 1.29 (d, J=6.6 Hz, 3H), 4.58-4.60 (m, 1H), 7.36-7.50 (m, 5H), 7.70 (s, 1H) and 10.94 (s, 1H).

Step e: Synthesis of 2-chloro-7-methyl-5,8-diphenyl-7,8-dihydropteridin-6(5H)-one To a stirred solution of 2-chloro-7-methyl-8-phenyl-7,8-dihydropteridin-6(5H)-one (1.59 g, 5.78 mmol) in dichloromethane (75 mL) was added triethylamine (8.07 ml, 57.8 mmol), cupric acetate (2.09 g, 11.56 mmol) and phenylboronic acid (1.41 g, 11.56 mmol) followed by 4 Å molecular sieves (2 g). The resulting mixture was stirred for 48 h at rt with an air balloon on the top. The reaction mixture was then filtered over celite to give a clear solution. The solution was washed with aqueous saturated sodium bicarbonate (50 mL×2), dried over anhydrous sodium sulfate and evaporated to give a crude material, which was then purified by silica gel column chromatography (eluent: 2% methanol in dichloromethane) to give the desired product (750 mg, 37%). $^1$HNMR (300 MHz, CDCl$_3$): δ 1.65 (d, J=6.9 Hz, 3H), 4.82 (q, J=6.9 Hz, 1H) and 7.36-7.65 (m, 11H).

Step f: Synthesis of 2-(1H-indazol-5-ylamino)-7-methyl-5,8-diphenyl-7,8-dihydropteridin-6(5H)-one

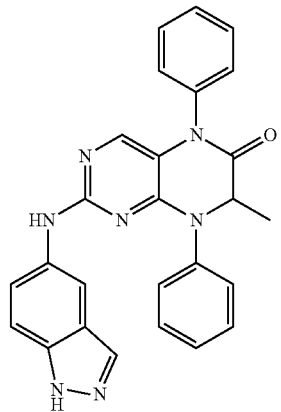 [SMILES: CC1C(=O)N(c2ccccc2)c2cnc(Nc3ccc4[nH]ncc4c3)nc2N1c1ccccc1]

To a mixture of 2-chloro-7-methyl-5,8-diphenyl-7,8-dihydropteridin-6(5H)-one (175 mg, 0.5 mmol), 5-aminoindazole (99 mg, 0.75 mmol), in trifluoroethanol (2 mL) in a microwave reactor vial was added trifluoroacetic acid (171 mg). The vial was then sealed and heated in a microwave reactor at 125° C. for 30 minutes. The reaction mixture was then diluted with ethyl acetate (25 mL) and washed with aqueous saturated aq. sodium bicarbonate. The organic layer was dried (Na$_2$SO$_4$) and evaporated to give a crude material, which was then purified by silica gel column chromatography (eluent: 2% methanol in dichloromethane) to give the desired product (40%).

Examples 179-183 were prepared according to procedures similar to the preparation of Example 178, using corresponding starting materials and intermediates. For example, for the synthesis of example 180, ethyl (2S)-2-hydroxypropanoate was used in the step a of the synthesis, 4-fluoroaniline was used in the step b of the synthesis, (3-cyanophenyl)boronic acid was used in the step e of the synthesis and 7-fluoro-1H-indazol-5-amine was used in the step f of the synthesis.

| Ex. # | Chemical Name | Analytical data |
|---|---|---|
| 184 | 3-[(7R)-2-(1H-indazol-5-ylamino)-7-methyl-6-oxo-8-(tetrahydro-2H-pyran-4-yl)-7,8-dihydropteridin-5(6H)-yl]benzonitrile | $^1$H NMR (CDCl$_3$, 300 MHz) δ 1.50 (d, J = 6.9 Hz, 3H), 1.75-1.79 (m, 1H), 1.92-2.00 (m, 1H), 2.12-2.17 (m, 2H), 3.51-3.61(m, 2H), 4.12-4.16 (m, 2H), 4.45 (q, J = 6.9 Hz, 1H), 4.56-4.62 (m, 1H), 6.96 (s, 1H), 7.18(s, 1H), 7.37-7.45 (m, 2H), 7.51-7.54 (m, 1H), 7.60-7.67 (m, 2H), 7.73-7.76 (m, 1H), 8.01(s, 1H), 8.09 (s, 1H), 10.09 (br s, 1H). MS(ES$^+$): m/z = 481.13 (100) [MH$^+$]. HPLC: t$_R$ = 2.03 (ZQ3, Polar_5 min). [α]$_D$ = −47.5(c = 0.8 in CH$_2$Cl$_2$). |
| 185 | 3-[(7R)-2-[(4-fluoro-1H-indazol-5-yl)amino]-7-methyl-6-oxo-8-(tetrahydro-2H-pyran-4-yl)-7,8-dihydropteridin-5(6H)-yl]benzonitrile | $^1$H NMR (CDCl$_3$, 300 MHz) δ 1.49 (d, J = 6.6 Hz, 3H), 1.70-1.74 (m, 1H), 1.80-1.92 (m, 1H), 2.04-2.14 (m, 2H), 3.39-3.56 (m, 2H), 4.05-4.12 (m, 2H), 4.40-4.57 (m, 2H), 6.88 (s, 1H), 7.14 (1H), 7.24-7.26 (m, 1H), 7.51 (d, J = 7.8 Hz, 1H), 7.58 (s, 1H), 7.64 (t, J = 7.5 Hz, 1H), 7.72-7.76 (m, 1H), 7.98-8.04 (m, 1H), 8.12 (s, 1H). MS(ES$^+$): m/z = 498.72 [MH$^+$]. HPLC: t$_R$ = 2.14 (ZQ3, Polar_5 min). |
| 186 | 3-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]benzonitrile | $^1$H NMR (CDCl$_3$, 400 MHz): δ 1.44 (d, J = 6.8 Hz, 3 H), 1.71 (m, 1 H), 1.89 (m, 1 H), 2.05-2.10 (m, 2 H), 3.48-3.56 (m, 2 H), 4.06-4.11 (m, 2 H), 4.40 (q, J = 6.8 Hz, 1 H), 4.55 (m, 1 H), 7.04 (s, 1 H), 7.13 (s, 1 H), 7.42 (dd, J = 1.6, 12.4 Hz, 1 H), 7.46 (d, J = 8.0 Hz, 1 H), 7.53 (m, 1 H), 7.58 (t, J = 6.4 Hz, 1 H), 7.59 (s, 1 H), 7.68 (dt, J = 1.6, 8.0 Hz, 1 H), 7.96 (d, J = 3.6 Hz, 1 H), 10.52 (s, br, 1 H). MS (ES$^+$): m/z = 499.39 [MH$^+$]. HPLC: t$_R$ = 0.75 min (TOF, polar_2 min). |
| 187 | (7R)-5-(3,4-dimethoxyphenyl)-2-[(3-fluoro-1H-indazol-5-yl)amino]-7-methyl-8-(tetrahydro-2H-pyran-4-yl)-7,8-dihydropteridin-6(5H)-one | 1H NMR (400 MHz, CD$_3$OD): δ 1.50 (d, J = 6.57 Hz, 3H), 1.78 (d, J = 12.63 Hz, 1H), 1.92-2.30 (m, 3H), 3.50-3.67 (m, 2H), 3.84 (s, 3H), 3.91 (s, 3H), 4.03-4.16 (m, 2H), 4.50 (q, J = 6.74 Hz, 1H), 4.64-4.76 (m, 1H), 6.77-6.92 (m, 2H), 7.05-7.17 (m, 2H), 7.36 (dd, J = 9.22, 1.89 Hz, 1H), 7.47 (dd, J = 9.1, 2.02 Hz, 1H), 8.08 (d, J = 1.2 Hz, 1H). MS(ES$^+$): m/z = 534.48[MH$^+$]. HPLC: t$_R$ = 0.75 (analytical_2 min, UPLC). |
| 188 | (7R)-5-(3,4-dimethoxyphenyl)-2-[(7-fluoro-1H-indazol-5-yl)amino]-7-methyl-8-(tetrahydro-2H-pyran-4-yl)-7,8-dihydropteridin-6(5H)-one | $^1$H NMR (400 MHz, CD$_3$OD): δ 1.50 (d, J = 6.5 Hz, 3H), 1.77 (d, J = 11.3 Hz, 1H), 2.08 (br. s., 2H), 2.26 (d, J = 8.5 Hz, 1H), 3.47-3.65 (m, 2H), 3.83 (s, 3H), 3.90 (s, 3H), 4.04-4.15 (m, 2H), 4.49 (d, J = 6.0 Hz, 1H), 4.59 (br. s., 1H), 6.87 (br. s., 2H), 7.12 (d, J = 8.3 Hz, 2H), 7.46 (d, J = 12.8 Hz, 1H), 7.79 (br. s., 1H), 8.03 (br. s., 1H). MS(ES$^+$): m/z = 534.45[MH$^+$]. HPLC: t$_R$ = 0.72 min (analytical_2 min, UPLC). |
| 189 | (7R)-2-[(7-fluoro-1H-indazol-5-yl)amino]-5-(3-fluorophenyl)-7-methyl-8-(tetrahydro-2H-pyran-4-yl)-7,8-dihydropteridin-6(5H)-one | $^1$H NMR (400 MHz, CD$_3$OD): δ 1.50 (d, J = 6.5 Hz, 3H), 1.77 (d, J = 11.3 Hz, 1H), 2.08 (br. s., 2H), 2.26 (d, J = 8.3 Hz, 1H), 3.45-3.62 (m, 2H), 4.00-4.16 (m, 2H), 4.50 (d, J = 6.5 Hz, 1H), 4.59 (br. s., 1H), 7.14 (d, J = 5.5 Hz, 2H), 7.28 (t, J = 7.8 Hz, 1H), 7.46 (d, J = 13.1 Hz, 1H), 7.55-7.66 (m, 1H), 7.79 (br. s., 1H), 8.04 (br. s., 1H). MS(ES$^+$): m/z = 492.36[MH$^+$]. HPLC: t$_R$ = 0.76 min (analytical_2 min, UPLC). |
| 190 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-methoxybenzonitrile | $^1$H NMR (400 MHz, CD$_3$OD): δ 8.02 (d, J = 3.3 Hz, 1H), 7.79 (d, J = 1.5 Hz, 1H), 7.66 (d, J = 2.0 Hz, 1H), 7.53-7.60 (m, 1H), 7.46 (d, J = 13.1 Hz, 1H), 7.36 (d, J = 9.1 Hz, 1H), 7.10 (s, 1H), 4.60 (br. s., 1H), 4.50 (q, J = 6.8 Hz, 1H), 4.05-4.13 (m, 2H), 4.03 (s, 3H), 3.49-3.62 (m, 2H), 2.25 (dd, J = 4.7, 12.3 Hz, 1H), 2.02-2.13 (m, 2H), 1.77 (d, J = 12.9 Hz, 1H), 1.49 (d, J = 6.6 Hz, 3H). MS (ES$^+$): m/z = 529.21 [MH$^+$]. UPLC: t$_R$ = 0.65 min (TOF: polar_2 min). |
| 191 | (7R)-2-[(7-fluoro-1H-indazol-5-yl)amino]-7-methyl-5-(pyridin-3-yl)-8-(tetrahydro-2H-pyran-4-yl)-7,8-dihydropteridin-6(5H)-one | $^1$H NMR (400 MHz, CD$_3$OD): δ 1.52 (d, J = 6.82 Hz, 4H), 1.74-1.86 (m, 1H), 2.03-2.13 (m, 2H), 3.49-3.64 (m, 4H), 4.09 (d, J = 13.8 Hz, 2H), 7.11 (s, 1H), 7.48 (d, J = 13.1 Hz, 1H), 7.65 (dd, J = 8.7, 4.9 Hz, 1H), 7.80 (d, J = 1.5 Hz, 1H), 7.84-7.91 (m, 1H), 8.02 (br. s., 1H), 8.50-8.50 (m, 1H), 8.67 (dd, J = 4.9, 1.39 Hz, 1H). MS(ES$^+$): m/z = 475.32 [MH$^+$]. HPLC: t$_R$ = 0.59 min (analytical_2 min, UPLC). |

-continued

| Ex. # | Chemical Name | Analytical data |
|---|---|---|
| 192 | (7R)-2-[(7-fluoro-1H-indazol-5-yl)amino]-5-(6-methoxypyridin-3-yl)-7-methyl-8-(tetrahydro-2H-pyran-4-yl)-7,8-dihydropteridin-6(5H)-one | $^1$H NMR (400 MHz, CD$_3$OD): δ 1.50 (d, J = 6.8 Hz, 3H), 1.77 (d, J = 11.3 Hz, 1H), 2.00-2.13 (m, 2H), 2.19-2.33 (m, 1H), 3.46-3.64 (m, 2H), 3.98 (s, 3H), 4.03-4.13 (m, 2H), 4.51 (q, J = 6.40 Hz, 1H), 4.59 (br. s., 1H), 6.98 (d, J = 8.5 Hz, 1H), 7.48 (d, J = 13.14 Hz, 1H), 7.61(d, J = 7.8 Hz, 1H), 7.80 (br. s., 1H), 7.99-8.14 (m, 2H). MS(ES$^+$): m/z = 505.57[MH$^+$]. HPLC: t$_R$ = 0.71 min (analytical_2 min, UPLC). |
| 193 | (7R)-2-[(7-fluoro-1H-indazol-5-yl)amino]-7-methyl-5-[6-(4-methylpiperazin-1-yl)pyridin-3-yl]-8-(tetrahydro-2H-pyran-4-yl)-7,8-dihydropteridin-6(5H)-one | 1H NMR (400 MHz, CDCl$_3$): δ 1.50 (d, J = 6.5 Hz, 3H), 1.79 (d, J = 12.13 Hz, 2H), 2.09-2.20 (m, 2H), 2.45 (br. s., 3H), 2.65 (br. s., 4H), 3.59 (ddd, J = 11.75, 9.85, 5.68 Hz, 2H), 3.73 (br. s., 4H), 4.06-4.21 (m, 2H), 4.46 (q, J = 6.82 Hz, 1H), 4.56-4.71 (m, 1H), 6.76 (d, J = 9.09 Hz, 1H), 7.04 (br. s., 1H), 7.31 (s, 1H), 7.35 (dd, J = 8.72, 2.15 Hz, 1H), 7.49 (dd, J = 12.63, 1.52 Hz, 1H), 7.66 (d, J = 1.52 Hz, 1H), 7.99-8.09 (m, 2H). MS(ES$^+$): m/z = 573.74 [MH$^+$]. HPLC: t$_R$ = 0.50 (analytical_2 min, UPLC). |
| 194 | 3-[(7R)-2-[(3,5-difluoro-4-hydroxyphenyl)amino]-7-methyl-6-oxo-8-(tetrahydro-2H-pyran-4-yl)-7,8-dihydropteridin-5(6H)-yl]benzonitrile | $^1$H NMR (400 MHz, CD$_3$OD): δ 7.84-7.90 (m, 1H), 7.70-7.81 (m, 2H), 7.64 (d, J = 8.1 Hz, 1H), 7.20-7.33 (m, J = 10.9 Hz, 2H), 7.08 (s, 1H), 4.67 (tt, J = 3.8, 12.1 Hz, 1H), 4.52 (q, J = 6.8 Hz, 1H), 4.04-4.15 (m, 2H), 3.60 (t, J = 11.7 Hz, 2H), 2.08-2.22 (m, 2H), 1.92-2.05 (m, J = 3.9, 11.7 Hz, 1H), 1.78 (d, J = 11.1 Hz, 1H), 1.50 (d, J = 6.6 Hz, 3H). |
| 195 | 2-Ethoxy-5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]benzonitrile | $^1$H NMR (400 MHz, CD$_3$OD): δ 8.02 (br. s., 1H), 7.79 (s, 1H), 7.64 (d, J = 2.3 Hz, 1H), 7.53 (d, J = 8.8 Hz, 1H), 7.46 (d, J = 13.1 Hz, 1H), 7.33 (d, J = 9.1 Hz, 1H), 7.10 (s, 1H), 4.59 (t, J = 11.5 Hz, 1H), 4.50 (q, J = 6.8 Hz, 1H), 4.28 (q, J = 7.0 Hz, 2H), 4.04-4.12 (m, 2H), 3.49-3.63 (m, 2H), 2.17-2.31 (m, 1H), 2.00-2.13 (m, 2H), 1.76 (d, J = 12.1 Hz, 1H), 1.45-1.53 (m, 6H). MS (ES$^+$): m/z = 543.22 [MH$^+$]. UPLC: t$_R$ = 0.71 min (TOF: polar_2 min). |
| 196 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-(propan-2-yloxy)benzonitrile | $^1$H NMR (400 MHz, CD$_3$OD): δ 8.02 (d, J = 2.8 Hz, 1H), 7.79 (s, 1H), 7.64 (d, J = 2.5 Hz, 1H), 7.52 (d, J = 8.8 Hz, 1H), 7.47 (d, J = 12.6 Hz, 1H), 7.36 (d, J = 9.1 Hz, 1H), 7.11 (s, 1H), 4.59 (d, J = 7.1 Hz, 1H), 4.50 (q, J = 6.7 Hz, 1H), 4.04-4.13 (m, 2H), 3.46-3.62 (m, 3H), 2.25 (dd, J = 4.5, 12.1 Hz, 1H), 2.08 (br. s., 2H), 1.77 (d, J = 12.6 Hz, 1H), 1.49 (d, J = 6.6 Hz, 3H), 1.44 (d, J = 6.1 Hz, 6H). MS (ES$^+$): m/z = 557.23 [MH$^+$]. UPLC: t$_R$ = 0.76 min (TOF: polar_2 min). |
| 197 | 2-Methoxy-5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]benzonitrile. | $^1$H NMR (400 MHz, CD$_3$OD): δ 7.80 (d, J = 1.8 Hz, 1H), 7.65 (d, J = 2.0 Hz, 1H), 7.56 (dd, J = 1.9, 9.0 Hz, 1H), 7.35 (d, J = 9.1 Hz, 1H), 7.19 (dd, J = 2.0, 8.3 Hz, 1H), 7.09 (s, 1H), 6.97 (d, J = 8.6 Hz, 1H), 4.55-4.65 (m, 1H), 4.49 (q, J = 6.7 Hz, 1H), 4.09 (d, J = 11.4 Hz, 2H), 4.03 (s, 3H), 3.58 (t, J = 11.7 Hz, 2H), 1.94-2.27 (m, 3H), 1.76 (d, J = 12.4 Hz, 1H), 1.48 (d, J = 6.8 Hz, 3H). MS (ES$^+$): m/z = 528.19 [MH$^+$]. UPLC: t$_R$ = 0.62 min (TOF: polar_2 min). |
| 198 | 2-Ethoxy-5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]benzonitrile. | $^1$H NMR (400 MHz, CD$_3$OD): δ 7.81 (d, J = 2.0 Hz, 1H), 7.64 (d, J = 2.3 Hz, 1H), 7.53 (dd, J = 2.0, 8.8 Hz, 1H), 7.33 (d, J = 9.1 Hz, 1H), 7.19 (dd, J = 2.0, 8.3 Hz, 1H), 7.09 (s, 1H), 6.97 (d, J = 8.3 Hz, 1H), 4.61 (tt, J = 3.6, 11.9 Hz, 1H), 4.50 (q, J = 6.8 Hz, 1H), 4.28 (q, J = 6.9 Hz, 2H), 4.06-4.11 (m, 2H), 3.52-3.64 (m, 2H), 2.07-2.26 (m, 2H), 1.94-2.06 (m, 2H), 1.73-1.80 (m, 1H), 1.46-1.51 (m, 5H). MS (ES$^+$): m/z = 542.21 [MH$^+$]. UPLC: t$_R$ = 0.68 min (TOF: polar_2 min). |
| 199 | 5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]-2-(propan-2-yloxy)benzonitrile | $^1$H NMR (400 MHz, CD$_3$OD): δ 7.80 (d, J = 1.8 Hz, 1H), 7.63 (s, 1H), 7.51 (d, J = 7.6 Hz, 1H), 7.35 (d, J = 8.8 Hz, 1H), 7.19 (dd, J = 1.9, 8.7 Hz, 1H), 7.10 (s, 1H), 6.96-7.00 (m, 1H), 4.60 (d, J = 11.6 Hz, 1H), 4.50 (q, J = 6.9 Hz, 1H), 4.09 (d, J = 10.9 Hz, 2H), 3.54-3.64 (m, 2H), 2.07-2.22 (m, 2H), 2.01 (dd, J = 4.4, 11.7 Hz, 1H), 1.77 (d, J = 10.4 Hz, 1H), 1.49 (d, J = 6.8 |

| Ex. # | Chemical Name | Analytical data |
|---|---|---|
| | | Hz, 3H), 1.44 (d, J = 6.1 Hz, 7H). MS (ES+): m/z = 556.23 [MH+]. UPLC: $t_R$ = 0.73 min (TOF: polar_2 min). |
| 200 | 2-methoxy-5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]benzonitrile | $^1$H NMR (400 MHz, CD$_3$OD): δ 8.62 (d, J = 2.3 Hz, 1H), 8.53 (d, J = 2.3 Hz, 1H), 8.04 (s, 1H), 7.65 (d, J = 2.0 Hz, 1H), 7.53 (dd, J = 2.0, 9.1 Hz, 1H), 7.33 (d, J = 9.1 Hz, 1H), 7.11 (s, 1H), 4.45-4.57 (m, 2H), 4.27 (q, J = 7.1 Hz, 2H), 3.99-4.10 (m, 2H), 3.43-3.59 (m, 2H), 2.23 (dq, J = 4.4, 12.2 Hz, 1H), 1.99-2.08 (m, 2H), 1.74 (d, J = 12.1 Hz, 1H), 1.52 (s, 6H). MS (ES+): m/z = 512.21 [MH+]. UPLC: $t_R$ = 0.58 min (TOF: polar_2 min). |
| 201 | 2-Ethoxy-5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]benzonitrile. | $^1$H NMR (400 MHz, CD$_3$OD): δ 8.62 (d, J = 2.3 Hz, 1H), 8.53 (d, J = 2.3 Hz, 1H), 8.04 (s, 1H), 7.65 (d, J = 2.0 Hz, 1H), 7.53 (dd, J = 2.0, 9.1 Hz, 1H), 7.33 (d, J = 9.1 Hz, 1H), 7.11 (s, 1H), 4.45-4.57 (m, 2H), 4.27 (q, J = 7.1 Hz, 2H), 3.99-4.10 (m, 2H), 3.43-3.59 (m, 2H), 2.23 (dq, J = 4.4, 12.2 Hz, 1H), 1.99-2.08 (m, 2H), 1.74 (d, J = 12.1 Hz, 1H), 1.52 (s, 6H). MS (ES+): m/z = 526.22 [MH+]. UPLC: $t_R$ = 0.64 min (TOF: polar_2 min). |
| 202 | 5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]-2-(propan-2-yloxy)benzonitrile | $^1$H NMR (400 MHz, CD$_3$OD): δ 8.63 (d, J = 2.0 Hz, 1H), 8.53 (d, J = 2.3 Hz, 1H), 8.04 (s, 1H), 7.64 (s, 1H), 7.52 (d, J = 7.8 Hz, 1H), 7.36 (d, J = 9.1 Hz, 1H), 7.12 (s, 1H), 4.44-4.60 (m, 2H), 4.00-4.13 (m, 2H), 3.40-3.60 (m, 3H), 2.17-2.30 (m, 1H), 2.02-2.08 (m, 2H), 1.75 (d, J = 12.6 Hz, 1H), 1.49 (d, J = 6.6 Hz, 3H), 1.44 (d, J = 6.1 Hz, 6H). MS (ES+): m/z = 540.24 [MH+]. UPLC: $t_R$ = 0.69 min (TOF: polar_2 min). |
| 203 | 5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]-2-methoxybenzonitrile. | $^1$H NMR (400 MHz, CD$_3$OD): δ 7.65 (br. s., 1H), 7.56 (d, J = 7.3 Hz, 1H), 7.51 (s, 1H), 7.31-7.39 (m, 2H), 7.13 (s, 1H), 4.65 (t, J = 12.0 Hz, 1H), 4.51 (q, J = 6.7 Hz, 1H), 4.10 (d, J = 11.1 Hz, 2H), 4.03 (s, 3H), 3.60 (t, J = 11.9 Hz, 2H), 2.09-2.25 (m, 2H), 1.96-2.08 (m, J = 4.5 Hz, 1H), 1.78 (d, J = 11.9 Hz, 1H), 1.49 (d, J = 6.6 Hz, 3H). MS (ES+): m/z = 546.19 [MH+]. UPLC: $t_R$ = 0.70 min (TOF: polar_2 min). |
| 204 | 2-Ethoxy-5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]benzonitrile. | $^1$H NMR (400 MHz, CD$_3$OD): δ 7.64 (s, 1H), 7.49-7.55 (m, 2H), 7.30-7.38 (m, 2H), 7.13 (s, 1H), 4.66 (s, 1H), 4.51 (d, J = 6.8 Hz, 1H), 4.10 (d, J = 11.9 Hz, 2H), 3.61 (t, J = 11.7 Hz, 2H), 2.09-2.23 (m, 2H), 1.96-2.07 (m, 1H), 1.78 (d, J = 13.1 Hz, 1H), 1.45-1.53 (m, 8H). MS (ES+): m/z = 560.21 [MH+]. UPLC: $t_R$ = 0.77 min (TOF: polar_2 min) |
| 205 | 5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]-2-(propan-2-yloxy)benzonitrile. | $^1$H NMR (400 MHz, CD$_3$OD): δ 7.60-7.64 (m, 1H), 7.48-7.54 (m, 2H), 7.31-7.38 (m, 2H), 7.12-7.15 (m, 1H), 4.54-4.72 (m, 1H), 4.40-4.54 (m, 1H), 4.06-4.15 (m, 2H), 3.55-3.65 (m, 3H), 2.10-2.18 (m, 2H), 1.96-2.06 (m, 1H), 1.74-1.81 (m, 1H), 1.47-1.50 (m, 3H), 1.43-1.45 (m, 6H). MS (ES+): m/z = 574.22 [MH+]. UPLC: $t_R$ = 0.81 min (TOF: polar_2 min). |
| 206 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-(4-methylpiperazin-1-yl)benzonitrile | $^1$H NMR (CDCl$_3$, 400 MHz): δ 1.48 (d, J = 6.8 Hz, 3 H), 1.76 (m, 1 H), 1.96 (dq, J = 3.6, 11.60 Hz, 1 H), 2.07-2.17 (m, 2 H), 2.38 (s, 3 H), 2.65 (t, J = 4.8 Hz, 4 H), 3.35 (t, J = 4.8 Hz, 4 H), 3.56 (q, J = 10.4 Hz, 2 H), 4.11-4.14 (m, 2 H), 4.43 (q, J = 6.8 Hz, 1 H), 4.59 (m, 1 H), 6.94 (s, 1 H), 7.09 (d, J = 8.8 Hz, 1 H), 7.24-7.25 (m, 2 H), 7.32 (dd, J = 2.0, 8.8 Hz, 1 H), 7.43 (d, J = 2.0 Hz, 1 H), 7.47 (d, J = 12.8 Hz, 1 H), 7.65 (s, 1 H), 8.01 (d, J = 2.8 Hz, 1 H). MS (ES+): m/z = 597.46 [MH+]. HPLC: $t_R$ = 0.54 min (TOF, polar_2 min). |

Examples 184-206 were prepared according to procedures similar to the preparation of Example 18, using corresponding starting materials and intermediates. For example, for the synthesis of example 186, tetrahydro-4H-pyran-4-one and D-Alanine methyl ester hydrochloride were used in the step a of the synthesis, (3-cyanophenyl)boronic acid was used in the step d of the synthesis and 7-fluoro-1H-indazol-5-amine was used in the step e of the synthesis.

| Ex. # | Chemical Name | Analytical data |
|---|---|---|
| 207 | 3-[(7R)-8-(4,4-dimethylcyclohexyl)-2-(1H-indazol-5-ylamino)-7-methyl-6-oxo-7,8-dihydropteridin-5(6H)-yl]benzonitrile | ¹H NMR (CDCl₃, 300 MHz) δ 0.93-0.95 (m, 6H), 1.39-1.46 (m, 5H), 1.51-1.61 (m, 4H), 1.82-1.84 (m, 1H), 1.97-1.99 (m, 1 H), 4.35-4.47 (m, 2H), 7.03 (s, 1H), 7.29-7.32 (m, 1H), 7.37-7.41 (m, 1H), 7.46-7.48 (m, 1H), 7.54 (s, 1H), 7.61 (t, J = 8.1 Hz, 1H), 7.70-7.72 (m, 1H), 7.89 (s, 1H), 8.10 (s, 1H). MS(ES⁺): m/z = 507.14 [MH⁺]. HPLC: t$_R$ = 2.82 (ZQ3, Polar_5 min). |
| 208 | (7R)-8-(4,4-dimethylcyclohexyl)-2-[(7-fluoro-1H-indazol-5-yl)amino]-7-methyl-5-(pyridin-3-yl)-7,8-dihydropteridin-6(5H)-one | ¹H NMR (400 MHz, CD₃OD): δ 1.00 (d, J = 5.5 Hz, 6H), 1.43-1.71 (m, 8H), 1.79 (qd, J = 12.5, 3.54 Hz, 1H), 1.96-2.08 (m, 2H), 4.39-4.51 (m, 1H), 4.55 (q, J = 6.8 Hz, 1H), 7.09 (s, 1H), 7.48 (d, J = 13.1 Hz, 1H), 7.65 (dd, J = 8.2, 4.9 Hz, 1H), 7.80 (d, J = 1.2 Hz, 1H), 7.86(dt, J = 8.0, 1.7 Hz, 1H), 7.99 (d, J = 2.7 Hz, 1H), 8.54 (d, J = 2.2 Hz, 1H), 8.67 (dd, J = 4.9, 1.1 Hz, 1H). MS(ES⁺): m/z = 501.44[MH⁺]. HPLC: t$_R$ = 0.93 min (analytical_2 min, UPLC). |
| 209 | 3-[(7R)-8-(4,4-dimethylcyclohexyl)-2-[(7-fluoro-1H-indazol-5-yl)amino]-7-methyl-6-oxo-7,8-dihydropteridin-5(6H)-yl]benzonitrile | ¹H NMR (400 MHz, CD₃OD): δ 1.01 (d, J = 5.3 Hz, 6H), 1.50-1.70 (m, 7H), 1.74-1.87 (m, 1H), 1.97-2.08 (m, 3H), 4.41-4.50 (m, 1H), 4.54 (q, J = 6.8 Hz, 1H), 7.08 (s, 1H), 7.49 (d, J = 13.3 Hz, 1H), 7.62-7.68 (m, 1H), 7.77 (t, J = 7.9 Hz, 1H), 7.80 (d, J = 1.5 Hz, 2H), 7.87-7.91 (m, 1H), 8.00 (d, J = 3.2 Hz, 1H). MS(ES⁺): m/z = 525.41[MH⁺]. HPLC: t$_R$ = 1.06 min (analytical_2 min, UPLC). |
| 210 | (7R)-5-(3,4-dimethoxyphenyl)-8-(4,4-dimethylcyclohexyl)-2-[(7-fluoro-1H-indazol-5-yl)amino]-7-methyl-7,8-dihydropteridin-6(5H)-one | ¹H NMR (400 MHz, CD₃OD): δ 0.94-1.07 (m, 6H), 1.42-1.52 (m, 5H), 1.53-1.68 (m, 3H), 1.73-1.87 (m, 1H), 1.94-2.09 (m, 2H), 3.82 (s, 3H), 3.89 (s, 3H), 4.27-4.45 (m, 1H), 4.50 (q, J = 6.6 Hz, 1H), 6.72-6.96 (m, 2H), 7.02-7.19 (m, 2H), 7.47 (d, J = 13.1 Hz, 1H), 7.78 (d, J = 1.2 Hz, 1H), 7.98 (d, J = 2.7 Hz, 1H). MS(ES⁺): m/z = 560.50[MH⁺]. HPLC: t$_R$ = 1.00 min (analytical_2 min, UPLC). |
| 211 | (7R)-8-(4,4-dimethylcyclohexyl)-2-[(7-fluoro-1H-indazol-5-yl)amino]-5-(3-fluorophenyl)-7-methyl-7,8-dihydropteridin-6(5H)-one | 1H NMR (400 MHz, CD₃OD): δ 1.00 (d, J = 5.31 Hz, 6H), 1.42-1.53 (m, 5H), 1.53-1.86 (m, 5H), 1.92-2.08 (m, 2H), 4.38-4.48 (m, 1H), 4.52 (q, J = 6.7 Hz, 1H), 7.07 (s, 1H), 7.11-7.19 (m, 2H), 7.28 (tdd, J = 8.5, 8.5, 2.4, 1.01 Hz, 1H), 7.48 (d, J = 12.8 Hz, 1H), 7.60 (td, J = 8.2, 6.3 Hz, 1H), 7.79 (d, J = 1.5 Hz, 1H), 7.99 (d, J = 3.2 Hz, 1H). MS(ES⁺): m/z = 518.41 [MH⁺]. HPLC: t$_R$ = 1.06 (analytical_2 min, UPLC). |
| 212 | 5-[(7R)-8-(4,4-dimethylcyclohexyl)-2-[(7-fluoro-1H-indazol-5-yl)amino]-7-methyl-6-oxo-7,8-dihydropteridin-5(6H)-yl]-2-(pyrrolidin-1-yl)benzonitrile | ¹H NMR (400 MHz, DMSO-d₆) δ 0.90 (s, 3 H) 0.93 (s, 3 H) 1.21-1.41 (m, 3 H) 1.44 (d, J = 6.8 Hz, 3 H) 1.49 (br. s., 3 H) 1.67-1.81 (m, 1 H) 1.81-1.92 (m, 1 H) 1.94-2.02 (m, 4 H) 3.59 (t, J = 6.5 Hz, 4 H) 4.17-4.35 (m, 1 H) 4.47-4.62 (m, 1 H) 6.90 (d, J = 9.3 Hz, 1 H) 7.04 (s, 1 H) 7.28-7.37 (m, 1 H) 7.45-7.53 (m, 1 H) 7.55 (s, 1 H) 7.81 (s, 1 H) 8.04-8.11 (m, 1 H) 9.26-10.01 (m, 1 H) 13.15-13.83 (m, 1 H). MS(ES⁺): m/z = 594.49 [MH⁺]. HPLC: t$_R$ = 1.12 (UPLC, Analytical_2 min). |
| 213 | (7R)-8-(4,4-dimethylcyclohexyl)-2-[(7-fluoro-1H-indazol-5-yl)amino]-7-methyl-5-[6-(morpholin-4-yl)pyridin-3-yl]-7,8-dihydropteridin-6(5H)-one | 1H NMR (400 MHz, CD₃OD) δ 0.85 (s, 3 H) 0.92 (s, 3 H) 1.14-1.25 (m, 1 H) 1.28-1.50 (m, 2 H) 1.55 (d, J = 2.7 Hz, 1 H) 1.66 (d, J = 6.8 Hz, 3 H) 1.68-1.75 (m, 1 H) 1.90 (d, J = 2.7 Hz, 2 H) 2.05-2.18 (m, 1 H) 3.59-3.64 (m, 4 H) 3.77-3.85 (m, 4 H) 4.18-4.33 (m, 1 H) 4.67 (d, J = 6.8 Hz, 1 H) 6.89 (s, 1 H) 7.00 (d, J = 9.0 Hz, 1 H) 7.34 (dd, J = 11.8, 1.5 Hz, 1 H) 7.53 (dd, J = 9.0, 2.5 Hz, 1 H) 7.68 (d, J = 1.7 Hz, 1 H) 8.07 (d, J = 2.5 Hz, 1 H) 8.15 (d, J = 3.2 Hz, 1 H). MS(ES⁺): m/z = 586.47 [MH⁺]. HPLC: t$_R$ = 0.97 (UPLC, Analytical_2 min). |
| 214 | (7R)-8-(4,4-dimethylcyclohexyl)-2-[(7-fluoro-1H-indazol-5-yl)amino]-7-methyl-5-[6-(pyrrolidin-1-yl)pyridin-3-yl]-7,8-dihydropteridin-6(5H)-one | ¹H NMR (400 MHz, CD₃OD) δ 0.83 (s, 3 H) 0.86-0.94 (m, 3 H) 1.19 (td, J = 13.0, 3.5 Hz, 1 H) 1.26-1.47 (m, 2 H) 1.54 (dd, J = 13.3, 1.7 Hz, 1 H) 1.64 (d, J = 6.8 Hz, 3 H) 1.69 (br. s., 1 H) 1.74-1.86 (m, 1 H) 1.89 (br. s., 1 H) 2.00-2.10 (m, 1 H) 2.10-2.21 (m, 4 H) 3.58 (t, J = 6.3 Hz, 4 H) 4.17-4.31 (m, 1 H) 4.66 (q, J = 6.6 Hz, 1 H) 6.96 (d, J = 9.3 Hz, 1 H) 7.06 (s, 1 H) 7.35 (d, J = 11.8 Hz, 1 H) 7.65-7.73 (m, 2 H) 8.04 (d, |

-continued

| Ex. # | Chemical Name | Analytical data |
|---|---|---|
| 215 | (7R)-8-(4,4-dimethylcyclohexyl)-2-[(7-fluoro-1H-indazol-5-yl)amino]-7-methyl-5-[6-(piperidin-1-yl)pyridin-3-yl]-7,8-dihydropteridin-6(5H)-one | J = 2.0 Hz, 1 H) 8.10-8.16 (m, 1 H). MS(ES$^+$): m/z = 570.42 [MH$^+$]. HPLC: t$_R$ = 0.90 (UPLC, Analytical__2 min).<br>$^1$H NMR (400 MHz, CDCl$_3$) δ 0.91 (s, 3 H) 0.96 (s, 3 H) 1.22-1.32 (m, 1 H) 1.36-1.45 (m, 1 H) 1.51 (dd, J = 13.3, 2.78 Hz, 1 H) 1.62 (dd, J = 13.3, 2.7 Hz, 1 H) 1.68 (d, J = 6.8 Hz, 3 H) 1.69-1.84 (m, 8 H) 1.94-2.11 (m, 2 H) 3.35 (dt, J = 3.2, 1.6 Hz, 1 H) 3.61-3.70 (m, 4 H) 4.30-4.44 (m, 1 H) 6.89 (d, J = 9.0 Hz, 1 H) 6.98-7.02 (m, 1 H) 7.34-7.41 (m, 2 H) 7.71 (d, J = 1.5 Hz, 1 H) 7.96 (d, J = 2.7 Hz, 1 H) 8.05-8.11 (m, 1 H). MS(ES$^+$): m/z = 584.42 [MH$^+$]. HPLC: t$_R$ = 1.11 (UPLC, Analytical__2 min). |

Examples 207-215 were prepared according to procedures similar to the preparation of Example 18, using corresponding starting materials and intermediates. For example, for the synthesis of example 209, 4,4-dimethylcyclohexanone and D-alanine methyl ester hydrochloride was used in the step a of the synthesis, (3-cyanophenyl)boronic acid was used in the step d of the synthesis and 7-fluoro-1H-indazol-5-amine was used in the step e of the synthesis.

| Ex.# | Chemical Name | Analytical data |
|---|---|---|
| 216 | 3-[(7R)-8-cyclopentyl-2-[(4-fluoro-1H-indazol-5-yl)amino]-7-methyl-6-oxo-7,8-dihydropteridin-5(6H)-yl]benzonitrile | $^1$H NMR (CDCl$_3$, 300 MHz) δ 1.46 (d, J = 6.9 Hz, 3H), 1.61-1.76 (m, 6H), 1.95-2.10 (m, 2H), 4.37-4.49 (m, 2H), 6.80 (s, 1H), 7.11 (s, 1H), 7.21-7.24 (m, 1H), 7.51-7.54 (m, 1H), 7.60-7.66 (m, 2H), 7.72-7.74 (m, 1H), 8.00-8.06 (m, 1H), 8.12 (br s, 1H), 10.15 (br s, 1H). MS(ES$^+$): m/z = 483.14 [MH$^+$]. HPLC: t$_R$ = 2.43 (ZQ3, Polar__5 min). |
| 217 | 3-[(7R)-8-cyclopentyl-7-ethyl-2-[(7-fluoro-1H-indazol-5-yl)amino]-6-oxo-7,8-dihydropteridin-5(6H)-yl]benzonitrile | $^1$H NMR (400 MHz, CD$_3$OD): δ 8.08 (d, J = 1.0 Hz, 1H), 7.93 (td, J = 1.3, 7.8 Hz, 1H), 7.80-7.84 (m, 2H), 7.76-7.80 (m, 1H), 7.66-7.72 (m, 1H), 7.63 (d, J = 8.8 Hz, 1H), 7.37 (dd, J = 1.8, 8.8 Hz, 1H), 6.67 (s, 1H), 4.56 (dd, J = 3.5, 6.8 Hz, 1H), 4.21 (t, J = 8.8 Hz, 1H), 1.84-2.17 (m, 6H), 1.45 (br. s., 4H), 1.03 (t, J = 7.5 Hz, 3H). MS (ES$^+$): m/z = 497.45 [MH$^+$]. UPLC: t$_R$ = 0.92 min (TOF: polar__2 min). |
| 218 | 3-[(7R)-8-cyclopentyl-2-[(7-fluoro-1H-indazol-5-yl)amino]-7-(hydroxymethyl)-6-oxo-7,8-dihydropteridin-5(6H)-yl]benzonitrile | $^1$H NMR (400 MHz, CD$_3$OD): δ 8.07 (d, J = 0.8 Hz, 1H), 7.93 (td, J = 1.3, 7.8 Hz, 1H), 7.75-7.85 (m, 3H), 7.67-7.73 (m, 1H), 7.62 (d, J = 8.8 Hz, 1H), 7.38 (dd, J = 2.0, 8.8 Hz, 1H), 4.59 (s, 1H), 4.24 (t, J = 8.7 Hz, 1H), 3.95-4.14 (m, 2H), 1.86-2.18 (m, 4H), 1.46 (d, J = 15.2 Hz, 4H). MS (ES$^+$): m/z = 499.44 [MH$^+$]. UPLC: t$_R$ = 0.74 min (TOF: polar__2 min). |
| 219 | 3-[(7R)-8-cyclopentyl-2-[(7-fluoro-1H-indazol-5-yl)amino]-7-methyl-6-oxo-7,8-dihydropteridin-5(6H)-yl]benzonitrile | $^1$H NMR (400 MHz, CD$_3$OD): δ 1.48 (d, J = 6.82 Hz, 3H), 1.59-1.71 (m, 2H), 1.75-1.95 (m, 4H), 1.99-2.18 (m, 2H), 4.41-4.61 (m, 2H), 7.05 (s, 1H), 7.45 (d, J = 13.1 Hz, 1H), 7.61-7.68 (m, 1H), 7.70-7.77 (m, 2H), 7.79 (s, 1H), 7.86 (d, J = 7.8 Hz, 1H), 7.98 (d, J = 3.2 Hz, 1H). MS(ES$^+$): m/z = 483.41 [MH$^+$]. HPLC: t$_R$ = 0.88 min (analytical__2 min, UPLC). |
| 220 | 3-[(7R)-8-cyclopentyl-7-(hydroxymethyl)-2-(1H-indazol-5-ylamino)-6-oxo-7,8-dihydropteridin-5(6H)-yl]benzonitrile | $^1$H NMR (400 MHz, CD$_3$OD): δ 8.07 (d, J = 0.8 Hz, 1H), 7.93 (td, J = 1.3, 7.8 Hz, 1H), 7.75-7.85 (m, 3H), 7.67-7.73 (m, 1H), 7.62 (d, J = 8.8 Hz, 1H), 7.38 (dd, J = 2.0, 8.8 Hz, 1H), 6.58 (s, 1H), 4.59 (s, 1H), 4.24 (t, J = 8.7 Hz, 1H), 3.95-4.14 (m, 2H), 1.86-2.18 (m, 4H), 1.46 (d, J = 15.2 Hz, 4H). MS (ES$^+$): m/z = 481.40 [MH$^+$]. UPLC: t$_R$ = 0.66 min (TOF: polar__2 min). |
| 221 | 3-[(7S)-8-cyclopentyl-2-[(7-fluoro-1H-indazol-5-yl)amino]-7-(fluoromethyl)-6-oxo-7,8-dihydropteridin-5(6H)-yl]benzonitrile | $^1$H NMR (400 MHz, CD$_3$OD): δ 7.99 (d, J = 3.0 Hz, 1H), 7.89 (td, J = 1.3, 8.0 Hz, 1H), 7.72-7.78 (m, 3H), 7.63-7.68 (m, 1H), 7.41 (d, J = 13.6 Hz, 1H), 6.95 (s, 1H), 4.77-4.83 (m, 1H), 4.62-4.75 (m, 2H), 4.48 (t, J = 8.7 Hz, 1H), 2.17 (dd, J = 3.4, 8.0 Hz, 1H), 2.02 (t, J = 8.2 Hz, 2H), 1.87-1.97 (m, 1H), 1.71-1.82 (m, 2H), 1.57-1.68 (m, 2H). MS (ES$^+$): m/z = 501.39 [MH$^+$]. UPLC: t$_R$ = 0.86 min (TOF: polar__2 min). |

-continued

| Ex.# | Chemical Name | Analytical data |
|------|---------------|-----------------|
| 222 | 3-[(7S)-8-cyclopentyl-7-(fluoromethyl)-2-(1H-indazol-5-ylamino)-6-oxo-7,8-dihydropteridin-5(6H)-yl]benzonitrile | $^1$H NMR (400 MHz, CD$_3$OD): δ 7.96-7.99 (m, 1H), 7.94 (s, 1H), 7.89 (td, J = 1.3, 8.0 Hz, 1H), 7.74-7.80 (m, 2H), 7.65 (ddd, J = 1.1, 2.0, 8.0 Hz, 1H), 7.44-7.47 (m, 2H), 6.92 (s, 1H), 4.62-4.84 (m, 2H), 4.37-4.48 (m, 1H), 1.87-2.17 (m, 5H), 1.66-1.77 (m, 2H), 1.53-1.63 (m, 2H). MS (ES$^+$): m/z = 483.32 [MH$^+$]. UPLC: t$_R$ = 0.79 min (TOF: polar__2 min). |

Examples 216-220 were prepared according to procedures similar to the preparation of Example 18, using corresponding starting materials and intermediates. For example, for the synthesis of example 218, methyl D-serinate and cyclopentanone were used in the step a of the synthesis, (3-cyanophenyl)boronic acid was used in the step d of the synthesis and 7-fluoro-1H-indazol-5-amine was used in the step e of the synthesis.

Example 221 was prepared according to chemistry shown below:

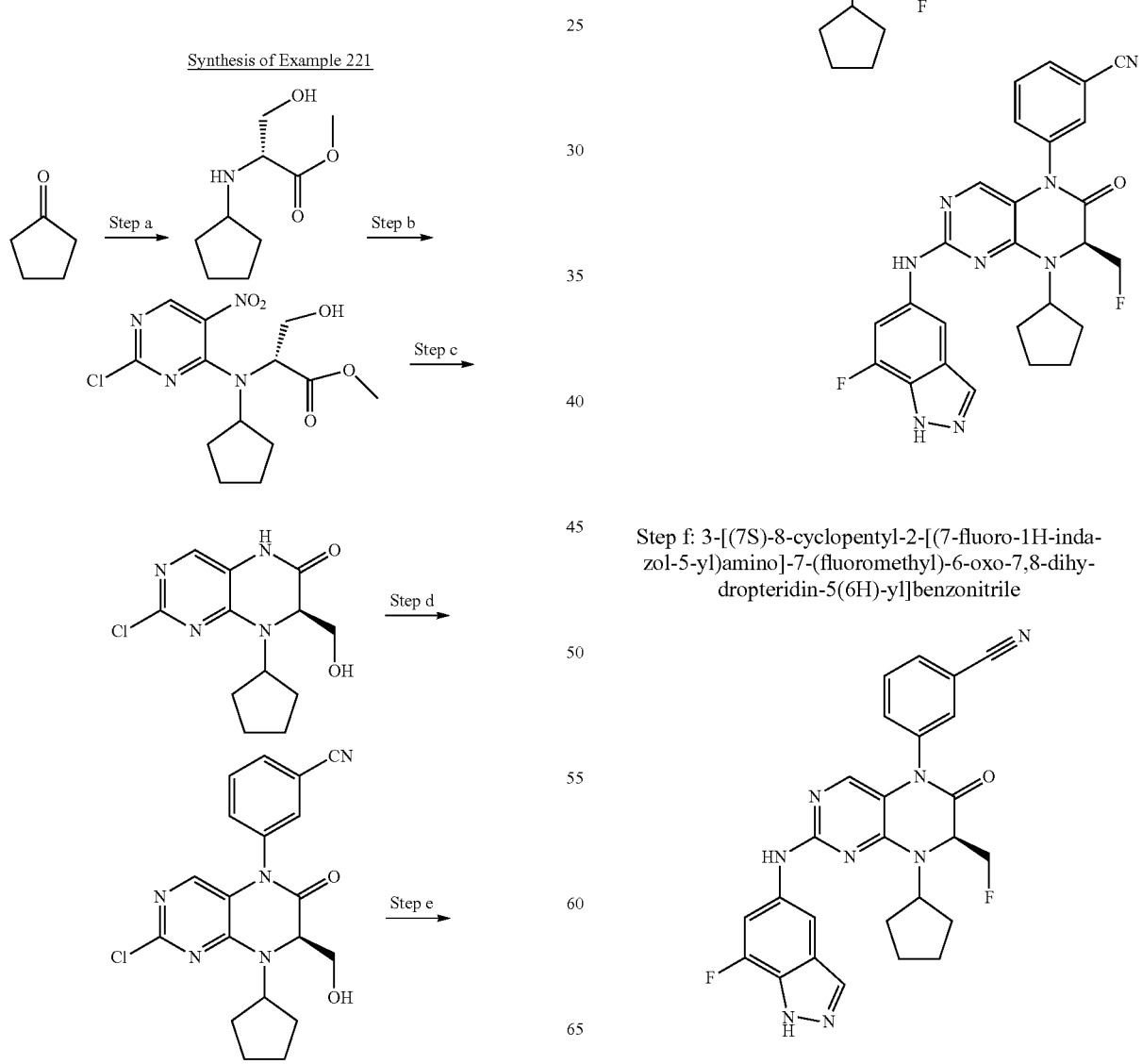

Step f: 3-[(7S)-8-cyclopentyl-2-[(7-fluoro-1H-indazol-5-yl)amino]-7-(fluoromethyl)-6-oxo-7,8-dihydropteridin-5(6H)-yl]benzonitrile This compound was prepared from 3-[(7S)-2-chloro-8-cyclopentyl-7-(fluoromethyl)-6-oxo-7,8-dihydropteridin-5(6H)-yl]benzonitrile and 7-fluoro-1H-indazol-5-amine, according to procedures similar to step e for the preparation of Example 18.

Step e: 3-[(7S)-2-chloro-8-cyclopentyl-7-(fluoromethyl)-6-oxo-7,8-dihydropteridin-5(6H)-yl]benzonitrile To a stirred solution of 3-[(7R)-2-chloro-8-cyclopentyl-7-(hydroxymethyl)-6-oxo-7,8-dihydropteridin-5(6H)-yl]benzonitrile (94 mg, 0.24 mmol) in anhydrous DCM (3 mL) was added diethylaminosulfur trifluoride (39 µL, 0.29 mmol) at −78° C. under nitrogen. The mixture was allowed to warm to rt and stirred for 18 h. The mixture was then cooled to 0° C. and quenched by saturated aqueous NaHCO$_3$ solution. The mixture was extracted with DCM (30 mL×2) and the combined organic layers were dried over Na$_2$SO$_4$, concentrated in vacuo to give a crude residue, which was purified using a silica gel flash chromatography [eluent: 0-50% EtOAc/Heptane] to afford the desired compound (24 mg, 25%). $^1$H NMR (400 MHz, CD$_3$OD): δ 7.89-7.94 (m, 1H), 7.74-7.80 (m, 2H), 7.61-7.66 (m, 1H), 7.01 (s, 1H), 4.87-5.00 (m, 1H), 4.70-4.83 (m, 1H), 4.31 (quin, J=8.4 Hz, 1H), 2.08-2.19 (m, 2H), 1.97-2.07 (m, 4H), 1.61-1.76 (m, 2H). MS (ES$^+$): m/z=386.32/388.29 [MH$^+$]. UPLC: t$_R$=1.33 min (TOF: polar_2 min).

3-[(7R)-2-Chloro-8-cyclopentyl-7-(hydroxymethyl)-6-oxo-7,8-dihydropteridin-5(6H)-yl]benzonitrile: this intermediate was prepared during synthesis of example 218. Examples 222 were prepared according to procedures similar to the preparation of Example 221, using corresponding starting materials and intermediates. More specifically, 1H-indazol-5-amine was used in the step f of the synthesis.

Examples 223 and 224 were prepared as cis/trans mixtures, according to procedures similar to the preparation of Example 18, using corresponding starting materials and intermediates, followed by separation by Supercritical Fluid Chromatography (SFC). More specifically, 4-methoxycyclohexanone and D-Alanine methyl ester hydrochloride were used in the step a of the synthesis, and 7-fluoro-1H-indazol-5-amine was used in the step e of the synthesis. Examples 225-235 were prepared according to procedures similar to the preparation of Example 18, using 4-methoxycyclohexanone, D-alanine methyl ester hydrochloride and other corresponding starting materials and intermediates, followed by Supercritical Fluid Chromatography (SFC) to give pure isomers. For example, for the synthesis of example 225, (3,4-dimethoxyphenyl)boronic acid was used during the synthesis.

Synthesis of examples 223-224

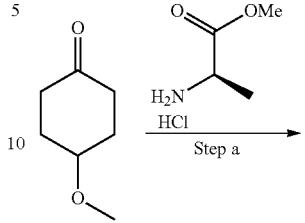

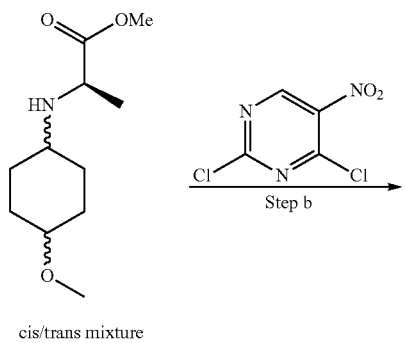

cis/trans mixture

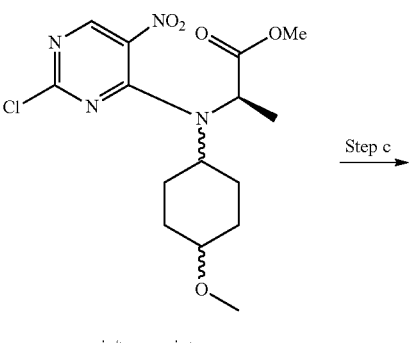

cis/trans mixture

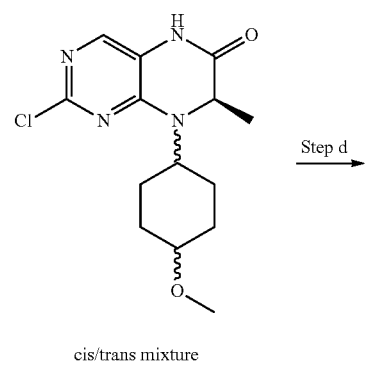

cis/trans mixture

-continued

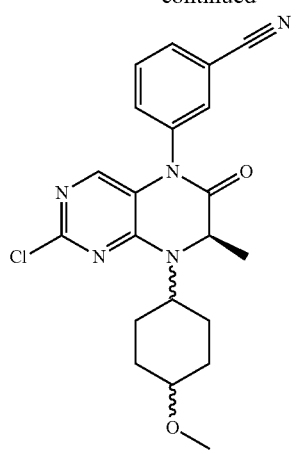

cis/trans mixture

Step e →

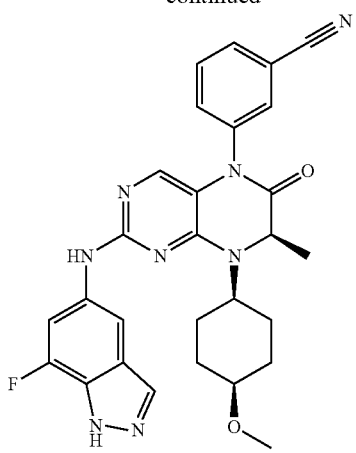

Example 223

+

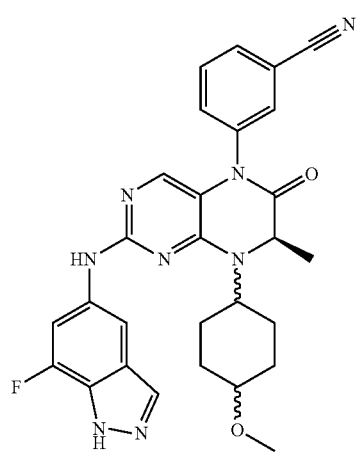

cis/trans mixture

Supercritical Fluid Chromatography(SFC) →

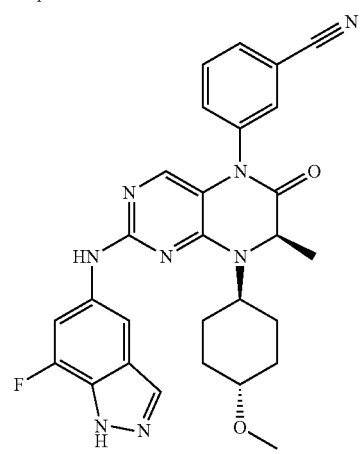

Example 224

| Ex. # | Chemical Name | Analytical data |
|---|---|---|
| 223 | 3-[(7R)-2-[(7-fluoro-1H-indazol-5-yl)amino]-8-(cis-4-methoxycyclohexyl)-7-methyl-6-oxo-7,8-dihydropteridin-5(6H)-yl]benzonitrile | $^1$H NMR (400 MHz, CD$_3$OD): δ 1.49 (d, J = 6.8 Hz, 3H), 1.56-1.69 (m, 3H), 1.85-2.03 (m, 2H), 2.07-2.22 (m, 3H), 3.37 (d, J = 0.5 Hz, 3H), 3.53 (br. s., 1H), 4.44-4.51 (m, 1H), 4.51-4.59 (m, 1H), 7.07 (s, 1H), 7.51 (d, J = 13.1 Hz, 1H), 7.64 (d, J = 8.0 Hz, 1H), 7.71-7.76 (m, 1H), 7.77-7.81 (m, 2H), 7.87 (d, J = 7.5 Hz, 1H), 7.99 (d, J = 3.0 Hz, 1H). MS(ES$^+$): m/z = 527.34[MH$^+$]. HPLC: t$_R$ = 0.86 min (analytical_2 min, UPLC). |
| 224 | 3-[(7R)-2-[(7-fluoro-1H-indazol-5-yl)amino]-8-(trans-4-methoxycyclohexyl)-7-methyl-6-oxo-7,8-dihydropteridin-5(6H)-yl]benzonitrile | $^1$H NMR (400 MHz, CD$_3$OD): δ 1.29-1.44 (m, 2H), 1.48 (d, J = 6.8 Hz, 3H), 1.65-2.03 (m, 3H), 2.21 (d, J = 11.3 Hz, 3H), 3.10-3.24 (m, 1H), 3.35 (s, 3H), 4.27-4.41 (m, 1H), 4.45 (q, J = 6.6 Hz, 1H), 7.07 (s, 1H), 7.44 (d, J = 12.6 Hz, 1H), 7.61 (d, J = 8.0 Hz, 1H), 7.69-7.78 (m, 3H), 7.84 (d, J = 8.0 Hz, 1H), 7.99 (d, J = 3.0 Hz, 1H). MS(ES$^+$): m/z = 527.30 [MH$^+$]. HPLC: t$_R$ = 0.77 min (analytical_2 min, UPLC). |
| 225 | (7R)-5-(3,4-dimethoxyphenyl)-2-[(7-fluoro-1H-indazol-5-yl)amino]-8-(trans-4-methoxycyclohexyl)-7-methyl-7,8-dihydropteridin-6(5H)-one | $^1$H NMR (400 MHz, CD$_3$OD): δ 8.01 (d, J = 2.8 Hz, 1H), 7.76 (d, J = 1.5 Hz, 1H), 7.43 (d, J = 12.9 Hz, 1H), 7.11 (d, J = 8.6 Hz, 1H), 7.07 (s, 1H), 6.78-6.89 (m, 2H), 4.44 (q, J = 6.8 Hz, 1H), 4.25-4.38 (m, 1H), 3.89 (s, 3H), 3.82 (s, 3H), 3.34-3.36 (m, 3H), 3.11-3.22 (m, 1H), 2.13-2.25 (m, 3H), 2.01 (dd, J = 3.0, 12.6 Hz, 1H), 1.74-1.90 (m, 2H), 1.47 (d, J = 6.8 Hz, 3H), 1.27-1.43 (m, 2H). MS (ES$^+$): |

-continued

| Ex. # | Chemical Name | Analytical data |
|---|---|---|
| 226 | (7R)-5-(3,4-dimethoxyphenyl)-2-[(7-fluoro-1H-indazol-5-yl)amino]-8-(cis-4-methoxycyclohexyl)-7-methyl-7,8-dihydropteridin-6(5H)-one | m/z = 562.25 [MH$^+$]. UPLC: tR = 0.77 min (TOF: polar_2 min).<br>$^1$H NMR (400 MHz, CD$_3$OD): δ 1.48 (d, J = 6.57 Hz, 3H), 1.54-1.69 (m, 3H), 1.84-2.04 (m, 2H), 2.08-2.22 (m, 3H), 3.35-3.40 (m, 3H), 3.53 (br. s., 1H), 3.83 (s, 3H), 3.90 (s, 3H), 4.42-4.49 (m, 1H), 4.49-4.56 (m, 1H), 6.76-6.91 (m, 2H), 7.03-7.16 (m, 2H), 7.50 (d, J = 13.14 Hz, 1H), 7.77 (s, 1H), 7.99 (d, J = 2.27 Hz, 1H). MS(ES$^+$): m/z = 562.20[MH$^+$]. HPLC: t$_R$ = 0.82 min (analytical_2 min, UPLC). |
| 227 | (7R)-2-[(7-fluoro-1H-indazol-5-yl)amino]-8-(cis-4-methoxycyclohexyl)-7-methyl-5-(pyridin-3-yl)-7,8-dihydropteridin-6(5H)-one | $^1$H NMR (400 MHz, CD$_3$OD): δ 1.50 (d, J = 6.82 Hz, 3H), 1.56-1.70 (m, 3H), 1.84-2.04 (m, 2H), 2.05-2.21 (m, 3H), 3.37 (s, 3H), 3.36-3.39 (m, 3H), 3.53 (br. s., 1H), 4.46-4.53 (m, 1H), 4.56 (br. s., 1H), 7.10 (br. s., 1H), 7.51 (d, J = 13.14 Hz, 1H), 7.65 (dd, J = 8.08, 4.80 Hz, 1H), 7.78 (d, J = 1.26 Hz, 1H), 7.86 (d, J = 8.08 Hz, 1H), 7.99 (d, J = 2.53 Hz, 1H), 8.54 (br. s., 1H), 8.67 (d, J = 4.04 Hz, 1H). MS(ES$^+$): m/z = 503.14[MH$^+$]. HPLC: t$_R$ = 0.72 min (analytical_2 min, UPLC). |
| 228 | 3-[(7R)-8-(cis-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile | $^1$H NMR (400 MHz, CD$_3$OD): δ 1.49 (d, J = 6.82 Hz, 3H), 1.57-1.71 (m, 3H), 1.83-2.21 (m, 5H), 3.38 (d, J = 1.01 Hz, 3H), 3.55 (br. s., 1H), 4.49 (q, J = 6.57 Hz, 2H), 6.97 (d, J = 8.34 Hz, 1H), 7.06 (s, 1H), 7.14-7.20 (m, 1H), 7.64 (d, J = 8.08 Hz, 1H), 7.71-7.76 (m, 1H), 7.76-7.80 (m, 1H), 7.84-7.91 (m, 2H). MS(ES$^+$): m/z = 526.36[MH$^+$]. HPLC: t$_R$ = 0.80 min (analytical_2 min, UPLC). |
| 229 | 3-[(7R)-8-(trans-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile | $^1$H NMR (400 MHz, CD$_3$OD): δ 1.32-1.44 (m, 2H), 1.48 (d, J = 6.8 Hz, 3H), 1.72-1.82 (m, 1H), 1.83-1.93 (m, 1H), 1.95-2.06 (m, 1H), 2.16-2.29 (m, 3H), 3.20-3.28 (m, 1H), 3.36-3.44 (m, 3H), 4.28-4.38 (m, 1H), 4.46 (q, J = 6.6 Hz, 1H), 6.98 (d, J = 8.3 Hz, 1H), 7.06 (s, 1H), 7.23 (dd, J = 8.3, 2.0 Hz, 1H), 7.62 (d, J = 8.0 Hz, 1H), 7.69-7.78 (m, 3H), 7.82-7.89 (m, 1H). MS(ES$^+$): m/z = 526.31 [MH$^+$]. HPLC: t$_R$ = 0.75 min (analytical_2 min, UPLC). |
| 230 | 3-[(7R)-8-(trans-4-methoxycyclohexyl)-7-methyl-6-oxo-2-(1H-pyrazolo[3,4-c]pyridin-5-ylamino)-7,8-dihydropteridin-5(6H)-yl]benzonitrile | $^1$H NMR (400 MHz, CD$_3$OD): δ 1.29-1.44 (m, 2H), 1.50 (d, J = 6.82 Hz, 3H), 1.74-2.07 (m, 3H), 2.23-2.33 (m, 3H), 3.20-3.20 (m, 1H), 3.40 (d, J = 0.7 Hz, 3H), 4.39-4.55 (m, 2H), 7.13 (m, 1H), 7.66 (d, J = 8.0 Hz, 1H), 7.76 (t, J = 7.9 Hz, 1H), 7.80 (s, 1H), 7.88 (d, J = 7.5 Hz, 1H), 8.09 (s, 1H), 8.40 (s, 1H), 8.75 (s, 1H). MS(ES$^+$): m/z = 510.22 [MH$^+$]. HPLC: t$_R$ = 0.77 min (analytical_2 min, UPLC). |
| 231 | 3-[(7R)-8-(trans-4-methoxycyclohexyl)-7-methyl-6-oxo-2-(1H-pyrazolo[3,4-b]pyridin-5-ylamino)-7,8-dihydropteridin-5(6H)-yl]benzonitrile | $^1$H NMR (400 MHz, CD$_3$OD): δ 1.33 (d, J = 2.0 Hz, 2H), 1.48 (d, J = 6.5 Hz, 3H), 1.72-1.88 (m, 2H), 1.93-2.07 (m, 1H), 2.17 (d, J = 7.5 Hz, 3H), 3.08-3.18 (m, 1H), 3.35 (s, 3H), 4.21-4.32 (m, 1H), 4.47 (q, J = 6.6 Hz, 1H), 7.06 (s, 1H), 7.65 (d, J = 8.0 Hz, 1H), 7.75 (t, J = 7.8 Hz, 1H), 7.78-7.79 (m, 1H), 7.88 (d, J = 7.8 Hz, 1H), 8.04 (s, 1H), 8.51 (d, J = 2.2 Hz, 1H), 8.61 (d, J = 2.2 Hz, 1H). MS(ES$^+$): m/z = 510.72[MH$^+$]. HPLC: t$_R$ = 0.69 min (analytical_2 min, UPLC). |
| 232 | 3-[(7R)-2-[(3,5-difluoro-4-hydroxyphenyl)amino]-8-(trans-4-methoxycyclohexyl)-7-methyl-6-oxo-7,8-dihydropteridin-5(6H)-yl]benzonitrile. | $^1$H NMR (400 MHz, CD$_3$OD): δ 7.84-7.91 (m, 1H), 7.72-7.82 (m, 2H), 7.64 (s, 1H), 7.25 (d, J = 10.4 Hz, 1H), 7.03-7.11 (m, 1H), 6.19 (s, 1H), 4.43-4.60 (m, 1H), 4.24-4.43 (m, 1H), 3.38 (d, J = 2.8 Hz, 3H), 2.19-2.27 (m, 2H), 2.07-2.16 (m, 1H), 1.93-2.07 (m, 1H), 1.73-1.91 (m, 2H), 1.21-1.54 (m, 6H). MS (ES$^+$): m/z = 521.62 [MH$^+$]. UPLC: t$_R$ = 0.87 min (TOF: polar_2 min). |
| 233 | (7R)-2-[(7-fluoro-1H-indazol-5-yl)amino]-8-(trans-4-methoxycyclohexyl)-7-methyl-5-[6-(4-methylpiperazin-1-yl)pyridin-3-yl]-7,8-dihydropteridin-6(5H)-one | MS(ES$^+$): m/z = 601.70[MH$^+$]. HPLC: t$_R$ = 0.66 min (analytical_2 min, UPLC). |
| 234 | 2-methoxy-5-[(7R)-8-(trans-4-methoxycyclohexyl)-7-methyl-6-oxo-2-(1H-pyrazolo[3,4-b]pyridin-5-ylamino)-7,8-dihydropteridin-5(6H)-yl]benzonitrile | $^1$H NMR (400 MHz, CD$_3$OD): δ 8.60 (d, J = 2.5 Hz, 1H), 8.50 (d, J = 2.3 Hz, 1H), 8.03 (s, 1H), 7.65 (d, J = 2.5 Hz, 1H), 7.56 (dd, J = 2.3, 8.8 Hz, 1H), 7.35 (d, J = 9.1 Hz, 1H), 7.08 (s, 1H), 4.45 (q, J = 6.8 Hz, 1H), 4.16-4.31 (m, 1H), 4.03 (s, 3H), 3.32-3.36 (m, 3H), 3.05-3.20 (m, 1H), 2.08-2.24 (m, 3H), 1.99 (dd, J = 3.2, 12.5 Hz, 1H), 1.68-1.87 (m, 2H), 1.46 |

-continued

| Ex. # | Chemical Name | Analytical data |
|---|---|---|
| 235 | 2-methoxy-5-[(7R)-8-(trans-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile | (d, J = 6.8 Hz, 3H), 1.21-1.39 (m, 2H). MS (ES$^+$): m/z = 540.43 [MH$^+$]. UPLC: t$_R$= 0.73 min (TOF: polar_2 min).<br>1H NMR (400 MHz, CD$_3$OD) δ 7.71 (d, J = 1.8 Hz, 1H), 7.64 (d, J = 2.3 Hz, 1H), 7.52-7.58 (m, 1H), 7.35 (d, J = 9.1 Hz, 1H), 7.22 (dd, J = 2.0, 8.3 Hz, 1H), 7.06 (s, 1H), 6.98 (d, J = 8.6 Hz, 1H), 4.45 (q, J = 6.7 Hz, 1H), 4.31 (t, J = 12.0 Hz, 1H), 4.03 (s, 3H), 3.38 (s, 3H), 2.17-2.26 (m, 3H), 2.02 (dd, J = 2.7, 10.0 Hz, 1H), 1.79 (br. s., 2H), 1.42 (br. s., 4H), 1.32-1.41 (m, 2H). MS (ES$^+$): m/z = 556.30 [M + H$^+$]. UPLC: t$_R$ = 0.78 min (TOF: Polar_2 min). |

Examples 236-252 were prepared according to procedures similar to the preparation of Example 18, using 4-methylcyclohexanone, D-alanine methyl ester hydrochloride and other corresponding starting materials and intermediates, followed by Supercritical Fluid Chromatography (SFC) to give pure isomers. For example, for the synthesis of example 238, (3,4-dimethoxyphenyl)boronic acid and 7-fluoro-1H-indazol-5-amine were used during the synthesis.

| Ex. # | Chemical Name | Analytical data |
|---|---|---|
| 236 | 3-[(7R)-2-[(7-fluoro-1H-indazol-5-yl)amino]-7-methyl-8-(cis-4-methylcyclohexyl)-6-oxo-7,8-dihydropteridin-5(6H)-yl]benzonitrile | $^1$H NMR (400 MHz, CD$_3$OD) δ 7.98 (d, J = 3.3 Hz, 1H), 7.84-7.89 (m, 1H), 7.79 (d, J = 1.3 Hz, 2H), 7.74 (t, J = 7.8 Hz, 1H), 7.64 (d, J = 8.1 Hz, 1H), 7.47 (dd, J = 1.3, 13.1 Hz, 1H), 7.07 (s, 1H), 4.41-4.56 (m, 2H), 1.94-2.11 (m, 3H), 1.65-1.89 (m, 5H), 1.59 (d, J = 12.1 Hz, 1H), 1.49 (d, J = 6.6 Hz, 3H), 1.06 (d, J = 7.1 Hz, 3H). MS (ES$^+$): m/z = 511.20 [M + H]$^+$. UPLC: t$_R$ = 0.97 min (TOF: Polar_2 min). |
| 237 | 3-[(7R)-2-[(7-fluoro-1H-indazol-5-yl)amino]-7-methyl-8-(trans-4-methylcyclohexyl)-6-oxo-7,8-dihydropteridin-5(6H)-yl]benzonitrile | $^1$H NMR (400 MHz, CD$_3$OD) δ 7.98 (d, J = 3.3 Hz, 1H), 7.84-7.89 (m, 1H), 7.71-7.81 (m, 3H), 7.64 (d, J = 8.1 Hz, 1H), 7.47 (d, J = 13.1 Hz, 1H), 7.05 (s, 1H), 4.37-4.52 (m, 2H), 2.16 (dd, J = 2.3, 9.3 Hz, 1H), 1.75-1.92 (m, 4H), 1.63-1.74 (m, 1H), 1.40-1.50 (m, 4H), 1.13-1.24 (m, 2H), 0.96 (d, J = 6.6 Hz, 3H). MS (ES$^+$): m/z = 511.21 [M + H]$^+$. UPLC: t$_R$ = 0.96 min (TOF: polar_2 min). |
| 238 | (7R)-5-(3,4-dimethoxyphenyl)-2-[(7-fluoro-1H-indazol-5-yl)amino]-7-methyl-8-(cis-4-methylcyclohexyl)-7,8-dihydropteridin-6(5H)-one | 1H NMR (400 MHz, CD$_3$OD): δ 1.06 (d, J = 7.1 Hz, 3H), 1.51 (d, J = 6.8 Hz, 3H), 1.61 (d, J = 11.3 Hz, 1H), 1.65-1.90 (m, 5H), 1.94-2.13 (m, 3H), 3.84 (s, 3H), 3.91 (s, 3H), 4.46 (t, J = 11.6 Hz, 1H), 4.51-4.58 (m, 1H), 6.77-6.92 (m, 2H), 7.08 (s, 1H), 7.11-7.12 (m, 1H), 7.48 (d, J = 12.8 Hz, 1H), 7.79 (d, J = 1.5 Hz, 1H), 8.00 (d, J = 3.0 Hz, 1H). MS(ES$^+$): m/z = 546.34 [MH$^+$]. HPLC: t$_R$ = 0.94 (analytical_2 min, UPLC). |
| 239 | (7R)-5-(3,4-dimethoxyphenyl)-2-[(7-fluoro-1H-indazol-5-yl)amino]-7-methyl-8-(trans-4-methylcyclohexyl)-7,8-dihydropteridin-6(5H)-one | 1H NMR (400 MHz, CD$_3$OD): δ 0.93 (d, J = 6.3 Hz, 3H), 1.05-1.23 (m, 2H), 1.29 (br. s., 1H), 1.52 (d, J = 6.8 Hz, 3H), 1.68-2.02 (m, 5H), 2.12 (d, J = 11.8 Hz, 1H), 3.83 (s, 3H), 3.90 (s, 3H), 4.33 (br. s., 1H), 4.51 (d, J = 6.8 Hz, 1H), 6.73-6.91 (m, 2H), 6.98 (s, 1H), 7.12 (d, J = 8.5 Hz, 1H), 7.42 (d, J = 12.8 Hz, 1H), 7.75 (d, J = 1.0 Hz, 1H), 8.03 (br. s., 1H). MS(ES$^+$): m/z = 545.99 [MH$^+$]. HPLC: t$_R$ = 0.93 (analytical_2 min, UPLC). |
| 240 | (7R)-2-[(7-fluoro-1H-indazol-5-yl)amino]-7-methyl-8-(cis-4-methylcyclohexyl)-5-(pyridin-3-yl)-7,8-dihydropteridin-6(5H)-one | 1H NMR (400 MHz, CD$_3$OD): δ 1.03 (d, J = 7.0 Hz, 3H), 1.55 (d, J = 6.5 Hz, 3H), 1.59-2.02 (m, 8H), 2.04-2.12 (m, 1H), 4.35-4.51 (m, 1H), 4.58 (q, J = 6.8 Hz, 1H), 7.05 (s, 1H), 7.45 (d, J = 12.6 Hz, 1H), 7.66 (dd, J = 8.0, 4.8 Hz, 1H), 7.77 (d, J = 1.5 Hz, 1H), 7.82-7.91 (m, 1H), 8.02 (br. s., 1H), 8.55 (d, J = 2.0 Hz, 1H), 8.68 (dd, J = 4.8, 1.2 Hz, 1H). MS(ES$^+$): m/z = 487.10 [MH$^+$]. HPLC: t$_R$ = 0.86 (analytical_2 min, UPLC). |
| 241 | (7R)-2-[(7-fluoro-1H-indazol-5-yl)amino]-7-methyl-8-(cis-4-methylcyclohexyl)-5-(pyridin-3-yl)-7,8-dihydropteridin-6(5H)-one | 1H NMR (400 MHz, CD$_3$OD): δ 0.83 (d, J = 5.8 Hz, 3H), 1.05 (d, J = 9.0 Hz, 3H), 1.63-1.73 (m, 4H), 1.73-1.93 (m, 3H), 1.94-2.10 (m, 2H), 4.09 (t, J = 11.2 Hz, 1H), 4.66 (d, J = 7.0 Hz, 1H), 6.84 (s, 1H), 7.29 (dd, J = 11.3, 1.2 Hz, 1H), 7.66 (d, J = 1.0 Hz, 1H), 7.72-7.86 (m, 1H), 8.00 (d, J = 8.3 Hz, 1H), 8.17 (d, J = 3.0 Hz, 1H), 8.58-8.84 (m, 2H). MS(ES$^+$): m/z = 487.10 [MH$^+$]. HPLC: t$_R$ = 0.86 (analytical_2 min, UPLC). |

-continued

| Ex. # | Chemical Name | Analytical data |
|---|---|---|
| 242 | (7R)-2-[(7-fluoro-1H-indazol-5-yl)amino]-7-methyl-8-(trans-4-methylcyclohexyl)-5-[6-(4-methylpiperazin-1-yl)pyridin-3-yl]-7,8-dihydropteridin-6(5H)-one | $^1$H NMR (400 MHz, CD$_3$OD): δ 0.96 (d, J = 3.7 Hz, 3H), 1.12-1.30 (m, 2H), 1.47 (d, J = 3.5 Hz, 4H), 1.65 (d, J = 12.6 Hz, 1H), 1.76-1.96 (m, 4H), 2.19 (d, J = 11.6 Hz, 1H), 2.38 (d, J = 2.7 Hz, 3H), 2.60 (br. s., 4H), 3.66 (br. s., 4H), 4.34-4.51 (m, 2H), 6.93 (d, J = 8.8 Hz, 1H), 7.16 (d, J = 3.2 Hz, 1H), 7.33-7.51 (m, 2H), 7.68-7.82 (m, 1H), 7.97 (d, J = 11.1 Hz, 2H). MS(ES$^+$): m/z = 585.73[MH$^+$]. HPLC: t$_R$ = 0.69 min (analytical_2 min, UPLC). |
| 243 | 3-[(7R)-2-[(3,5-difluoro-4-hydroxyphenyl)amino]-7-methyl-8-(trans-4-methylcyclohexyl)-6-oxo-7,8-dihydropteridin-5(6H)-yl]benzonitrile. | $^1$H NMR (400 MHz, CD$_3$OD): δ 7.86 (d, J = 7.6 Hz, 1H), 7.71-7.79 (m, 2H), 7.63 (d, J = 8.1 Hz, 1H), 7.22-7.32 (m, 2H), 7.05 (s, 1H), 4.39-4.53 (m, 2H), 2.12-2.22 (m, 1H), 1.77-1.95 (m, 4H), 1.62-1.74 (m, 1H), 1.43-1.53 (m, 4H), 1.17-1.32 (m, 2H), 0.97 (d, J = 6.3 Hz, 3H). MS (ES$^+$): m/z = 505.63 [MH$^+$]. UPLC: t$_R$ = 1.09 min (TOF: polar_2 min). |
| 244 | 2-methoxy-5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]benzonitrile | $^1$H NMR (400 MHz, CD$_3$OD): δ 7.82 (s, 1H), 7.64 (br. s., 1H), 7.55 (d, J = 9.1 Hz, 1H), 7.35 (d, J = 8.6 Hz, 1H), 7.18 (d, J = 8.3 Hz, 1H), 7.06 (s, 1H), 6.97 (d, J = 8.6 Hz, 1H), 4.47 (q, J = 6.2 Hz, 1H), 4.39 (t, J = 12.3 Hz, 1H), 4.03 (s, 3H), 2.15 (s, 2H), 1.84-1.94 (m, 3H), 1.62-1.83 (m, 2H), 1.47 (d, J = 6.8 Hz, 4H), 1.14-1.37 (m, 3H), 0.98 (d, J = 6.3 Hz, 3H). MS (ES$^+$): m/z = 540.62 [MH$^+$]. UPLC: t$_R$ = 0.94 min (TOF: polar_2 min). |
| 245 | 2-Methoxy-5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]benzonitrile | $^1$H NMR (400 MHz, CD$_3$OD): δ 8.60 (s, 1H), 8.53 (d, J = 2.5 Hz, 1H), 8.01 (s, 1H), 7.65 (br. s., 1H), 7.55 (s, 1H), 7.36 (d, J = 9.1 Hz, 1H), 7.08 (s, 1H), 4.47 (d, J = 6.8 Hz, 1H), 4.25-4.38 (m, 1H), 4.03 (s, 3H), 2.07-2.15 (m, 1H), 1.76-1.93 (m, 4H), 1.47 (d, J = 6.6 Hz, 3H), 1.29 (br. s., 2H), 1.15 (br. s., 2H), 0.94 (d, J = 6.6 Hz, 3H). MS (ES$^+$): m/z = 524.71 [MH$^+$]. UPLC: t$_R$ = 0.91 min (TOF: polar_2 min). |
| 246 | 2-Ethoxy-5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]benzonitrile | $^1$H NMR (400 MHz, CD$_3$OD): δ 8.60 (d, J = 2.3 Hz, 1H), 8.53 (d, J = 2.3 Hz, 1H), 8.01 (s, 1H), 7.64 (s, 1H), 7.53 (d, J = 7.1 Hz, 1H), 7.33 (d, J = 8.8 Hz, 1H), 7.08 (s, 1H), 4.47 (d, J = 6.8 Hz, 1H), 4.30-4.38 (m, 1H), 2.11 (d, J = 12.6 Hz, 1H), 1.74-1.92 (m, 4H), 1.64-1.73 (m, 1H), 1.50 (s, 7H), 1.33-1.42 (m, 1H), 1.26-1.32 (m, 1H), 1.06-1.20 (m, 2H), 0.94 (d, J = 6.3 Hz, 3H). MS (ES$^+$): m/z = 538.69 [MH$^+$]. UPLC: t$_R$ = 0.96 min (TOF: polar_2 min). |
| 247 | 2-Ethoxy-5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]benzonitrile | $^1$H NMR (400 MHz, CD$_3$OD): δ 7.82 (d, J = 2.0 Hz, 1H), 7.63 (s, 1H), 7.49-7.56 (m, 1H), 7.33 (d, J = 9.1 Hz, 1H), 7.18 (dd, J = 2.0, 8.6 Hz, 1H), 7.06 (s, 1H), 6.97 (d, J = 8.6 Hz, 1H), 4.47 (d, J = 6.8 Hz, 1H), 4.34-4.43 (m, 1H), 2.10-2.21 (m, 1H), 1.89 (br. s., 3H), 1.74-1.84 (m, 1H), 1.66-1.74 (m, 1H), 1.45-1.53 (m, 7H), 1.27-1.35 (m, 3H), 0.98 (d, J = 6.6 Hz, 3H). MS (ES$^+$): m/z = 554.67 [MH$^+$]. UPLC: t$_R$ = 1.00 min (TOF: polar_2 min). |
| 248 | 5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]-2-(propan-2-yloxy)benzonitrile. | $^1$H NMR (400 MHz, CD$_3$OD): δ 8.60 (d, J = 2.3 Hz, 1H), 8.54 (d, J = 2.5 Hz, 1H), 8.01 (s, 1H), 7.63 (s, 1H), 7.51 (d, J = 7.6 Hz, 1H), 7.35 (d, J = 8.8 Hz, 1H), 7.09 (s, 1H), 4.47 (q, J = 7.0 Hz, 1H), 4.32 (t, J = 12.0 Hz, 1H), 2.11 (d, J = 12.4 Hz, 1H), 1.75-1.97 (m, 4H), 1.60-1.74 (m, 1H), 1.35-1.52 (m, 11H), 1.02-1.22 (m, 2H), 0.94 (d, J = 6.6 Hz, 3H). MS (ES$^+$): m/z = 552.27 [MH$^+$]. UPLC: t$_R$ = 0.86 min (TOF: polar_2 min). |
| 249 | 5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]-2-(propan-2-yloxy)benzonitrile | $^1$H NMR (400 MHz, CD$_3$OD): δ 7.82 (d, J = 2.0 Hz, 1H), 7.62 (s, 1H), 7.51 (d, J = 8.6 Hz, 1H), 7.35 (d, J = 9.1 Hz, 1H), 7.18 (dd, J = 2.0, 8.6 Hz, 1H), 7.07 (s, 1H), 6.97 (d, J = 8.3 Hz, 1H), 4.33-4.51 (m, 2H), 2.10-2.19 (m, 1H), 1.84-1.93 (m, 3H), 1.64-1.83 (m, 2H), 1.40-1.51 (m, 10H), 1.29 (s, 3H), 0.98 (d, J = 6.6 Hz, 3H). MS (ES$^+$): m/z = 568.26 [MH$^+$]. UPLC: t$_R$ = 0.88 min (TOF: polar_2 min). |
| 250 | 3-[(7R)-2-[(2,2-dioxido-1,3-dihydro-2,1-benzothiazol-5-yl)amino]-7-methyl-8-(trans-4-methylcyclohexyl)-6-oxo-7,8-dihydropteridin-5(6H)-yl]benzonitrile. | $^1$H NMR (400 MHz, CD$_3$OD): δ 7.86 (d, J = 7.8 Hz, 1H), 7.70-7.78 (m, 2H), 7.59-7.65 (m, 1H), 7.54-7.57 (m, 1H), 7.44 (dd, J = 1.9, 8.5 Hz, 1H), 7.01 (s, 1H), 6.79 (d, J = 8.6 Hz, 1H), 4.47 (d, J = 6.8 Hz, 1H), 4.34-4.38 (m, 2H), 2.09-2.17 (m, 1H), 1.89 (d, J = 10.9 Hz, 3H), 1.63-1.82 (m, 2H), 1.47 (d, J = 6.6 Hz, 4H), 1.28 (s, 1H), 1.15 (t, J = 11.7 Hz, 2H), 0.97 (d, J = 6.6 Hz, 3H). MS (ES$^+$): m/z = 544.40 [MH$^+$]. UPLC: t$_R$ = 0.95 min (TOF: polar_2 min). |

| Ex. # | Chemical Name | Analytical data |
|---|---|---|
| 251 | 5-[(7R)-2-[(7-fluoro-1H-indazol-5-yl)amino]-7-methyl-8-(trans-4-methylcyclohexyl)-6-oxo-7,8-dihydropteridin-5(6H)-yl]-2-(4-methylpiperazin-1-yl)benzonitrile | $^1$H NMR (CDCl$_3$, 400 MHz): δ 0.98 (d, J = 6.0 Hz, 3 H), 1.19-1.26 (m, 2 H), 1.47 (d, J = 6.4 Hz, 3 H), 1.54-1.64 (m, 2 H), 1.76-1.92 (m, 4 H), 2.21 (m, 1 H), 2.39 (s, 3 H), 2.66 (t, J = 4.8 Hz, 4 H), 3.35 (t, J = 4.8 Hz, 4 H), 4.41 (m, 1 H), 4.43 (q, J = 6.4 Hz, 1 H), 7.01 (s, 1 H), 7.09 (d, J = 8.8 Hz, 1 H), 7.21 (s, 1 H), 7.32 (dd, J = 2.4, 8.8 Hz, 1 H), 7.43 (d, J = 2.8 Hz, 1 H), 7.45 (dd, J = 1.6, 11.6 Hz, 1 H), 7.71 (d, J = 1.6 Hz, 1 H), 8.00 (d, J = 3.6 Hz, 1 H). MS (ES$^+$): m/z = 609.51 [MH$^+$]. HPLC: t$_R$ = 0.76 min (TOF, polar_2 min). |
| 252 | 5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]-2-(4-methylpiperazin-1-yl)benzonitrile | $^1$H NMR (CDCl$_3$, 400 MHz): δ 0.99 (d, J = 6.4 Hz, 3 H), 1.16-1.28 (m, 2 H), 1.40-1.65 (m, 2 H), 1.50 (d, J = 6.4 Hz, 3 H), 1.77-1.97 (m, 4 H), 2.39 (m, 1 H), 2.41 (s, 3 H), 2.69 (t, J = 4.8 Hz, 4 H), 3.40 (t, J = 4.8 Hz, 4 H), 4.48 (m, 1 H), 4.50 (q, J = 6.4 Hz, 1 H), 7.14 (d, J = 8.8 Hz, 1 H), 7.37 (d, J = 7.6 Hz, 1 H), 7.41 (s, 1 H), 7.47 (s, 1 H), 8.02 (s, 1 H), 8.79 (d, J = 2.0 Hz, 1 H), 8.99 (d, J = 2.0 Hz, 1 H), 9.52 (s, 1 H). MS (ES$^+$): m/z = 592.47 [MH$^+$]. HPLC: t$_R$ = 0.69 min (TOF, polar_2 min). |

Examples 253-259 were prepared according to procedures similar to the preparation of Example 18, using 4-(trifluoromethyl)cyclohexanone, D-alanine methyl ester hydrochloride and other corresponding starting materials and intermediates, followed by Supercritical Fluid Chromatography (SFC) to give pure isomers. For example, for the synthesis of example 257, (3,4-dimethoxyphenyl)boronic acid and 7-fluoro-1H-indazol-5-amine were used during the synthesis.

| Ex. # | Chemical Structure and Name | Analytical data |
|---|---|---|
| 253 | 3-[(7R)-2-(1H-indazol-5-ylamino)-7-methyl-6-oxo-8-[trans-4-(trifluoromethyl)cyclohexyl]-7,8-dihydropteridin-5(6H)-yl]benzonitrile | $^1$H NMR (400 MHz, CDCl$_3$) δ 1.49 (d, J = 6.5 Hz, 3 H) 1.57-1.68 (m, 4 H) 1.82 (dd, J = 12.6, 3.2 Hz, 1 H) 2.00 (d, J = 12.1 Hz, 1 H) 2.12-2.24 (m, 2H) 2.33 (br. s., 1 H) 4.42 (q, J = 6.6 Hz, 2 H) 7.00 (s, 1 H) 7.19 (s, 1 H) 7.43-7.56 (m, 2 H) 7.59 (s, 1 H) 7.62-7.69 (m, 2 H) 7.75 (dt, J = 7.7, 1.2 Hz, 1 H) 8.02 (d, J = 3.5 Hz, 1 H) 10.01-10.61 (m, 1 H). MS(ES$^+$): m/z = 565.8 [MH$^+$]. SFC: t$_R$ = 22.55 min |
| 254 | 3-[(7R)-2-(1H-indazol-5-ylamino)-7-methyl-6-oxo-8-[cis-4-(trifluoromethyl)cyclohexyl]-7,8-dihydropteridin-5(6H)-yl]benzonitrile | $^1$H NMR (400 MHz, CDCl$_3$) δ 1.48 (d, J = 6.82 Hz, 3 H) 1.57 (br. s., 3 H) 1.84 (br. s., 3 H) 2.11 (br. s., 2 H) 2.22 (br. s., 2 H) 2.34-2.49 (m, 1 H) 4.45 (d, J = 6.57 Hz, 2 H) 6.92 (s, 1 H) 7.18 (s, 1 H) 7.48-7.55 (m, 2H) 7.56-7.70 (m, 3 H) 7.71-7.79 (m, 1 H) 8.01 (d, J = 3.54 Hz, 1 H) 9.77-10.84 (m, 1 H). MS(ES$^+$): m/z = 565.8 [MH$^+$]. SFC: t$_R$ = 17.88 min |
| 255 | (7R)-2-[(7-fluoro-1H-indazol-5-yl)amino]-7-methyl-5-(pyridin-3-yl)-8-[cis-4-(trifluoromethyl)cyclohexyl]-7,8-dihydropteridin-6(5H)-one | $^1$H NMR (400 MHz, Pyridine-d$_5$) δ 10.50 (s, 1H), 8.97 (d, J = 2.5 Hz, 1H), 8.81 (dd, J = 1.5, 4.8 Hz, 1H), 8.42-8.52 (m, 2H), 8.14 (dd, J = 1.4, 13.5 Hz, 1H), 7.86-7.94 (m, 1H), 7.48 (dd, J = 4.8, 8.1 Hz, 1H), 5.00 (s, 1H), 4.66 (q, J = 6.7 Hz, 1H), 4.44-4.56 (m, 1H), 2.34 (d, J = 3.3 Hz, 1H), 1.91-2.18 (m, 4H), 1.59-1.83 (m, 3H), 1.42-1.56 (m, 4H), 1.27-1.36 (m, 1H). MS (ES$^+$): m/z = 541.23 [M + H]$^+$. UPLC: t$_R$ = 0.87 min (TOF: polar_2 min). |
| 256 | (7R)-2-[(7-fluoro-1H-indazol-5-yl)amino]-7-methyl-5-(pyridin-3-yl)-8-[trans-4-(trifluoromethyl)cyclohexyl]-7,8-dihydropteridin-6(5H)-one | $^1$H NMR (400 MHz, Pyridine-d$_5$) δ 15.18 (br. s., 1H), 10.56 (s, 1H), 8.98 (s, 1H), 8.82 (d, J = 4.5 Hz, 1H), 8.46 (br. s., 2H), 8.14 (d, J = 13.4 Hz, 1H), 7.92 (d, J = 7.8 Hz, 1H), 7.49 (dd, J = 4.8, 7.8 Hz, 1H), 5.01 (br. s., 1H), 4.64 (q, J = 6.6 Hz, 1H), 4.25-4.39 (m, 1H), 2.20 (d, J = 10.4 Hz, 1H), 1.91-2.12 (m, 3H), 1.68-1.86 (m, 2H), 1.29-1.65 (m, 6H). MS (ES$^+$): m/z = 540.86 [M + H]$^+$. UPLC: t$_R$ = 0.87 min (TOF: polar_2 min). |
| 257 | (7R)-5-(3,4-dimethoxyphenyl)-2-[(7-fluoro-1H-indazol-5-yl)amino]-7-methyl-8-[cis-4-(trifluoromethyl)cyclohexyl]-7,8-dihydropteridin-6(5H)-one | $^1$H NMR (400 MHz, Pyridine-d$_5$) δ 10.38 (br. s., 1H), 8.39-8.53 (m, 2H), 8.16 (d, J = 13.6 Hz, 1H), 7.67 (s, 1H), 7.18-7.30 (m, 2H), 4.67 (q, J = 6.6 Hz, 1H), 4.46-4.58 (m, 1H), 3.82 (s, 3H), 3.72 (s, 3H), 3.58-3.65 (m, 1H), 2.34 (br. s., 1H), 1.91-2.21 (m, 4H), 1.61-1.84 (m, 3H), 1.44-1.58 (m, 4H), 1.23-1.35 (m, 1H). MS (ES$^+$): m/z = 599.98 [M + H]$^+$. UPLC: t$_R$ = 0.91 min (TOF: polar_2 min). |
| 258 | (7R)-5-(3,4-dimethoxyphenyl)-2-[(7-fluoro-1H-indazol-5-yl)amino]-7-methyl-8-[trans-4- | $^1$H NMR (400 MHz, Pyridine-d$_5$) δ 10.45 (br. s., 1H), 8.40-8.51 (m, 2H), 8.16 (dd, J = 1.3, 13.4 Hz, 1H), 7.66 (s, 1H), 7.22 (s, 2H), 4.65 (q, J = 6.7 Hz, |

-continued

| Ex. # | Chemical Structure and Name | Analytical data |
|---|---|---|
|  | (trifluoromethyl)cyclohexyl]-7,8-dihydropteridin-6(5H)-one | 1H), 4.27-4.41 (m, 1H), 3.78-3.86 (m, 3H), 3.73 (s, 3H), 3.62 (s, 1H), 2.23 (d, J = 11.6 Hz, 1H), 1.93-2.15 (m, 3H), 1.72-1.90 (m, 2H), 1.37-1.67 (m, 6H), 1.19-1.34 (m, 1H). MS (ES+): m/z = 599.98 [M + H]+. UPLC: $t_R$ = 0.91 min (TOF: polar_2 min). |
| 259 | 3-[(7R)-2-[(3,5-difluoro-4-hydroxyphenyl)amino]-7-methyl-6-oxo-8-[trans-4-(trifluoromethyl)cyclohexyl]-7,8-dihydropteridin-5(6H)-yl]benzonitrile | $^1$H NMR (400 MHz, CD$_3$OD): δ 7.84-7.90 (m, 1H), 7.71-7.80 (m, 2H), 7.63 (d, J = 8.3 Hz, 1H), 7.20-7.33 (m, J = 10.6 Hz, 2H), 7.07 (s, 1H), 4.50 (q, J = 6.7 Hz, 1H), 4.41 (tt, J = 3.6, 11.9 Hz, 1H), 2.22-2.33 (m, 2H), 2.08-2.18 (m, 2H), 1.91-2.08 (m, 2H), 1.82 (dq, J = 3.2, 12.4 Hz, 1H), 1.52-1.69 (m, 2H), 1.49 (d, J = 6.8 Hz, 3H). MS (ES+): m/z = 559.31 [MH+]. UPLC: $t_R$ = 1.09 min (TOF: polar_2 min). |

Example 260 was prepared by following procedure:

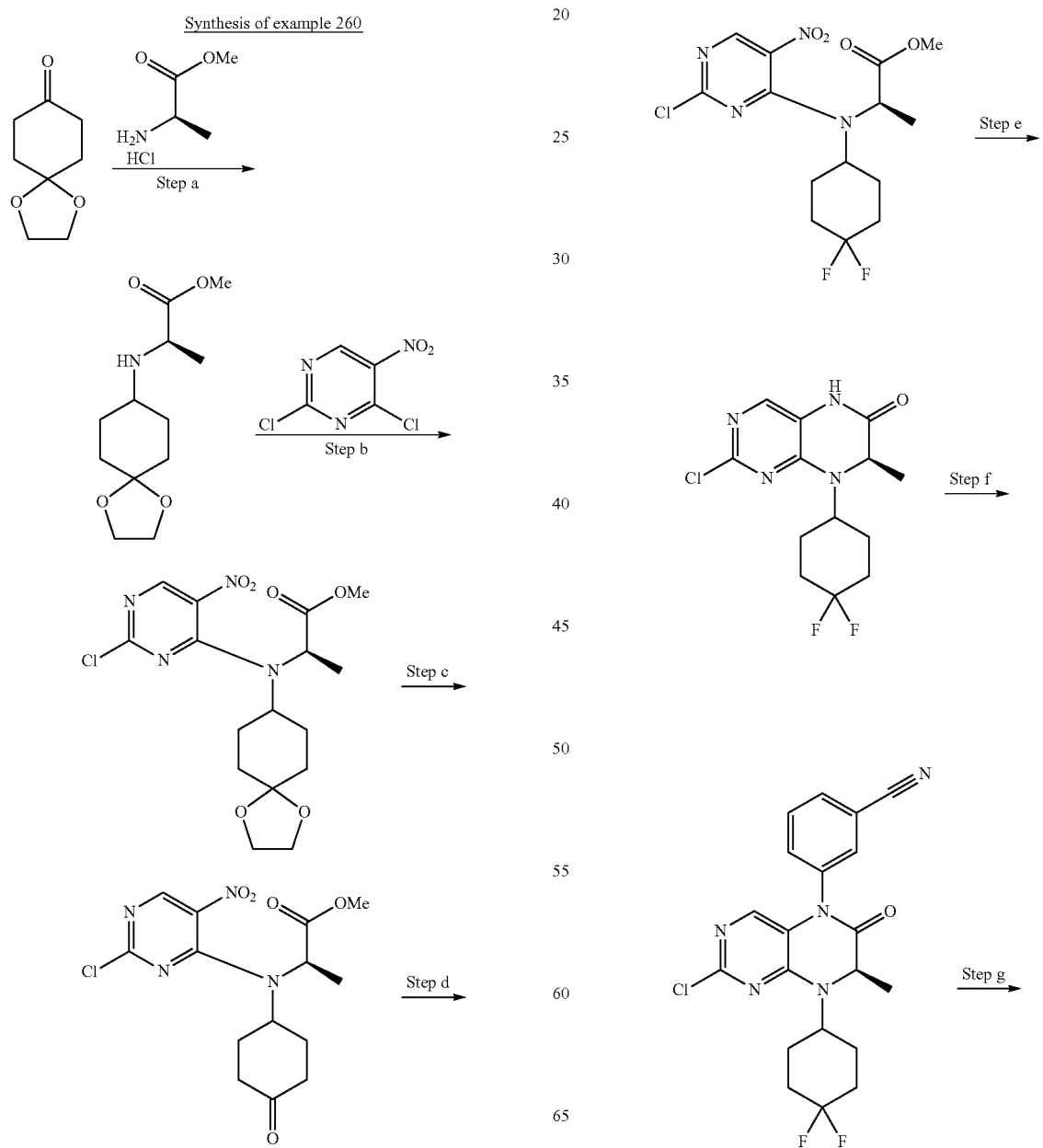

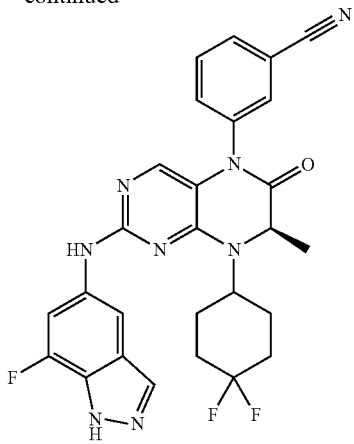

Step a: Synthesis of methyl N-1,4-dioxaspiro[4.5]dec-8-yl-D-alaninate

To a stirred mixture of D-alanine methyl ester hydrochloride (1, 12 g, 85.9 mmol) in anhydrous dichloromethane (120 mL) was added potassium acetate (8.5 g, 85.9 mmol) and the resulting reaction mixture was stirred at rt for ten minutes. The reaction was then cooled to 10° C. and treated with 1,4-dioxaspiro[4.5]decan-8-one (2, 13.4 g, 85.9 mmol), followed by the addition of sodium triacetoxyborohydride (22.6 g, 106.6 mmol) in portions over a period of ten minutes. The resulting reaction mixture was stirred at rt for 16 h. Saturated aqueous sodium bicarbonate solution was then added to the reaction and the mixture was stirred for another 30 minutes. Dichloromethane layer was separated and the aqueous layer was extracted with dichloromethane (100 mL×3). Organic layers were combined, washed with brine, dried over sodium sulfate, and evaporated to give the crude product as colorless oil (14 g), which was used for next step without any further purifications. $^1$HNMR (300 MHz, CDCl$_3$): δ 1.22 (d, 3H), 1.40-1.61 (m, 4H), 1.65-1.90 (m, 4H), 2.42-2.55 (m, 1H), 3.42 (q, 1H), 3.72 (s, 3H), 3.98 (s, 4H).

Step b: Synthesis of methyl N-(2-chloro-5-nitropyrimidin-4-yl)-N-1,4-dioxaspiro[4.5]dec-8-yl-D-alaninate To a stirred mixture of 2,4-dichloro-5-nitropyrimidine (4, 12 g, 62.1 mmol), potassium carbonate (11.7 g, 84.78 mmol) in acetone (100 mL) was added methyl N-1,4-dioxaspiro[4.5]dec-8-yl-D-alaninate (13.8 g, 62.1 mmol) at rt. The reaction mixture was stirred for 16 h at rt. The bulk of solvent was removed under reduced pressure to give a residue, which was diluted with ethyl acetate (100 mL), washed with water, dried over sodium sulfate. The solvent was evaporated to give a crude material, which was then purified by silica gel flash chromatography (eluent: ethyl acetate-hexane mixture (v:v=5:95)) to afforded the desired product (10.1 g). $^1$HNMR (300 MHz, CDCl$_3$): δ 1.55-1.64 (m, 3H), 1.70-1.99 (m, 6H), 2.05-2.20 (m, 3H), 3.06-3.15 (m, 1H), 3.75 (s, 3H), 3.99 (t, 4H), 8.61 (s, 1H).

Step c: Synthesis of methyl N-(2-chloro-5-nitropyrimidin-4-yl)-N-(4-oxocyclohexyl)-D-alaninate A stirred solution of methyl N-(2-chloro-5-nitropyrimidin-4-yl)-N-1,4-dioxaspiro[4.5]dec-8-yl-D-alaninate (17 g, 42.5 mmol) in dioxane (450 mL, contains 1M HCl) was heated to reflux for 16 h. The bulk of solvent was then removed under reduced pressure, the crude material was neutralized with aq. NaHCO$_3$, and extracted with ethyl acetate (300 mL×3). Organic layers were combined, dried over sodium sulfate, and evaporated to give the crude material, which was then purified by silica gel column chromatography to give the desired product (10 g). $^1$HNMR (300 MHz, CDCl$_3$): δ 1.66 (d, J=6.9 Hz, 3H), 1.99-2.18 (m, 2H), 2.34-2.57 (m, 6H), 3.56-3.59 (m, 1H), 3.76 (s, 3H), 4.04 (q, J=6.9, 13.8 Hz, 1H), 8.70 (s, 1H).

Step d: Synthesis of methyl N-(2-chloro-5-nitropyrimidin-4-yl)-N-(4,4-difluorocyclohexyl)-D-alaninate To a stirred solution of triethylamine trihydrofluoride (2.72 mL, 16.7 mmol) and triethylamine (1.17 mL, 8.41 mmol) in dichloromethane (30 mL) was added Xtalfluor-E (2.9 g, 12.6 mmol) at 0° C. To the solution was then added methyl N-(2-chloro-5-nitropyrimidin-4-yl)-N-(4-oxocyclohexyl)-D-alaninate (3 g, 8.37 mmol) slowly. An additional amount of Xtalfluor-E (2.9 g, 12.6 mmol) was added after 3 h, and resulting mixture was stirred at rt for 9 h. The reaction mixture was quenched with a 5% aqueous NaHCO$_3$ solution. The resulting mixture was extracted with dichloromethane (40 mL×3). The organic phases were combined, dried over Na$_2$SO$_4$, evaporated to give the crude material, which was then purified by silica gel column chromatography to give the desired product (2.2 g). $^1$HNMR (300 MHz, CDCl$_3$): δ 1.60-1.99 (m, 6H), 2.19-2.24 (m, 3H), 3.16-3.25 (m, 3H), 3.75 (s, 3H), 4.06 (q, J=6.9 Hz, 1H), 8.65 (s, 1H).

Step e: Synthesis of (7R)-2-chloro-8-(4,4-difluorocyclohexyl)-7-methyl-7,8-dihydropteridin-6(5H)-one To a stirred solution of methyl N-(2-chloro-5-nitropyrimidin-4-yl)-N-(4,4-difluorocyclohexyl)-D-alaninate (3.9 g, 9.24 mmol) in ethanol (120 mL) was added iron powder (5.12 g, 91.0 mmol).

The resulting mixture was then heated to reflux. 1N aqueous hydrochloric acid (8 ml) was then added to the mixture in small portions. The reaction mixture was refluxed for 8 h. After cooling to rt, the insoluble material was removed by filtration, the bulk of ethanol was evaporated to give a crude material, which was then purified by silica gel column chromatography (eluent: 5% methanol in dichloromethane) to give the desired product (2.3 g). $^1$HNMR (300 MHz, CDCl$_3$): δ 1.43 (d, J=6.9 Hz, 3H), 1.81-2.24 (m, 8H), 4.28 (q, J=6.6 Hz, 1H), 4.43-4.51 (m, 1H), 7.76 (s, 1H), 9.46 (s, 1H).

Step f: Synthesis of 3-[(7R)-2-chloro-8-(4,4-difluorocyclohexyl)-7-methyl-6-oxo-7,8-dihydropteridin-5(6H)-yl]benzonitrile To a stirred solution of (7R)-2-chloro-8-(4,4-difluorocyclohexyl)-7-methyl-7,8-dihydropteridin-6(5H)-one (1.80 g, 5.7 mmol) in dichloromethane (75 mL) was added triethylamine (8.07 ml, 57.8 mmol), cupric acetate (2.09 g, 11.56 mmol) and (3-cyanophenyl)boronic acid (1.69 g, 11.56 mmol) followed by 4 Å molecular sieves (2 g). The reaction mixture was stirred for 48 h at rt with an air balloon on the top. The reaction mixture was then filtered over celite to give a clear solution. The solution was washed with aqueous saturated sodium bicarbonate (50 mL×2), dried over anhydrous sodium sulfate and evaporated to give a crude material, which was then purified by silica gel column chromatography (eluent: 2% methanol in dichloromethane) to give the desired product (51%). $^1$HNMR (300 MHz, CDCl$_3$): δ 1.50 (d, J=6.9 Hz, 3H), 1.80-2.24 (m, 8H), 4.40-4.61 (m, 2H), 7.20-7.26 (m, 1H), 7.47 (d, J=7.5 Hz, 1H), 7.55 (s, 1H), 7.69 (t, J=7.8 Hz, 1H), 7.80 (d, J=8.1 Hz, 1H).

Step g: Synthesis of 3-[(7R)-8-(4,4-difluorocyclo-hexyl)-2-[(7-fluoro-1H-indazol-5-yl)amino]-7-methyl-6-oxo-7,8-dihydropteridin-5(6H)-yl]benzonitrile

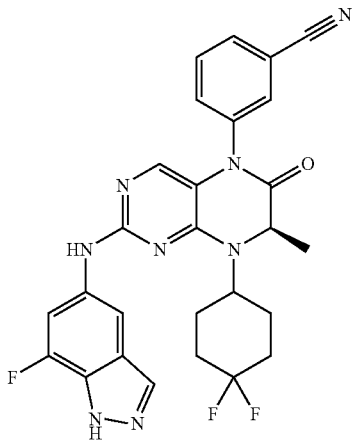 [SMILES: C[C@@H]1C(=O)N(c2cccc(C#N)c2)c2cnc(Nc3cc(F)c4[nH]ncc4c3)nc2N1C1CCC(F)(F)CC1]

To a solution of 3-[(7R)-2-chloro-8-(4,4-difluorocyclohexyl)-7-methyl-6-oxo-7,8-dihydropteridin-5(6H)-yl]benzonitrile (208 mg, 0.5 mmol), 7-fluoro-1H-indazol-5-amine (113 mg, 0.75 mmol) in trifluoroethanol (2 mL) in a microwave reaction vial was added trifluoroacetic acid (171 mg). The vial was then sealed and heated in a microwave reactor at 125° C. for 30 minutes. The reaction mixture was then diluted with ethyl acetate (25 mL) and washed with aqueous saturated aq. sodium bicarbonate. The organic layer was dried ($Na_2SO_4$) and evaporated to give a crude material, which was then purified by silica gel column chromatography (eluent: 2% methanol in dichloromethane) to give the desired product (40%).

Examples 261-286 were prepared according to procedures similar to the preparation of Example 260, using corresponding starting materials and intermediates. For example, for the synthesis of example 262, (3,4-dimethoxyphenyl)boronic acid was used in the step f of the synthesis.

| Ex. # | Chemical Name | Analytical data |
|---|---|---|
| 260 | 3-[(7R)-8-(4,4-difluorocyclohexyl)-2-[(7-fluoro-1H-indazol-5-yl)amino]-7-methyl-6-oxo-7,8-dihydropteridin-5(6H)-yl]benzonitrile | $^1$H NMR (400 MHz, CD$_3$OD): δ 7.93-8.03 (m, 1H), 7.85-7.90 (m, 1H), 7.71-7.81 (m, 3H), 7.65 (d, J = 8.1 Hz, 1H), 7.50 (d, J = 12.9 Hz, 1H), 7.06-7.13 (m, 1H), 4.43-4.60 (m, 2H), 1.85-2.31 (m, 7H), 1.45-1.54 (m, 3H), 1.32 (br. s., 1H). MS (ES$^+$): m/z = 533.41 [MH$^+$]. UPLC: t$_R$ = 0.90 min (TOF: polar_2 min). |
| 261 | 3-[(7R)-8-(4,4-difluorocyclohexyl)-2-(1H-indazol-5-ylamino)-7-methyl-6-oxo-7,8-dihydropteridin-5(6H)-yl]benzonitrile | $^1$H NMR (400 MHz, CDCl$_3$) δ 1.26 (s, 2 H) 1.49 (d, J = 6.8 Hz, 3 H) 1.88 (d, J = 8.5 Hz, 2 H) 1.95-2.05 (m, 1 H) 2.05-2.19 (m, 1 H) 2.28 (d, J = 7.5 Hz, 2 H) 4.42 (d, J = 6.8 Hz, 2 H) 6.91 (s, 1H) 7.20 (s, 1 H) 7.40-7.47 (m, 2 H) 7.52 (d, J = 8.0 Hz, 1 H) 7.59 (s, 1 H) 7.65 (t, J = 7.9 Hz, 1 H) 7.75 (dt, J = 7.8, 1.26 Hz, 1 H) 8.00 (s, 1 H) 8.03 (s, 1 H) 9.87-10.27 (m, 1 H). MS(ES$^+$): m/z = 515.6 [MH$^+$]. |
| 262 | (7R)-8-(4,4-difluorocyclohexyl)-5-(3,4-dimethoxyphenyl)-2-[(7-fluoro-1H-indazol-5-yl)amino]-7-methyl-7,8-dihydropteridin-6(5H)-one | MS(ES$^+$): m/z = 568.82 (60) [MH$^+$]. HPLC: t$_R$ = 2.46 (ZQ3, Polar_5 min). |
| 263 | (7R)-8-(4,4-difluorocyclohexyl)-2-[(7-fluoro-1H-indazol-5-yl)amino]-5-(3-fluorophenyl)-7-methyl-7,8-dihydropteridin-6(5H)-one | MS(ES$^+$): m/z = 526.93 (80) [MH$^+$]. HPLC: t$_R$ = 2.71 (ZQ3, Polar_5 min). |
| 264 | (7R)-8-(4,4-difluorocyclohexyl)-2-[(7-fluoro-1H-indazol-5-yl)amino]-7-methyl-5-(pyridin-3-yl)-7,8-dihydropteridin-6(5H)-one | $^1$H NMR (400 MHz, CD$_3$OD): δ 8.67 (dd, J = 1.4, 4.9 Hz, 1H), 8.54 (d, J = 2.0 Hz, 1H), 7.99 (d, J = 2.8 Hz, 1H), 7.82-7.90 (m, 1H), 7.72 (d, J = 1.8 Hz, 1H), 7.65 (dd, J = 4.8, 8.1 Hz, 1H), 7.50 (d, J = 12.9 Hz, 1H), 7.11 (s, 1H), 4.43-4.61 (m, 2H), 1.83-2.32 (m, 8H), 1.49 (d, J = 6.8 Hz, 3H). MS (ES$^+$): m/z = 509.18 [MH$^+$]. UPLC: t$_R$ = 0.76 min (TOF: polar_2 min). |
| 265 | 3-[(7R)-8-(4,4-difluorocyclohexyl)-7-methyl-6-oxo-2-[(2-oxo-2,3-dihydro-1H-benzimidazol-5-yl)amino]-7,8-dihydropteridin-5(6H)-yl]benzonitrile | $^1$H NMR (400 MHz, CD$_3$OD): δ 7.86 (td, J = 1.3, 7.8 Hz, 1H), 7.71-7.79 (m, 2H), 7.59-7.66 (m, 1H), 7.29 (d, J = 1.8 Hz, 1H), 7.16 (dd, J = 2.0, 8.6 Hz, 1H), 7.03 (s, 1H), 6.95 (d, J = 8.6 Hz, 1H), 4.46 (q, J = 6.7 Hz, 2H), 1.78-2.28 (m, 9H), 1.47 (d, J = 6.8 Hz, 3H). MS (ES$^+$): m/z = 531.34 [MH$^+$]. UPLC: t$_R$ = 0.75 min (TOF: polar_2 min). |
| 266 | 3-[(7R)-8-(4,4-difluorocyclohexyl)-7-methyl-6-oxo-2-[(2-oxo-2,3-dihydro-1,3-benzoxazol-6-yl)amino]-7,8- | $^1$H NMR (400 MHz, CD$_3$OD): δ 7.86 (td, J = 1.4, 7.8 Hz, 1H), 7.71-7.80 (m, 3H), 7.60-7.67 (m, 1H), 7.19 (dd, J = 2.0, 8.6 Hz, 1H), 7.08 (s, 1H), 6.97 (d, J = 8.3 Hz, 1H), 4.41-4.56 (m, 2H), |

-continued

| Ex. # | Chemical Name | Analytical data |
|---|---|---|
| | dihydropteridin-5(6H)-yl]benzonitrile | 1.85-2.30 (m, 8H), 1.48 (d, J = 6.8 Hz, 3H). MS (ES$^+$): m/z = 533.32 [MH$^+$]. UPLC: t$_R$ = 0.86 min (TOF: polar__2 min). |
| 267 | 3-[(7R)-8-(4,4-difluorocyclohexyl)-7-methyl-6-oxo-2-[(2-oxo-2,3-dihydro-1,3-benzothiazol-6-yl)amino]-7,8-dihydropteridin-5(6H)-yl]benzonitrile | $^1$H NMR (400 MHz, CD$_3$OD): δ 7.84-7.89 (m, 2H), 7.71-7.79 (m, 2H), 7.63 (d, J = 8.6 Hz, 1H), 7.35 (dd, J = 2.3, 8.6 Hz, 1H), 7.02-7.09 (m, 2H), 4.40-4.56 (m, 2H), 2.02-2.30 (m, 5H), 1.86-1.99 (m, 3H), 1.47 (d, J = 6.8 Hz, 3H). MS (ES$^+$): m/z = 548.11 [MH$^+$]. UPLC: t$_R$ = 0.90 min (TOF: polar__2 min). |
| 268 | 3-[(7R)-8-(4,4-difluorocyclohexyl)-7-methyl-6-oxo-2-(1H-pyrazolo[3,4-c]pyridin-5-ylamino)-7,8-dihydropteridin-5(6H)-yl]benzonitrile | $^1$H NMR (400 MHz, CD$_3$OD): δ 8.74 (s, 1H), 8.35 (s, 1H), 8.04 (s, 1H), 7.88 (d, J = 7.8 Hz, 1H), 7.71-7.82 (m, 2H), 7.66 (d, J = 8.1 Hz, 1H), 7.16 (s, 1H), 4.51 (q, J = 6.7 Hz, 2H), 2.15 (s, 8H), 1.50 (d, J = 6.8 Hz, 3H). MS (ES$^+$): m/z = 516.32 [MH$^+$]. UPLC: t$_R$ = 0.85 min (TOF: polar__2 min). |
| 269 | 4-{[(7R)-5-(3-cyanophenyl)-8-(4,4-difluorocyclohexyl)-7-methyl-6-oxo-5,6,7,8-tetrahydropteridin-2-yl]amino}benzoic acid | $^1$H NMR (400 MHz, CD$_3$OD): δ 7.84-7.95 (m, 3H), 7.71-7.81 (m, 4H), 7.65 (d, J = 8.3 Hz, 1H), 7.15 (br. s., 1H), 4.46-4.60 (m, 2H), 2.16-2.34 (m, 4H), 1.90-2.12 (m, 4H), 1.49 (d, J = 6.8 Hz, 3H). MS (ES$^+$): m/z = 519.34 [MH$^+$]. UPLC: t$_R$ = 1.00 min (TOF: polar__2 min). |
| 270 | 3-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]benzonitrile | $^1$H NMR (400 MHz, CD$_3$OD): δ 8.67 (d, J = 2.3 Hz, 1H), 8.45 (d, J = 2.5 Hz, 1H), 8.02 (s, 1H), 7.84-7.91 (m, 1H), 7.72-7.81 (m, 2H), 7.65 (d, J = 8.1 Hz, 1H), 7.09 (s, 1H), 4.48 (q, J = 6.7 Hz, 2H), 2.10-2.25 (m, 4H), 1.84-2.07 (m, 4H), 1.48 (d, J = 6.8 Hz, 3H). MS (ES$^+$): m/z = 516.16 [MH$^+$]. UPLC: t$_R$ = 0.81 min (TOF: polar__2 min). |
| 271 | 4-{[(7R)-5-(3-cyanophenyl)-8-(4,4-difluorocyclohexyl)-7-methyl-6-oxo-5,6,7,8-tetrahydropteridin-2-yl]amino}-2-fluorobenzoic acid | $^1$H NMR (400 MHz, CD$_3$OD): δ 7.86-7.94 (m, 2H), 7.72-7.85 (m, 3H), 7.66 (d, J = 7.8 Hz, 1H), 7.14-7.36 (m, 2H), 4.62 (t, J = 11.7 Hz, 1H), 4.52 (q, J = 6.8 Hz, 1H), 2.20-2.38 (m, 3H), 1.90-2.19 (m, 5H), 1.46-1.55 (m, 3H). MS (ES$^+$): m/z = 537.30 [MH$^+$]. UPLC: t$_R$ = 1.09 min (TOF: polar__2 min). |
| 272 | 4-{[(7R)-5-(3-cyanophenyl)-8-(4,4-difluorocyclohexyl)-7-methyl-6-oxo-5,6,7,8-tetrahydropteridin-2-yl]amino}-2-fluorobenzamide | $^1$H NMR (400 MHz, CD$_3$OD): δ 7.85-7.96 (m, 2H), 7.71-7.83 (m, 3H), 7.61-7.68 (m, 1H), 7.33 (dd, J = 1.8, 8.6 Hz, 1H), 7.18 (s, 1H), 4.62 (t, J = 11.7 Hz, 1H), 4.52 (q, J = 6.7 Hz, 1H), 1.87-2.36 (m, 8H), 1.50 (d, J = 6.8 Hz, 3H). MS (ES$^+$): m/z = 536.02 [MH$^+$]. UPLC: t$_R$ = 1.02 min (TOF: polar__2 min). |
| 273 | 4-{[(7R)-5-(3-cyanophenyl)-8-(4,4-difluorocyclohexyl)-7-methyl-6-oxo-5,6,7,8-tetrahydropteridin-2-yl]amino}benzenesulfonamide | $^1$H NMR (400 MHz, CD$_3$OD): δ 7.85-7.90 (m, 1H), 7.72-7.84 (m, 6H), 7.65 (d, J = 8.1 Hz, 1H), 7.13-7.17 (m, 1H), 4.46-4.61 (m, 2H), 1.90-2.34 (m, 8H), 1.49 (d, J = 6.8 Hz, 3H). MS (ES$^+$): m/z = 554.28 [MH$^+$]. UPLC: t$_R$ = 0.97 min (TOF: polar__2 min). |
| 274 | 3-[(7R)-2-[(4-cyanophenyl)amino]-8-(4,4-difluorocyclohexyl)-7-methyl-6-oxo-7,8-dihydropteridin-5(6H)-yl]benzonitrile | $^1$H NMR (400 MHz, CD$_3$OD): δ 7.72-7.90 (m, 5H), 7.65 (d, J = 8.1 Hz, 1H), 7.55-7.60 (m, 2H), 7.16 (s, 1H), 4.51 (q, J = 6.7 Hz, 2H), 1.89-2.32 (m, 8H), 1.49 (d, J = 6.8 Hz, 3H). MS (ES$^+$): m/z = 500.33 [MH$^+$]. UPLC: t$_R$ = 1.23 min (TOF: polar__2 min). |
| 275 | 3-[(7R)-2-{[4-amino-3-(trifluoromethyl)phenyl]amino}-8-(4,4-difluorocyclohexyl)-7-methyl-6-oxo-7,8-dihydropteridin-5(6H)-yl]benzonitrile | $^1$H NMR (400 MHz, CD$_3$OD): δ 7.82-7.89 (m, 1H), 7.70-7.79 (m, 2H), 7.59-7.66 (m, 2H), 7.39 (dd, J = 2.1, 9.0 Hz, 1H), 7.04 (s, 1H), 6.82 (d, J = 8.6 Hz, 1H), 4.38-4.58 (m, 2H), 1.81-2.26 (m, 8H), 1.46 (d, J = 6.8 Hz, 3H). MS (ES$^+$): m/z = 558.31 [MH$^+$]. UPLC: t$_R$ = 1.01 min (TOF: polar__2 min). |
| 276 | 3-[(7R)-8-(4,4-difluorocyclohexyl)-2-[(3,5-difluoro-4-hydroxyphenyl)amino]-7-methyl-6-oxo-7,8-dihydropteridin-5(6H)-yl]benzonitrile | $^1$H NMR (400 MHz, CD$_3$OD): δ 7.86 (dd, J = 1.0, 7.8 Hz, 1H), 7.71-7.79 (m, 2H), 7.63 (d, J = 8.1 Hz, 1H), 7.20-7.31 (m, 2H), 7.08 (s, 1H), 4.57 (t, J = 11.9 Hz, 1H), 4.49 (q, J = 6.8 Hz, 1H), 2.18-2.33 (m, 3H), 2.04-2.16 (m, 2H), 1.98-2.01 (m, 1H), 1.86-1.95 (m, 2H), 1.48 (d, J = 6.6 Hz, 3H). MS (ES$^+$): m/z = 527.58 [MH$^+$]. UPLC: t$_R$ = 1.00 min (TOF: polar__2 min). |
| 277 | 3-[(7R)-8-(4,4-difluorocyclohexyl)-2-[(4-fluoro-2-oxo-2,3-dihydro-1,3-benzoxazol-6-yl)amino]-7-methyl-6-oxo-7,8- | $^1$H NMR (400 MHz, CD$_3$OD): δ 1.45-1.52 (m, 3H), 1.80-2.36 (m, 8H), 4.45-4.58 (m, 2H), 7.10 (s, 1H), 7.36 (dd, J = 12.5, 1.6 Hz, 1H), 7.44 (s, 1H), 7.65 (d, J = 7.8 Hz, 1H), 7.75 (t, J = 7.9 Hz, 1H), 7.79 (s, 1H), 7.83-7.90 (m, 1H). MS(ES$^+$): |

| Ex. # | Chemical Name | Analytical data |
|---|---|---|
| | dihydropteridin-5(6H)-yl]benzonitrile | m/z = 550.61 [MH$^+$]. HPLC: t$_R$ = 0.98 min (analytical_2min, UPLC). |
| 278 | 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-(propan-2-yloxy)benzonitrile | $^1$H NMR (400 MHz, CD$_3$OD): δ 1.44 (dd, J = 5.9, 1.6 Hz, 6H), 1.46-1.53 (m, 3H), 1.78-2.18 (m, 6H), 2.19-2.32 (m, 2H), 2.33-2.41 (m, 1H), 4.41-4.61 (m, 2H), 7.06-7.24 (m, 1H), 7.31 (d, J = 8.8 Hz, 1H), 7.37 (d, J = 12.3 Hz, 1H), 7.42-7.53 (m, 2H), 7.56 (br. s., 1H). MS(ES$^+$): m/z = 608.44[MH$^+$]. HPLC: t$_R$ = 1.16 min (analytical_2 min, UPLC). |
| 279 | 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-methoxybenzonitrile | $^1$H NMR (400 MHz, CD$_3$OD): δ 1.47 (d, J = 6.5 Hz, 3H), 1.72-2.04 (m, 4H), 2.08-2.31 (m, 4H), 4.03 (s, 3H), 4.38-4.53 (m, 2H), 7.11 (s, 1H), 7.36 (d, J = 9.0 Hz, 1H), 7.57 (d, J = 8.5 Hz, 1H), 7.65 (s, 1H), 8.02 (s, 1H), 8.44 (d, J = 1.7 Hz, 1H), 8.66 (s, 1H). MS(ES$^+$): m/z = 546.15[MH$^+$]. HPLC: t$_R$ = 0.89 min (analytical_2 min, UPLC). |
| 280 | 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-ethoxybenzonitrile | 1H NMR (400 MHz, CD$_3$OD): δ 1.45-1.54 (m, 6H), 1.84-2.39 (m, 8H), 4.27 (q, J = 6.9 Hz, 2H), 4.47 (q, J = 6.8 Hz, 1H), 4.56 (t, J = 11.4 Hz, 1H), 7.16 (br. s., 1H), 7.30 (d, J = 9.0 Hz, 1H), 7.37 (dd, J = 12.5, 1.6 Hz, 1H), 7.45 (s, 1H), 7.51 (d, J = 8.8 Hz, 1H), 7.58 (br. s., 1H). MS(ES$^+$): m/z = 594.38 [MH$^+$]. HPLC: t$_R$ = 1.09 (analytical_2 min, UPLC). |
| 281 | 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-methoxybenzonitrile | MS(ES$^+$): m/z = 580.36[MH$^+$]. HPLC: t$_R$ = 1.02 min (analytical_2 min, UPLC). |
| 282 | 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-ethoxybenzonitrile | $^1$H NMR (400 MHz, CD$_3$OD): δ 1.41-1.61 (m, 6H), 1.78-2.03 (m, 4H), 2.10-2.25 (m, 4H), 4.28 (q, J = 6.9 Hz, 2H), 4.38-4.53 (m, 2H), 7.12 (s, 1H), 7.28-7.43 (m, 1H), 7.46-7.60 (m, 1H), 7.65 (d, J = 2.2 Hz, 1H), 8.02 (s, 1H), 8.32-8.49 (m, 1H), 8.67 (d, J = 2.02 Hz, 1H). MS(ES$^+$): m/z = 560.40[MH$^+$]. HPLC: t$_R$ = 0.97 min (analytical_2 min, UPLC). |
| 283 | 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-methoxybenzonitrile | $^1$H NMR (400 MHz, CD$_3$OD): δ 1.44-1.54 (m, 3H), 1.80-2.37 (m, 8H), 4.02 (d, J = 1.0 Hz, 3H), 4.39-4.57 (m, 2H), 6.86-7.02 (m, 1H), 7.16 (d, J = 8.5 Hz, 2H), 7.30 (d, J = 8.8 Hz, 1H), 7.46-7.61 (m, 2H), 7.71-7.80 (m, 1H). MS(ES$^+$): m/z = 562.31[MH$^+$]. HPLC: t$_R$ = 0.87 min (analytical_2 min, UPLC). |
| 284 | 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-ethoxybenzonitrile | $^1$H NMR (400 MHz, CD$_3$OD): δ 1.43-1.54 (m, 6H), 1.79-2.37 (m, 8H), 4.26 (q, J = 6.8 Hz, 2H), 4.40-4.54 (m, 2H), 6.96 (d, J = 8.3 Hz, 1H), 7.17 (d, J = 8.0 Hz, 2H), 7.28 (d, J = 8.8 Hz, 1H), 7.49 (d, J = 8.5 Hz, 1H), 7.56 (br. s., 1H), 7.75 (d, J = 1.7 Hz, 1H). MS(ES$^+$): m/z = 576.35[MH$^+$]. HPLC: t$_R$ = 0.93 min (analytical_2 min, UPLC). |
| 285 | 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-(propan-2-yloxy)benzonitrile | $^1$H NMR (400 MHz, CD$_3$OD): δ 1.43 (d, J = 6.0 Hz, 6H), 1.47 (d, J = 6.8 Hz, 3H), 1.77-2.33 (m, 8H), 4.39-4.56 (m, 2H), 4.81 (d, J = 6.0 Hz, 1H), 6.96 (d, J = 8.5 Hz, 1H), 7.17 (d, J = 8.3 Hz, 2H), 7.28 (d, J = 9.0 Hz, 1H), 7.47 (d, J = 8.3 Hz, 1H), 7.54 (br. s., 1H), 7.76 (s, 1H). MS(ES$^+$): m/z = 590.36[MH$^+$]. HPLC: t$_R$ = 0.98 min (analytical_2 min, UPLC). |
| 286 | 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-(propan-2-yloxy)benzonitrile | $^1$H NMR (400 MHz, CD$_3$OD): δ 1.44 (d, J = 6.0, 6H), 1.47 (d, J = 6.8, 3H), 1.79-2.28 (m, 8H), 4.30-4.50 (m, 2H), 4.78 (t, J = 5.6 Hz, 1H), 7.15 (br. s., 1H), 7.24 (d, J = 8.3 Hz, 1H), 7.40-7.55 (m, 2H), 7.97 (s, 1H), 8.40 (s, 1H), 8.65 (br. s., 1H). MS(ES$^+$): m/z = 574.31[MH$^+$]. HPLC: t$_R$ = 0.95 min (analytical_2 min, UPLC). |

Examples 287-295 were prepared according to procedures similar to the preparation of Example 18, using corresponding starting materials and intermediates. For example, for the synthesis of example 287, methyl (2R)-2-aminobutanoate hydrochloride and cyclohexanone were used in the step a of the synthesis, (3-cyanophenyl)boronic acid was used in the step d of the synthesis and 7-fluoro-1H-indazol-5-amine was used in the step e of the synthesis.

Examples 296 were prepared according to procedures similar for the preparation of Example 18, using corresponding starting materials and intermediates. More specifically, methyl (2R)-2-aminobutanoate hydrochloride and cyclopentanone were used in the step a of the synthesis, (3-cyanophenyl)boronic acid was used in the step d of the synthesis and 1H-indazol-5-amine was used in the step e of the synthesis.

| Ex. # | Chemical Name | Analytical data |
|---|---|---|
| 287 | 3-[(7R)-8-cyclohexyl-7-ethyl-2-[(7-fluoro-1H-indazol-5-yl)amino]-6-oxo-7,8-dihydropteridin-5(6H)-yl]benzonitrile | 1H NMR (400 MHz, CD$_3$OD) δ 7.98 (d, J = 3.0 Hz, 1H), 7.87 (d, J = 7.8 Hz, 1H), 7.74-7.79 (m, 3H), 7.63 (d, J = 8.3 Hz, 1H), 7.47 (d, J = 12.4 Hz, 1H), 7.01 (s, 1H), 4.38 (dd, J = 4.5, 7.6 Hz, 2H), 2.22 (d, J = 11.9 Hz, 1H), 1.79-1.98 (m, 6H), 1.57-1.77 (m, 2H), 1.48 (q, J = 12.5 Hz, 2H), 1.24 (d, J = 13.1 Hz, 1H), 1.03 (t, J = 7.5 Hz, 3H). MS (ES$^+$): m/z = 511.44 [M + H]$^+$. UPLC: t$_R$ = 0.98 min (TOF: polar__2 min). |
| 288 | (7R)-8-cyclohexyl-7-ethyl-2-[(7-fluoro-1H-indazol-5-yl)amino]-5-(pyridin-3-yl)-7,8-dihydropteridin-6(5H)-one | $^1$H NMR (400 MHz, CD$_3$OD): δ 8.68 (dd, J = 1.0, 4.8 Hz, 1H), 8.53 (d, J = 2.3 Hz, 1H), 8.00 (d, J = 2.8 Hz, 1H), 7.85 (d, J = 8.3 Hz, 1H), 7.79 (d, J = 1.5 Hz, 1H), 7.66 (dd, J = 5.1, 8.1 Hz, 1H), 7.48 (d, J = 12.9 Hz, 1H), 7.04 (s, 1H), 4.41 (dd, J = 4.5, 7.6 Hz, 2H), 2.23 (d, J = 11.4 Hz, 1H), 1.82-2.00 (m, 6H), 1.59-1.78 (m, 2H), 1.50 (q, J = 13.1 Hz, 2H), 1.21-1.32 (m, 1H), 1.04 (t, J = 7.6 Hz, 3H). MS (ES$^+$): m/z = 487.36 [MH$^+$]. UPLC: t$_R$ = 0.85 min (TOF: polar__2 min). |
| 289 | (7R)-8-cyclohexyl-5-(3,4-dimethoxyphenyl)-7-ethyl-2-[(7-fluoro-1H-indazol-5-yl)amino]-7,8-dihydropteridin-6(5H)-one. | $^1$H NMR (400 MHz, CD$_3$OD): δ 7.99 (d, J = 3.3 Hz, 1H), 7.78 (d, J = 1.5 Hz, 1H), 7.47 (d, J = 12.4 Hz, 1H), 7.13 (d, J = 8.6 Hz, 1H), 7.03 (s, 1H), 6.80-6.88 (m, 2H), 4.39 (dd, J = 3.9, 8.0 Hz, 2H), 3.91 (s, 3H), 3.80-3.86 (m, 3H), 2.23 (d, J = 12.1 Hz, 1H), 1.82-1.99 (m, 6H), 1.60-1.77 (m, 3H), 1.41-1.53 (m, 2H), 1.03 (t, J = 7.6 Hz, 3H). MS (ES$^+$): m/z = 546.40 [MH$^+$]. UPLC: t$_R$ = 0.94 min (TOF: polar__2 min). |
| 290 | (7R)-8-cyclohexyl-7-ethyl-2-[(7-fluoro-1H-indazol-5-yl)amino]-5-(3-fluorophenyl)-7,8-dihydropteridin-6(5H)-one | $^1$H NMR (400 MHz, CD$_3$OD): δ 7.98 (d, J = 3.3 Hz, 1H), 7.78 (d, J = 1.5 Hz, 1H), 7.56-7.64 (m, 1H), 7.47 (d, J = 13.4 Hz, 1H), 7.24-7.31 (m, 1H), 7.09-7.15 (m, 2H), 7.02 (s, 1H), 4.34-4.45 (m, 2H), 2.22 (d, J = 10.6 Hz, 1H), 1.80-2.00 (m, 6H), 1.58-1.76 (m, 2H), 1.40-1.55 (m, 2H), 1.19-1.30 (m, 1H), 1.02 (t, J = 7.6 Hz, 3H). MS (ES$^+$): m/z = 504.40[MH$^+$]. UPLC: t$_R$ = 1.00 min (TOF: polar__2 min). |
| 291 | (7R)-8-cyclohexyl-7-ethyl-2-[(7-fluoro-1H-indazol-5-yl)amino]-5-[3-(trifluoromethyl)phenyl]-7,8-dihydropteridin-6(5H)-one. | $^1$H NMR (400 MHz, CD$_3$OD): δ 7.99 (d, J = 3.0 Hz, 1H), 7.76-7.86 (m, 3H), 7.61-7.65 (m, 1H), 7.58 (d, J = 7.6 Hz, 1H), 7.47 (d, J = 12.6 Hz, 1H), 6.98 (s, 1H), 4.36-4.46 (m, 2H), 2.23 (d, J = 11.6 Hz, 1H), 1.82-2.00 (m, 6H), 1.59-1.76 (m, 2H), 1.40-1.55 (m, 2H), 1.31-1.38 (m, 1H), 1.04 (t, J = 7.5 Hz, 3H). MS (ES$^+$): m/z = 554.36 [MH$^+$]. UPLC: t$_R$ = 1.11 min (TOF: polar__2 min). |
| 292 | (7R)-8-cyclohexyl-7-ethyl-2-[(7-fluoro-1H-indazol-5-yl)amino]-5-[6-(morpholin-4-yl)pyridin-3-yl]-7,8-dihydropteridin-6(5H)-one | $^1$H NMR (400 MHz, CD$_3$OD): δ 7.99 (br. s., 2H), 7.77 (d, J = 1.3 Hz, 1H), 7.42-7.50 (m, 2H), 7.08 (s, 1H), 6.96 (d, J = 9.1 Hz, 1H), 4.38 (dd, J = 4.2, 8.0 Hz, 2H), 3.77-3.84 (m, 4H), 3.55-3.60 (m, 4H), 2.22 (d, J = 9.3 Hz, 1H), 1.80-1.96 (m, 6H), 1.61-1.76 (m, 2H), 1.41-1.52 (m, 2H), 1.35 (br. s., 1H), 1.00 (t, J = 7.5 Hz, 3H). MS (ES$^+$): m/z = 572.57[MH$^+$]. UPLC: t$_R$ = 0.93 min (TOF: polar__2 min). |
| 293 | (7R)-8-cyclohexyl-5-[6-(dimethylamino)pyridin-3-yl]-7-ethyl-2-[(7-fluoro-1H-indazol-5-yl)amino]-7,8-dihydropteridin-6(5H)-one | $^1$H NMR (400 MHz, CD$_3$OD): δ 7.89-7.94 (m, 1H), 7.74-7.80 (m, 2H), 7.61-7.66 (m, 1H), 7.01 (s, 1H), 4.87-5.00 (m, 1H), 4.70-4.83 (m, 1H), 4.31 (quin, J = 8.4 Hz, 1H), 2.08-2.19 (m, 2H), 1.97-2.07 (m, 4H), 1.61-1.76 (m, 2H). MS (ES$^+$): m/z = 530.47 [MH$^+$]. UPLC: t$_R$ = 0.86 min (TOF: polar__2 min). |
| 294 | (7R)-8-cyclohexyl-7-ethyl-2-[(7-fluoro-1H-indazol-5-yl)amino]-5-(3-fluoro-4-methoxyphenyl)-7,8-dihydropteridin-6(5H)-one | $^1$H NMR (400 MHz, CD$_3$OD): δ 7.98 (d, J = 3.3 Hz, 1H), 7.77 (d, J = 1.5 Hz, 1H), 7.46 (d, J = 12.9 Hz, 1H), 7.28 (t, J = 9.0 Hz, 1H), 6.99-7.12 (m, 3H), 4.37 (dd, J = 3.9, 8.0 Hz, 2H), 3.95 (s, 3H), 2.22 (d, J = 11.9 Hz, 1H), 1.80-1.97 (m, 6H), 1.58-1.77 (m, 2H), 1.48 (q, J = 12.6 Hz, 2H), 1.23 (d, J = 13.4 Hz, 1H), 1.01 (t, J = 7.5 Hz, 3H). MS (ES$^+$): m/z = 534.44 [MH$^+$]. UPLC: t$_R$ = 1.00 min (TOF: polar__2 min). |
| 295 | 3-[(7R)-8-cyclohexyl-7-ethyl-2-[(3-fluoro-1H-indazol-5-yl)amino]-6-oxo-7,8- | $^1$H NMR (400 MHz, CD$_3$OD): δ 8.08 (d, J = 1.3 Hz, 1H), 7.85-7.90 (m, 1H), 7.73-7.78 (m, 2H), 7.63 (d, J = 8.6 Hz, 1H), 7.44-7.49 (m, 1H), 7.35 |

-continued

| Ex. # | Chemical Name | Analytical data |
|---|---|---|
|  | dihydropteridin-5(6H)-yl]benzonitrile | (dd, J = 1.8, 9.1 Hz, 1H), 7.02 (s, 1H), 4.40-4.50 (m, 1H), 4.38 (dd, J = 4.9, 7.5 Hz, 1H), 2.19 (d, J = 10.4 Hz, 1H), 1.80-1.98 (m, 6H), 1.59-1.75 (m, 2H), 1.42-1.56 (m, 2H), 1.20-1.30 (m, 1H), 1.03 (t, J = 7.6 Hz, 3H). MS (ES+): m/z = 511.47 [MH+]. UPLC: $t_R$ = 1.01 min (TOF: polar_2 min). |
| 296 | 3-[(7R)-8-cyclopentyl-7-ethyl-2-(1H-indazol-5-ylamino)-6-oxo-7,8-dihydropteridin-5(6H)-yl]benzonitrile | $^1$H NMR (400 MHz, CD$_3$OD): δ 8.08 (d, J = 1.0 Hz, 1H), 7.93 (td, J = 1.3, 7.8 Hz, 1H), 7.80-7.84 (m, 2H), 7.76-7.80 (m, 1H), 7.66-7.72 (m, 1H), 7.63 (d, J = 8.8 Hz, 1H), 7.37 (dd, J = 1.8, 8.8 Hz, 1H), 6.67 (s, 1H), 4.56 (dd, J = 3.5, 6.8 Hz, 1H), 4.21 (t, J = 8.8 Hz, 1H), 1.84-2.17 (m, 6H), 1.45 (br. s., 4H), 1.03 (t, J = 7.5 Hz, 3H). MS (ES+): m/z = 479.48 [MH+]. UPLC: $t_R$ = 0.89 min (TOF: polar_2 min). |

Examples 297-299 were prepared according to procedures similar to the preparation of Example 18, using corresponding starting materials and intermediates. For example, for the synthesis of example 297, spiro[2.5]octan-6-one and D-alanine methyl ester hydrochloride were used in the step a of the synthesis, (3-cyanophenyl)boronic acid was used in the step d of the synthesis and 7-fluoro-1H-indazol-5-amine was used in the step e of the synthesis.

Examples 300-302 were prepared according to procedures similar to the preparation of Example 18, using corresponding starting materials and intermediates. For example, for the synthesis of example 302, ($^2$H$_{10}$)cyclohexanone and D-alanine methyl ester hydrochloride were used in the step a of the synthesis, (3-cyanophenyl)boronic acid was used in the step d of the synthesis, 7-fluoro-1H-indazol-5-amine was used in the step e of the synthesis.

| Ex. # | Chemical Name | Analytical data |
|---|---|---|
| 297 | 3-[(7R)-2-[(7-fluoro-1H-indazol-5-yl)amino]-7-methyl-6-oxo-8-(spiro[2.5]oct-6-yl)-7,8-dihydropteridin-5(6H)-yl]benzonitrile | $^1$H NMR (400 MHz, CD$_3$OD): δ 7.99 (br. s., 1H), 7.87 (d, J = 8.3 Hz, 1H), 7.71-7.81 (m, 3H), 7.65 (d, J = 8.6 Hz, 1H), 7.50 (d, J = 13.6 Hz, 1H), 7.08 (s, 1H), 4.49-4.63 (m, 2H), 2.19 (d, J = 10.9 Hz, 1H), 1.93-2.08 (m, 3H), 1.73-1.84 (m, 2H), 1.50 (d, J = 6.6 Hz, 3H), 1.00-1.10 (m, 2H), 0.28-0.41 (m, 4H). MS (ES+): m/z = 523.29 [MH+]. UPLC: $t_R$ = 1.00 min (TOF: polar_2 min). |
| 298 | (7R)-2-[(7-fluoro-1H-indazol-5-yl)amino]-7-methyl-5-(pyridin-3-yl)-8-(spiro[2.5]oct-6-yl)-7,8-dihydropteridin-6(5H)-one. | $^1$H NMR (400 MHz, CD$_3$OD): δ 8.67 (d, J = 3.5 Hz, 1H), 8.54 (d, J = 2.5 Hz, 1H), 7.98 (d, J = 3.0 Hz, 1H), 7.86 (d, J = 8.8 Hz, 1H), 7.80 (d, J = 1.0 Hz, 1H), 7.65 (dd, J = 4.8, 8.1 Hz, 1H), 7.51 (d, J = 13.9 Hz, 1H), 7.10 (s, 1H), 4.49-4.64 (m, 2H), 2.18 (br. s., 1H), 2.01 (q, J = 13.6 Hz, 3H), 1.74-1.87 (m, 2H), 1.52 (d, J = 6.8 Hz, 3H), 1.06 (br. s., 2H), 0.28-0.43 (m, 4H). MS (ES+): m/z = 499.14 [MH+]. UPLC: $t_R$ = 0.88 min (TOF: polar_2 min). |
| 299 | (7R)-5-(3,4-dimethoxyphenyl)-2-[(7-fluoro-1H-indazol-5-yl)amino]-7-methyl-8-(spiro[2.5]oct-6-yl)-7,8-dihydropteridin-6(5H)-one | $^1$H NMR (400 MHz, CD$_3$OD): δ 7.98 (d, J = 2.3 Hz, 1H), 7.79 (d, J = 1.5 Hz, 1H), 7.49 (d, J = 12.6 Hz, 1H), 7.06-7.15 (m, 2H), 6.86 (br. s., 2H), 4.45-4.61 (m, 2H), 3.90 (s, 3H), 3.83 (s, 3H), 2.19 (d, J = 11.6 Hz, 1H), 1.95-2.08 (m, 2H), 1.69-1.83 (m, 1H), 1.50 (d, J = 6.8 Hz, 4H), 0.98-1.12 (m, 3H), 0.27-0.41 (m, 4H). MS (ES+): m/z = 558.04 [MH+]. UPLC: $t_R$ = 0.96 min (TOF: polar_2 min). |

| Ex. # | Chemical Name | Analytical data |
|---|---|---|
| 300 | (7R)-8-[(2,2,3,3,4,4,5,5,6,6-$^2$H$_{10}$)cyclohexyl]-5-(3,4-dimethoxyphenyl)-2-[(7-fluoro-1H-indazol-5-yl)amino]-7-methyl-7,8-dihydropteridin-6(5H)-one | $^1$H NMR (400 MHz, CD$_3$OD): δ 1.48 (d, J = 6.8 Hz, 3H), 3.84 (s, 3H), 3.91 (s, 3H), 4.40-4.53 (m, 2H), 6.87 (br. s., 2H), 7.09 (s, 1H), 7.12 (d, J = 8.5 Hz, 1H), 7.49 (d, J = 13.3 Hz, 1H), 7.79 (d, J = 1.5 Hz, 1H), 7.99 (d, J = 3.0 Hz, 1H). MS(ES+): m/z = 542.12 [MH+]. HPLC: $t_R$ = 0.86 min (analytical_2 min, UPLC). |

-continued

| Ex. # | Chemical Name | Analytical data |
|---|---|---|
| 301 | (7R)-8-[(2,2,3,3,4,4,5,5,6,6-$^2$H$_{10}$)cyclohexyl]-2-[(7-fluoro-1H-indazol-5-yl)amino]-7-methyl-5-(pyridin-3-yl)-7,8-dihydropteridin-6(5H)-one | $^1$H NMR (400 MHz, CD$_3$OD): δ 1.51 (d, J = 6.8 Hz, 3H), 4.45 (s, 1H), 4.48-4.55 (m, 1H), 7.10 (s, 1H), 7.48 (d, J = 12.6 Hz, 1H), 7.64 (dd, J = 8.0, 4.8 Hz, 1H), 7.78 (dd, J = 1.7, 1.0 Hz, 1H), 7.82 (d, J = 8.0 Hz, 1H), 7.96 (d, J = 3.0 Hz, 1H), 8.51 (d, J = 2.2 Hz, 1H), 8.66 (dd, J = 4.9, 1.1 Hz, 1H). MS(ES$^+$): m/z = 483.25 [MH$^+$]. HPLC: t$_R$ = 0.78 min (analytical__2 min, UPLC). |
| 302 | 3-[(7R)-8-[(2,2,3,3,4,4,5,5,6,6-$^2$H$_{10}$)cyclohexyl]-2-[(7-fluoro-1H-indazol-5-yl)amino]-7-methyl-6-oxo-7,8-dihydropteridin-5(6H)-yl]benzonitrile | $^1$H NMR (400 MHz, CD$_3$OD): δ 1.49 (d, J = 6.8 Hz, 3H), 4.43 (s, 1H), 4.50 (d, J = 6.8 Hz, 1H), 7.06 (br. s., 1H), 7.49 (d, J = 13.1 Hz, 1H), 7.64 (d, J = 8.0 Hz, 1H), 7.75 (t, J = 7.9 Hz, 1H), 7.79 (d, J = 1.5 Hz, 2H), 7.87 (dt, J = 7.8, 1.2 Hz, 1H), 7.99 (d, J = 3.0 Hz, 1H). MS(ES$^+$): m/z = 507.30[MH$^+$]. HPLC: t$_R$ = 0.90 min (analytical__2 min, UPLC). |
| 303 | (7R)-8-cyclohexyl-2-[(7-fluoro-1H-indazol-5-yl)amino]-7-methyl-5-(1-oxidopyridin-3-yl)-7,8-dihydropteridin-6(5H)-one | $^1$H NMR (DMSO-d$_6$, 400 MHz): δ 13.41 (brs, exchanges with D$_2$O, 1H), 9.32 (s, exchanges with D$_2$O, 1H), 8.44 (dd, J = 1.6, 1.6 Hz, 1H), 8.32 (ddd, J = 6.4, 1.6, 1.2 Hz, 1H), 8.01 (brs, 1H), 7.95 (d, J = 1.2 Hz, 1H), 7.61-7.55 (m, 2H), 7.40 (dd, J = 8.2, 0.6 Hz, 1H), 7.33 (s, 1H), 4.46 (q, J = 6.8 Hz, 1H), 4.38 (tt, J = 12.0, 3.6 Hz, 1H), 1.96-1.51 (m, 6H), 1.50-1.39 (m, 2H), 1.38 (d, J = 6.8 Hz, 3H), 1.29-1.20 (m, 2H). MS(ES$^+$): m/z = 489.37 [MH$^+$]. HPLC: t$_R$ = 0.78 min (analytical__2 min, UPLC). |
| 304 | (7R)-8-(4,4-dimethylcyclohexyl)-2-[(7-fluoro-1H-indazol-5-yl)amino]-7-methyl-5-(1-oxidopyridin-3-yl)-7,8-dihydropteridin-6(5H)-one | $^1$H NMR (CD$_3$OD, 400 MHz): δ 0.94 (s, 3 H), 0.96 (s, 3 H), 1.31 (t, J = 11.2 Hz, 1 H), 1.41-1.56 (m, 3 H), 1.44 (d, J = 6.8 Hz, 3 H), 1.67 (m, 1 H), 1.90-1.98 (m, 2 H), 2.61 (m, 1 H), 4.32 (t, J = 12.0 Hz, 1 H), 4.51 (q, J = 6.8 Hz, 1 H), 7.26 (s, 1 H), 7.47 (d, J = 13.2 Hz, 1 H), 7.60-7.68 (m, 2 H), 7.81 (d, J = 1.6 Hz, 1 H), 7.95 (d, J = 3.2 Hz, 1 H), 8.41 (d, J = 6.4 Hz, 1 H), 8.58 (t, J = 1.6 Hz, 1 H). MS (ES$^+$): m/z = 517.63 [MH$^+$]. HPLC: t$_R$ = 0.83 min (TOF, polar__2 min). |

Example 303 was prepared by the following procedure:

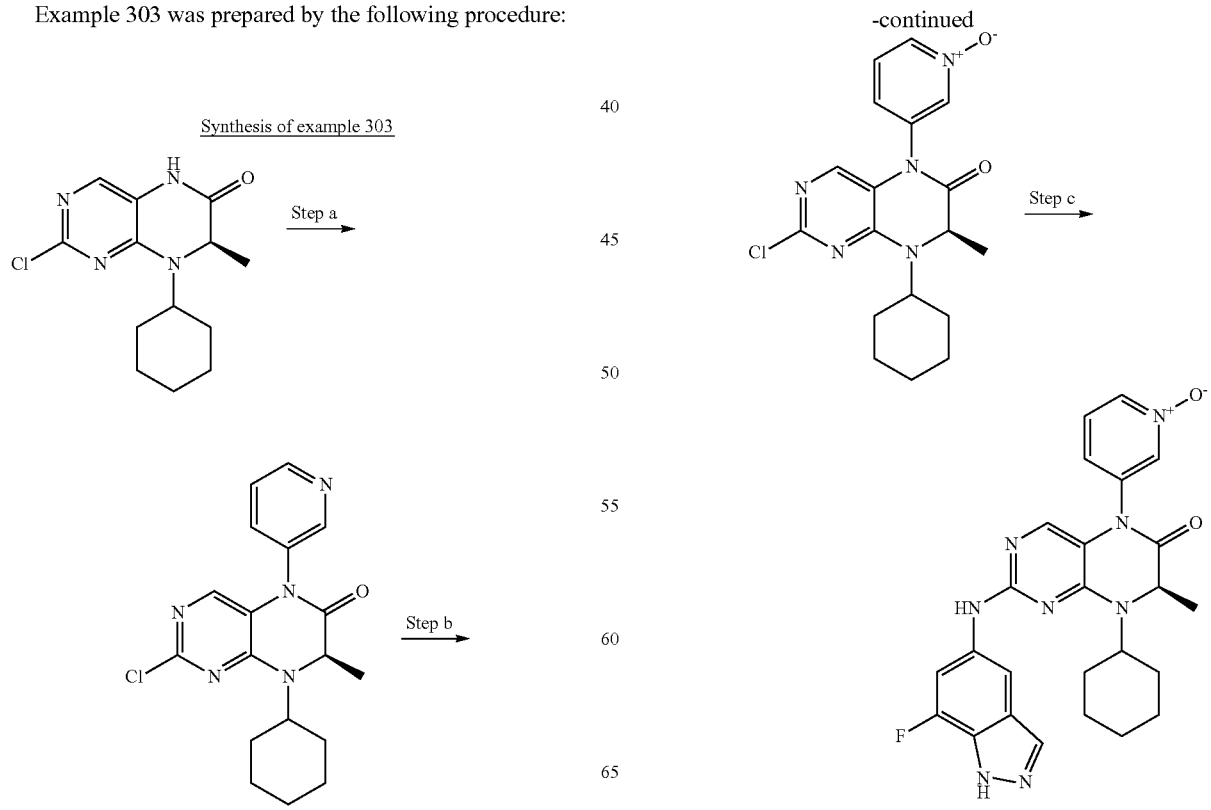

Step c: (7R)-8-cyclohexyl-2-[(7-fluoro-1H-indazol-5-yl)amino]-7-methyl-5-(1-oxidopyridin-3-yl)-7,8-dihydropteridin-6(5H)-one

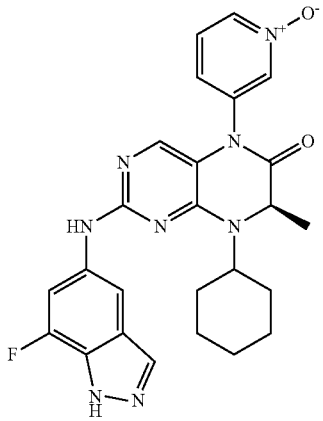 [SMILES: C[C@@H]1C(=O)N(c2ccc[n+]([O-])c2)c2cnc(Nc3cc(F)c4[nH]ncc4c3)nc2N1C1CCCCC1]

To a solution of (7R)-2-chloro-8-cyclohexyl-7-methyl-5-(1-oxidopyridin-3-yl)-7,8-dihydropteridin-6(5H)-one (30.4 mg, 0.081 mmol) and 7-fluoro-1H-indazol-5-amine (37.2 mg, 0.25 mmol) in trifluoroethanol (2.0 mL, 27 mmol) in a microwave reactor vial was added trifluoroacetic acid (42 mg, 0.37 mmol). The vial was then sealed, and the mixture was stirred at 100° C. (oil bath). More 7-fluoro-1H-indazol-5-amine (29.5 mg, 0.195 mmol) and trifluoroacetic acid (0.025 mL, 0.32 mmol) was added after 15 h, and heating at 100° C. was continued for additional 24 h. The reaction mixture was cooled to rt and quenched with saturated aq. NaHCO$_3$ solution (5 mL). The resulting mixture was extracted with 5% MeOH in dichloromethane (15 mL×4). The combined organic layers were washed with water and brine, dried over Na$_2$SO$_4$, filtered, and concentrated in vacuo to give a crude residue, which was then purified by silica gel column chromatography (eluent: 8% methanol in dichloromethane) to give the desired product (24%).

Step b: Synthesis of (7R)-2-chloro-8-cyclohexyl-7-methyl-5-(1-oxidopyridin-3-yl)-7,8-dihydropteridin-6(5H)-one To a stirred solution of (7R)-2-chloro-8-cyclohexyl-7-methyl-5-(pyridin-3-yl)-7,8-dihydropteridin-6(5H)-one (51.2 mg, 0.143 mmol) in dichloromethane (2.5 mL) was added mCPBA (77% max, 33.7 mg, 0.150 mmol) at rt, and the solution was stirred at rt. More mCPBA (77% max, 10.2 mg, 0.0455 mmol) was added after 2.5 h, and stirring at rt was continued for additional 4 h. The reaction solution was diluted with dichloromethane (15 mL), washed with aq. NaHCO$_3$ solution (20 mL×2), dried over Na$_2$SO$_4$, and concentrated in vacuo to give a crude residue, which was then purified by silica gel column chromatography (eluent: 5% methanol in dichloromethane) to give the desired product (0.116 mmol, 81% yield). $^1$H NMR (CDCl$_3$, 400 MHz): δ 8.30 (d, J=6.8 Hz, 1H), 8.17 (s, 1H), 7.45 (dd, J=8.4, 6.8 Hz, 1H), 7.33 (s, 1H), 7.16 (d, J=8.4 Hz, 1H), 4.49 (q, J=6.8 Hz, 1H), 4.49-4.39 (m$_e$, 1H), 2.17-2.10 (m, 1H), 1.96-1.87 (m, 2H), 1.83-1.64 (m, 3H), 1.55-1.43 (m, 3H), 1.47 (d, J=6.8 Hz, 3H), 1.25-1.14 (m, 1H). MS(ES$^+$): m/z=374.13/376.21 [MH$^+$].

Step a: (7R)-2-chloro-8-cyclohexyl-7-methyl-5-(pyridin-3-yl)-7,8-dihydropteridin-6(5H)-one was prepared from (7R)-2-chloro-8-cyclohexyl-7-methyl-7,8-dihydropteridin-6(5H)-one and pyridin-3-ylboronic acid, according to procedures similar to step d for the preparation of Example 18. Examples 304 was prepared according to procedures similar to the preparation of Example 303, using corresponding starting materials and intermediates.

| Ex. # | Chemical Name | Analytical data |
|---|---|---|
| 305 | 2-(1H-indazol-5-ylamino)-8-(3-methylbutyl)-5-phenyl-5,8-dihydropteridine-6,7-dione | $^1$H NMR (DMSO-d$_6$, 400 MHz) δ 0.92 (d, J = 6.8 Hz, 6H), 1.56-1.73 (m, 3H), 4.21 (t, J = 7.2 Hz, 2H), 7.35 (s, 1H), 7.39-7.42 (m, 3H), 7.48-7.59 (m, 2H), 7.61 (t, J = 6.8 Hz, 2H), 7.87 (s, 1H), 8.10 (s, 1H), 9.60 (s, 1H). MS(ES$^+$): m/z = 442.06 [MH$^+$]. HPLC: t$_R$ = 2.72 (ZQ3, Polar_5 min). |
| 306 | 8-(3-methylbutyl)-2-[(2-oxo-2,3-dihydro-1H-indol-5-yl)amino]-5-phenyl-5,8-dihydropteridine-6,7-dione | $^1$H NMR (CDCl$_3$ and CD$_3$OD, 300 MHz) δ 0.85 (d, J = 6.3 Hz, 6H), 1.51-1.56 (m, 3H), 3.36 (s, 2H), 4.17-4.22 (m, 2H), 6.99 (d, J = 8.1 Hz, 2H), 7.15-7.19 (m, 2H), 7.22-7.25 (m, 1H), 7.33 (br. s, 1H), 7.42-7.50 (m, 4H). MS (ES$^+$): m/z = 456.96 (100) [MH$^+$]. HPLC: t$_R$ = 2.60 (ZQ3, Polar_5 min). |
| 307 | 8-cyclopentyl-2-(1H-indazol-5-ylamino)-5-phenyl-5,8-dihydropteridine-6,7-dione | $^1$H NMR (CDCl$_3$ and CD$_3$OD, 400 MHz) δ 1.79-1.85 (m, 5H), 2.09-2.20 (m, 3H), 5.61-5.64 (m, 1H), 7.19-7.21 (m, 2H), 7.27-7.29 (m, 1H), 7.36(d, J = 9.2 Hz, 1H), 7.44-7.51 (m, 4H), 7.82 (s, 1H), 7.87 (s, 1H). MS(ES$^+$): m/z = 440.04 [MH$^+$]. HPLC: t$_R$ = 2.55 (ZQ3, Polar_5 min). |

Example 305 was prepared by the following procedures:

Synthesis of example 305

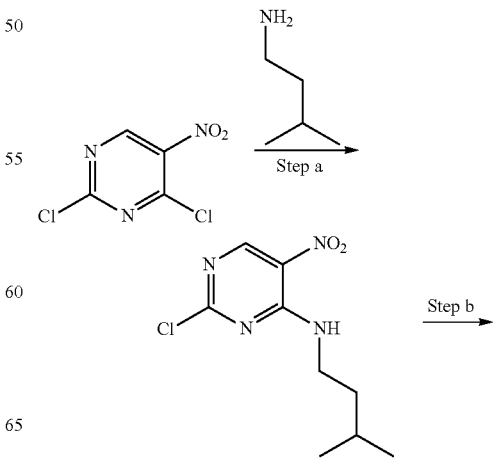

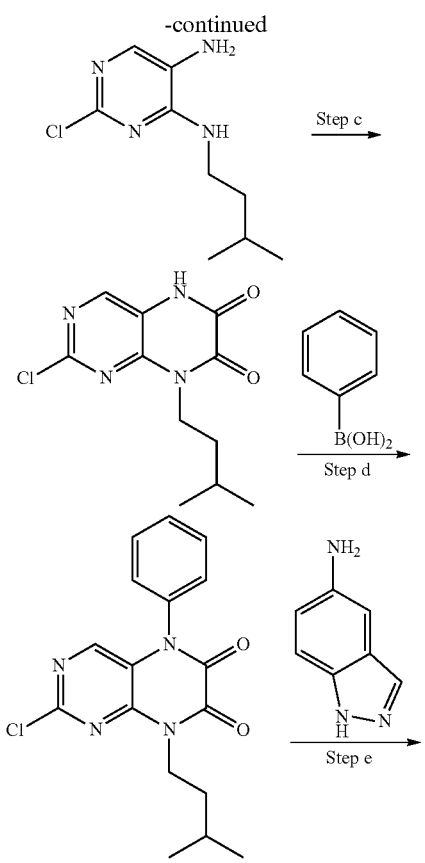

Step a: Synthesis of 2-chloro-N-(3-methylbutyl)-5-nitropyrimidin-4-amine

To a stirred solution of 2,4-dichloro-5-nitropyrimidine (13.8 g, 99.28 mmol) and 3-methylbutan-1-amine (7.0 g, 80.45 mmol) in dichloroethane (150 mL) was added imidazole (3.78 g, 55.58 mmol) at 0° C., the resulting mixture was stirred at 0° C. for 30 minutes then stirred at rt for 16 h. The solvent was removed under reduced pressure to give a crude residue was purified by silica gel column chromatography (eluent: 2% ethyl acetate in hexane) to yield 5.5 g of the desired compound. $^1$H NMR (CDCl$_3$, 300 MHz) δ 0.98 (d, J=6.8 Hz, 6H), 1.56-1.81 (m, 3H), 3.60-3.75 (m, 2H), 8.40 (br s, 1H), 9.01 (s, 1H); MS m/z 245[M+H+].

Step b: synthesis of 2-chloro-N$^4$-(3-methylbutyl) pyrimidine-4,5-diamine

To a stirred solution of 2-chloro-N-(3-methylbutyl)-5-nitropyrimidin-4-amine (800 mg, 3.27 mmol) in ethanol (40 ml) was added iron powder (1.8 g). The resulting mixture was heated to reflux before 2 N aqueous hydrochloric acid (4 mL) was added in small portion over 10 min. The reaction was then refluxed for 2 h. The reaction mixture was cooled to rt, filtered to remove inorganic material. The solution was then concentrated under reduced pressure to afforded the desired compound (500 mg), which was used for next step without any further purifications. $^1$H NMR (CDCl$_3$, 300 MHz) δ 0.92 (d, J=6.8 Hz, 6H), 1.42-1.80 (m, 3H), 3.42-3.60 (m, 2H), 5.01-5.15 (br s 1H), 7.60 (s, 1H).

Step c: Synthesis of 2-chloro-8-(3-methylbutyl)-5,8-dihydropteridine-6,7-dione

To a stirred solution of 2-chloro-N$^4$-(3-methylbutyl)pyrimidine-4,5-diamine (2.8 g, 13.08 mmol) in toluene (40 mL) was added triethylamine (4.23 g, 41.88 mmol) and ethyl chlorooxoacetate (1.95 g, 14.33). The mixture was then heated to reflux for 16 h. It was then cooled to rt, the bulk of solvent was removed under reduced pressure to give a crude residue, which was purified by silica gel column chromatography (eluent: 70% ethyl acetate in hexane) afforded the desired product (2.1 g). $^1$H NMR (CDCl$_3$, 300 MHz) δ 1.01 (d, J=6.6 Hz, 6H), 1.60-1.82 (m, 3H), 4.20-4.35 (m, 2H), 8.35 (s, 1H).

Step d: Synthesis of 2-chloro-8-(3-methylbutyl)-5-phenyl-5,8-dihydropteridine-6,7-dione To a stirred solution of 2-chloro-8-(3-methylbutyl)-5,8-dihydropteridine-6,7-dione (500 mg, 1.86 mmol), triethylamine (1.88 g, 18.61 mmol) in dichloromethane (20 mL) was added copper acetate (678 mg, 3.73 mmol), phenyl boronic acid (455 mg, 3.73 mmol) and molecular sieves (4 Å, 2 g). The resulting mixture was and stirred at rt for 60 h with an air balloon. The reaction mixture was then diluted with dichloromethane (20 mL) and filtered through celite to remove insoluble material. The bulk of solvent from filtration was then removed under reduced pressure to give a crude residue, which was purified by a silica gel column chromatography (eluent: 40% ethyl acetate in hexanes) to provided the desired compound (110 mg). $^1$H NMR (CDCl$_3$, 300 MHz) δ 1.05 (d, J=6.8 Hz, 6H), 1.60-1.79 (m, 3H), 4.38-4.42 (m, 2H), 7.21-7.38 (m, 3H), 7.48-7.65 (m, 2H), 7.79 (s, 1H).

Step e: Synthesis of 2-(1H-indazol-5-ylamino)-8-(3-methylbutyl)-5-phenyl-5,8-dihydropteridine-6,7-dione This compound was prepared from 2-chloro-8-(3-methylbutyl)-5-phenyl-5,8-dihydropteridine-6,7-dione and 5-aminoindazole, according to procedures similar to the preparation of example 18 from (7R)-2-chloro-8-cyclohexyl-7-methyl-5-phenyl-7,8-dihydropteridin-6(5H)-one. Examples 306 and 307 was prepared according to procedures similar for the preparation of Example 305, using corresponding starting materials and intermediates. For example, for synthesis of example 307, cyclopentanamine was used in the step a of the synthesis.

| Ex. # | Chemical Name | Analytical data |
|---|---|---|
| 308 | (7R)-5-(3,4-dimethoxyphenyl)-2-[(7-fluoro-1H-indazol-5-yl)amino]-7-methyl-8-(4-oxocyclohexyl)-7,8-dihydropteridin-6(5H)-one | $^1$H NMR (400 MHz, CD$_3$OD) δ 7.97-8.04 (m, 1H), 7.70-7.83 (m, 1H), 7.40-7.52 (m, 1H), 7.08-7.15 (m, 2H), 6.80-6.90 (m, 2H), 4.70-4.81 (m, 1H), 4.41-4.54 (m, 1H), 3.90 (s, 3H), 3.83 (s, 3H), 2.53-2.70 (m, 1H), 2.39-2.50 (m, 2H), 2.02-2.32 (m, 3H), 1.58-1.81 (m, 2H), 1.45-1.53 (m, 3H). MS (ES$^+$): m/z = 546.64 [MH$^+$]. UPLC: $t_R$ = 0.67 min (TOF: polar_2 min). |
| 309 | 3-[(7R)-8-(cis-4-hydroxycyclohexyl)-2-(1H-indazol-5-ylamino)-7-methyl-6-oxo-7,8-dihydropteridin-5(6H)-yl]benzonitrile | MS (ES$^+$): m/z = 495.38 [MH$^+$]. HPLC: $t_R$ = 0.71 min (TOF, polar_2 min). |

Examples 308 and 309 were prepared according to procedures similar for the preparation of Example 18, using corresponding starting materials and intermediates.

| Ex. # | Chemical Name | Analytical data |
|---|---|---|
| 310 | 7-(1H-indazol-5-ylamino)-2-methyl-1-(3-methylbutyl)-4-phenyl-1,4-dihydropyrido[3,4-b]pyrazin-3(2H)-one | $^1$H NMR (400 MHz, CD$_3$OD) δ 0.88 (d, J = 6.4 Hz, 3H), 0.95 (d, J = 6.4 Hz, 3H), 1.41 (d, J = 6.82 Hz, 3H), 1.55-1.65 (m, 3H), 3.18-3.28 (m, 1 H), 3.39-3.49 (m, 1 H), 4.26 (q, J = 6.74 Hz, 1 H), 6.10 (s, 1 H), 6.79 (s, 1 H), 7.27-7.34 (m, 3 H), 7.49-7.55 (m, 2 H), 7.56-7.62 (m, 2 H), 7.75 (d, J = 1.52 Hz, 1 H), 7.97(s, 1 H). MS(ES$^+$): m/z 441.19 [MH$^+$]. HPLC: $t_R$ = 2.55(ZQ3, Polar_5 min). |

Example 310 was prepared according to the following procedures:

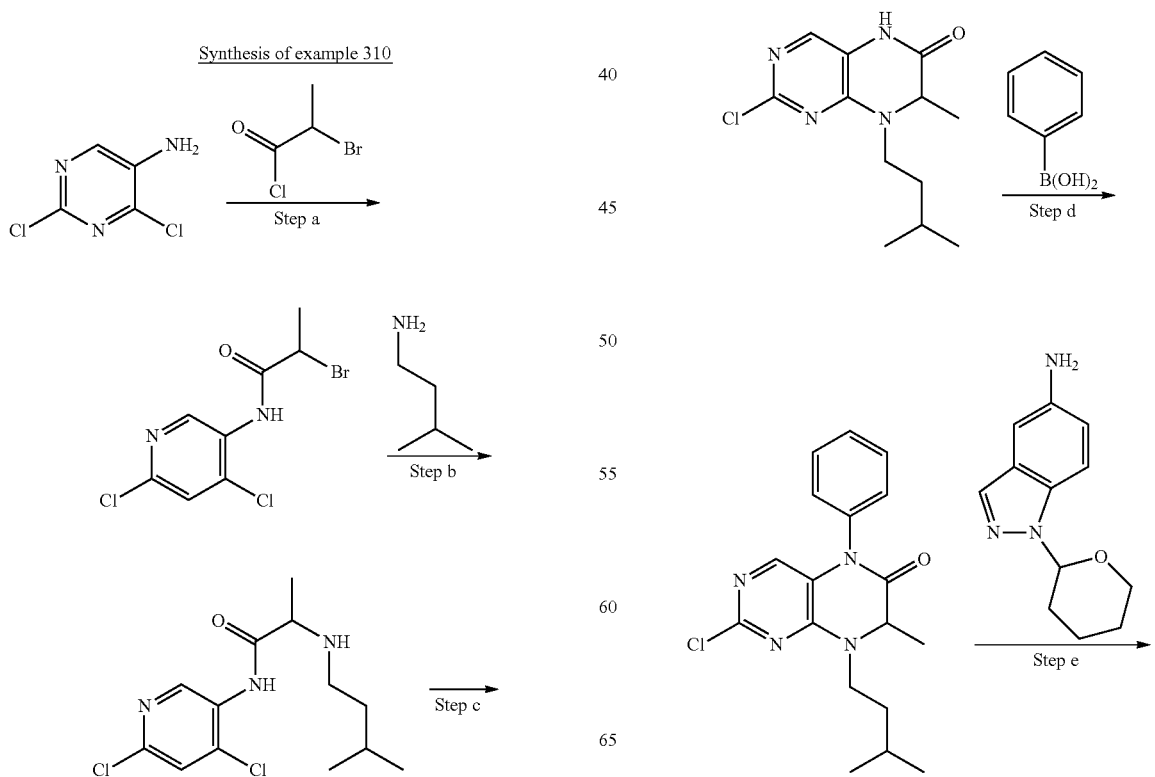

-continued

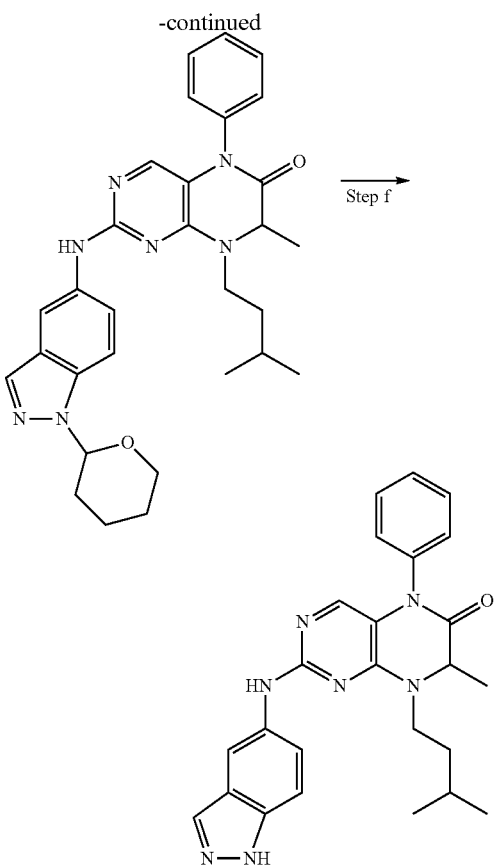

Step a: Synthesis of 2-bromo-N-(4,6-dichloropyridin-3-yl)propanamide

To a stirred mixture of 4,6-dichloro-pyridin-3-yl-amine dihydrochloride (1.50 g, 3.08 mmol) in a mixture of ether (6 mL) and ethyl acetate (5 mL) at 0° C. was added a solution of potassium carbonate (426 mg, 3.0 mmol) in water (4 mL), followed by 2-bromopropionoic acid chloride (2, 0.34 mL) in drop wise over a period of 30 min. The reaction mixture was then stirred at rt for 45 min. The solids formed (desired product) was filtered and the solvent layer was extracted with ethyl acetate (20 mL×3). The combined organic phases were dried over $Na_2SO_4$, evaporated and to give a crude product, which was purified from re-crystallization from ether to give desired compound (Yield: 55% yield). $^1$HNMR (CDCl$_3$, 300 MHz) δ 2.01 (m, 3H), 4.62 (m, 1H), 7.41 (s, 1H), 8.58 (br s, 1H), 9.35 (s, 1H).

Step b: Synthesis of N-(4,6-dichloropyridin-3-yl)-N$^2$-(3-methylbutyl)alaninamide To a stirred solution of 2-bromo-N-(4,6-dichloropyridin-3-yl)propanamide (500 mg, 1.68 mmol) in DMF (4 mL) was added potassium carbonate (465 mg, 3.36 mmol) and isoamylamine (4, 0.512 mg, 5.88 mmol), the reaction mixture was then heated to 80° C. and stirred at the same temperature for 2 h. The reaction mixture was then cooled to rt, diluted with water (20 mL) and extracted with ethyl acetate (25 mL×3). The combined organic phases were washed with water, dried over $Na_2SO_4$ and evaporated to give a crude residue, which was purified by silica gel column chromatography (eluent: 25% ethyl acetate in hexane) to give desired product (Yield: 69%). $^1$HNMR (CDCl$_3$, 300 MHz) δ 0.91-0.98 (m, 6H), 1.39-1.43 (m, 3H), 1.60-1.75 (m, 2H), 2.59-2.76 (m, 2H), 3.22-3.31 (m, 2H), 7.41 (s, 1H), 9.51 (s, 1H), 10.20 (br s, 1H).

Step c: Synthesis of 7-chloro-2-methyl-1-(3-methylbutyl)-1,4-dihydropyrido[3,4-b]pyrazin-3(2H)-one To a stirred solution of N-(4,6-dichloropyridin-3-yl)-N$^2$-(3-methylbutyl)alaninamide (350 mg, 1.15 mmol) in DMF (1.0 mL) was added tri-basic potassium phosphate (250 mg, 1.20 mmol). The reaction mixture was heated to 125° C. and stirred at the same temperature for 3 h. The reaction was then cooled to rt, diluted with water (5 mL) and the aqueous phase was extracted with ethyl acetate (25 mL×3). The combined organic phases were washed with water, dried over $Na_2SO_4$ and evaporated to give desired product (Yield: 33%), which was used for next step without any further purifications. $^1$HNMR (CDCl$_3$, 300 MHz) δ 0.90-1.01 (m, 6H), 1.33 (d, 3H), 1.52-1.75 (m, 2H), 1.80 (s, 1H), 3.10-3.19 (m, 1H), 3.31-3.42 (m, 1H), 4.07 (q, 1H), 6.51 (s, 1H), 7.65 (s, 1H), 9.41 (br s, 1H).

Step d: Synthesis of 7-chloro-2-methyl-1-(3-methylbutyl)-4-phenyl-1,4-dihydropyrido[3,4-b]pyrazin-3(2H)-one To a stirred solution of 7-chloro-2-methyl-1-(3-methylbutyl)-1,4-dihydropyrido[3,4-b]pyrazin-3(2H)-one (103 mg, 0.38 mmol) in dichloromethane (7 mL) was added triethylamine (0.53 mL, 3.8 mmol), cupric acetate (140 mg, 0.77 mmol) and phenylboronic acid (94 mg, 0.77 mmol) followed by 4 Å molecular sieves (2.0 g). The reaction mixture was stirred for 30 h at rt with an air balloon. It was then filtered over celite to remove inorganic material, the organic phase was washed with aqueous sodium carbonate, dried with $Na_2SO_4$, and the solvent was removed under reduced pressure to give a crude residue, which was purified by silica gel flash column chromatography (eluent: 40% ethyl acetate in hexane) to give the desired product (Yield: 49%). $^1$HNMR (CDCl$_3$, 300 MHz) δ 1.07-1.18 (m, 6H), 1.47 (d, J=6.6 Hz, 3H), 1.69-1.86 (m, 4H), 3.18-3.26 (m, 1H), 3.48-3.58 (m, 1H), 4.32 (q, J=6.9 Hz, 1H), 6.62 (s, 1H), 6.87-7.05 (m, 1H), 7.27-7.35 (m, 2H), 7.39 (s, 1H), 7.53-7.65 (m, 3H).

Step e: Synthesis of 2-methyl-1-(3-methylbutyl)-4-phenyl-7-{[1-(tetrahydro-2H-pyran-2-yl)-1H-indazol-5-yl]amino}-1,4-dihydropyrido[3,4-b]pyrazin-3(2H)-one

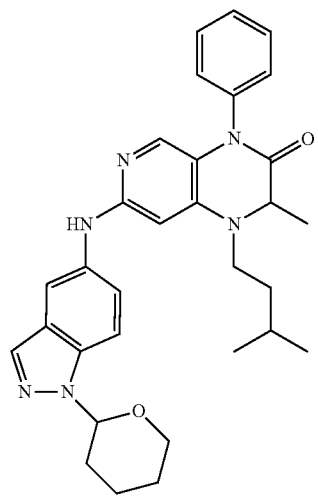 [SMILES: CC(C)CCN1c2cc(Nc3ccc4c(cnn4C4CCCCO4)c3)ncc2N(c2ccccc2)C(=O)C1C]

To a stirred mixture of 7-chloro-2-methyl-1-(3-methylbutyl)-4-phenyl-1,4-dihydropyrido[3,4-b]pyrazin-3(2H)-one (25.00 mg, 0.073 mmol) and 5-amino-1-(tetrahydropyranyl)-1H-indazole (23 mg, 0.11 mmol) in toluene (2.00 mL) was added bis(dibenzylideneacetone)palladium (10.0 mg, 0.011 mmol), 2,2'-Bis-diphenylphosphanyl-[1,1']binaphthalenyl (13.5 mg, 0.022 mmol) and $Cs_2CO_3$ (71 mg, 0.22 mmol). The resulting mixture was heated at 95° C. for 5 h. LC-MS indicated completion of reaction. The bulk of solvent was removed under reduced pressure to give a crude residue, which was purified by flash column chromatography on silica gel (eluent: 2% methanol in dichloromethane) to give the desired product: (Yield: 65%) MS(ES+): m/z 525.21 [MH+]. HPLC: $t_R$=3.26 (ZQ3, Polar_5 min).

Step f: Synthesis of 7-(1H-indazol-5-ylamino)-2-methyl-1-(3-methylbutyl)-4-phenyl-1,4-dihydropyrido[3,4-b]pyrazin-3(2H)-one tive Thin-Layer Chromatography (developing solvent: 2% methanol in dichloromethane) to give the desired product (yield: 60%) $^1$H NMR (400 MHz, $CD_3OD$) b 0.88 (d, J=6.4 Hz, 3H), 0.95 (d, J=6.4 Hz, 3H), 1.41 (d, J=6.82 Hz, 3H), 1.55-1.65 (m, 3H), 3.18-3.28 (m, 1H), 3.39-3.49 (m, 1H), 4.26 (q, J=6.74 Hz, 1H), 6.10 (s, 1H), 6.79 (s, 1H), 7.27-7.34 (m, 3H), 7.49-7.55 (m, 2H), 7.56-7.62 (m, 2H), 7.75 (d, J=1.52 Hz, 1H), 7.97 (s, 1H). MS(ES+): m/z 441.19 [MH+]. HPLC: $t_R$=2.55 (ZQ3, Polar_5 min).

| Ex. # | Chemical Name | Analytical data |
|---|---|---|
| 311 | 3-[(7R)-8-(3,3-dimethylcyclobutyl)-2-[(7-fluoro-1H-indazol-5-yl)amino]-7-methyl-6-oxo-7,8-dihydropteridin-5(6H)-yl]benzonitrile | $^1$H NMR ($CDCl_3$, 300 MHz) δ 1.16 (s, 3H), 1.30 (s, 3H), 1.38 (d, J = 6.6 Hz, 3H), 1.86-1.99 (m, 2H), 2.15-2.24 (m, 1H), 2.45-2.52 (m, 1H), 4.40-4.50 (m, 2H), 7.03-7.18 (m, 2H), 7.44-7.48 (m, 1H), 7.53-7.56 (m, 1H), 7.62-7.68 (m, 2H), 7.73-7.76 (m, 2H), 8.03 (brs, 1H); $[α]_D$ = +18 (c = 0.55 in $CH_2Cl_2$). MS(ES+): m/z 496.75 [MH+]. HPLC: $t_R$ = 2.80 (ZQ3, Polar_5 min). |
| 312 | 3-[(7R)-8-(3,3-dimethylcyclobutyl)-7-methyl-6-oxo-2-(1H-pyrazolo[3,4-b]pyridin-5-ylamino)-7,8-dihydropteridin-5(6H)-yl]benzonitrile | $^1$H NMR ($CDCl_3$, 300 MHz) δ 1.13 (s, 3H), 1.23 (s, 3H), 1.44 (d, J = 6.9 Hz, 3H), 1.82-1.99 (m, 2H), 2.15-2.20 (m, 1H), 2.30-2.38 (m, 1H), 4.44-4.48 (m, 2H), 7.14 (s, 1H), 7.55 (d, J = 8.7 Hz, 1H), 7.62 (s, 1H), 7.69 (t, J = 7.5 Hz, 1H), 7.99 (d, J = 7.5 Hz, 1H), 8.04 (s, 1H), 8.66 (s, 2H), 8.90 (brs, 1H). MS(ES+): m/z 479.74 [MH+]. HPLC: $t_R$ = 2.58 (ZQ3, Polar_5 min). |
| 313 | 3-[(7R)-8-(3,3-difluorocyclobutyl)-2-[(7-fluoro-1H-indazol-5-yl)amino]-7-methyl-6-oxo-7,8-dihydropteridin-5(6H)-yl]benzonitrile | MS(ES+): m/z 504.77 [MH+]. HPLC: $t_R$ = 2.69 (ZQ3, Polar_5 min). |

Example 311 was synthesized from 3,3-dimethylcyclobutanamine hydrochloride based on following chemistry (steps a-e), according to similar procedures described in steps b-f for synthesis of example 178.

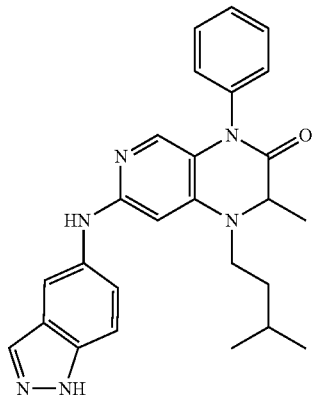 [SMILES: CC(C)CCN1c2cc(Nc3ccc4[nH]ncc4c3)ncc2N(c2ccccc2)C(=O)C1C]

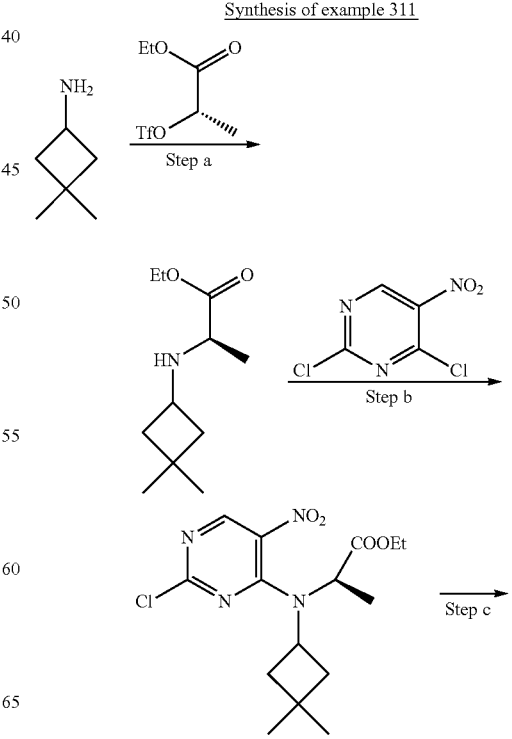

Synthesis of example 311

To a stirred solution of 2-methyl-1-(3-methylbutyl)-4-phenyl-7-{[1-(tetrahydro-2H-pyran-2-yl)-1H-indazol-5-yl]amino}-1,4-dihydropyrido[3,4-b]pyrazin-3(2H)-one (15 mg) in dioxane (2 mL) was added 2N aq. HCl (2 mL) at rt. The resulting mixture was stirred at rt for 2 h. LC-MS indicated completion of reaction. Dichloromethane (30 mL) was added to the reaction mixture, the organic phase was washed with aq. $NaHCO_3$, dried over anhydrous sodium sulfate, and evaporated to give a residue, which was purified by prepara-

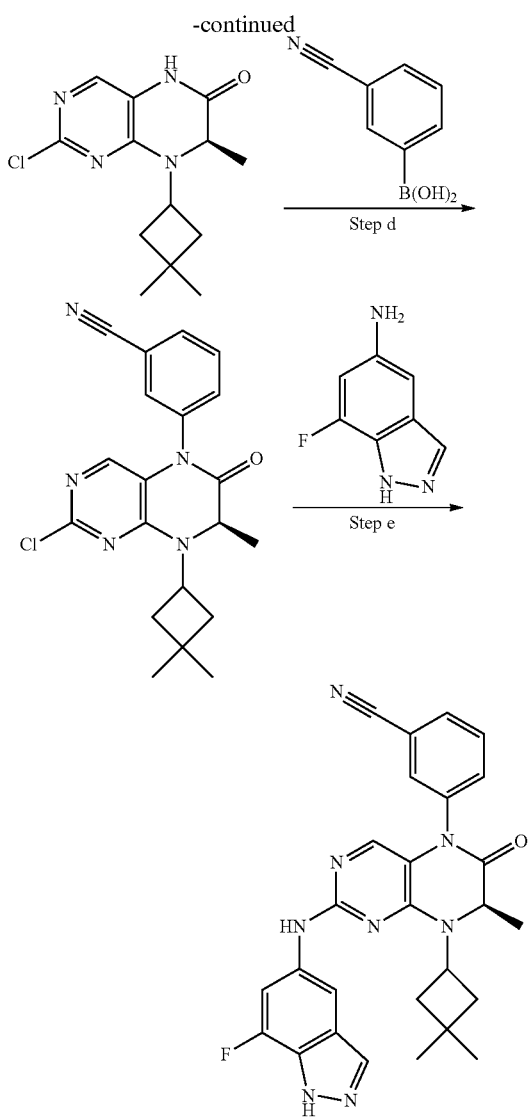

Examples 312 and 313 were prepared according to procedures similar for the preparation of Example 311, using corresponding starting materials and intermediates. COMPOSITIONS The invention includes pharmaceutical compositions comprising a compound or pharmaceutically acceptable salt thereof of the invention, which is formulated for a desired mode of administration with or without one or more pharmaceutically acceptable and useful carriers.

The compounds can also be included in pharmaceutical compositions in combination with one or more other therapeutically active compounds.

The pharmaceutical compositions of the present invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Biological Properties

In some embodiments, compounds of the invention are inhibitors of kinases. Without limitation to the invention, compounds of the invention have been determined to have utility in their RSK inhibition activity. In some embodiments, the compounds are inhibitors of one or more of RSK1-4. In some embodiments, the compounds are inhibitors of all isoforms RSK1-4. In some embodiments, the compounds are inhibitors of at least RSK1-2. Of note, the example compounds assayed for RSK1 and RSK2 were found to have activity against both kinases.

In some embodiments, a compound of the invention inhibits RSK1 and/or RSK2 in a biochemical assay with an $IC_{50}$ of about 100 nM or less. The assay can be such as that described herein or another assay. In some embodiments, the $IC_{50}$s may be about 10 nM or less, about 100 nM or less, or about 1 µM or less.

In some embodiments, the compound is selective for RSK1 and/or RSK2 with respect to certain other non-RSK kinases. In some embodiments, the compound is selective for all of RSK1-4 over certain other kinases. In some embodiments the selectivity is with respect to one or more of: polo-like kinase 1 (PLK1), aurora kinases, or KDR. In some embodiments, this selectivity is about 10-fold or more, about 25-fold or more, about 50-fold or more, about 100-fold or more, or about 500-fold or more in assays such as biochemical or cellular assays.

In some embodiments, the compound is sufficiently orally bioavailable for effective human administration. In some embodiments, the compound is characterized by a suitable therapeutic window upon human administration, oral or otherwise.

RSK1 & RSK2 Omnia Assay Protocol for Compound $IC_{50}$ Determination

The Omnia Assay (Invitrogen) has been optimized for His-tagged full length RSK1 (RPS6KA1, Millipore 14-509) and for His-tagged full-length RSK2 (RPS6KA3, Invitrogen PV3323). In this assay system, Omnia ST Peptide 6 (Invitrogen KNZ1061) functions as a substrate for RSK1 or RSK2. Phosphorylation of this SOX-containing peptide results in an increase in fluorescence at 485 nm upon excitation at 360 nm.

Assays are carried out in 384-well OptiPlates (Perkin Elmer 6007290) in a total volume of 20 µL containing RSK1 (120 µM) or RSK2 (135 µM), Omnia ST Peptide 6 (5 µM), ATP (15 µM, $K_m$=16.3 µM), and test compound (variable) in RSK assay buffer (50 mM HEPES, pH 7.5, 10 mM $MgCl_2$, 0.01% Tween-20, 1% glycerol, 1 mM DTT, 1 mM EGTA, 0.01% BSA) with 1% DMSO.

$IC_{50}$s for test compounds are typically determined using an 11-point three-fold serial dilution with a final assay concentration ranging either from 170 µM to 10 µM or from 17 µM to 1 µM. All compound concentrations are assayed in duplicate. Initial compound dilutions are prepared at 100× concentration in 100% DMSO from a 10 mM stock solution. Compounds are further diluted 1:25 in assay buffer resulting in a 4× concentrated solution.

To run the assay 5 µL of the above 4× concentrated compound solution (or 4% DMSO for positive controls) is added to the assay plate followed by 5 µL of a solution containing peptide (20 µM) and ATP (60 µM) in assay buffer. The reaction is initiated by the addition of 10 µL of RSK1 (240 µM) or RSK2 (270 µM) in assay buffer, or assay buffer alone for negative controls. The increase in fluorescence due to peptide phosphorylation is monitored continuously as a function of time using a Spectramax M5 plate reader (Molecular Devices) equipped with SoftMax Pro software.

The slopes from the linear portion of progress curves are used to determine $IC_{50}$ values by non-linear curve-fitting to a four-parameter equation using GraphPad Prism (GraphPad Software, Inc.) or XLFit (IDBS). $IC_{50}$'s are determined in duplicate (n=2) and $K_i$ values are calculated from $IC_{50}$ values using the Cheng-Prusoff equation assuming a competitive mode of inhibition.

The RSK2 biochemical potency of compounds described herein are shown in Table 1. Results are shown in Table 1 according to the key: A, $IC_{50} \leq 0.1$ µM; B, $0.1$ µM$<IC_{50} \leq 1$ µM; C, $IC_{50} > 1$ µM.

TABLE 1

| Example # | Mean RSK2 Biochem IC50 |
|---|---|
| 1 | A |
| 2 | A |
| 3 | A |
| 4 | C |
| 5 | B |
| 6 | B |
| 7 | C |
| 8 | C |

TABLE 1-continued

| Example # | Mean RSK2 Biochem IC50 |
|---|---|
| 9 | C |
| 10 | C |
| 11 | C |
| 12 | C |
| 13 | B |
| 14 | A |
| 15 | C |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | B |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | B |
| 60 | A |
| 61 | A |
| 62 | B |
| 63 | A |
| 64 | A |
| 65 | A |
| 66 | A |
| 67 | B |
| 68 | A |
| 69 | A |
| 70 | A |
| 71 | A |
| 72 | A |
| 73 | C |
| 74 | A |
| 75 | A |
| 76 | A |
| 77 | B |
| 78 | C |
| 79 | A |
| 80 | A |
| 81 | A |
| 82 | A |
| 83 | A |
| 84 | B |
| 85 | A |
| 86 | A |
| 87 | A |
| 88 | A |
| 89 | A |
| 90 | A |
| 91 | A |
| 92 | A |
| 93 | A |
| 94 | B |
| 95 | A |
| 96 | A |
| 97 | A |
| 98 | A |
| 99 | A |
| 100 | A |
| 101 | C |
| 102 | B |
| 103 | B |
| 104 | A |
| 105 | A |
| 106 | A |
| 107 | B |
| 108 | A |
| 109 | B |
| 110 | A |
| 111 | A |
| 112 | A |
| 113 | A |
| 114 | A |
| 115 | A |
| 116 | A |
| 117 | B |
| 118 | A |
| 119 | C |
| 120 | A |
| 121 | A |
| 122 | A |
| 123 | B |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | A |
| 156 | B |
| 157 | B |
| 158 | A |
| 159 | A |
| 160 | A |
| 161 | A |
| 162 | C |
| 163 | C |
| 164 | A |

TABLE 1-continued

| Example # | Mean RSK2 Biochem IC50 |
|---|---|
| 165 | A |
| 166 | A |
| 167 | B |
| 168 | B |
| 169 | A |
| 170 | C |
| 171 | A |
| 172 | A |
| 173 | A |
| 174 | A |
| 175 | A |
| 176 | A |
| 177 | A |
| 178 | A |
| 179 | B |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | A |
| 230 | B |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |

TABLE 1-continued

| Example # | Mean RSK2 Biochem IC50 |
|---|---|
| 243 | A |
| 244 | A |
| 245 | A |
| 246 | A |
| 247 | A |
| 248 | A |
| 249 | A |
| 250 | B |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | C |
| 266 | A |
| 267 | A |
| 268 | B |
| 269 | A |
| 270 | A |
| 271 | A |
| 272 | A |
| 273 | A |
| 274 | B |
| 275 | C |
| 276 | A |
| 277 | A |
| 278 | A |
| 279 | A |
| 280 | A |
| 281 | A |
| 282 | A |
| 283 | B |
| 284 | B |
| 285 | A |
| 286 | B |
| 287 | A |
| 288 | A |
| 289 | A |
| 290 | A |
| 291 | A |
| 292 | A |
| 293 | A |
| 294 | A |
| 295 | A |
| 296 | A |
| 297 | A |
| 298 | A |
| 299 | A |
| 300 | A |
| 301 | A |
| 302 | A |
| 303 | A |
| 304 | A |
| 305 | C |
| 306 | C |
| 307 | B |
| 308 | A |
| 309 | C |
| 310 | B |

The RSK1 biochemical potency of examples 23, 29, 57, 66 are shown in Table 2. Results are shown in Table 2 according to the key: A, $IC_{50} \leq 0.1\ \mu M$; B, $0.1\ \mu M < IC_{50} \leq 1\ \mu M$; C, $IC_{50} > 1\ \mu M$.

TABLE 2

| Example # | Mean RSK1 Biochem IC$_{50}$ |
| --- | --- |
| 23 | A |
| 29 | A |
| 57 | A |
| 66 | A |

Uses

In view of their biological activity, compounds of the invention and compositions thereof are useful whenever inhibition of RSK may be beneficial. The compounds may be useful in the treatment and/or prevention of various diseases and conditions such as hyperproliferative disorders such as cancer. Cancers can include solid tumors, leukemias, and lymphomas. In some embodiments, the condition is other than cancer.

In some embodiments, the invention includes a method of inhibiting at least RSK1 and RSK2 in a cell, comprising contacting the cell with an effective amount of the compound or salt. In some embodiments, the invention includes inhibiting cell proliferation or cell growth by contacting cells with an effective amount of the compound or salt.

In some embodiments, the invention includes a method of treating cancer mediated at least in part by RSK1 and RSK2, comprising administering to a human in need thereof a therapeutically effective amount of the compound.

In some embodiments, the invention includes the compound or salt thereof formulated for use in treating human disease such as but not limited to cancer that is mediated at least in part by RSK1 and RSK2.

In some embodiments, the cancer may be a solid tumor, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma (HCC), ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung (NSCLC), breast, or pancreatic cancer. In some aspects, the above methods are used to treat one or more of ovarian, gastric, head and neck, prostate, hepatocellular, renal, glioma, glioma, or sarcoma cancer.

In some embodiments, the invention includes a method of treating a cancer selected from breast, prostate, multiple myeloma, head and neck squamous cell carcinoma (HNSCC), or acute myeloid leukemia (AML), comprising administering to a human in need thereof a therapeutically effective amount of the compound or salt thereof.

In some embodiments, the invention includes a method of treating a cardiovascular, inflammatory, allergic, pulmonary, fibrotic, or renal disease that is mediated at least in part by RSK1 and/or RSK2, comprising administering to a human in need thereof a therapeutically effective amount of the compound or salt.

In some embodiments, the invention includes a method as described above, further comprising administering a therapeutically effective amount of at least one additional anti-cancer agent that is known at any time to be effective in such combination.

In some embodiments, the invention includes use of a therapeutically effective amount of a compound or salt the invention in the manufacture of a medicament for use in any of the treatment methods described herein.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system, may be effectively treated by the administration of from about 0.01 mg to 1 g of the compound per kilogram of body weight per day, about 0.01 mg to 100 mg/kg, about 0.01 mg to 10 mg/kg, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

GENERAL DEFINITIONS AND ABBREVIATIONS

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons.

The term "active agent" of the invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group.

In the case of multiple variable positions or substituents, any combination of group or variable subsets is also contemplated. Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "($C_{a-b}$)" or "$C_a$-$C_b$," meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_0$alkyl means a single covalent chemical bond when a linking group and means hydrogen when a terminal group.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "-"), the connections of compound name moieties are at the rightmost recited moiety. That is, the substituent name starts with a terminal moiety, continues with any bridging moieties, and ends with the connecting moiety. For example, "heteroarylthio$C_{1-4}$alkyl is a heteroaryl group connected through a thio sulfur to a $C_{1-4}$ alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O-(haloalkyl) group. Representative examples include, but are not limited to, trifluoromethoxy, tribromomethoxy, and the like.

"Haloalkyl" means an alkyl that is substituted with one or more same or different halo atoms.

"Hydroxyalkyl" means an alkyl that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated or unsaturated. Ring systems can be bridged and can include fused rings. The size of ring systems may be described using terminology such as "$_{x-y}$cyclic," which means a cyclic ring system that can have from x to y ring atoms. For example, the term "$_{9-10}$carbocyclic" means a 5,6 or 6,6 fused bicyclic carbocyclic ring system which can be satd., unsatd. or aromatic. It also means a phenyl fused to one 5 or 6 membered satd. or unsatd. carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity, including monocyclic, fused, and bridged systems. For example, a 3-10 membered carbocyclic means any chemically feasible ring systems having from 3 to 10 ring atoms.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means planar ring moieties containing 4n+2 pi electrons, wherein n is an integer.

The term "aryl" means an aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl that is substituted with an aryl group as defined above; e.g., —$CH_2$ phenyl, —$(CH_2)_2$phenyl, —$(CH_2)_3$phenyl, $CH_3CH(CH_3)CH_2$phenyl, and the like and derivatives thereof.

The term "heterocyclic" means a cyclic ring moiety containing at least one heteroatom (N, O, or $S(O)_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo(4,5-b)pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to: 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl also includes N-oxide moieties where applicable. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, and the like.

"Heteroaralkyl" group means alkyl that is substituted with a heteroaryl group; e.g., —CH$_2$ pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo

[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5,6 or 6,6 bicyclic heterocyclic ring moiety, which can be satd., unsatd. or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8 hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-ihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydrobenzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

"Aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

One in the art understands that an "oxo" requires a second bond from the atom to which the oxo is attached. Accordingly, it is understood that oxo cannot be substituted onto an aryl or heteroaryl ring.

The term "halo" or "halogen" means fluoro, chloro, bromo, or iodo.

"Acyl" means a —C(O)R group, where R can be selected from the nonlimiting group of hydrogen or optionally substituted alkyl, trihalomethyl, unsubstituted cycloalkyl, aryl. "Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "cancer" in an refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

The following abbreviations are used:
min. minute(s)
h hour(s)
d day(s)
RT or rt room temperature
$t_R$ retention time
L liter
mL milliliter
mmol millimole
μmol micromole
equiv. or eq. equivalents
NMR nuclear magnetic resonance MDP(S) mass-directed HPLC purification (system)
LC/MS liquid chromatography mass spectrometry
HPLC high performance liquid chromatography
TLC thin layer chromatography
CDCl$_3$ deuterated chloroform
CD$_3$OD or MeOD deuterated methanol
DMSO-d$_6$ deuterated dimethylsulfoxide
LDA lithium diisopropylamide
DCM dichloromethane
THF tetrahydrofuran
EtOAc ethyl acetate
MeCN acetonitrile
DMSO dimethylsulfoxide
Boc tert-butyloxycarbonyl
DME 1,2-dimethoxyethane
DMF N,N-dimethylformamide
DIPEA diisopropylethylamine
PS-DIEA polymer-supported diisopropylethylamine
PS-PPh$_3$-Pd polymer-supported Pd(PPh$_3$)$_4$
EDC 1-(3-dimethylaminopropyl)-3-ethylcarbodiimide
HOBt 1-hydroxybenzotriazole
DMAP 4-dimethylaminopyridine
TBTU O-(benzotriazol-1-yl)-N,N,N',N'-tetramethyluronium tetrafluoroborate
TEMPO 2,2,6,6-tetramethylpiperidine-1-oxyl
TFA trifluoroacetic acid
OTf Trifluoromethanesulfonate

The invention claimed is:

1. A compound of Formula I:

or a pharmaceutically acceptable salt thereof, wherein:
A$_1$ is N;
A$_2$ is C(O) or C(R$^5$)(R$^6$);
R$^1$ is phenyl optionally fused to 5-10 membered cyclic, or R$^1$ is 5-6 membered heteroaryl optionally fused to 5-10 membered cyclic, either of which is optionally substituted by one or more R$^7$;
each R$^7$ is independently halo, nitro, —CN, —OR$^{10}$, —NR$^{10}$R$^{11}$, —C(O)R$^{10}$, —C(O)OR$^{10}$, —C(O)NR$^{10}$R$^{11}$, —SR$^{10}$, —R$^{10}$, —NR$^{12}$C(O)NR$^{10}$R$^{11}$, —OC(O)R$^{10}$, —NR$^{12}$C(O)R$^1$, —NR$^{12}$C(O)OR$^{10}$, —OC(O)NR$^{10}$R$^{11}$, —C(O)—C(O)OR$^{10}$, —S(O$_{1-2}$)R$^{10}$, —S(O$_{1-2}$)NR$^{10}$R$^{11}$, —NR$^{12}$S(O$_{1-2}$)R$^{10}$, —NR$^{12}$S(O$_{1-2}$)NR$^{10}$R$^{11}$, —NR$^{12}$S(O$_{1-2}$)OR$^{10}$, or —OS(O$_{1-2}$)NR$^{10}$R$^{11}$; or —PR$^{10}$R$^{11}$, —P(OR$^{10}$)(OR$^{11}$), —PR$^{10}$(OR$^{11}$), —P(O)R$^{10}$R$^{11}$, —P(O)(OR$^{10}$)(OR$^{11}$), —P(O)R$^{10}$(OR$^{11}$), —BR$^{10}$R$^{11}$, —B(OR$^{10}$)(OR$^{11}$), —NHS(O)(R$^{10}$)=NR$^{11}$, or —R$^{10}$—S(O)(R$^{11}$)=NR$^{12}$; wherein in the case of a non-aromatic moiety, an R$^7$ can also be oxo;
each R$^{10}$, R$^{11}$, and R$^{12}$ is independently H or C$_{1-6}$aliphatic, each independently optionally substituted by one or more halo, oxo, nitro, —CN, —OR$^{13}$, —NR$^{13}$R$^{14}$, —C(O)R$^{13}$, —C(O)OR$^{13}$, —C(O)NR$^{13}$R$^{14}$, —SR$^{13}$, —R$^{14}$, —NR$^{15}$C(O)NR$^{13}$R$^{14}$, —OC(O)R$^{13}$, —NR$^{14}$C(O)R$^{13}$, —NR$^{14}$C(O)OR$^{13}$, —OC(O)NR$^{13}$R$^{14}$, —C(O)—C(O)OR$^{13}$, —S(O$_{1-2}$)R$^{13}$, —S(O$_{1-2}$)NR$^{13}$R$^{14}$, or —NR$^{13}$S(O$_{1-2}$)R$^{14}$; —NR$^{15}$S(O$_{1-2}$)NR$^{13}$R$^{14}$, —NR$^{15}$S(O$_{1-2}$)OR$^{13}$, or —OS(O$_{1-2}$)NR$^{13}$R$^{14}$, or by —PR$^{13}$R$^{14}$, —P(OR$^{13}$)(OR$^{14}$), —PR$^{13}$(OR$^{14}$), —P(O)R$^{13}$R$^{14}$, —P(O)(OR$^{13}$)(OR$^{14}$), —P(O)R$^{13}$(OR$^{14}$), —BR$^{13}$R$^{14}$, —B(OR$^{13}$)(OR$^{14}$), —NHS(O)(R$^{13}$)=NR$^{14}$, or —R$^{13}$—S(O)(R$^{14}$)=NR$^{15}$;
wherein any R$^{10}$/R$^{11}$ pair attached to the same atom, together with said atom to which they are attached, can form a 3-6 membered cyclic that can include one or more heteroatoms selected from O, NR$^{18}$, or S(O$_{0-2}$);
each R$^{13}$, R$^{14}$, and R$^{15}$ is independently H or C$_{1-3}$aliphatic, each independently optionally substituted by one or more halo, —CN, —OR$^{16}$, —NR$^{16}$R$^{17}$, —C(O)R$^{16}$, —C(O)OR$^{16}$, —C(O)NR$^{16}$, or —OC(O)R$^{16}$;
wherein any R$^{13}$/R$^{14}$ pair attached to the same atom, together with said atom to which they are attached, can form a 3-6 membered cyclic that can include one or more heteroatoms selected from O, NR$^{19}$, or S(O$_{0-2}$);
each R$^{16}$, R$^{17}$, R$^{18}$, and R$^{19}$ is independently H or C$_{1-3}$aliphatic;
R$^2$ is phenyl or 5-6 membered heteroaryl each optionally substituted with one or more R$^{20}$; or R$^2$ is H or C$_{1-8}$aliphatic that is optionally interrupted by one or more heteroatoms and optionally substituted by one or more R$^{21}$;
R$^3$ is C$_{4-8}$carbocyclic optionally fused to 5-10 membered cyclic or 5-6 membered heteroaryl optionally fused to 5-10 membered cyclic, either of which is optionally substituted by one or more R$^8$;
R$^4$ is H, halo, C$_{1-3}$aliphatic, or —OC$_{1-3}$aliphatic;
each R$^5$ and R$^6$ is independently H, C$_{1-6}$aliphatic, or 3-10 membered cyclic, any of which is optionally substituted by one or more halo, —OH, —OC$_{1-3}$aliphatic, —NR$^{40}$R$^{41}$, 5-6 membered heteroaryl, or —C(O)NR$^{40}$R$^{41}$;
each R$^8$ is independently halo, nitro, —CN, —OR$^{30}$, —NR$^{30}$R$^{31}$, —C(O)R$^{30}$, —C(O)OR$^{30}$, —C(O)NR$^{30}$R$^{31}$, —SR$^{30}$, —R$^{30}$, —NR$^{32}$C(O)NR$^{30}$R$^{31}$, —OC(O)R$^{30}$, —NR$^{32}$C(O)R$^{30}$, —NR$^{32}$C(O)OR$^{30}$, —OC(O)NR$^{30}$R$^{31}$, —C(O)—C(O)OR$^{30}$, —S(O$_{1-2}$)R$^{30}$, —S(O$_{1-2}$)NR$^{30}$R$^{31}$, —NR$^{32}$S(O$_{1-2}$)R$^{30}$, —NR$^{32}$S(O$_{1-2}$)NR$^{30}$R$^{31}$, —NR$^{31}$S(O$_{1-2}$)OR$^{32}$, or —OS(O$_{1-2}$)NR$^{30}$R$^{31}$; or —PR$^{30}$R$^{31}$, —P(OR$^{30}$)(OR$^{31}$), —PR$^{30}$(OR$^{31}$), —P(O)R$^{30}$R$^{31}$, —P(O)(OR$^{30}$)(OR$^{31}$), —P(O)R$^{30}$(OR$^{31}$), —BR$^{30}$R$^{31}$, —B(OR$^{30}$)(OR$^{31}$), —NHS(O)(R$^{30}$)=NR$^{31}$, or —R$^{30}$—S(O)(R$^{31}$)=NR$^{32}$; wherein in the case of a non-aromatic moiety, an R$^8$ can also be oxo;
each R$^{20}$ and R$^{21}$ is independently oxo, —R$^{22}$, halo, —CN, —OR$^{22}$, —SR$^{22}$, —NR$^{22}$R$^{23}$, —C(O)R$^{22}$, —C(O)OR$^{22}$, —C(O)NR$^{22}$, —OC(O)R$^{22}$, NR$^{22}$C(O)R$^{23}$, —S(O$_{1-2}$)R$^{22}$, —S(O$_{1-2}$)NR$^{22}$R$^{23}$, or —NR$^{22}$S(O$_{1-2}$)R$^{23}$;
each R$^{22}$ and R$^{23}$ is independently H or C$_{1-3}$aliphatic, each independently optionally substituted by one or more oxo, —R$^{50}$, halo, —CN, —OR$^{50}$, —SR$^{50}$, —NR$^{50}$R$^{51}$, —C(O)R$^{50}$, —C(O)OR$^{50}$, —C(O)NR$^{50}$, —OC(O)R$^{50}$, NR$^{50}$C(O)R$^{51}$, —S(O$_{1-2}$)R$^{50}$, —S(O$_{1-2}$)NR$^{50}$R$^{51}$, or —NR$^{50}$S(O$_{1-2}$)R$^{51}$;
wherein any R$^{22}$/R$^{23}$ pair attached to the same atom, together with said atom to which they are attached, can form a 3-6 membered cyclic that can include one or more heteroatoms selected from O, NR$^{52}$, or S(O$_{0-2}$);
each R$^{30}$, R$^{31}$, and R$^{32}$ is independently H or C$_{1-6}$aliphatic, each independently optionally substituted by one or more halo, oxo, nitro, —CN, —OR$^{33}$, —NR$^{33}$R$^{34}$, —C(O)R$^{33}$, —C(O)OR$^{33}$, —C(O)NR$^{33}$R$^{34}$, —SR$^{33}$, —R$^{34}$, —OC(O)R$^{33}$, —NR$^{34}$C(O)R$^{33}$, —NR$^{34}$C(O)OR$^{33}$, —N=CR$^{33}$R$^{34}$, —OC(O)NR$^{33}$R$^{34}$, —C(O)—C (O)OR$^{33}$, —S(O$_{1-2}$)R$^{33}$, —S(O$_{1-2}$)NR$^{33}$R$^{34}$, or —NR$^{33}$S(O$_{1-2}$)R$^{34}$; or by —PR$^{33}$R$^{34}$, —P(OR$^{33}$)(OR$^{34}$), —PR$^{33}$(OR$^{34}$), —P(O)R$^{33}$R$^{34}$, —P(O)(OR$^{33}$)(OR$^{34}$), —P(O)R$^{33}$(OR$^{34}$), BR$^{33}$R$^{34}$, —B(OR$^{33}$)(OR$^{34}$), —NHS(O)(R$^{33}$)=NR$^{34}$, or —R$^{33}$—S(O)(R$^{34}$)=NR$^{35}$;

wherein any R$^{30}$/R$^{31}$ pair attached to the same atom, together with said atom to which they are attached, can form a 3-6 membered cyclic that can include one or more heteroatoms selected from O, NR$^{38}$, or S(O$_{0-2}$);

each R$^{30}$, R$^{34}$, and R$^{35}$ is independently H or C$_{1-3}$aliphatic, each independently optionally substituted by one or more halo, —CN, —OR$^{36}$, —NR$^{36}$R$^{37}$, —C(O)R$^{36}$, —C(O)OR$^{36}$, —C(O)NR$^{36}$, or —OC(O)R$^{36}$;

wherein any R$^{33}$/R$^{34}$ pair attached to the same atom, together with said atom to which they are attached, can form a 3-6 membered cyclic that can include one or more heteroatoms selected from O, NR$^{39}$, or S(O$_{0-2}$);

each R$^{36}$, R$^{37}$, R$^{38}$, and R$^{39}$ is independently H or C$_{1-3}$aliphatic;

each R$^{40}$ and R$^{41}$ is independently H or C$_{1-3}$aliphatic, and R$^{40}$ and R$^{41}$, together with the atom to which they are attached, can form a 3-6 membered cyclic optionally including one or more heteroatoms; and each R$^{50}$, R$^{51}$ and R$^{52}$ is independently H or C$_{1-3}$aliphatic.

2. The compound or salt of claim 1, wherein:
each R$^5$ and R$^6$ is independently H or C$_{1-6}$aliphatic optionally substituted by one or more halo, —OH, —OC$_{1-3}$aliphatic, —NR$^{40}$R$^{41}$, 5-6 membered heteroaryl, or —C(O)NR$^{40}$R$^{41}$; and each R$^{40}$ and R$^{41}$ is independently H or C$_{1-3}$aliphatic, and R$^{40}$ and R$^{41}$, together with the atom to which they are attached, can form a 3-6 membered cyclic optionally including one or more heteroatoms.

3. The compound or salt of claim 2, wherein:
R$^2$ is phenyl or 5-6 membered heteroaryl, each optionally substituted by one or more R$^{20}$;
or R$^2$ is C$_{1-8}$aliphatic optionally interrupted by one or more heteroatoms and optionally substituted by one or more R$^{21}$;

each R$^{20}$ and R$^{21}$ is independently oxo, —R$^{22}$, halo, —CN, —OR$^{22}$, —SR$^{22}$, —NR$^{22}$R$^{23}$, —C(O)R$^{22}$, —C(O)OR$^{22}$, —C(O)NR$^{22}$, —OC(O)R$^{22}$, NR$^{22}$C(O)R$^{23}$, —S(O$_{1-2}$)R$^{22}$, —S(O$_{1-2}$)NR$^{22}$R$^{23}$, or —NR$^{22}$S(O$_{1-2}$)R$^{23}$;

each R$^{22}$ and R$^{23}$ is independently H or C$_{1-3}$aliphatic, each independently optionally substituted by one or more oxo, —R$^{50}$, halo, —CN, —OR$^{50}$, —SR$^{50}$, —NR$^{50}$R$^{51}$, —C(O)R$^{50}$, —C(O)OR$^{50}$, —C(O)NR$^{50}$, —OC(O)R$^{50}$, NR$^{50}$C(O)R$^{51}$, —S(O$_{1-2}$)R$^{50}$, —S(O$_{1-2}$)NR$^{50}$R$^{51}$, or —NR$^{50}$S(O$_{1-2}$)R$^{51}$;

wherein any R$^{22}$/R$^{23}$ pair attached to the same atom, together with said atom to which they are attached, can form a 3-6 membered cyclic that can include one or more heteroatoms selected from O, NR$^{52}$, or S(O$_{0-2}$); and each R$^{50}$, R$^{51}$ and R$^{52}$ is independently H or C$_{1-3}$aliphatic.

4. The compound or salt of claim 3, wherein:
R$^3$ is phenyl optionally fused to 5-10 membered cyclic, or R$^3$ is 5-6 membered heteroaryl optionally fused to 5-10 membered cyclic, either of which is optionally substituted by one or more R$^8$;

each R$^8$ is independently halo, nitro, —CN, OR$^{30}$, —NR$^{30}$R$^{31}$, —C(O)R$^{30}$, —C(O)OR$^{30}$, —C(O)NR$^{30}$R$^{31}$, —SR$^{30}$, —R$^{30}$, —NR$^{32}$C(O)NR$^{30}$R$^{31}$, —OC(O)R$^{30}$, —NR$^{32}$C(O)R$^{30}$, —NR$^{32}$C(O)OR$^{30}$, —OC(O)NR$^{30}$R$^{31}$, —C(O)—C(O)OR$^{30}$, —S(O$_{1-2}$)R$^{30}$, —S(O$_{1-2}$)NR$^{30}$R$^{31}$, —NR$^{32}$S(O$_{1-2}$)R$^{30}$, —NR$^{32}$S(O$_{1-2}$)NR$^{30}$R$^{31}$, —NR$^{31}$S(O$_{1-2}$)OR$^{32}$, or —OS(O$_{1-2}$)NR$^{30}$R$^{31}$; or —PR$^{30}$R$^{31}$, —P(OR$^{30}$)(OR$^{31}$), —PR$^{30}$(OR$^{31}$), —P(O)R$^{30}$R$^{31}$, —P(O)(OR$^{30}$)(OR$^{31}$), —P(O)R$^{30}$(OR$^{31}$), —BR$^{30}$R$^{31}$, —B(OR$^{30}$)(OR$^{31}$), —NHS(O)(R$^{30}$)=NR$^{31}$, or —R$^{30}$—S(O)(R$^{31}$)=NR$^{32}$; wherein in the case of a non-aromatic moiety, an R$^8$ can also be oxo;

each R$^{30}$, R$^{31}$, and R$^{32}$ is independently H or C$_{1-6}$aliphatic, each independently optionally substituted by one or more halo, oxo, nitro, —CN, —OR$^{33}$, —NR$^{33}$R$^{34}$, —C(O)R$^{33}$, —C(O)OR$^{33}$, —C(O)NR$^{33}$R$^{34}$, —SR$^{33}$, —R$^{34}$, —OC(O)R$^{33}$, —NR$^{34}$C(O)R$^{33}$, —NR$^{34}$C(O)OR$^{33}$, —N=CR$^{33}$R$^{34}$, —OC(O)NR$^{33}$R$^{34}$, —C(O)—C(O)OR$^{33}$, —S(O$_{1-2}$)R$^{33}$, —S(O$_{1-2}$)NR$^{33}$R$^{34}$, or —NR$^{33}$S(O$_{1-2}$)R$^{34}$; or by —PR$^{33}$R$^{34}$, —P(OR$^{33}$)(OR$^{34}$), —PR$^{33}$(OR$^{34}$), —P(O)R$^{33}$R$^{34}$, —P(O)(OR$^{33}$)(OR$^{34}$), —P(O)R$^{33}$(OR$^{34}$), —BR$^{33}$R$^{34}$, —B(OR$^{33}$)(OR$^{34}$), —NHS(O)(R$^{33}$)=NR$^{34}$, or —R$^{33}$—S(O)(R$^{34}$)=NR$^{35}$;

wherein any R$^{30}$/R$^{31}$ pair attached to the same atom, together with said atom to which they are attached, can form a 3-6 membered cyclic that can include one or more heteroatoms selected from O, NR$^{38}$, or S(O$_{0-2}$);

each R$^{33}$, R$^{34}$, and R$^{35}$ is independently H or C$_{1-3}$aliphatic, each independently optionally substituted by one or more halo, —CN, —OR$^{36}$, —NR$^{36}$R$^{37}$, —C(O)R$^{36}$, —C(O)OR$^{36}$, —C(O)NR$^{36}$, or —OC(O)R$^{36}$;

wherein any R$^{33}$/R$^{34}$ pair attached to the same atom, together with said atom to which they are attached, can form a 3-6 membered cyclic that can include one or more heteroatoms selected from O, NR$^{39}$, or S(O$_{0-2}$); and each R$^{36}$, R$^{37}$, R$^{38}$, and R$^{39}$ is independently H or C$_{1-3}$aliphatic.

5. The compound or salt of claim 4, wherein:
R$^8$ is independently halo, nitro, —CN, —OR$^{30}$, —NR$^{30}$R$^{31}$, —C(O)R$^{30}$, —C(O)OR$^{30}$, —C(O)NR$^{30}$R$^{31}$, —SR$^{30}$, —R$^{30}$, —NR$^{32}$C(O)NR$^{30}$R$^{31}$, —OC(O)R$^{30}$, —NR$^{32}$C(O)R$^{30}$, —NR$^{32}$C(O)OR$^{30}$, —OC(O)NR$^{30}$R$^{31}$, —C(O)—C(O)OR$^{30}$, —S(O$_{1-2}$)R$^{30}$, —S(O$_{1-2}$)NR$^{30}$R$^{31}$, —NR$^{32}$S(O$_{1-2}$)R$^{30}$, —NR$^{32}$S(O$_{1-2}$)NR$^{30}$R$^{31}$, or —OS(O$_{1-2}$)NR$^{30}$R$^{31}$;

in the case of a non-aromatic moiety, an R$^8$ can also be oxo; and each R$^{30}$, R$^{31}$, and R$^{32}$ is independently H or C$_{1-3}$aliphatic.

6. The compound or salt of claim 5, having the formula:

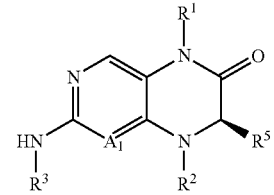

wherein R$^5$ is C$_{1-3}$aliphatic.

7. The compound or salt of claim 6, wherein R$^5$ is CH$_3$.

8. The compound or salt of claim 1, wherein:
A$_1$ is N;
A$_2$ is CH((R)-methyl);
R$^1$ is phenyl or pyridyl, either of which is optionally substituted by 1-2 independent halo, —CN, —CH$_3$, or —OC$_{1-3}$alkyl;
R$^2$ is C$_{3-6}$aliphatic selected from branched and cyclic aliphatic optionally interrupted by 1-2 heteroatoms, and optionally substituted by 1-2 independent halo, —CH$_3$, or —OCH$_3$;

R³ is selected from:

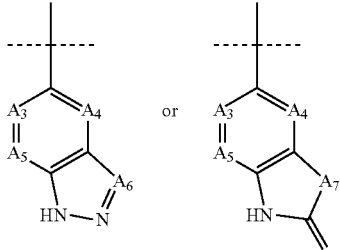

wherein each A₃, A₄, A₅, and A₆ is independently CH or N; A₇ is CH₂, O, or S;

and wherein either of the above is optionally substituted by 1-3 independent halo, —CH₃, or —OCH₃ groups.

9. The compound or salt of claim 1 selected from:

| | |
|---|---|
| 1 | 2-(1H-indazol-5-ylamino)-7-methyl-8-(3-methylbutyl)-5-phenyl-7,8-dihydropteridin-6(5H)-one |
| 2 | 2-[(3,5-difluoro-4-hydroxyphenyl)amino]-7-methyl-8-(3-methylbutyl)-5-phenyl-7,8-dihydropteridin-6(5H)-one |
| 3 | 7-methyl-8-(3-methylbutyl)-2-[(2-oxo-2,3-dihydro-1H-indol-5-yl)amino]-5-phenyl-7,8-dihydropteridin-6(5H)-one |
| 4 | diethyl (4-{[7-methyl-8-(3-methylbutyl)-6-oxo-5-phenyl-5,6,7,8-tetrahydropteridin-2-yl]amino}benzyl)phosphonate |
| 5 | N-methyl-2-(4-{[7-methyl-8-(3-methylbutyl)-6-oxo-5-phenyl-5,6,7,8-tetrahydropteridin-2-yl]amino}phenyl)acetamide |
| 6 | N,N-dimethyl-2-(4-{[7-methyl-8-(3-methylbutyl)-6-oxo-5-phenyl-5,6,7,8-tetrahydropteridin-2-yl]amino}phenyl)acetamide |
| 7 | N-methyl-1-(4-{[7-methyl-8-(3-methylbutyl)-6-oxo-5-phenyl-5,6,7,8-tetrahydropteridin-2-yl]amino}phenyl)methanesulfonamide |
| 8 | N,N-dimethyl-1-(4-{[7-methyl-8-(3-methylbutyl)-6-oxo-5-phenyl-5,6,7,8-tetrahydropteridin-2-yl]amino}phenyl)methanesulfonamide |
| 9 | methyl 4-{[7-methyl-8-(3-methylbutyl)-6-oxo-5-phenyl-5,6,7,8-tetrahydropteridin-2-yl]amino}benzoate |
| 10 | methyl 3-{[7-methyl-8-(3-methylbutyl)-6-oxo-5-phenyl-5,6,7,8-tetrahydropteridin-2-yl]amino}benzoate |
| 11 | 2-[(trans-4-hydroxycyclohexyl)amino]-7-methyl-8-(3-methylbutyl)-5-phenyl-7,8-dihydropteridin-6(5H)-one |
| 12 | 2-[(cis-4-hydroxycyclohexyl)amino]-7-methyl-8-(3-methylbutyl)-5-phenyl-7,8-dihydropteridin-6(5H)-one |
| 13 | 2-(1H-indazol-5-ylamino)-7-methyl-5-phenyl-8-(propan-2-yl)-7,8-dihydropteridin-6(5H)-one |
| 14 | 4-{[7-methyl-8-(3-methylbutyl)-6-oxo-5-phenyl-5,6,7,8-tetrahydropteridin-2-yl]amino}benzoic acid |
| 15 | 3-{[7-methyl-8-(3-methylbutyl)-6-oxo-5-phenyl-5,6,7,8-tetrahydropteridin-2-yl]amino}benzoic acid |
| 16 | (7R)-2-(1H-indazol-5-ylamino)-7-methyl-8-(3-methylbutyl)-5-phenyl-7,8-dihydropteridin-6(5H)-one |
| 17 | (7S)-2-(1H-indazol-5-ylamino)-7-methyl-8-(3-methylbutyl)-5-phenyl-7,8-dihydropteridin-6(5H)-one |
| 18 | (7R)-8-cyclohexyl-2-(1H-indazol-5-ylamino)-7-methyl-5-phenyl-7,8-dihydropteridin-6(5H)-one |
| 19 | 4-[(7R)-8-cyclohexyl-2-(1H-indazol-5-ylamino)-7-methyl-6-oxo-7,8-dihydropteridin-5(6H)-yl]benzonitrile |
| 20 | (7R)-8-cyclohexyl-2-(1H-indazol-5-ylamino)-7-methyl-5-(pyridin-4-yl)-7,8-dihydropteridin-6(5H)-one |
| 21 | (7R)-5-(4-chlorophenyl)-8-cyclohexyl-2-(1H-indazol-5-ylamino)-7-methyl-7,8-dihydropteridin-6(5H)-one |
| 22 | (7R)-8-cyclohexyl-2-(1H-indazol-5-ylamino)-7-methyl-5-(4-methylphenyl)-7,8-dihydropteridin-6(5H)-one |
| 23 | (7R)-8-cyclohexyl-2-(1H-indazol-5-ylamino)-7-methyl-5-(pyridin-3-yl)-7,8-dihydropteridin-6(5H)-one |
| 24 | (7R)-8-cyclohexyl-5-(4-fluorophenyl)-2-(1H-indazol-5-ylamino)-7-methyl-7,8-dihydropteridin-6(5H)-one |
| 25 | (7R)-8-cyclohexyl-5-(3-fluorophenyl)-2-(1H-indazol-5-ylamino)-7-methyl-7,8-dihydropteridin-6(5H)-one |
| 26 | (7R)-8-cyclohexyl-2-(1H-indazol-5-ylamino)-5-(4-methoxyphenyl)-7-methyl-7,8-dihydropteridin-6(5H)-one |
| 27 | 4-[(7R)-8-cyclohexyl-2-(1H-indazol-5-ylamino)-7-methyl-6-oxo-7,8-dihydropteridin-5(6H)-yl]-N,N-dimethylbenzamide |
| 28 | (7R)-8-cyclohexyl-2-(1H-indazol-5-ylamino)-5-(3-methoxyphenyl)-7-methyl-7,8-dihydropteridin-6(5H)-one |
| 29 | 3-[(7R)-8-cyclohexyl-2-(1H-indazol-5-ylamino)-7-methyl-6-oxo-7,8-dihydropteridin-5(6H)-yl]benzonitrile |
| 30 | (7R)-8-cyclohexyl-2-(1H-indazol-5-ylamino)-7-methyl-5-(3-methylphenyl)-7,8-dihydropteridin-6(5H)-one |
| 31 | (7R)-5-(3-chlorophenyl)-8-cyclohexyl-2-(1H-indazol-5-ylamino)-7-methyl-7,8-dihydropteridin-6(5H)-one |
| 32 | 3-[(7R)-8-cyclohexyl-2-(1H-indazol-5-ylamino)-7-methyl-6-oxo-7,8-dihydropteridin-5(6H)-yl]-N,N-dimethylbenzamide |
| 33 | (7R)-8-cyclohexyl-2-(1H-indazol-5-ylamino)-7-methyl-5-[4-(trifluoromethoxy)phenyl]-7,8-dihydropteridin-6(5H)-one |
| 34 | (7R)-8-cyclohexyl-2-(1H-indazol-5-ylamino)-7-methyl-5-[3-(trifluoromethoxy)phenyl]-7,8-dihydropteridin-6(5H)-one |
| 35 | (7R)-8-cyclohexyl-2-(1H-indazol-5-ylamino)-7-methyl-5-[4-(trifluoromethyl)phenyl]-7,8-dihydropteridin-6(5H)-one |
| 36 | (7R)-8-cyclohexyl-2-(1H-indazol-5-ylamino)-7-methyl-5-[3-(trifluoromethyl)phenyl]-7,8-dihydropteridin-6(5H)-one |
| 37 | 4-[(7R)-8-cyclohexyl-2-(1H-indazol-5-ylamino)-7-methyl-6-oxo-7,8-dihydropteridin-5(6H)-yl]-N-methylbenzenesulfonamide |
| 38 | (7R)-8-cyclohexyl-2-(1H-indazol-5-ylamino)-7-methyl-5-(3,4,5-trimethoxyphenyl)-7,8-dihydropteridin-6(5H)-one |
| 39 | (7R)-5-(1,3-benzodioxol-5-yl)-8-cyclohexyl-2-(1H-indazol-5-ylamino)-7-methyl-7,8-dihydropteridin-6(5H)-one |
| 40 | (7R)-8-cyclohexyl-2-(1H-indazol-5-ylamino)-7-methyl-5-[4-(methylsulfonyl)phenyl]-7,8-dihydropteridin-6(5H)-one |
| 41 | (7R)-8-cyclohexyl-5-[4-(dimethylamino)phenyl]-2-(1H-indazol-5-ylamino)-7-methyl-7,8-dihydropteridin-6(5H)-one |
| 42 | 3-[(7R)-8-cyclohexyl-2-(1H-indazol-5-ylamino)-7-methyl-6-oxo-7,8-dihydropteridin-5(6H)-yl]-N-methylbenzenesulfonamide |
| 43 | (7R)-8-cyclohexyl-2-(1H-indazol-5-ylamino)-7-methyl-5-[3-(methylsulfonyl)phenyl]-7,8-dihydropteridin-6(5H)-one |
| 44 | (7R)-8-cyclohexyl-5-[3-(dimethylamino)phenyl]-2-(1H-indazol-5-ylamino)-7-methyl-7,8-dihydropteridin-6(5H)-one |
| 45 | (7R)-8-cyclohexyl-2-(1H-indazol-5-ylamino)-7-methyl-5-(naphthalen-2-yl)-7,8-dihydropteridin-6(5H)-one |
| 46 | 3-[(7R)-8-cyclohexyl-2-(1H-indazol-5-ylamino)-7-methyl-6-oxo-7,8-dihydropteridin-5(6H)-yl]-N-methylbenzamide |
| 47 | N-{4-[(7R)-8-cyclohexyl-2-(1H-indazol-5-ylamino)-7-methyl-6-oxo-7,8-dihydropteridin-5(6H)-yl]phenyl}methanesulfonamide |
| 48 | (7R)-8-cyclohexyl-2-(1H-indazol-5-ylamino)-5-(6-methoxypyridin-3-yl)-7-methyl-7,8-dihydropteridin-6(5H)-one |
| 49 | (7R)-8-cyclohexyl-5-(3,4-difluorophenyl)-2-(1H-indazol-5-ylamino)-7-methyl-7,8-dihydropteridin-6(5H)-one |
| 50 | (7R)-8-cyclohexyl-2-(1H-indazol-5-ylamino)-7-methyl-5-(quinolin-3-yl)-7,8-dihydropteridin-6(5H)-one |
| 51 | 3-[(7R)-8-cyclohexyl-7-methyl-6-oxo-2-[(2-oxo-2,3-dihydro-1H-indol-5-yl)amino]-7,8-dihydropteridin-5(6H)-yl]benzonitrile |
| 52 | methyl 4-[(7R)-8-cyclohexyl-2-(1H-indazol-5-ylamino)-7-methyl-6-oxo-7,8-dihydropteridin-5(6H)-yl]benzoate |
| 53 | 5-[(7R)-8-cyclohexyl-2-(1H-indazol-5-ylamino)-7-methyl-6-oxo-7,8-dihydropteridin-5(6H)-yl]-2-methylbenzonitrile |
| 54 | (7R)-8-cyclohexyl-5-(4-fluoro-3-methoxyphenyl)-2-(1H-indazol-5-ylamino)-7-methyl-7,8-dihydropteridin-6(5H)-one |
| 55 | (7R)-8-cyclohexyl-5-(3-fluoro-4-methoxyphenyl)-2-(1H-indazol-5-ylamino)-7-methyl-7,8-dihydropteridin-6(5H)-one |
| 56 | 3-[(7R)-8-cyclohexyl-2-[(6-fluoro-1H-indazol-5-yl)amino]-7-methyl-6-oxo-7,8-dihydropteridin-5(6H)-yl]benzonitrile |
| 57 | (7R)-8-cyclohexyl-2-(1H-indazol-5-ylamino)-7-methyl-5-(thiophen-3-yl)-7,8-dihydropteridin-6(5H)-one |
| 58 | (7R)-8-cyclohexyl-2-(1H-indazol-5-ylamino)-7-methyl-5-(1-methyl-1H-pyrazol-4-yl)-7,8-dihydropteridin-6(5H)-one |
| 59 | 3-[(7R)-8-cyclohexyl-7-methyl-2-[(7-methyl-1H-indazol-5-yl)amino]-6-oxo-7,8-dihydropteridin-5(6H)-yl]benzonitrile |
| 60 | 8-cyclohexyl-7-methyl-2-[(2-oxo-2,3-dihydro-1H-indol-5-yl)amino]-5-phenyl-7,8-dihydropteridin-6(5H)-one |
| 61 | 8-cyclohexyl-2-(1H-indazol-5-ylamino)-7-methyl-5-phenyl-7,8-dihydropteridin-6(5H)-one |
| 62 | (7S)-8-cyclohexyl-2-(1H-indazol-5-ylamino)-7-methyl-5-phenyl-7,8-dihydropteridin-6(5H)-one |
| 63 | 4-[(7R)-8-cyclohexyl-2-(1H-indazol-5-ylamino)-7-methyl-6-oxo-7,8-dihydropteridin-5(6H)-yl]benzoic acid |
| 64 | 8-cyclopentyl-2-(1H-indazol-5-ylamino)-7-methyl-5-phenyl-7,8-dihydropteridin-6(5H)-one |
| 65 | 8-cyclopentyl-7-methyl-2-[(2-oxo-2,3-dihydro-1H-indol-5-yl)amino]-5-phenyl-7,8-dihydropteridin-6(5H)-one |
| 66 | (7R)-8-cyclopentyl-2-(1H-indazol-5-ylamino)-7-methyl-5-phenyl-7,8-dihydropteridin-6(5H)-one |

-continued

| | |
|---|---|
| 67 | (7S)-8-cyclopentyl-2-(1H-indazol-5-ylamino)-7-methyl-5-phenyl-7,8-dihydropteridin-6(5H)-one |
| 68 | (7R)-8-cyclopentyl-7-methyl-2-[(2-oxo-2,3-dihydro-1H-indol-5-yl)amino]-5-phenyl-7,8-dihydropteridin-6(5H)-one |
| 69 | 3-[(7R)-8-cyclopentyl-2-(1H-indazol-5-ylamino)-7-methyl-6-oxo-7,8-dihydropteridin-5(6H)-yl]benzonitrile |
| 70 | 2-(1H-indazol-5-ylamino)-7,7-dimethyl-8-(3-methylbutyl)-5-phenyl-7,8-dihydropteridin-6(5H)-one |
| 71 | 3-[(7R)-8-(cyclobutylmethyl)-2-(1H-indazol-5-ylamino)-7-methyl-6-oxo-7,8-dihydropteridin-5(6H)-yl]benzonitrile |
| 72 | (7R)-8-(cyclohexylmethyl)-2-(1H-indazol-5-ylamino)-7-methyl-5-phenyl-7,8-dihydropteridin-6(5H)-one |
| 73 | (7R)-8-[2-(dimethylamino)ethyl]-2-(1H-indazol-5-ylamino)-7-methyl-5-phenyl-7,8-dihydropteridin-6(5H)-one |
| 74 | (7R)-2-(1H-indazol-5-ylamino)-7-methyl-5-phenyl-8-(tetrahydro-2H-pyran-4-ylmethyl)-7,8-dihydropteridin-6(5H)-one |
| 75 | (7R)-8-(cyclopentylmethyl)-2-(1H-indazol-5-ylamino)-7-methyl-5-phenyl-7,8-dihydropteridin-6(5H)-one |
| 76 | (7R)-8-benzyl-2-(1H-indazol-5-ylamino)-7-methyl-5-phenyl-7,8-dihydropteridin-6(5H)-one |
| 77 | (7R)-8-(3-hydroxypropyl)-2-(1H-indazol-5-ylamino)-7-methyl-5-phenyl-7,8-dihydropteridin-6(5H)-one |
| 78 | (7R)-2-(1H-indazol-5-ylamino)-7-methyl-5-phenyl-8-(piperidin-4-ylmethyl)-7,8-dihydropteridin-6(5H)-one |
| 79 | (7R)-2-(1H-indazol-5-ylamino)-7-methyl-8-(2-methylpropyl)-5-phenyl-7,8-dihydropteridin-6(5H)-one |
| 80 | 3-[(7R)-2-(1H-indazol-5-ylamino)-7-methyl-6-oxo-8-(tetrahydro-2H-pyran-4-ylmethyl)-7,8-dihydropteridin-5(6H)-yl]benzonitrile |
| 81 | 3-[(7R)-8-(cyclopentylmethyl)-2-(1H-indazol-5-ylamino)-7-methyl-6-oxo-7,8-dihydropteridin-5(6H)-yl]benzonitrile |
| 82 | 3-[(7R)-2-(1H-indazol-5-ylamino)-7-methyl-6-oxo-8-(tetrahydrofuran-3-ylmethyl)-7,8-dihydropteridin-5(6H)-yl]benzonitrile |
| 83 | 3-[(7R)-8-[(3,3-difluorocyclobutyl)methyl]-2-(1H-indazol-5-ylamino)-7-methyl-6-oxo-7,8-dihydropteridin-5(6H)-yl]benzonitrile |
| 85 | (7R)-5-(3,4-dimethoxyphenyl)-2-[(7-fluoro-1H-indazol-5-yl)amino]-7-methyl-8-(3-methylbutyl)-7,8-dihydropteridin-6(5H)-one |
| 86 | 3-[(7R)-2-[(7-fluoro-1H-indazol-5-yl)amino]-7-methyl-8-(3-methylbutyl)-6-oxo-7,8-dihydropteridin-5(6H)-yl]benzonitrile |
| 87 | (7R)-2-[(7-fluoro-1H-indazol-5-yl)amino]-7-methyl-8-(3-methylbutyl)-5-(pyridin-3-yl)-7,8-dihydropteridin-6(5H)-one |
| 88 | (7R)-5-(3,4-dimethoxyphenyl)-2-[(4-fluoro-2-oxo-2,3-dihydro-1,3-benzoxazol-6-yl)amino]-7-methyl-8-(3-methylbutyl)-7,8-dihydropteridin-6(5H)-one |
| 89 | 3-[(7R)-2-[(3,5-difluoro-4-hydroxyphenyl)amino]-7-methyl-8-(3-methylbutyl)-6-oxo-7,8-dihydropteridin-5(6H)-yl]benzonitrile |
| 90 | 3-[(7R)-2-[(4-fluoro-2-oxo-2,3-dihydro-1,3-benzoxazol-6-yl)amino]-7-methyl-8-(3-methylbutyl)-6-oxo-7,8-dihydropteridin-5(6H)-yl]benzonitrile |
| 91 | 5-[(7R)-2-[(7-fluoro-1H-indazol-5-yl)amino]-7-methyl-8-(3-methylbutyl)-6-oxo-7,8-dihydropteridin-5(6H)-yl]-2-methoxybenzonitrile |
| 92 | 2-ethoxy-5-[(7R)-2-[(7-fluoro-1H-indazol-5--yl)amino]-7-methyl-8-(3-methylbutyl)-6-oxo-7,8-dihydropteridin-5(6H)-yl]benzonitrile |
| 93 | 5-[(7R)-2-[(7-fluoro-1H-indazol-5-yl)amino]-7-methyl-8-(3-methylbutyl)-6-oxo-7,8-dihydropteridin-5(6H)-yl]-2-(propan-2-yloxy)benzonitrile |
| 94 | 7-methyl-2-[(2-oxo-2,3-dihydro-1H-indol-5-yl)amino]-5-phenyl-8-(propan-2-yl)-7,8-dihydropteridin-6(5H)-one |
| 95 | (7R)-8-cyclohexyl-5-(3,5-difluorophenyl)-2-(1H-indazol-5-ylamino)-7-methyl-7,8-dihydropteridin-6(5H)-one |
| 96 | 5-[(7R)-8-cyclohexyl-2-(1H-indazol-5-ylamino)-7-methyl-6-oxo-7,8-dihydropteridin-5(6H)-yl]-2-fluorobenzonitrile |
| 97 | 3-[(7R)-2-[(7-chloro-1H-indazol-5-yl)amino]-8-cyclohexyl-7-methyl-6-oxo-7,8-dihydropteridin-5(6H)-yl]benzonitrile |
| 98 | (7R)-8-cyclohexyl-2-(1H-indazol-5-ylamino)-7-methyl-5-[6-(methylsulfanyl)pyridin-3-yl]-7,8-dihydropteridin-6(5H)-one |
| 99 | (7R)-8-cyclohexyl-5-(3-fluoro-5-methoxyphenyl)-2-(1H-indazol-5-ylamino)-7-methyl-7,8-dihydropteridin-6(5H)-one |
| 100 | 3-[(7R)-8-cyclohexyl-2-[(4-fluoro-1H-indazol-5-yl)amino]-7-methyl-6-oxo-7,8-dihydropteridin-5(6H)-yl]benzonitrile |
| 101 | 3-[(7R)-2-[(4-chloro-1H-indazol-5-yl)amino]-8-cyclohexyl-7-methyl-6-oxo-7,8-dihydropteridin-5(6H)-yl]benzonitrile |
| 102 | 3-[(7R)-8-cyclohexyl-2-[(4-methoxy-1H-indazol-5-yl)amino]-7-methyl-6-oxo-7,8-dihydropteridin-5(6H)-yl]benzonitrile |
| 103 | 3-[(7R)-8-cyclohexyl-7-methyl-2-[(3-methyl-1H-indazol-5-yl)amino]-6-oxo-7,8-dihydropteridin-5(6H)-yl]benzonitrile |
| 104 | 5-[(7R)-8-cyclohexyl-2-(1H-indazol-5-ylamino)-7-methyl-6-oxo-7,8-dihydropteridin-5(6H)-yl]-2-methoxybenzonitrile |
| 105 | 2-chloro-5-[(7R)-8-cyclohexyl-2-(1H-indazol-5-ylamino)-7-methyl-6-oxo-7,8-dihydropteridin-5(6H)-yl]benzonitrile |
| 106 | 3-[(7R)-8-cyclohexyl-2-[(7-fluoro-1H-indazol-5-yl)amino]-7-methyl-6-oxo-7,8-dihydropteridin-5(6H)-yl]benzonitrile |
| 107 | 3-[(7R)-8-cyclohexyl-2-[(7-fluoro-1H-indazol-4-yl)amino]-7-methyl-6-oxo-7,8-dihydropteridin-5(6H)-yl]benzonitrile |
| 108 | 3-[(7R)-2-[(3-chloro-1H-indazol-5-yl)amino]-8-cyclohexyl-7-methyl-6-oxo-7,8-dihydropteridin-5(6H)-yl]benzonitrile |
| 109 | 3-[(7R)-2-(1,2-benzothiazol-5-ylamino)-8-cyclohexyl-7-methyl-6-oxo-7,8-dihydropteridin-5(6H)-yl]benzonitrile |
| 110 | (7R)-8-cyclohexyl-2-(1H-indazol-5-ylamino)-5-[3-(methoxymethyl)phenyl]-7-methyl-7,8-dihydropteridin-6(5H)-one |
| 111 | (7R)-8-cyclohexyl-5-(3,4-dimethoxyphenyl)-2-(1H-indazol-5-ylamino)-7-methyl-7,8-dihydropteridin-6(5H)-one |
| 112 | 3-[(7R)-8-cyclohexyl-2-(1H-indazol-5-ylamino)-7-methyl-6-oxo-7,8-dihydropteridin-5(6H)-yl]-5-fluorobenzonitrile |
| 113 | (7R)-8-cyclohexyl-2-(1H-indazol-5-ylamino)-7-methyl-5-(6-methylpyridin-3-yl)-7,8-dihydropteridin-6(5H)-one |
| 114 | (7R)-8-cyclohexyl-2-(1H-indazol-5-ylamino)-7-methyl-5-[3-(methylsulfinyl)phenyl]-7,8-dihydropteridin-6(5H)-one |
| 115 | 3-[(7R)-8-cyclohexyl-2-[(3-fluoro-1H-indazol-5-yl)amino]-7-methyl-6-oxo-7,8-dihydropteridin-5(6H)-yl]benzonitrile |
| 116 | 3-[(7R)-8-cyclohexyl-2-[(3-methoxy-1H-indazol-5-yl)amino]-7-methyl-6-oxo-7,8-dihydropteridin-5(6H)-yl]benzonitrile |
| 117 | 3-[(7R)-8-cyclohexyl-7-methyl-2-[(4-methyl-1H-indazol-5-yl)amino]-6-oxo-7,8-dihydropteridin-5(6H)-yl]benzonitrile |
| 118 | 3-[(7R)-2-[(6-chloro-1H-indazol-5-yl)amino]-8-cyclohexyl-7-methyl-6-oxo-7,8-dihydropteridin-5(6H)-yl]benzonitrile |
| 119 | 3-[(7R)-8-cyclohexyl-2-[(6-methoxy-1H-indazol-5-yl)amino]-7-methyl-6-oxo-7,8-dihydropteridin-5(6H)-yl]benzonitrile |
| 120 | (7R)-8-cyclohexyl-2-[(4-fluoro-1H-indazol-5-yl)amino]-5-(3-fluorophenyl)-7-methyl-7,8-dihydropteridin-6(5H)-one |
| 121 | (7R)-8-cyclohexyl-5-(3-fluoro-4-methylphenyl)-2-(1H-indazol-5-ylamino)-7-methyl-7,8-dihydropteridin-6(5H)-one |
| 122 | (7R)-8-cyclohexyl-2-[(4-fluoro-1H-indazol-5-yl)amino]-7-methyl-5-(pyridin-3-yl)-7,8-dihydropteridin-6(5H)-one |
| 123 | 3-[(7R)-8-cyclohexyl-2-[(7-methoxy-1H-indazol-5-yl)amino]-7-methyl-6-oxo-7,8-dihydropteridin-5(6H)-yl]benzonitrile |
| 124 | 4-[(7R)-8-cyclohexyl-2-(1H-indazol-5-ylamino)-7-methyl-6-oxo-7,8-dihydropteridin-5(6H)-yl]thiophene-2-carboxylic acid |
| 125 | (7R)-8-cyclohexyl-2-(1H-indazol-5-ylamino)-5-(3-methoxy-4-methylphenyl)-7-methyl-7,8-dihydropteridin-6(5H)-one |
| 126 | (7R)-8-cyclohexyl-2-(1H-indazol-5-ylamino)-7-methyl-5-[4-(morpholin-4-yl)phenyl]-7,8-dihydropteridin-6(5H)-one |
| 127 | (7R)-8-cyclohexyl-5-[3-(hydroxymethyl)phenyl]-2-(1H-indazol-5-ylamino)-7-methyl-7,8-dihydropteridin-6(5H)-one |
| 128 | 5-[(7R)-8-cyclohexyl-2-(1H-indazol-5-ylamino)-7-methyl-6-oxo-7,8-dihydropteridin-5(6H)-yl]pyridine-3-carbonitrile |
| 129 | (7R)-8-cyclohexyl-5-[6-(dimethylamino)pyridin-3-yl]-2-(1H-indazol-5-ylamino)-7-methyl-7,8-dihydropteridin-6(5H)-one |
| 130 | 3-[(7R)-8-cyclohexyl-2-[(4,7-difluoro-1H-indazol-5-yl)amino]-7-methyl-6-oxo-7,8-dihydropteridin-5(6H)-yl]benzonitrile |
| 131 | 3-[(7R)-8-cyclohexyl-2-[(3,7-difluoro-1H-indazol-5-yl)amino]-7-methyl-6-oxo-7,8-dihydropteridin-5(6H)-yl]benzonitrile |
| 132 | (7R)-8-cyclohexyl-5-(3,4-dimethoxyphenyl)-2-[(7-fluoro-1H-indazol-5-yl)amino]-7-methyl-7,8-dihydropteridin-6(5H)-one |
| 133 | (7R)-8-cyclohexyl-2-[(7-fluoro-1H-indazol-5-yl)amino]-7-methyl-5-(quinolin-7-yl)-7,8-dihydropteridin-6(5H)-one |
| 134 | (7R)-8-cyclohexyl-2-[(7-fluoro-1H-indazol-5-yl)amino]-7-methyl-5-[4-(morpholin-4-yl)phenyl]-7,8-dihydropteridin-6(5H)-one |
| 135 | (7R)-8-cyclohexyl-2-[(7-fluoro-1H-indazol-5-yl)amino]-7-methyl-5-(pyridin-3-yl)-7,8-dihydropteridin-6(5H)-one |
| 136 | 5-[(7R)-8-cyclohexyl-2-[(7-fluoro-1H-indazol-5-yl)amino]-7-methyl-6-oxo-7,8-dihydropteridin-5(6H)-yl]-2-methoxybenzonitrile |
| 137 | (7R)-8-cyclohexyl-2-[(7-fluoro-1H-indazol-5-yl)amino]-5-(3-fluorophenyl)-7-methyl-7,8-dihydropteridin-6(5H)-one |
| 138 | (7R)-8-cyclohexyl-2-[(7-fluoro-1H-indazol-5-yl)amino]-5-(6-methoxypyridin-3-yl)-7-methyl-7,8-dihydropteridin-6(5H)-one |
| 139 | (7R)-8-cyclohexyl-2-[(7-fluoro-1H-indazol-5-yl)amino]-7-methyl-5-[6-(4-methylpiperazin-1-yl)pyridin-3-yl]-7,8-dihydropteridin-6(5H)-one. |
| 140 | 3-[(7R)-8-cyclopentyl-7-ethyl-2-(1H-indazol-5-ylamino)-6-oxo-7,8-dihydropteridin-5(6H)-yl]benzonitrile |

| # | Compound |
|---|---|
| 141 | (7R)-8-cyclohexyl-2-[(7-fluoro-1H-indazol-5-yl)amino]-7-methyl-5-[6-(pyrrolidin-1-yl)pyridin-3-yl]-7,8-dihydropteridin-6(5H)-one |
| 142 | (7R)-8-cyclohexyl-2-[(7-fluoro-1H-indazol-5-yl)amino]-7-methyl-5-[6-(piperidin-1-yl)pyridin-3-yl]-7,8-dihydropteridin-6(5H)-one |
| 143 | (7R)-8-cyclohexyl-5-[6-(dimethylamino)pyridin-3-yl]-2-[(7-fluoro-1H-indazol-5-yl)amino]-7-methyl-7,8-dihydropteridin-6(5H)-one |
| 144 | 3-[(7R)-8-cyclohexyl-2-[(3,4-difluoro-1H-indazol-5-yl)amino]-7-methyl-6-oxo-7,8-dihydropteridin-5(6H)-yl]benzonitrile |
| 145 | 3-[(7R)-8-cyclohexyl-2-[(7-fluoro-2-oxo-2,3-dihydro-1H-indol-5-yl)amino]-7-methyl-6-oxo-7,8-dihydropteridin-5(6H)-yl]benzonitrile |
| 146 | 3-[(7R)-8-cyclohexyl-7-methyl-6-oxo-2-[(3,4,7-trifluoro-1H-indazol-5-yl)amino]-7,8-dihydropteridin-5(6H)-yl]benzonitrile |
| 147 | (7R)-8-cyclohexyl-2-[(7-fluoro-1H-indazol-5-yl)amino]-5-[6-(4-hydroxypiperidin-1-yl)pyridin-3-yl]-7-methyl-7,8-dihydropteridin-6(5H)-one. |
| 148 | 4-{[(7R)-8-cyclohexyl-5-(3,4-dimethoxyphenyl)-7-methyl-6-oxo-5,6,7,8-tetrahydropteridin-2-yl]amino}benzoic acid |
| 149 | 3-[(7R)-8-cyclohexyl-7-methyl-6-oxo-2-[(2-oxo-2,3-dihydro-1,3-benzoxazol-6-yl)amino]-7,8-dihydropteridin-(6H)-yl]benzonitrile |
| 150 | (7R)-8-cyclohexyl-5-(3,4-dimethoxyphenyl)-7-methyl-2-[(2-oxo-2,3-dihydro-1,3-benzoxazol-6-yl)amino]-7,8-dihydropteridin-6(5H)-one |
| 151 | (7R)-8-cyclohexyl-7-methyl-2-[(2-oxo-2,3-dihydro-1,3-benzoxazol-6-yl)amino]-5-(pyridin-3-yl)-7,8-dihydropteridin-6(5H)-one |
| 152 | 3-[(7R)-8-cyclohexyl-7-methyl-6-oxo-2-(1H-pyrazolo[3,4-b]pyridin-5-ylamino)-7,8-dihydropteridin-5(6H)-yl]benzonitrile |
| 153 | (7R)-8-cyclohexyl-5-(3,4-dimethoxyphenyl)-7-methyl-2-(1H-pyrazolo[3,4-B]pyridin-5-ylamino)-7,8-dihydropteridin-6(5H)-one. |
| 154 | (7R)-8-cyclohexyl-7-methyl-2-(1H-pyrazolo[3,4-b]pyridin-5-ylamino)-5-(pyridin-3-yl)-7,8-dihydropteridin-6(5H)-one |
| 155 | 4-{[(7R)-5-(3-cyanophenyl)-8-cyclohexyl-7-methyl-6-oxo-5,6,7,8-tetrahydropteridin-2-yl]amino}benzoic acid. |
| 156 | 3-[(7R)-8-cyclohexyl-7-methyl-6-oxo-2-(phenylamino)-7,8-dihydropteridin-5(6H)-yl]benzonitrile |
| 157 | 5-{[(7R)-5-(3-cyanophenyl)-8-cyclohexyl-7-methyl-6-oxo-5,6,7,8-tetrahydropteridin-2-yl]amino}-1H-indazole-3-carbonitrile. |
| 158 | 3-[(7R)-8-cyclohexyl-2-[(3,5-difluoro-4-hydroxyphenyl)amino]-7-methyl-6-oxo-7,8-dihydropteridin-5(6H)-yl]benzonitrile |
| 159 | (7R)-8-cyclohexyl-2-[(3,5-difluoro-4-hydroxyphenyl)amino]-5-(3,4-dimethoxyphenyl)-7-methyl-7,8-dihydroptendin-6(5H)-one |
| 160 | (7R)-8-cyclohexyl-2-[(3,5-difluoro-4-hydroxyphenyl)amino]-7-methyl-5-(pyridin-3-yl)-7,8-dihydropteridin-(5H)-one. |
| 161 | 3-[(7R)-8-cyclohexyl-7-methyl-6-oxo-2-[(1-oxo-2,3-dihydro-1H-isoindol-5-yl)amino]-7,8-dihydroptendin-5(6H)-yl]benzonitrile |
| 164 | 5-[(7R)-8-cyclohexyl-7-methyl-6-oxo-2-(1H-pyrazolo[3,4-b]pyridin-5-ylamino)-7,8-dihydropteridin-5(6H)-yl]-2-methoxybenzonitrile. |
| 165 | 5-[(7R)-8-cyclohexyl-7-methyl-6-oxo-2-[(2-oxo-2,3-dihydro-1,3-benzoxazol-6-yl)amino]-7,8-dihydropteridin-5(6H)-yl]-2-methoxybenzonitrile |
| 166 | 3-[(7R)-8-cyclohexyl-7-methyl-6-oxo-2-[(3-oxo-2,3-dihydro-1,2-benzoxazol-6-yl)amino]-7,8-dihydropteridin-5(6H)-yl]benzonitrile |
| 167 | 3-[(7R)-8-cyclohexyl-7-methyl-6-oxo-2-(1H-pyrazolo[4,3-b]pyridin-5-ylamino)-7,8-dihydropteridin-5(6H)-yl]benzonitrile |
| 168 | 3-[(7R)-8-cyclohexyl-2-[(5-hydroxypyridin-2-yl)amino]-7-methyl-6-oxo-7,8-dihydropteridin-5(6H)-yl]benzonitrile |
| 169 | 3-[(7R)-8-cyclohexyl-2-[(4-fluoro-2-oxo-2,3-dihydro-1,3-benzoxazol-6-yl)amino]-7-methyl-6-oxo-7,8-dihydropteridin-5(6H)-yl]benzonitrile |
| 171 | 3-[(7R)-8-cyclohexyl-2-{[4-(hydroxymethyl)phenyl]aminol-7-methyl-6-oxo-7,8-dihydropteridin-5(6H)-yl]benzonitrile |
| 172 | 3-[(7R)-8-cyclohexyl-7-methyl-6-oxo-2-[(2-oxo-2,3-dihydro[1,3]oxazolo[4,5-b]pyridin-6-yl)amino]-7,8-dihydropteridin-5(6H)-yl]benzonitrile |
| 173 | 5-[(7R)-8-cyclohexyl-2-[(7-fluoro-1H-indazol-5-yl)amino]-7-methyl-6-oxo-7,8-dihydropteridin-5(6H)-yl]-2-(4-methylpiperazin-1-yl)benzonitrile |
| 174 | 3-[(7R)-8-cyclohexyl-2-[(2,2-dioxido-1,3-dihydro-2,1-benzothiazol-5-yl)amino]-7-methyl-6-oxo-7,8-dihydropteridin-5(6H)-yl]benzonitrile |
| 175 | (7R)-8-cyclohexyl-7-methyl-5-(1-methyl-2-oxo-1,2-dihydropyridin-4-yl)-2-(1H-pyrazolo[3,4-b]pyridin-5-ylamino)-7,8-dihydropteridin-6(5H)-one |
| 176 | (7R)-8-cyclohexyl-2-[(7-fluoro-1H-indazol-5-yl)amino]-7-methyl-5-(1-methyl-2-oxo-1,2-dihydropyridin-4-yl)-7,8-dihydropteridin-6(5H)-one |
| 177 | methyl 4-[(7R)-8-cyclohexyl-2-(1H-indazol-5-ylamino)-7-methyl-6-oxo-7,8-dihydropteridin-5(6H)-yl]thiophene-2-carboxylate |
| 178 | 2-(1H-indazol-5-ylamino)-7-methyl-5,8-diphenyl-7,8-dihydropteridin-6(5H)-one |
| 179 | 7-methyl-2-[(2-oxo-2,3-dihydro-1H-indo1-5-yl)amino]-5,8-diphenyl-7,8-dihydropteridin-6(5H)-one |
| 180 | 3-[(7R)-2-[(7-fluoro-1H-indazol-5-yl)amino]-8-(4-fluorophenyl)-7-methyl-6-oxo-7,8-dihydropteridin-5(6H)-ypenzonitrile |
| 181 | 3-[(7R)-2-[(7-fluoro-1H-indazol-5-yl)amino]-8-(3-methoxyphenyl)-7-methyl-6-oxo-7,8-dihydropteridin-5(6H)-yl]benzonitrile |
| 182 | 3-[(7R)-2-[(7-fluoro-1H-indazol-5-yl)amino]-8-(4-methoxyphenyl)-7-methyl-6-oxo-7,8-dihydropteridin-5(6H)-yl]benzonitrile |
| 183 | 3-[(7R)-2-[(7-fluoro-1H-indazol-5-yl)amino]-8-(3-fluorophenyl)-7-methyl-6-oxo-7,8-dihydropteridin-5(6H)-yl]benzonitrile |
| 184 | 3-[(7R)-2-(1H-indazol-5-ylamino)-7-methyl-6-oxo-8-(tetrahydro-2H-pyran-4-yl)-7,8-dihydropteridin-5(6H)-yl]benzonitrile |
| 185 | 3-[(7R)-2-[(4-fluoro-1H-indazol-5-yl)amino]-7-methyl-6-oxo-8-(tetrahydro-2H-pyran-4-yl)-7,8-dihydropteridin-5(6H)-yl]benzonitrile |
| 186 | 3-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]benzonitrile |
| 187 | (7R)-5-(3,4-dimethoxyphenyl)-2-[(3-fluoro-1H-indazol-5-yl)amino]-7-methyl-8-(tetrahydro-2H-pyran-4-yl)-7,8-dihydropteridin-6(5H)-one |
| 188 | (7R)-5-(3,4-dimethoxyphenyl)-2-[(7-fluoro-1H-indazol-5-yl)amino]-7-methyl-8-(tetrahydro-2H-pyran-4-yl)-7,8-dihydropteridin-6(5H)-one |
| 189 | (7R)-2-[(7-fluoro-1H-indazol-5-yl)amino]-5-(3-fluorophenyl)-7-methyl-8-(tetrahydro-2H-pyran-4-yl)-7,8-dihydropteridin-6(5H)-one |
| 190 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-methoxybenzonitrile |
| 191 | (7R)-2-[(7-fluoro-1H-indazol-5-yl)amino]-7-methyl-5-(pyridin-3-yl)-8-(tetrahydro-2H-pyran-4-yl)-7,8-dihydropteridin-6(5H)-one |
| 192 | (7R)-2-[(7-fluoro-1H-indazol-5-yl)amino]-5-(6-methoxypyridin-3-yl)-7-methyl-8-(tetrahydro-2H-pyran-4-yl)-7,8-dihydropteridin-6(5H)-one |
| 193 | (7R)-2-[(7-fluoro-1H-indazol-5-yl)amino]-7-methyl-5-[6-(4-methylpiperazin-1-yl)pyridin-3-yl]-8-(tetrahydro-2H-pyran-4-yl)-7,8-dihydropteridin-6(5H)-one |
| 194 | 3-[(7R)-2-[(3,5-difluoro-4-hydroxyphenyl)amino]-7-methyl-6-oxo-8-(tetrahydro-2H-pyran-4-yl)-7,8-dihydropteridin-5(6H)-yl]benzonitrile |
| 195 | 2-Ethoxy-5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]benzonitrile |
| 196 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-(propan-2-yloxy)benzonitrile |
| 197 | 2-Methoxy-5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]benzonitrile. |
| 198 | 2-Ethoxy-5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]benzonitrile |
| 199 | 5-[(7R)-7-methyl-6-oxo-2-[(2-oxo-2,3-dihydro-1,3-benzoxazol-6-yl)amino]-8-(tetrahydro-2H-pyran-4-yl)-7,8-dihydropteridin-5(6H)-yl]-2-(propan-2-yloxy)benzonitrile |
| 200 | 2-methoxy-5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]benzonitrile |
| 201 | 2-Ethoxy-5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]benzonitrile. |
| 202 | 5-[(7R)-7-methyl-6-oxo-2-(1H-pyrazolo[3,4-b]pyridin-5-ylamino)-8-(tetrahydro-2H-pyran-4-yl)-7,8-dihydropteridin-5(6H)-yl]-2-(propan-2-yloxy)benzonitrile |
| 203 | 5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]-2-methoxybenzonitrile. |
| 204 | 2-Ethoxy-5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]benzonitrile. |
| 205 | 5-[(7R)-2-[(4-fluoro-2-oxo-2,3-dihydro-1,3-benzoxazol-6-yl)amino]-7-methyl-6-oxo-8-(tetrahydro-2H-pyran-4-yl)-7,8-dihydropteridin-5(6H)-yl]-2-(propan-2-yloxy)benzonitrile |

| # | Name |
|---|---|
| 206 | 5-[(7R)-2-[(7-fluoro-1H-indazol-5-yl)amino]-7-methyl-6-oxo-8-(tetrahydro-2H-pyran-4-yl)-7,8-dihydropteridin-5(6H)-yl]-2-(4-methylpiperazin-1-yl)benzonitrile |
| 207 | 3-[(7R)-8-(4,4-dimethylcyclohexyl)-2-(1H-indazol-5-ylamino)-7-methyl-6-oxo-7,8-dihydropteridin-5(6H)-yl]benzonitrile |
| 208 | (7R)-8-(4,4-dimethylcyclohexyl)-2-[(7-fluoro-1H-indazol-5-yl)amino]-7-methyl-5-(pyridin-3-yl)-7,8-dihydropteridin-6(5H)-one |
| 209 | 3-[(7R)-8-(4,4-dimethylcyclohexyl)-2-[(7-fluoro-1H-indazol-5-yl)amino]-7-methyl-6-oxo-7,8-dihydropteridin-5(6H)-yl]benzonitrile |
| 210 | (7R)-5-(3,4-dimethoxyphenyl)-8-(4,4-dimethylcyclohexyl)-2-[(7-fluoro-1H-indazol-5-yl)amino]-7-methyl-7,8-dihydropteridin-6(5H)-one |
| 211 | (7R)-8-(4,4-dimethylcyclohexyl)-2-[(7-fluoro-1H-indazol-5-yl)amino]-5-(3-fluorophenyl)-7-methyl-7,8-dihydropteridin-6(5H)-one |
| 212 | 5-[(7R)-8-(4,4-dimethylcyclohexyl)-2-[(7-fluoro-1H-indazol-5-yl)amino]-7-methyl-6-oxo-7,8-dihydropteridin-5(6H)-yl]-2-(pyrrolidin-1-yl)benzonitrile |
| 213 | (7R)-8-(4,4-dimethylcyclohexyl)-2-[(7-fluoro-1H-indazol-5-yl)amino]-7-methyl-5-[6-(morpholin-4-Apyridin-3-yl)-7,8-dihydropteridin-6(5H)-one |
| 214 | (7R)-8-(4,4-dimethylcyclohexyl)-2-[(7-fluoro-1H-indazol-5-yl)amino]-7-methyl-5-[6-(pyrrolidin-1-yl)pyridin-3-yl]-7,8-dihydropteridin-6(5H)-one |
| 215 | (7R)-8-(4,4-dimethylcyclohexyl)-2-[(7-fluoro-1H-indazol-5-yl)amino]-7-methyl-5-[6-(piperidin-1-yl)pyridin-3-yl]-7,8-dihydropteridin-6(5H)-one |
| 216 | 3-[(7R)-8-cyclopentyl-2-[(4-fluoro-1H-indazol-5-yl)amino]-7-methyl-6-oxo-7,8-dihydropteridin-5(6H)-yl]benzonitrile |
| 217 | 3-[(7R)-8-cyclopentyl-7-ethyl-2-[(7-fluoro-1H-indazol-5-yl)amino]-6-oxo-7,8-dihydropteridin-5(6H)-yl]benzonitrile |
| 218 | 3-[(7R)-8-cyclopentyl-2-[(7-fluoro-1H-indazol-5-yl)amino]-7-(hydroxymethyl)-6-oxo-7,8-dihydropteridin-5(6H)-yl]benzonitrile |
| 219 | 3-[(7R)-8-cyclopentyl-2-[(7-fluoro-1H-indazol-5-yl)amino]-7-methyl-6-oxo-7,8-dihydropteridin-5(6H)-yl]benzonitrile |
| 220 | 3-[(7R)-8-cyclopentyl-7-(hydroxymethyl)-2-(1H-indazol-5-ylamino)-6-oxo-7,8-dihydropteridin-5(6H)-yl]benzonitrile |
| 221 | 3-[(7S)-8-cyclopentyl-2-[(7-fluoro-1H-indazol-5-yl)amino]-7-(fluoromethyl)-6-oxo-7,8-dihydropteridin-5(6H)-yl]benzonitrile |
| 222 | 3-[(7S)-8-cyclopentyl-7-(fluoromethyl)-2-(1H-indazol-5-ylamino)-6-oxo-7,8-dihydropteridin-5(6H)-yl]benzonitrile |
| 223 | 3-[(7R)-2-[(7-fluoro-1H-indazol-5-yl)amino]-8-(cis-4-methoxycyclohexyl)-7-methyl-6-oxo-7,8-dihydropteridin-5(6H)-yl]benzonitrile |
| 224 | 3-[(7R)-2-[(7-fluoro-1H-indazol-5-yl)amino]-8-(trans-4-methoxycyclohexyl)-7-methyl-6-oxo-7,8-dihydropteridin-5(6H)-yl]benzonitrile |
| 225 | (7R)-5-(3,4-dimethoxyphenyl)-2-[(7-fluoro-1H-indazol-5-yl)amino]-8-(trans-4-methoxycyclohexyl)-7-methyl-7,8-dihydropteridin-6(5H)-one |
| 226 | (7R)-5-(3,4-dimethoxyphenyl)-2-[(7-fluoro-1H-indazol-5-yl)amino]-8-(cis-4-methoxycyclohexyl)-7-methyl-7,8-dihydropteridin-6(5H)-one |
| 227 | (7R)-2-[(7-fluoro-1H-indazol-5-yl)amino]-8-(cis-4-methoxycyclohexyl)-7-methyl-5-(pyridin-3-yl)-7,8-dihydropteridin-6(5H)-one |
| 228 | 3-[(7R)-8-(cis-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile |
| 229 | 3-[(7R)-8-(trans-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile |
| 230 | 3-[(7R)-8-(trans-4-methoxycyclohexyl)-7-methyl-6-oxo-2-(1H-pyrazolo[3,4-c]pyridin-5-ylamino)-7,8-dihydropteridin-5(6H)-yl]benzonitrile |
| 231 | 3-[(7R)-8-(trans-4-methoxycyclohexyl)-7-methyl-6-oxo-2-(1H-pyrazolo[3,4-b]pyridin-5-ylamino)-7,8-dihydropteridin-5(6H)-yl]benzonitrile |
| 232 | 3-[(7R)-2-[(3,5-difluoro-4-hydroxyphenyl)amino]-8-(trans-4-methoxycyclohexyl)-7-methyl-6-oxo-7,8-dihydropteridin-5(6H)-yl]benzonitrile. |
| 233 | (7R)-2-[(7-fluoro-1H-indazol-5-yl)amino]-8-(trans-4-methoxycyclohexyl)-7-methyl-5-[6-(4-methylpiperazin-1-yl)pyridin-3-yl]-7,8-dihydropteridin-6(5H)-one |
| 234 | 2-methoxy-5-[(7R)-8-(trans-4-methoxycyclohexyl)-7-methyl-6-oxo-2-(1H-pyrazolo[3,4-b]pyridin-5-ylamino)-7,8-dihydropteridin-5(6H)-yl]benzonitrile |
| 235 | 2-methoxy-5-[(7R)-8-(trans-4-methoxycyclohexyl)-7-methyl-6-oxo-2-[(2-oxo-2,3-dihydro-1,3-benzoxazol-6-yl)amino]-7,8-dihydropteridin-5(6H)-yl]benzonitrile |
| 236 | 3-[(7R)-2-[(7-fluoro-1H-indazol-5-yl)amino]-7-methyl-8-(cis-4-methylcyclohexyl)-6-oxo-7,8-dihydropteridin-5(6H)-yl]benzonitrile |
| 237 | 3-[(7R)-2-[(7-fluoro-1H-indazol-5-yl)amino]-7-methyl-8-(trans-4-methylcyclohexyl)-6-oxo-7,8-dihydropteridin-5(6H)-yl]benzonitrile |
| 238 | (7R)-5-(3,4-dimethoxyphenyl)-2-[(7-fluoro-1H-indazol-5-yl)amino]-7-methyl-8-(cis-4-methylcyclohexyl)-7,8-dihydropteridin-6(5H)-one |
| 239 | (7R)-5-(3,4-dimethoxyphenyl)-2-[(7-fluoro-1H-indazol-5-yl)amino]-7-methyl-8-(trans-4-methylcyclohexyl)-7,8-dihydropteridin-6(5H)-one |
| 240 | (7R)-2-[(7-fluoro-1H-indazol-5-yl)amino]-7-methyl-8-(cis-4-methylcyclohexyl)-5-(pyridin-3-yl)-7,8-dihydropteridin-6(5H)-one |
| 241 | (7R)-2-[(7-fluoro-1H-indazol-5-yl)amino]-7-methyl-8-(cis-4-methylcyclohexyl)-5-(pyridin-3-yl)-7,8-dihydropteridin-6(5H)-one |
| 242 | (7R)-2-[(7-fluoro-1H-indazol-5-yl)amino]-7-methyl-8-(trans-4-methylcyclohexyl)-5-[6-(4-methylpiperazin-1-yl)pyridin-3-yl]-7,8-dihydropteridin-6(5H)-one |
| 243 | 3-[(7R)-2-[(3,5-difluoro-4-hydroxyphenyl)amino]-7-methyl-8-(trans-4-methylcyclohexyl)-6-oxo-7,8-dihydropteridin-5(6H)-yl]benzonitrile. |
| 244 | 2-methoxy-5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]benzonitrile |
| 245 | 2-Methoxy-5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]benzonitrile |
| 246 | 2-Ethoxy-5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]benzonitrile |
| 247 | 2-Ethoxy-5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]benzonitrile |
| 248 | 5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]-2-(propan-2-yloxy)benzonitrile |
| 249 | 5-[(7R)-7-methyl-8-(trans-4-methylcyclohexyl)-6-oxo-2-[(2-oxo-2,3-dihydro-1,3-benzoxazol-6-yl)amino]-7,8-dihydropteridin-5(6H)-yl]-2-(propan-2-yloxy)benzonitrile |
| 250 | 3-[(7R)-2-[(2,2-dioxido-1,3-dihydro-2,1-benzothiazol-5-yl)amino]-7-methyl-8-(trans-4-methylcyclohexyl)-6-oxo-7,8-dihydropteridin-5(6H)-yl]benzonitrile. |
| 251 | 5-[(7R)-2-[(7-fluoro-1H-indazol-5-yl)amino]-7-methyl-8-(trans-4-methylcyclohexyl)-6-oxo-7,8-dihydropteridin-5(6H)-yl]-2-(4-methylpiperazin-1-yl)benzonitrile |
| 252 | 5-[(7R)-7-methyl-8-(trans-4-methylcyclohexyl)-6-oxo-2-(1H-pyrazolo[3,4-b]pyridin-5-ylamino)-7,8-dihydropteridin-5(6H)-yl]-2-(4-methylpiperazin-1-yl)benzonitrile |
| 253 | 3-[(7R)-2-(1H-indazol-5-ylamino)-7-methyl-6-oxo-8-[trans-4-(trifluoromethyl)cyclohexyl]-7,8-dihydropteridin-5(6H)-yl]benzonitrile |
| 254 | 3-[(7R)-2-(1H-indazol-5-ylamino)-7-methyl-6-oxo-8-[cis-4-(trifluoromethyl)cyclohexyl]-7,8-dihydropteridin-5(6H)-yl]benzonitrile |
| 255 | (7R)-2-[(7-fluoro-1H-indazol-5-yl)amino]-7-methyl-5-(pyridin-3-yl)-8-[cis-4-(trifluoromethyl)cyclohexyl]-7,8-dihydropteridin-6(5H)-one |
| 256 | (7R)-2-[(7-fluoro-1H-indazol-5-yl)amino]-7-methyl-5-(pyridin-3-yl)-8-[trans-4-(trifluoromethyl)cyclohexyl]-7,8-dihydropteridin-6(5H)-one |
| 257 | (7R)-5-(3,4-dimethoxyphenyl)-2-[(7-fluoro-1H-indazol-5-yl)amino]-7-methyl-8-[cis-4-(trifluoromethyl)cyclohexyl]-7,8-dihydropteridin-6(5H)-one |
| 258 | (7R)-5-(3,4-dimethoxyphenyl)-2-[(7-fluoro-1H-indazol-5-yl)amino]-7-methyl-8-[trans-4-(trifluoromethyl)cyclohexyl]-7,8-dihydropteridin-6(5H)-one |
| 259 | 3-[(7R)-2-[(3,5-difluoro-4-hydroxyphenyl)amino]-7-methyl-6-oxo-8-[trans-4-(trifluoromethyl)cyclohexyl]-7,8-dihydropteridin-5(6H)-yl]benzonitrile |
| 260 | 3-[(7R)-8-(4,4-difluorocyclohexyl)-2-[(7-fluoro-1H-indazol-5-yl)amino]-7-methyl-6-oxo-7,8-dihydropteridin-5(6H)-yl]benzonitrile |

261 3-[(7R)-8-(4,4-difluorocyclohexyl)-2-(1H-indazol-5-ylamino)-7-methyl-6-oxo-7,8-dihydropteridin-5(6H)-yl]benzonitrile
262 (7R)-8-(4,4-difluorocyclohexyl)-5-(3,4-dimethoxyphenyl)-2-[(7-fluoro-1H-indazol-5-yl)amino]-7-methyl-7,8-dihydropteridin-6(5H)-one
263 (7R)-8-(4,4-difluorocyclohexyl)-2-[(7-fluoro-1H-indazol-5-yl)amino]-5-(3-fluorophenyl)-7-methyl-7,8-dihydropteridin-6(5H)-one
264 (7R)-8-(4,4-difluorocyclohexyl)-2-[(7-fluoro-1H-indazol-5-yl)amino]-7-methyl-5-(pyridin-3-yl)-7,8-dihydropteridin-6(5H)-one
265 3-[(7R)-8-(4,4-difluorocyclohexyl)-7-methyl-6-oxo-2-[(2-oxo-2,3-dihydro-1H-benzimidazol-5-yl)amino]-7,8-dihydropteridin-5(6H)-yl]benzonitrile
266 3-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]benzonitrile
267 3-[(7R)-8-(4,4-difluorocyclohexyl)-7-methyl-6-oxo-2-[(2-oxo-2,3-dihydro-1,3-benzothiazol-6-yl)amino]-7,8-dihydropteridin-5(6H)-yl]benzonitrile
268 3-[(7R)-8-(4,4-difluorocyclohexyl)-7-methyl-6-oxo-2-(1H-pyrazolo[3,4-c]pyridin-5-ylamino)-7,8-dihydropteridin-5(6H)-yl]benzonitrile
269 4-{[(7R)-5-(3-cyanophenyl)-8-(4,4-difluorocyclohexyl)-7-methyl-6-oxo-5,6,7,8-tetrahydropteridin-2-yl]amino}benzoic acid
270 3-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]benzonitrile
271 4-{[(7R)-5-(3-cyanophenyl)-8-(4,4-difluorocyclohexyl)-7-methyl-6-oxo-5,6,7,8-tetrahydropteridin-2-yl]amino}-2-fluorobenzoic acid
272 4-{[(7R)-5-(3-cyanophenyl)-8-(4,4-difluorocyclohexyl)-7-methyl-6-oxo-5,6,7,8-tetrahydropteridin-2-yl]amino}-2-fluorobenzamide
273 4-{[(7R)-5-(3-cyanophenyl)-8-(4,4-difluorocyclohexyl)-7-methyl-6-oxo-5,6,7,8-tetrahydropteridin-2-yl]amino}benzenesulfonamide
274 3-[(7R)-2-[(4-cyanophenyl)amino]-8-(4,4-difluorocyclohexyl)-7-methyl-6-oxo-7,8-dihydropteridin-5(6H)-yl]benzonitrile
275 3-[(7R)-2-{[4-amino-3-(trifluoromethyl)phenyl]amino]-8-(4,4-difluorocyclohexyl)-7-methyl-6-oxo-7,8-dihydropteridin-5(6H)-yl]benzonitrile
276 3-[(7R)-8-(4,4-difluorocyclohexyl)-2-[(3,5-difluoro-4-hydroxyphenyl)amino]-7-methyl-6-oxo-7,8-dihydropteridin-5(6H)-yl]benzonitrile
277 3-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]benzonitrile
278 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-(propan-2-yloxy)benzonitrile
279 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-methoxybenzonitrile
280 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-ethoxybenzonitrile
281 5-[(7R)-8-(4,4-difluorocyclohexyl)-2-[(4-fluoro-2-oxo-2,3-dihydro-1,3-benzoxazol-6-yl)amino]-7-methyl-6-oxo-7,8-dihydropteridin-5(6H)-yl]-2-methoxybenzonitrile
282 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-ethoxybenzonitrile
283 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-methoxybenzonitrile
284 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-ethoxybenzonitrile
285 5-[(7R)-8-(4,4-difluorocyclohexyl)-7-methyl-6-oxo-2-[(2-oxo-2,3-dihydro-1,3-benzoxazol-6-yl)amino]-7,8-dihydropteridin-5(6H)-yl]-2-(propan-2-yloxy)benzonitrile
286 5-[(7R)-8-(4,4-difluorocyclohexyl)-7-methyl-6-oxo-2-(1H-pyrazolo[3,4-b]pyridin-5-ylamino)-7,8-dihydropteridin-5(6H)-yl]-2-(propan-2-yloxy)benzonitrile
287 3-[(7R)-8-cyclohexyl-7-ethyl-2-[(7-fluoro-1H-indazol-5-yl)amino]-6-oxo-7,8-dihydropteridin-5(6H)-yl]benzonitrile
288 (7R)-8-cyclohexyl-7-ethyl-2-[(7-fluoro-1H-indazol-5-yl)amino]-5-(pyridin-3-yl)-7,8-dihydropteridin-6(5H)-one
289 (7R)-8-cyclohexyl-5-(3,4-dimethoxyphenyl)-7-ethyl-2-[(7-fluoro-1H-indazol-5-yl)amino]-7,8-dihydropteridin-6(5H)-one.
290 (7R)-8-cyclohexyl-7-ethyl-2-[(7-fluoro-1H-indazol-5-yl)amino]-5-(3-fluorophenyl)-7,8-dihydropteridin-6(5H)-one
291 (7R)-8-cyclohexyl-7-ethyl-2-[(7-fluoro-1H-indazol-5-yl)amino]-5-[3-(trifluoromethyl)phenyl]-7,8-dihydropteridin-6(5H)-one.
292 (7R)-8-cyclohexyl-7-ethyl-2-[(7-fluoro-1H-indazol-5-yl)amino]-5-[6-(morpholin-4-yl)pyridin-3-yl]-7,8-dihydropteridin-6(5H)-one
293 (7R)-8-cyclohexyl-5-[6-(dimethylamino)pyridin-3-yl]-7-ethyl-2-[(7-fluoro-1H-indazol-5-yl)amino]-7,8-dihydropteridin-6(5H)-one
294 (7R)-8-cyclohexyl-7-ethyl-2-[(7-fluoro-1H-indazol-5-yl)amino]-5-(3-fluoro-4-methoxyphenyl)-7,8-dihydropteridin-6(5H)-one
295 3-[(7R)-8-cyclohexyl-7-ethyl-2-[(3-fluoro-1H-indazol-5-yl)amino]-6-oxo-7,8-dihydropteridin-5(6H)-yl]benzonitrile
296 3-[(7R)-8-cyclopentyl-7-ethyl-2-(1H-indazol-5-ylamino)-6-oxo-7,8-dihydropteridin-5(6H)-yl]benzonitrile
297 3-[(7R)-2-[(7-fluoro-1H-indazol-5-yl)amino]-7-methyl-6-oxo-8-(spiro[2.5]oct-6-yl)-7,8-dihydropteridin-5(6H)-yl]benzonitrile
298 (7R)-2-[(7-fluoro-1H-indazol-5-yl)amino]-7-methyl-5-(pyridin-3-yl)-8-(spiro[2.5]oct-6-yl)-7,8-dihydropteridin-6(5H)-one.
299 (7R)-5-(3,4-dimethoxyphenyl)-2-[(7-fluoro-1H-indazol-5-yl)amino]-7-methyl-8-(spiro[2.5]oct-6-yl)-7,8-dihydropteridin-6(5H)-one
300 (7R)-8-[(2,2,3,3,4,4,5,5,6,6-2H10)cyclohexyl]-5-(3,4-dimethoxyphenyl)-2-[(7-fluoro-1H-indazol-5-yl)amino]-7-methyl-7,8-dihydropteridin-6(5H)-one
301 (7R)-8-[(2,2,3,3,4,4,5,5,6,6-2H10)cyclohexyl]-2-[(7-fluoro-1H-indazol-5-yl)amino]-7-methyl-5-(pyridin-3-yl)-7,8-dihydropteridin-6(5H)-one
302 3-[(7R)-8-[(2,2,3,3,4,4,5,5,6,6-2H10)cyclohexyl]-2-[(7-fluoro-1H-indazol-5-yl)amino]-7-methyl-6-oxo-7,8-dihydropteridin-5(6H)-yl]benzonitrile
303 (7R)-8-cyclohexyl-2-[(7-fluoro-1H-indazol-5-yl)amino]-7-methyl-5-(1-oxidopyridin-3-yl)-7,8-dihydropteridin-6(5H)-one
304 (7R)-8-(4,4-dimethylcyclohexyl)-2-[(7-fluoro-1H-indazol-5-yl)amino]-7-methyl-5-(1-oxidopyridin-3-yl)-7,8-dihydropteridin-6(5H)-one
305 2-(1H-indazol-5-ylamino)-8-(3-methylbutyl)-5-phenyl-5,8-dihydropteridine-6,7-dione
306 8-(3-methylbutyl)-2-[(2-oxo-2,3-dihydro-1H-indol-5-yl)amino]-5-phenyl-5,8-dihydropteridine-6,7-dione
307 8-cyclopentyl-2-(1H-indazol-5-ylamino)-5-phenyl-5,8-dihydropteridine-6,7-dione
308 (7R)-5-(3,4-dimethoxyphenyl)-2-[(7-fluoro-1H-indazol-5-yl)amino]-7-methyl-8-(4-oxocyclohexyl)-7,8-dihydropteridin-6(5H)-one
309 3-[(7R)-8-(cis-4-hydroxycyclohexyl)-2-(1H-indazol-5-ylamino)-7-methyl-6-oxo-7,8-dihydropteridin-5(6H)-yl]benzonitrile
311 3-[(7R)-8-(3,3-dimethylcyclobutyl)-2-[(7-fluoro-1H-indazol-5-yl)amino]-7-methyl-6-oxo-7,8-dihydropteridin-5(6H)-yl]benzonitrile
312 3-[(7R)-8-(3,3-dimethylcyclobutyl)-7-methyl-6-oxo-2-(1H-pyrazolo[3,4-b]pyridin-5-ylamino)-7,8-dihydropteridin-5(6H)-yl]benzonitrile
313 3-[(7R)-8-(3,3-difluorocyclobutyl)-2-[(7-fluoro-1H-indazol-5-yl)amino]-7-methyl-6-oxo-7,8-dihydropteridin-5(6H)-yl]benzonitrile.

10. A pharmaceutical composition comprising the compound or salt of claim 1, formulated with one or more pharmaceutical carriers.

\* \* \* \* \*